United States Patent
Walji et al.

(10) Patent No.: US 9,808,542 B2
(45) Date of Patent: Nov. 7, 2017

(54) PYRROLO[2,3-C]PYRIDINES AS IMAGING AGENTS FOR NEUROFIBRILLARY

(71) Applicant: MERCK SHARP & DOHME CORP., Rahway, NJ (US)

(72) Inventors: Abbas W. Walji, Lansdale, PA (US); Eric Hostetler, Collegeville, PA (US); Thomas J. Greshock, Collegeville, PA (US); Jing Li, Lansdale, PA (US); Keith P. Moore, Doylestown, PA (US); Idriss Bennacef, Ambler, PA (US); James Mulhearn, Elkins, PA (US); Harold Selnick, Ambler, PA (US); Yaode Wang, Beijing (CN); Kun Yang, Beijing (CN); Jianmin Fu, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/317,333

(22) PCT Filed: Jun. 9, 2015

(86) PCT No.: PCT/US2015/034794
§ 371 (c)(1),
(2) Date: Dec. 12, 2016

(87) PCT Pub. No.: WO2015/191506
PCT Pub. Date: Dec. 17, 2015

(65) Prior Publication Data
US 2017/0119912 A1 May 4, 2017

(30) Foreign Application Priority Data
Jun. 13, 2014 (WO) ................ PCT/CN2014/079834

(51) Int. Cl.
*A61K 51/04* (2006.01)
*C07D 519/00* (2006.01)
*C07D 471/04* (2006.01)

(52) U.S. Cl.
CPC ...... *A61K 51/0455* (2013.01); *A61K 51/0459* (2013.01); *C07D 471/04* (2013.01); *C07D 519/00* (2013.01); *C07B 2200/05* (2013.01)

(58) Field of Classification Search
CPC ............ A61K 51/0455; A61K 51/0459; C07D 471/04; C07D 519/00; C07B 2200/05
See application file for complete search history.

(56) References Cited

U.S. PATENT DOCUMENTS 5,451,566 A 9/1995 Mathews
2008/0027044 A1 1/2008 Lewis et al.
2009/0203903 A1 8/2009 Cosford et al.
2009/0233945 A9 9/2009 Chessari et al.
2013/0102587 A1 4/2013 Evans et al.
2014/0275040 A1 9/2014 Espensen et al.
2015/0031672 A1 1/2015 Ren et al.

FOREIGN PATENT DOCUMENTS

| CN | 101223166 | 7/2008 |
|---|---|---|
| CN | 101796052 | 8/2010 |
| CN | 103450152 | 12/2013 |
| WO | WO2008103615 | 8/2008 |
| WO | WO2010129816 | 11/2010 |
| WO | WO2012106343 | 8/2012 |
| WO | WO2014140592 | 9/2014 |

OTHER PUBLICATIONS

Berge et al., Pharmaceutical Salts, J. Pharm Sci., 1977, pp. 1-19, 66(1).
Bulic et al., Development of Tau Aggregation Inhibitors for, Angewandte Chemie, 2009, 1740-1752, 48.
Bulic et al., Progress and Developments in Tau Aggregation Inhibitors for, J. Med. Chem, 2013, 4135:55, 56(11).
Eliel et al., Stereochemistry of Organic Compounds, Stereochemistry of Carbon Compounds, 1994, pp. 1119-1190, John Wiley and Sons, New York.
Pubchem, Compound Summary for CID 90433905, Create Date: Feb. 13, 2015. (retrieved on Jul. 31, 2015). Retrieved from Internet. <URL>:https://pubchem.ncbi.nim.nih.gov/compound/90433905?from=summary>. entire document.

*Primary Examiner* — Matt Mauro
(74) *Attorney, Agent, or Firm* — Sylvia A. Ayler; John C. Todaro

(57) ABSTRACT

The present invention is directed to pyrrolopyridine compounds of formula (I) or their pharmaceutically acceptable salts, which may be suitable for imaging tau aggregates, b-sheet aggregates, beta-amyloid aggregates or alpha-synuclein aggregates, and hence are useful in binding and imaging tau aggregates in Alzheimer's patients. More specifically, this invention relates to a method of using the compounds of this invention as tracers in positron emission tomography (PET) imaging to study tau deposits in brain in vivo to allow diagnosis of Alzheimer's disease and other neurodegenerative diseases characterized by tau pathology. The invention further relates to a method of measuring clinical efficacy of therapeutic agents for Alzheimer's disease and other neurodegenerative diseases characterized by tau pathology.

37 Claims, 1 Drawing Sheet

PYRROLO[2,3-C]PYRIDINES AS IMAGING AGENTS FOR NEUROFIBRILLARY

CROSS REFERENCE TO RELATED APPLICATIONS

Figure 1:
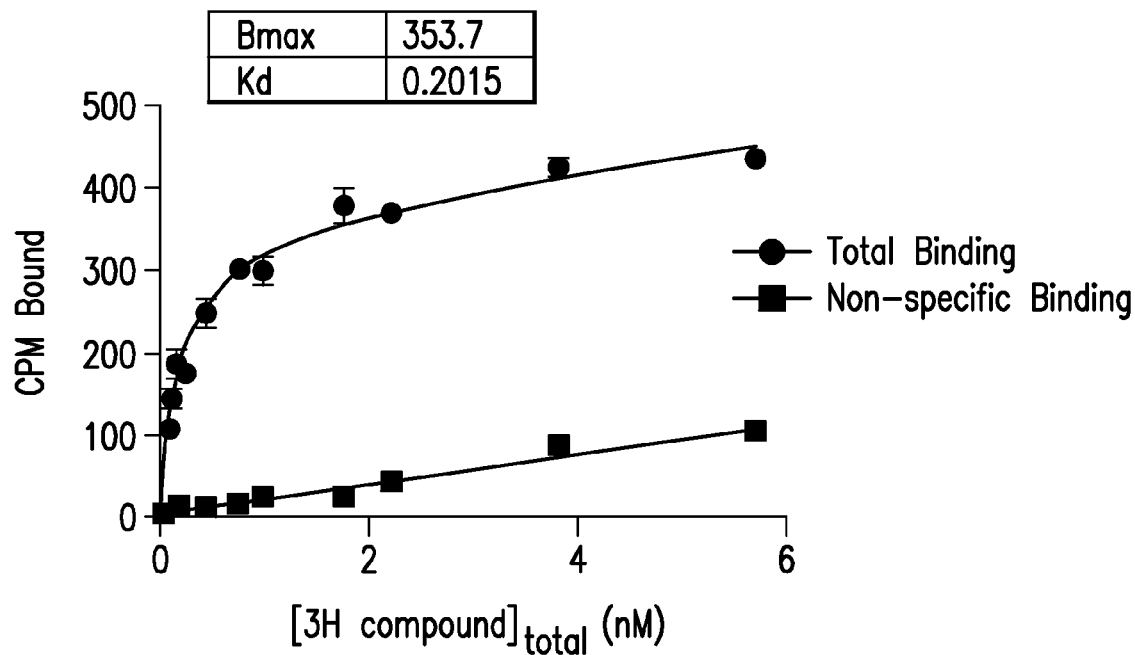

This application is the National Stage of International Application No. PCT/US2015/034794 filed on Jun. 9, 2015, which claims the benefit under International Application No PCT/CN2014/079834, filed Jun. 13, 2014.

FIELD OF THE INVENTION

The invention is directed to novel pyrrolopyridine compounds, their salts, pharmaceutical compositions comprising them, and therapeutic uses and processes for making such compounds. This invention is further directed to $^{2}H$, $^{3}H$, $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{76}Br$, $^{77}Br$, $^{123}I$, $^{125}I$, $^{124}I$ and $^{131}I$ isotopically labeled substituted pyrrolopyridine derivative compounds of this invention. In particular, the present invention is directed to $^{11}C$, $^{13}C$, $^{14}C$, $^{18}F$, $^{125}I$, $^{15}O$, $^{13}N$, $^{35}S$, $^{2}H$, and $^{3}H$ isotopes of novel pyrrolopyridine compounds and methods of their preparation.

The present invention also relates to novel pyrrolopyridine compounds which may be suitable for imaging tau aggregates, β-sheet aggregates, β-amyloid aggregates, α-synuclein aggregates or trans-active response DNA binding protein 43 kDa and hence are useful in binding and imaging tau aggregates in Alzheimer's patients. More specifically, this invention relates to a method of using the compounds of this invention as tracers in positron emission tomography (PET) imaging to study tau deposits in brain in vivo to allow diagnosis of Alzheimer's disease. The invention further relates to a method of measuring clinical efficacy of therapeutic agents targeting tau pathology.

BACKGROUND OF THE INVENTION

Alzheimer's disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid B peptide (AB).

In Alzheimer's, two main proteins form abnormal polymers (aggregates) in the brain that are believed to result from misfolding during aggregation of one of twenty nonhomologous human proteins. The intracellular neurofibrillary tangles-NFT's are made from the microtubule-associated protein (tau protein) and the extracellular "amyloid" plaques consist mainly of polymerized AB-peptide. Both are toxic to the brain neurons and are the result of fibers formed from the subunit protein by stacking of beta strands. See B. Bulic, E. Mandelkow et al. *Angewandte Chemie International Edition*, Vol. 48, Issue 10, pgs. 1740-1752, 2009 and B. Bulic, et al. *J. Med. Chem* 2013 Jun. 13; 56(11):4135-55. See also US2014275040, CN103450152, US2009203903, US2009233945, WO2012106343, US20150031672, WO2010129816, WO2008103615, and US20080027044.

Tubulin-associated unit, or Tau, is a microtubule-associated protein that is thought to play a critical role in the etiology of Alzheimer's disease (AD) based on several lines of evidence. First, intracellular aggregates of hyperphosphorylated tau (NFTs) are invariably found in the brains of patients with AD and several other neurodegenerative diseases. Second, the extent of NFT pathology in the brain of AD patients is closely correlated with cognitive function. Finally, while mutations in tau have not been shown to cause AD, such mutations do cause another form of dementia known as frontotemporal dementia with parkinsonism (FTDP). Therefore, approaches aimed at reducing NFTs and/or hyperphosphorylated tau represent disease modifying treatments for AD.

Currently histological analysis of autopsy materials is the primary means of detecting tau aggregates. A tau PET tracer would be a valuable non-invasive tool for spatial and temporal quantification of neurofibrillary tangles (NFTs) in human brain, since post-mortem studies have shown NFT burden to better correlate with cognitive decline. A tau PET tracer will be a critical disease-relevant tool for quantifying a stabilization or decrease of NFT formation for disease-modifying Alzheimer's disease therapeutics. Additionally, a tau PET tracer could be useful for patient selection for AD clinical trials. In this mode, a tau PET tracer could be developed as a companion diagnostic. In addition to AD, there are other neurodegenerative diseases characterized by the deposition of tau aggregates (frontotemporal dementia (FTD), progressive supranuclear palsy (PSP), corticobasal degeneration (CBD), chronic traumatic encephalopathy (CTE), Pick's disease, etc.).

Therefore, a need exists for neuroimaging radiotracers that would allow in vivo imaging of tau pathology thereby providing insight into the deposition of tau aggregates in the human brain. The successful neuroimaging radiotracer must cross the blood-brain barrier and posses high affinity and specificity for tau aggregates and therefore must have appropriate lipophilicity (log D 1-3) and low molecular weight (, <450), show rapid clearance from blood and low non-specific binding. The neuroimaging radiotracer will play a role in diagnosis by identifying patients with excess tau aggregates in the brain and therefore at risk for developing AD as well as shed light on the degree of tau aggregation, effect on the brain over time, the correlation with cognition and aid in the analysis of the efficacy of a tau inhibitor.

In a typical PET study, a small amount of radiotracer is administered to the experimental animal, normal human or patient being tested. The radiotracer then circulates in the blood of the subject and may be absorbed in certain tissues. The radiotracer may be preferentially retained in some of these tissues because of specific enzymatic conversion or by specific binding to macromolecular structures such as proteins. Using sophisticated imaging instrumentation to detect positron emission, the amount of radiotracer is then non-invasively assessed in the various tissues in the body. The resulting data are analyzed to provide quantitative spatial information of the in vivo biological process for which the tracer was designed. PET gives pharmaceutical research investigators the capability to assess biochemical changes or metabolic effects of a drug candidate in vivo for extended periods of time, and PET can be used to measure drug distribution, thus allowing the evaluation of the pharmacokinetics and pharmacodynamics of a particular drug candidate under study. Importantly, PET tracers can be designed and used to quantitate the presence of binding sites in tissues. Consequently, interest in PET tracers for drug development has been expanding based on the development of isotopically labeled biochemicals and appropriate detection devices to detect the radioactivity by external imaging.

While the primary use of the isotopically labeled compounds of this invention is in positron emission tomography, which is an in vivo analysis technique, certain of the isotopically labeled compounds can be used for methods other than PET analyses. In particular, $^{14}C$ and $^{3}H$ labeled compounds can be used in in vitro and in vivo methods for the determination of binding, receptor occupancy and metabolic studies including covalent labeling. In particular, various isotopically labeled compounds find utility in magnetic resonance imaging, autoradiography and other similar analytical tools.

SUMMARY OF THE INVENTION

The invention is directed to a class of pyrrolopyridine compounds of formula I, their salts, pharmaceutical compositions comprising them, diagnostic and therapeutic uses and processes for making such compounds. In particular, the invention is directed to a class of pyrrolopyridine compounds of formula I which may be useful for binding and imaging tau aggregates, β-sheet aggregates, beta-amyloid aggregates or alpha-synuclein aggregates, and hence are useful in binding and imaging tau aggregates in Alzheimer's patients. This invention also relates to use of the compounds as an imaging tool to improve diagnosis of patients likely to develop Alzheimer's disease by determining if said patients present with excess of tau aggregates in the brain. This invention further relates to finding an imaging tool that will be used to diagnosis and monitor the progression of AD. This invention also relates use of the pyrrolopyridine compound to monitor and measure treatment when an anti-tau aggregate drug becomes available. This invention also may be useful for imaging and detecting for other neurodegenerative diseases characterized by the deposition of tau aggregates such as frontotemporal dementia (FTD), progressive supranuclear palsy (PSP), corticobasal degeneration (CBD), chronic traumatic encephalopathy (CTE), Pick's disease, etc. This invention further relates to a pharmaceutical composition containing a compound of formula I and a pharmaceutically acceptable carrier.

Also included are isotopically labeled compounds of this invention. Another aspect of the invention relates to use of the isotopically labeled compounds as neuroimaging radiotracers for in vivo imaging of the brain for tau aggregates in the diagnosis, monitoring, and/or treatment of AD. Another aspect of the invention is use of the isotopically labeled compounds in positron emission tomography, which is an in vivo analysis technique in the diagnosis, monitoring, and/or treatment of AD. The $^{14}C$ and $^{3}H$ labeled compounds can be used in in vitro and in vivo methods for the determination of binding, receptor occupancy and metabolic studies including covalent labeling. In particular, various isotopically labeled compounds find utility in magnetic resonance imaging, autoradiography and other similar analytical tools. Thus, another aspect of this invention is further directed to $^{2}H$, $^{3}H$, $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{76}Br$, $^{77}Br$, $^{123}I$, $^{124}I$, $^{125}I$, and $^{131}I$ isotopically labeled substituted pyrrolopyridine derivative compounds of formula I. In particular, the present invention is directed to $^{11}C$, $^{13}C$, $^{14}C$, $^{18}F$, $^{123}I$, $^{15}O$, $^{13}N$ $^{35}S$, $^{2}H$, and $^{3}H$ isotopes of substituted pyrrolopyridine derivative compounds, compositions and methods of their preparation and use as radiotracers or PET tracers in diagnosing and measuring the effects of a compound in the treatment of AD. The present invention also relates to non-toxic tau protein binding compounds that can rapidly cross the blood brain barrier, have low non-specific binding properties and are rapidly cleared from the system. This and other aspects of the invention will be realized upon review of the specification in its entirety.

FIGURES

Figure 2:
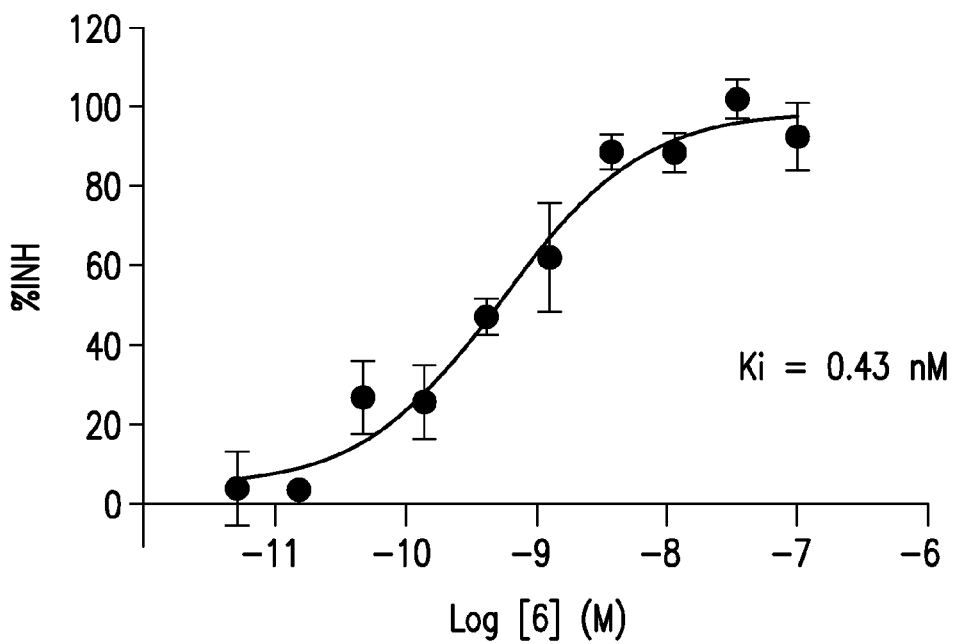

FIG. 1: shows saturation binding of [$^{3}H$]-6 (Example 49) in AD brain homogenates FIG. 2: shows compound 6 (unlabeled) self-displaced [$^{3}H$]-6 with Ki value of 0.43 nM

DETAILED DESCRIPTION OF THE INVENTION

The present invention is directed to quinoline amide compounds of generic formula (I)

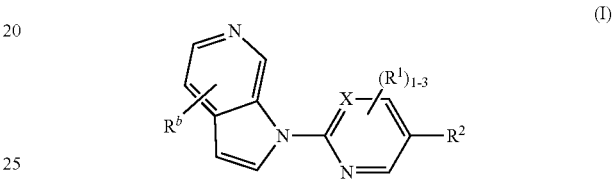

or a pharmaceutically acceptable salt thereof wherein;
X represents CH, or N;
R represents hydrogen, or —$C_{1-6}$alkyl, said alkyl optionally substituted with 1 to 3 groups of $R^{a}$;
$R^{1}$ represents hydrogen, —$C_{1-6}$alkyl, —CN, —$(CH_{2})_{n}$NH $(CH_{2})_{n}N(R)_{2}$, —$C_{2-6}$alkenyl, —$(CH_{2})_{n}$OR, or —$(CH_{2})_{n}$ halogen;
$R^{2}$ represents —$C_{1-6}$alkyl, —$OC_{1-6}$ alkyl, —$C_{2-6}$alkenyl$R^{3}$, —$C_{2-6}$alkynyl$R^{3}$, —$(CH_{2})_{n}$OR, —$(CH_{2})_{n}$halogen, —$O(CH_{2})_{n}$halogen, —$C_{6-10}$ aryl, —$C_{5-10}$ heterocyclyl, —$N(R)_{2}$, —$O(CH_{2})_{n}R^{a}$, —$N(CH_{3})(CH_{2})_{n}$OR, —NRC(O) R, —$NH(CH_{2})_{n}$halo, —$NC(O)C_{6-10}$ aryl, —$NC(O)C_{5-10}$ heterocyclyl, —$N(CH_{3})(CH_{2})_{n}$halogen, —$C(O)NC_{6-10}$ aryl, said alkyl, aryl, and heterocyclyl optionally substituted with 1 to 3 groups of $R^{a}$;
or an adjacent $R^{1}$ can combine with $R^{2}$ to form a nine to ten membered bicyclic ring together with the ring to which $R^{1}$ and $R^{2}$ are attached, optionally interrupted with N, S, and/or O, said bicyclic ring optionally substituted with 1 to 3 groups of $R^{a}$;
$R^{3}$ represents hydrogen, —$C_{1-6}$alkyl, —$(CH_{2})_{n}$halogen, —$(CH_{2})_{n}N(R)_{2}$, —$(CH_{2})_{n}NR(CH_{2})_{n}N(R)_{2}$, —$C_{6-10}$ aryl, —$C_{5-10}$ heteroaryl, said alkyl, aryl, and heteroaryl optionally substituted with 1 to 3 groups of $R^{a}$;
$R^{a}$ represents —CN, $CF_{3}$, —$C_{1-6}$ alkyl, —$C_{2-6}$alkenyl, —$C_{2-6}$alkynyl, $C_{6-10}$ aryl, —$C_{5-10}$ heterocyclyl, —CN, $NO_{2}$, $(CH_{2})_{n}$halogen, —$O(CH_{2})_{n}$halogen, $(CH_{2})_{n}$OR, —$O(CH_{2})_{n}$ $C_{6-10}$ aryl, —$(CH_{2})_{n}N(R)_{2}$, —$C(O)N(R)_{2}$, —$N(CH_{3})(CH_{2})_{n}$ OR, —NRCOR, —COR, —$NH(CH_{2})_{n}$halo, —NC(O)C $C_{6-10}$ aryl, —$N(CH_{3})(CH_{2})_{n}$halogen, $C(O)C_{6-10}$ aryl, or —$CO_{2}R$, said alkyl, alkenyl, alkynyl, aryl, and heterocyclyl optionally substituted with 1 to 3 groups of $R^{b}$;
$R^{b}$ represents hydrogen, —$C_{1-6}$alkyl, —OR, —$(CH_{2})_{n}$ $N(R)_{2}$, or halogen;
and
n represents 0-4.

One aspect of this invention is realized when $R^{b}$ is selected from the group consisting of hydrogen, methoxy, amino, methyl amino, and hydroxy.

Another aspect of this invention is realized when n is 0. Another aspect of this invention is realized when n is 1. Still another aspect of this invention is realized when n is 2. Yet another aspect of this invention is realized when n is 3. Another aspect of this invention is realized when n is 0-2.

Another embodiment of the invention of formula I is realized when $R^a$ is selected from the group consisting of —$C_{1-6}$alkyl, —$(CH_2)_n$halogen, —$O(CH_2)_n$halogen, CN, $NO_2$, $(CH_2)_nOR$, —$(CH_2)_nN(R)_2$, —$N(CH_3)(CH_2)_nOR$, —$NH(CH_2)_n$halo, and —$N(CH_3)(CH_2)_n$halogen. Still another subembodiment of this aspect of the invention is realized when $R^a$ is selected from the group consisting of $CH_3$, $CH_2CH_3$, $OCH_3$, OH, —$(CH_2)_nNHCH_3$, —$NH_2$, halogen, —$(CH_2)_nN(CH_3)_2$, $NO_2$, CN, —$N(CH_3)(CH_2)_nOH$, —$N(CH_3)(CH_2)_nF$, and $O(CH_2)_nF$.

Another aspect of this invention is realized when X is CH and all other variables are as originally described.

Another aspect of this invention is realized when X is N and all other variables are as originally described.

Still another aspect of this invention is realized when R is hydrogen.

Yet another aspect of this invention is realized when R is optionally substituted —$C_{1-6}$alkyl.

Another aspect of this invention is realized when $R^1$ is hydrogen.

Another aspect of this invention is realized when $R^1$—$C_{1-6}$alkyl, said alkyl optionally substituted with 1 to 3 groups of $R^a$.

Another aspect of this invention is realized when $R^1$ is CN.

Another aspect of this invention is realized when $R^1$ is —$C_{2-6}$alkenyl, said alkenyl optionally substituted with 1 to 3 groups of $R^a$.

Another aspect of this invention is realized when $R^1$ is $(CH_2)_nOR$.

Another aspect of this invention is realized when $R^1$ is —$(CH_2)_nN(CH_2)_nN(R)_2$.

Still another aspect of this invention is realized when $R^1$ is $(CH_2)_n$halogen.

It is understood that when X is N and adjacent $R^1$ and $R^2$ does not combine to form a bicyclic ring the number of $R^1$ substituents is 1 to 2.

Yet another aspect of this invention is realized when $R^2$ is selected from the group consisting of —$C_{2-6}$alkenyl$R^3$, —$C_{2-6}$alkynyl$R^3$, —$NC(O)C_{6-10}$ aryl, —$NC(O)C_{5-10}$ heterocyclyl, —$C_{6-10}$ aryl, and —$C_{5-10}$ heterocyclyl said aryl and heterocyclyl optionally substituted with 1 to 3 groups of $R^a$. A subembodiment of this aspect of the invention is realized when $R^2$ is —$C_{2-6}$ alkenyl$R^3$. A subembodiment of this aspect of the invention is realized when $R^2$ is —$C_{2-6}$alkynyl$R^3$. A subembodiment of this aspect of the invention is realized when $R^2$ is —$NC(O)$ $C_{6-10}$ aryl, said ary optionally substituted. A subembodiment of this aspect of the invention is realized when $R^2$ is —$NC(O)C_{5-10}$ heterocyclyl, said heterocyclyl optionally substituted. A subembodiment of this aspect of the invention is realized when $R^2$ is optionally substituted —$C_{6-10}$ aryl. A subembodiment of this aspect of the invention is realized when the aryl of $R^2$ is optionally substituted phenyl or napthyl. A subembodiment of this aspect of the invention is realized when $R^2$ is optionally substituted —$C_{5-10}$ heterocyclyl. A subembodiment of this aspect of the invention is realized when the heterocyclyl of $R^2$ is selected from the group consisting of optionally substituted pyridyl, thiazolyl, pyrimidinyl, piperizinyl, pyrazolyl, pyrazinyl, imidazolyl, and triazolyl.

Another aspect of this invention is realized when $R^3$ is —$C_{1-6}$alkyl, said alkyl optionally substituted with 1 to 3 groups of $R^a$. A subembodiment of this aspect of the invention is realized when the alkyl is methyl, ethyl, or propyl.

Another aspect of this invention is realized when $R^3$ is —$(CH_2)_n$halogen. A subembodiment of this aspect of the invention is realized when the halogen is fluorine or chlorine.

Another aspect of this invention is realized when $R^3$ is $C_{6-10}$ aryl, said aryl optionally substituted with 1 to 3 groups of $R^a$. A subembodiment of this invention is realized when the aryl is optionally substituted phenyl or napthyl.

Another aspect of this invention is realized when $R^3$ is —$C_{5-10}$ heteroaryl, said heteroaryl optionally substituted with 1 to 3 groups of $R^a$. A subembodiment of this aspect of the invention is realized when the heteroaryl is selected from the group consisting of optionally substituted pyridyl and thiazolyl.

Another aspect of this invention is realized when $R^3$ is —$(CH_2)_nN(R)_2$, or —$(CH_2)_nNR(CH_2)_nN(R)_2$.

Still another aspect of this invention is realized when $R^2$ is combined with an adjacent $R^1$ and the ring to which $R^1$ and $R^2$ are attached, to form a 9 to 10 membered bicycle ring, said bicyclic ring optionally interrupted with N, S, and/or O, and said bicyclic ring optionally substituted with 1 to 3 groups of $R^a$. A subembodiment of this aspect of the invention is realized when the bicyclic ring is optionally interrupted with one of N, S and/or O. Another subembodiment of this aspect of the invention is realized when the bicycle formed is optionally substituted pyrrolopyridinyl, furopyridinyl, naphthryidinyl, tetrahydronaphthyridinyl, quinazolinyl, quinolinyl, or isoquinolinyl. A subembodiment of this aspect of the invention is realized when the bicycle formed is optionally substituted pyrrolopyridinyl. Another subembodiment of this aspect of the invention is realized when the bicycle formed is optionally substituted naphthryidinyl or tetrahydronaphthyridinyl. Another subembodiment of this aspect of the invention is realized when the bicycle formed is optionally substituted quinazolinyl. Another subembodiment of this aspect of the invention is realized when the bicycle formed is optionally substituted quinolinyl. Another subembodiment of this aspect of the invention is realized when the bicycle formed is optionally substituted isoquinolinyl. Another subembodiment of this aspect of the invention is realized when the bicycle formed is optionally substituted furopyridinyl.

Still another subembodiment of this aspect of the invention is realized when X is CH and $R^2$ is selected from the group consisting of —$C_{2-6}$ alkenyl$R^3$, —$C_{2-6}$ alkynyl$R^3$, —$C_{6-10}$ aryl, and —$C_{5-10}$ heterocyclyl said aryl and heterocyclyl optionally substituted with 1 to 3 groups of $R^a$.

Another subembodiment of this aspect of the invention is realized when X is CH and $R^2$ is —$C_{2-6}$alkenyl$R^3$. A subembodiment of this aspect of the invention is realized when $R^3$ is selected from the group consisting of methyl, ethyl, propyl, $(CH_2)_nF$, —$(CH_2)_nN(R)_2$, —$(CH_2)_nNR(CH_2)_nN(R)_2$, optionally substituted phenyl, pyridyl and thiazolyl.

Another subembodiment of this aspect of the invention is realized when X is CH and $R^2$ is —$C_{2-6}$ alkynyl$R^3$. A subembodiment of this aspect of the invention is realized when $R^3$ is selected from the group consisting of methyl, ethyl, propyl, $(CH_2)_nF$, —$(CF_2)_nN(R)_2$, —$(CH_2)_nNR(CH_2)_nN(R)_2$, optionally substituted phenyl, pyridyl and thiazolyl.

Still another subembodiment of this aspect of the invention is realized when X is CH and $R^2$ is optionally substituted —C$_{6-10}$ aryl. A subembodiment of this aspect of the invention is realized when R$^2$ is optionally substituted phenyl or naphthyl.

Yet another subembodiment of this aspect of the invention is realized when X is CH and R$^2$ is optionally substituted —C$_{5-10}$ heterocyclyl. A subembodiment of this aspect of the invention is realized when R$^2$ is optionally substituted O(CH$_2$)$_n$pyridyl, NC(O)phenyl, C(O)phenyl, naphthyl, naphthyridinyl, pyridyl, triazolyl, pyrimidinyl, thiazolyl, pyrazinyl, or imidazolyl.

Another aspect of this invention is realized when X is CH and R$^2$ is combined with an adjacent R$^1$ to form a 9 to 10 membered bicycle ring optionally interrupted with N, S and/or O, said bicycle optionally substituted with 1 to 3 groups of R$^a$. A subembodiment of this aspect of the invention is realized when the bicycle formed is optionally substituted pyrrolopyridinyl, furopyridinyl, naphthridinyl, tetrahydronaphthyridinyl, quinolinyl, or isoquinolinyl.

Still another subembodiment of this aspect of the invention is realized when X is N and R$^2$ is selected from the group consisting of —C$_{2-6}$ alkenylR$^3$, —C$_{2-6}$ alkynylR$^3$, —C$_{6-10}$ aryl, and —C$_{5-10}$ heterocyclyl said aryl and heterocyclyl optionally substituted with 1 to 3 groups of R$^a$.

Another subembodiment of this aspect of the invention is realized when X is N and R$^2$ is —C$_{2-6}$alkenylR$^3$. A subembodiment of this aspect of the invention is realized when R$^3$ is selected from the group consisting of methyl, ethyl, propyl, (CH$_2$)$_n$F, —(CH$_2$)$_n$N(R)$_2$, —(CH$_2$)$_n$NR(CH$_2$)$_n$N(R)$_2$, optionally substituted phenyl, pyridyl and thiazolyl.

Another subembodiment of this aspect of the invention is realized when X is N and R$^2$ is —C$_{2-6}$ alkynylR$^3$. A subembodiment of this aspect of the invention is realized when R$^3$ is selected from the group consisting of methyl, ethyl, propyl, (CH$_2$)$_n$F, —(CH$_2$)$_n$N(R)$_2$, —(CH$_2$)$_n$NR(CH$_2$)$_n$N(R)$_2$, optionally substituted phenyl, pyridyl and thiazolyl.

Still another subembodiment of this aspect of the invention is realized when X is N and R$^2$ is optionally substituted —C$_{6-10}$ aryl. A subembodiment of this aspect of the invention is realized when R$^2$ is optionally substituted phenyl or naphthyl.

Yet another subembodiment of this aspect of the invention is realized when X is N and R$^2$ is optionally substituted —C$_{5-10}$ heterocyclyl. A subembodiment of this aspect of the invention is realized when R$^2$ is optionally substituted O(CH$_2$)$_n$pyridyl, NC(O)phenyl, C(O)phenyl, naphthyl, naphthyridinyl, pyridyl, triazolyl, pyrimidinyl, thiazolyl, pyrazinyl, or imidazolyl.

Another aspect of this invention is realized when X is N and R$^2$ is combined with an adjacent R$^1$ together with the ring to which R$^1$ and R$^2$ are attached, to form a 9 to 10 membered bicycle ring optionally interrupted with N, S and/or O, said bicycle optionally substituted with 1 to 3 groups of R$^a$. A subembodiment of this aspect of the invention is realized when the bicycle formed is optionally substituted quinazolinyl.

Another aspect of the invention is realized when the compounds of formula I are selected from isotopically labeled $^2$H, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$CL, $^{82}$Br, $^{76}$Br, $^{77}$Br, $^{123}$I, $^{124}$I, $^{125}$I and $^{131}$I.

Still another aspect of this invention is realized with the compound of structural formula Ia:

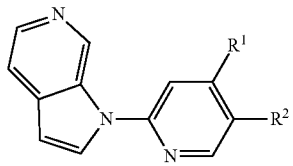

or a pharmaceutically acceptable salt thereof, wherein R$^1$, and R$^2$ are as described herein. A subembodiment of formula Ia is realized when R$^1$ is hydrogen, halogen, —(CH$_2$)$_n$N(CH$_2$)$_n$N(R)$_2$, optionally substituted C$_{1-6}$ alkyl or optionally substituted C$_{2-6}$ alkenyl. A subembodiment of the invention is realized when compounds of formula Ia are selected from isotopically labeled $^2$H, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$CL, $^{82}$Br, $^{76}$Br, $^{77}$Br, $^{123}$I, $^{124}$I, $^{125}$I and $^{131}$I.

Another subembodiment of formula Ia is realized when R$^2$ is selected from the group consisting of —C$_{2-6}$alkenylR$^3$, —C$_{2-6}$alkynylR$^3$, (CH$_2$)$_n$OR, —O(CH$_2$)$_n$halogen, C$_{6-10}$ aryl, —C$_5$ heterocyclyl, —N(R)$_2$, —O(CH$_2$)$_n$R$^a$, —N(CH$_3$)(CH$_2$)$_n$OR, —NH(CH$_2$)$_n$halogen, —NC(O) C$_{6-10}$ aryl, —N(CH$_3$)(CH$_2$)$_n$halogen, C(O)NC$_{6-10}$ aryl, said aryl, and heterocyclyl optionally substituted with 1 to 3 groups of R$^a$, and R$^3$ is selected from the group consisting of hydrogen, —(CH$_2$)$_n$halogen, —(CH$_2$)$_n$N(R)$_2$, (CH$_2$)$_n$NR(CH$_2$)$_n$N(R)$_2$, C$_{6-10}$ aryl, —C$_{5-10}$ heteroaryl, said aryl, and heteroaryl optionally substituted with 1 to 3 groups of R$^a$.

Another subembodiment of this aspect of formula Ia is realized when R$^2$ is selected from the group consisting of C$_2$alkenylR$^3$, C$_2$alkynylR$^3$, O(CH$_2$)$_n$F, N(CH$_2$)$_n$F, N(R)$_2$, and optionally substituted O(CH$_2$)$_n$pyridyl, NC(O)phenyl, C(O)phenyl, naphthyl, naphthyridinyl, pyridyl, triazolyl, pyrimidinyl, thiazolyl, pyrazinyl, and imidazolyl and R$^3$ is selected from the group consisting of methyl, ethyl, propyl, (CH$_2$)$_n$F, —(CH$_2$)$_n$N(R)$_2$, —(CH$_2$)$_n$NR(CH$_2$)$_n$N(R)$_2$, optionally substituted phenyl, pyridyl and thiazolyl and R$^1$ is selected from the group consisting of hydrogen, fluorine, or chlorine, —(CH$_2$)$_n$N(CH$_2$)$_n$N(R)$_2$. or optionally substituted C$_{1-6}$ alkyl and C$_{2-6}$ alkenyl.

Still another aspect of the invention of formula I is realized when R$^2$ combines with an adjacent R$^1$ together with the ring to which R$^1$ and R$^2$ are attached, to form a 9 to 10 membered bicycle optionally interrupted by N, S, O, said bicycle optionally substituted by 1 to 3 groups of R$^a$. A subembodiment of this aspect of the invention is realized when R$^2$ combines with an adjacent R$^1$ together with the ring to which R$^1$ and R$^2$ are attached, to form optionally substituted naphthyridinyl, tetrahydronaphthyridinyl, furopyridinyl, isoquinolinyl, or pyrrolopyridinyl. Another subembodiment of this aspect of the invention is realized when R$^2$ combines with an adjacent R$^1$ together with the ring to which R$^1$ and R$^2$ are attached, to form optionally substituted naphthyridinyl. Another subembodiment of this aspect of the invention is realized when R$^2$ combines with an adjacent R$^1$ together with the ring to which R$^1$ and R$^2$ are attached, to form optionally substituted tetrahydronaphthyridinyl. Another subembodiment of this aspect of the invention is realized when R$^2$ combines with an adjacent R$^1$ together with the ring to which R$^1$ and R$^2$ are attached, to form optionally substituted furopyridinyl. Another subembodiment of this aspect of the invention is realized when R$^2$ combines with an adjacent R$^1$ together with the ring to which R$^1$ and R$^2$ are attached, to form optionally substituted isoquinolinyl. Another subembodiment of this aspect of the invention is realized when R² combines with an adjacent R¹ together with the ring to which R¹ and R² are attached, to form optionally substituted pyrrolopyridinyl. A subembodiment of this aspect of the invention is realized wherein an adjacent R¹ and R² when combined is represented by structural formula Ib1, Ib2, Ib3, or Ib4:

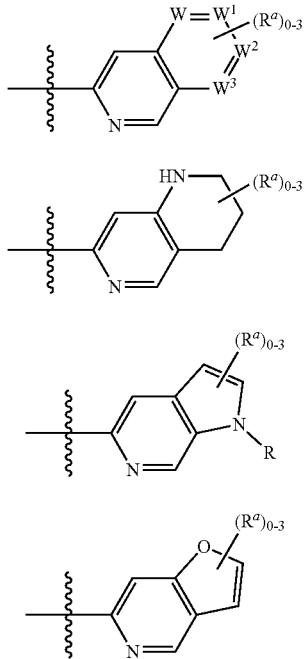

wherein W, W¹, W², and W³ are independently selected from —CH— or —N— and R and Ra are as originally described. A subembodiment of this aspect of the invention is realized when W, W¹, W², and W³ are all —CH—. Another subembodiment of this aspect of the invention is realized when at least one of W, W¹, W², and W³ is —N— and the others are —CH—.

Another aspect of the invention of formula I is represented by structural formula II:

II

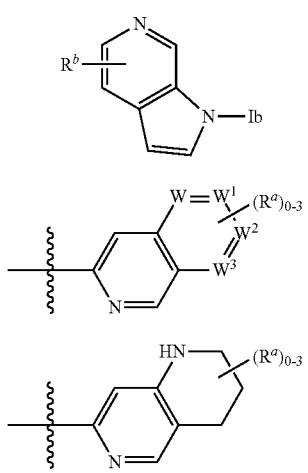

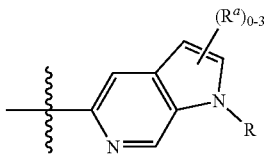

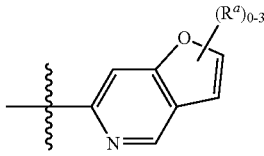

or a pharmaceutically acceptable salt there of wherein Ib=Ib1, Ib2, Ib3, or Ib4, and W, W¹, W², W³, R, $R^a$ and $R^b$ are as previously described. A subembodiment of the invention is realized when compounds of formula II are selected from isotopically labeled $^2$H, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$CL, $^{82}$Br, $^{76}$Br, $^{77}$Br, $^{123}$I, $^{124}$I, $^{125}$I and $^{131}$I. An aspect of this embodiment of the invention is realized when the compound isotopically labeled with $^{18}$F. Another subembodiment of the invention of formula II is realized when $R^a$ is selected from the group consisting of —$C_{1-6}$ alkyl, —$(CH_2)_n$halogen, —$O(CH_2)_n$halogen, CN, $NO_2$, $(CH_2)_nOR$, —$(CH_2)_nN(R)_2$, —$N(CH_3)(CH_2)_nOR$, —$NH(CH_2)_n$halo, and —$N(CH_3)(CH_2)_n$halogen. Still another subembodiment of this aspect of the invention is realized when $R^a$ is selected from the group consisting of $CH_3$, $CH_2CH_3$, $OCH_3$, OH, —$(CH_2)_nNHCH_3$, —$NH_2$, halogen, —$(CH_2)_nN(CH_3)_2$, $NO_2$, CN, —$N(CH_3)(CH_2)_nOH$, —$N(CH_3)(CH_2)_nF$, and $O(CH_2)_nF$.

Another embodiment of the invention of formula II is realized when Ib is Ib1, $R^a$ is selected from the group consisting of —$C_{1-6}$ alkyl, —$(CH_2)_n$halogen, —$O(CH_2)_n$halogen, CN, $NO_2$, $(CH_2)_nOR$, —$(CH_2)_nN(R)_2$, —$N(CH_3)(CH_2)_nOR$, —$NH(CH_2)_n$halo, and —$N(CH_3)(CH_2)_n$halogen, and W, W¹, W², and W³ are all —CH—.

Another embodiment of the invention of formula II is realized when Ib is Ib1, $R^a$ is selected from the group consisting of —$C_{1-6}$ alkyl, —$(CH_2)_n$halogen, —$O(CH_2)_n$halogen, CN, $NO_2$, $(CH_2)_nOR$, —$(CH_2)_nN(R)_2$, —$N(CH_3)(CH_2)_nOR$, —$NH(CH_2)_n$halo, and —$N(CH_3)(CH_2)_n$halogen, and at least one of W, W¹, W², and W³ is —N.

Another embodiment of the invention of formula II is realized when Ib is Ib2 and $R^a$ is selected from the group consisting of —$C_{1-6}$ alkyl, —$(CH_2)_n$halogen, —$O(CH_2)_n$halogen, CN, $NO_2$, $(CH_2)_nOR$, —$(CH_2)_nN(R)_2$, —$N(CH_3)(CH_2)_nOR$, —$NH(CH_2)_n$halo, and —$N(CH_3)(CH_2)_n$halogen.

Another embodiment of the invention of formula II is realized when Ib is Ib3 and $R^a$ is selected from the group consisting of $R^a$ is selected from the group consisting of —$C_{1-6}$alkyl, —$(CH_2)_n$halogen, —$O(CH_2)_n$halogen, CN, $NO_2$, $(CH_2)_nOR$, —$(CH_2)_nN(R)_2$, —$N(CH_3)(CH_2)_nOR$, —$NH(CH_2)_n$halo, and —$N(CH_3)(CH_2)_n$halogen.

Another embodiment of the invention of formula II is realized when Ib is Ib4 and $R^a$ is selected from the group consisting of $R^a$ is selected from the group consisting of —$C_{1-6}$alkyl, —$(CH_2)_n$halogen, —$O(CH_2)_n$halogen, CN, $NO_2$, $(CH_2)_nOR$, —$(CH_2)_nN(R)_2$, —$N(CH_3)(CH_2)_nOR$, —$NH(CH_2)_n$halo, and —$N(CH_3)(CH_2)_n$halogen.

Another aspect of the invention of formula I is represented by structural formula III:

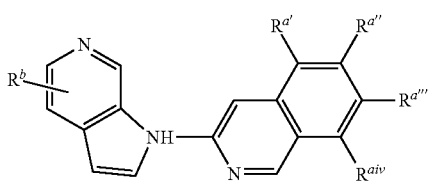

III wherein $R^{a'}$, $R^{a''}$, $R^{a'''}$, and $R^{aiv}$ independently are selected from hydrogen and $R^a$, and $R^a$ and $R^b$ are as originally described. A subembodiment of the invention is realized when compounds of formula III are selected from isotopically labeled $^2$H, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$CL, $^{82}$Br, $^{76}$Br, $^{77}$Br, $^{123}$I, $^{124}$I, $^{125}$I and $^{131}$I. An aspect of this embodiment of the invention is realized when the compound is isotopically labeled with $^{18}$F or $^{123}$I. A subembodiment of the invention of formula III is realized $R^{a'}$, $R^{a''}$, $R^{a'''}$, and $R^{aiv}$ independently are selected from the group consisting of hydrogen, —$C_{1-6}$ alkyl, —$(CH_2)_n$halogen, —$O(CH_2)_n$halogen, CN, $NO_2$, $(CH_2)OR$, —$(CH_2)_nN(R)_2$, —$N(CH_3)(CH_2)_nOR$, —$NH(CH_2)$halo, and —$N(CH_3)(CH_2)_n$halogen and $R^b$ is selected from the group consisting of hydrogen, $C_{1-6}$alkyl, —OR, —$(CH_2)_nN(R)_2$, or halogen. A subembodiment of this aspect of the invention is realized when $R^{a'}$, $R^{a''}$, $R^{a'''}$, and $R^{aiv}$ are independently selected from the group consisting of hydrogen, amino, fluoro, and iodo and $R^b$ is selected from the group consisting of hydrogen, methoxy, amino, methyl amino, dimethylamino, and hydroxy. Another subembodiment of this aspect of the invention is realized when $R^{a'}$, $R^{a''}$, $R^{a'''}$, and $R^{aiv}$ are independently selected from the group consisting of hydrogen, amino, fluoro, and iodo and $R^b$ is hydrogen. Another subembodiment of this aspect of the invention is realized when one of $R^{a'}$, $R^{a''}$, $R^{a'''}$, and $R^{aiv}$ is amino, one of $R^{a'}$, $R^{a''}$, $R^{a'''}$, and $R^{aiv}$ is fluoro and the others of $R^{a'}$, $R^{a''}$, $R^{a'''}$, and $R^{aiv}$ are hydrogen and $R^b$ is hydrogen. Still another subembodiment of this aspect of the invention is realized when one of $R^{a'}$, $R^{a''}$, $R^{a'''}$, and $R^{aiv}$ is amino, one of $R^{a'}$, $R^{a''}$, $R^{a'''}$, and $R^{aiv}$ is iodo and the others of $R^{a'}$, $R^{a''}$, $R^{a'''}$, and $R^{aiv}$ are hydrogen and $R^b$ is hydrogen. Yet another subembodiment of this aspect of the invention is realized when one of $R^{a'}$, $R^{a''}$, $R^{a'''}$, and $R^{aiv}$ is iodo and the others of $R^{a'}$, $R^{a''}$, $R^{a'''}$, and $R^{aiv}$ are hydrogen and $R^b$ is hydrogen. Still another subembodiment of this aspect of the invention is realized when one of $R^{a'}$, $R^{a''}$, $R^{a'''}$, and $R^{aiv}$ is fluoro and the others of $R^{a'}$, $R^{a''}$, $R^{a'''}$, and $R^{aiv}$ are hydrogen and $R^b$ is hydrogen.

Still another aspect of the invention of formula I is realized when X is N and $R^2$ is combined with an adjacent $R^1$ to form a 9 to 10 membered bicycle ring optionally interrupted with N, S and/or O, said bicycle optionally substituted with 1 to 3 groups of $R^a$. A subembodiment of this aspect of the invention is realized when the bicycle formed is optionally substituted quinazolinyl.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190)

When any variable (e.g. aryl, heterocycle, $R^{1a}$, $R^6$ etc.) occurs more than one time in any constituent, its definition on each occurrence is independent at every other occurrence. Also, combinations of substituents/or variables are permissible only if such combinations result in stable compounds, is chemically feasible and/or valency permits.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge.

"Halogen" or "halo" as used herein means fluoro, chloro, bromo and iodo.

As used herein, alkenyl is $C_2$-$C_6$ alkenyl.

As used herein alkynyl is $C_2$-$C_6$ alkynyl.

As used herein, "cycloalkyl" is intended to include cyclic saturated aliphatic hydrocarbon groups having the specified number of carbon atoms. Preferably, cycloalkyl is $C_3$-$C_{10}$ cycloalkyl. Examples of such cycloalkyl elements include, but are not limited to, cyclopropyl, cyclobutyl, cyclopentyl, cyclohexyl and cycloheptyl.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, furopyridinyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, pyrrolopyridinyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl.

Preferably, heterocyclyl is selected from furopyridinyl, imidazolyl, indolyl, isoquinolinylisothiazolyl, morpholinyl, naphthyridinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, pyrrolopyridinyl, quinazolinyl, quinolinyl, quinoxalinyl, tetrahydrofuryl, tetrahydroisoquinolinyl, tetrahydroquinolinyl, thiazolyl, thiazolinyl, thienofuryl, thienothienyl, thienyl, and triazolyl.

"Heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, tetrahydroisoquinolinyl, tetrahydroquinolinyl, thiazolyl, thienofuryl, thienothienyl, thienyl, triazolyl and the like.

Examples of an "effective amount" include amounts that enable imaging of amyloid deposit(s) in vivo, that yield acceptable toxicity and bioavailability levels for pharmaceutical use, and/or prevent cell degeneration and toxicity associated with fibril formation.

For use in medicine, the salts of the compounds of formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

As indicated herein the present invention includes isotopically labeled compounds of the invention. An "isotopically-labeled", "radio-labeled", "tracer", "radiotracer", "labeled tracer" or "radioligand" compound, is a compound where one or more atoms are replaced or substituted by an atom having an atomic mass or mass number different from the atomic mass or mass number typically found in nature (i.e., naturally occurring). Suitable radionuclides (i.e. "detectable isotopes") that may be incorporated in compounds of the present invention include but are not limited to $^2$H, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{76}$Br, $^{77}$Br, $^{123}$I, $^{124}$I, and $^{131}$I. The isotopically labeled compounds of the invention need only to be enriched with a detectable isotope to, or above, the degree which allows detection with a technique suitable for the particular application. The radionuclide that is incorporated in the instant radiolabeled compounds will depend on the specific application of that radiolabeled compound. In another embodiment of the invention the radionuclides are represented by $^{11}$C, $^{13}$C, $^{14}$C, $^{18}$F, $^{15}$O, $^{13}$N, $^{35}$S, $^2$H, and $^3$H, preferably $^{11}$C, and $^{18}$F.

This invention further relates to a pharmaceutical composition comprising an effective amount of at least one compound of formula I and a pharmaceutically acceptable carrier. The composition may comprise, but is not limited to, one or more buffering agents, wetting agents, emulsifiers, suspending agents, lubricants, adsorbents, surfactants, preservatives and the like. The composition may be formulated as a solid, liquid, gel or suspension for oral administration (e.g., drench, bolus, tablet, powder, capsule, mouth spray, emulsion); parenteral administration (e.g., subcutaneous, intramuscular, intravenous, epidural injection); topical application (e.g., cream, ointment, controlled-released patch, spray); intravaginal, intrarectal, transdermal, ocular, or nasal administration.

This invention provides radiolabeled pyrrolopyridinyl derivatives as tau imaging agents and synthetic precursor compounds from which they are prepared. The compounds of formula I are active against age-related diseases such as Alzheimer, as well as other tauopathies and neurodegenerative diseases, such as progressive supranuclear palsy, chronic traumatic encephalopathy, frontotemporal dementia, Pick's disease, corticobasal degeneration, etc. The compounds of this invention may also be used in combination with a broad range of cognition deficit enhancement agents. Thus, in another embodiment of this invention a compound of formula (I) or a pharmaceutically acceptable salt thereof, or a pharmaceutical composition or formulation comprising a compound of formula (I) is administered concurrently, simultaneously, sequentially or separately with another pharmaceutically active compound or compounds used in Alzheimer's therapies including for example donepezil, memantine, tacrine and equivalents and pharmaceutically active isomer(s) and metabolite(s) thereof.

This invention further relates to a method of treating or preventing a tau-related pathology in a patient comprising administering a therapeutically effective amount of a compound of formula I. This invention also provides a method for treating neurodegenerative disorders such as dementia, Cognitive Deficit in Schizophrenia, Mild Cognitive Impairment, Age Associated Memory Impairment, Age-Related Cognitive Decline, and the like.

An ultimate objective of the present invention is to provide a radiopharmaceutical agent, useful in tau imaging that has high specific radioactivity and high target tissue selectivity by virtue of its high affinity for tau aggregates. The tissue selectivity is capable of further enhancement by coupling this highly selective radiopharmaceutical with targeting agents, such as microparticles.

In another aspect of this invention the claimed compounds have an unexpectedly low binding potential in tau free cortical gray matter and adjacent white matter, which provides improved profiles with regard to binding potential in white matter.

In accordance with the present invention, the most preferred method for imaging tau deposits in a patient, wherein an isotopically labeled novel pyrrolopyridine derivative is employed as the imaging agent, comprises the following steps: the patient is placed in a supine position in the PET camera, and a sufficient amount (<10 mCi) of an isotopically labeled pyrrolopyridine derivative is administered to the brain tissue of the patient. An emission scan of the cerebral region is performed. The technique for performing an emission scan of the head is well known to those of skilled in the art. PET techniques are described in Freeman et al., Freeman and Johnson's Clinical Radionuclide Imaging. 3rd. Ed. Vol. 1 (1984); Grune & Stratton, N.Y.; Ennis et Q. Vascular Radionuclide Imaging: A Clinical Atlas, John Wiley & Sons, New York (1983).

The term "labeled tracer" refers to any molecule which can be used to follow or detect a defined activity in vivo, for example, a preferred tracer is one that accumulates in the regions where tau aggregates may be found. Preferably, the labeled tracer is one that can be viewed in a living experimental animal, healthy human or patient (referred to as a subject), for example, by positron emission tomograph (PET) scanning. Suitable labels include, but are not limited to radioisotopes, fluorochromes, chemiluminescent compounds, dyes, and proteins, including enzymes.

The present invention also provides methods of determining in vivo activity of an enzyme or other molecule. More specifically, a tracer, which specifically tracks the targeted activity, is selected and labeled. In a preferred embodiment, the tracer tracks binding activity of tau protein in the brain and central nervous system. The tracer provides the means to evaluate various neuronal processes, including, regulation of neurotransmitter release, and long-term potentiation. The present invention gives researchers the means to study the biochemical mechanisms of pain, anxiety/depression, drug addiction and withdrawal, disorders of the basal ganglia, eating disorders, obesity, long-term depression, learning and memory, developmental synaptic plasticity, hypoxic-ischemic damage and neuronal cell death, epileptic seizures, visual processing, as well as the pathogenesis of several neurodegenerative disorders.

Biomarkers of Alzheimer's disease state, prognosis and progression will all be useful for general diagnostic utilities as well as for clinical development plans for therapeutic agents for Alzheimer's disease. The present invention will provide biomarker information as patients are enrolled in clinical trials for new Alzheimer's treatments to assist in patient selection and assignment to cohorts. The present invention will serve as one of the biomarkers of disease state in order to get the correct patients into the proper PhIIb trial cohort. In addition, the present invention can serve as one marker of disease prognosis as an entry inclusion criterion in order to enhance the probability that the disease will progress in the placebo treatment arm, an issue that has plagued recent AD clinical trials. Finally, the present invention can serve as one biomarker of disease progression to monitor the clinical course of patients on therapy and could provide an independent biomarker measure of treatment response by a therapeutic drug.

Compounds within this invention are inhibitors and/or binders of aggregated tau protein. Compounds, and isotopically labeled variants thereof, may be useful for the diagnosis and/or treatment of Alzheimer's disease, depression, schizophrenia, or Parkinson's disease. Means of detecting labels are well known to those skilled in the art. For example, isotopic labels may be detected using imaging techniques, photographic film or scintillation counters. In a preferred embodiment, the label is detected in vivo in the brain of the subject by imaging techniques, for example positron emission tomography (PET).

The labeled compound of the invention preferably contains at least one radionuclide as a label. Positron-emitting radionuclides are all candidates for usage. In the context of this invention the radionuclide is preferably selected from $^{11}C$, $^{13}C$, $^{14}C$, $^{18}F$, $^{15}O$, $^{13}N$, $^{35}S$, $^{2}H$, and $^{3}H$, more preferably from $^{11}C$, and $^{18}F$.

The tracer can be selected in accordance with the detection method chosen. Before conducting the method of the present invention, a diagnostically effective amount of a labeled or unlabeled compound of the invention is administered to a living body, including a human.

The diagnostically effective amount of the labeled or unlabeled compound of the invention to be administered before conducting the in-vivo method for the present invention is within a range of from 0.1 ng to 100 mg per kg body weight, preferably within a range of from 1 ng to 10 mg per kg body weight.

The isotopically labeled compounds of this invention are prepared by incorporating an isotope such as $^{11}C$, $^{13}C$, $^{14}C$, $^{18}F$, $^{15}O$, $^{13}N$, $^{35}S$, $^{2}H$, and $^{3}H$ into the substrate molecule. This is accomplished by utilizing reagents that have had one or more of the atoms contained therein made radioactive by placing them in a source of radioactivity such as a nuclear reactor, a cyclotron and the like. Additionally many isotopically labeled reagents, such as $^{2}H_2O$, $^{3}H_3Cl$, $^{14}C_6H_5Br$, $ClCH_2^{14}COCl$ and the like, are commercially available. The isotopically labeled reagents are then used in standard organic chemistry synthetic techniques to incorporate the isotope atom, or atoms, into a compound of Formula I as described below. The following Schemes illustrate how to make the compounds of formula I.

The compounds of the present invention have utility in diagnosing, monitoring, and measuring Alzheimer's disease and other non-AD tauopathies such as frontotemporal dementia (FTD), progressive supranuclear palsy (PSP), corticobasal degeneration (CBD), chronic traumatic encephalopathy (CTE), Pick's disease, etc. Other conditions that may be diagnosed by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, head trauma, stroke, pancreatitis, inclusion body myositis, other peripheral amyloidoses, diabetes, autism and atherosclerosis.

In preferred embodiments, the compounds of the invention are useful in diagnosing, monitoring or measuring Alzheimer's Disease, non-AD tauopathies, neurodegenerative disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I) to (VIII), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The present invention also provides a method for the synthesis of compounds useful as intermediates in the preparation of compounds of the invention.

The compounds described herein can be prepared according to the procedures of the following schemes and examples, using appropriate materials and are further exemplified by the following specific examples. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electrospray ion-mass spectroscopy (ESI). $^1$H NMR spectra were recorded at 400-500 MHz. Compounds described herein were synthesized as a racemic mixture unless otherwise stated in the experimental procedures.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

LIST OF ABBREVIATIONS

Anal.=analytical
n-BuLi=n-butyl lithium
br=broad
calc.=calculated
m-CPBA=3-chloroperoxybenzoic acid
d=doublet
DEA=diethylamine
DIPEA=N,N-diisopropylethylamine
DMF=dimethylformamide
ESI=electrospray ionization
EtOAc=ethyl acetate
EtOH=ethanol
HPLC=high-pressure liquid chromatography
IPA=iso-propyl alcohol
IPAc=iso-propyl acetate
KF=Karl-Fischer titration (to determine water content)
KOt-Bu=potassium tert-butoxide
LCMS=liquid chromatography-mass spectrometry
LiHMDS=lithium hexamethyl silazane
m=multiplet
MeCN=acetonitrile
MeOH=methyl alcohol
MPa=milipascal
MS=mass spectroscopy
MTBE=methyl tert-butyl ether
NHS=normal human serum
NMR=nuclear magnetic resonance spectroscopy
Piv=pivalate, 2,2-dimethylpropanoyl
Pd/C=palladium on carbon
rt=room temperature
s=singlet
SFC=supercritical fluid chromatography
t=triplet
TLC=thin-layer chromatography
p-TsOH=para-toluene sulfonic acid
THF=tetrahydrofuran
wt %=percentage by weight The following examples are provided to illustrate the invention and are not to be construed as limiting the scope of the invention in any manner.

TABLE 1

| Compound # | Structure | Synthesis Reference Example # | MS (M + 1) | Tau Ki (nM) | Amyloid Ki (nM) |
|---|---|---|---|---|---|
| 1 | 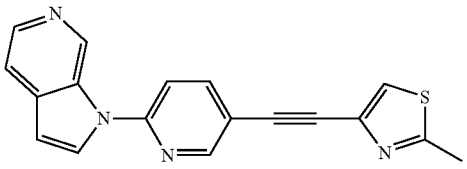 | 1 | 317.0 | — | — |
| 2 | 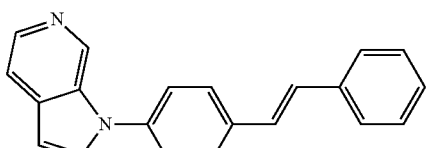 | 2 | 298.0 | — | — |

TABLE 1-continued
| Compound # | Structure | Synthesis Reference Example # | MS (M + 1) | Tau Ki (nM) | Amyloid Ki (nM) |
|---|---|---|---|---|---|
| 3 | 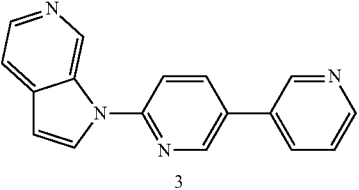 [SMILES: c1cncc(-c2ccc(-n3ccc4ccncc43)nc2)c1]<br>3 | 3 | 273.0 | — | — |
| 4 | 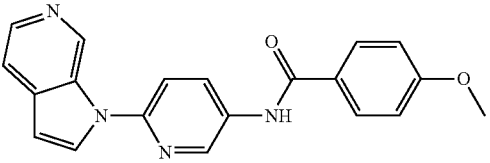<br>4 | 4 | 345.0 | — | — |
| 5 | 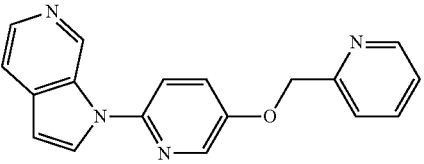<br>5 | 5 | 303.0 | — | — |
| 6 | 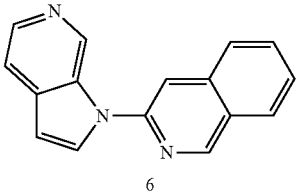 [SMILES: c1ccc2cc(-n3ccc4ccncc43)ncc2c1]<br>6 | 6 | 246.0 | 0.54 | 10000 |
| 7 | 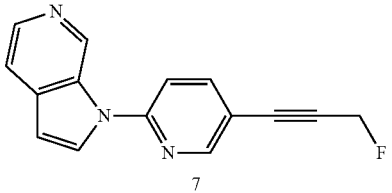 [SMILES: FCC#Cc1ccc(-n2ccc3ccncc32)nc1]<br>7 | 7 | 252.0 | 1.65 | 10000 |
| 8 | 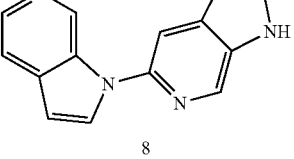<br>8 | 8 | 235.0 | 0.48 | 22270 |
| 9 | 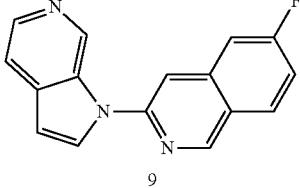<br>9 | 9 | 264.0 | 0.22 | 10000 |

TABLE 1-continued

| Compound # | Structure | Synthesis Reference Example # | MS (M + 1) | Tau Ki (nM) | Amyloid Ki (nM) |
|---|---|---|---|---|---|
| 10 | 10 | 10 | 239.0 | — | 10290 |
| 11 | 11 | 11 | 372.0 | — | — |
| 11-5 | 11-5 | 11-5 | 261.0 | 0.40 | 10000 |
| 12 | 12 | 12 | 261.1 | 0.29 | 10000 |
| 13 | 13 | 13 | 276.1 | 0.29 | 10000 |
| 14 | 14 | 14 | 321.2 | 2.28 | 10000 |
| 14-1 | 14-1 | 14 | 275.1 | 0.33 | 10000 |

TABLE 1-continued

| Compound # | Structure | Synthesis Reference Example # | MS (M + 1) | Tau Ki (nM) | Amyloid Ki (nM) |
| --- | --- | --- | --- | --- | --- |
| 15 | 15 | 15 | 262.1 | 0.53 | 10000 |
| 16 | 16 | 16 | 308.1 | 0.41 | 10000 |
| 17 | 17 | 17 | 294.2 | 0.43 | 10000 |
| 18 | 18 | 18 | 279.0 | 0.43 | 10000 |
| 19 | 19 | 19 | 249.1 | 0.62 | 10000 |
| 20 | 20 | 20 | 372.1 | 0.75 | 10000 |
| 21 | 21 | 21 | 266.1 | 4.10 | 10000 |

TABLE 1-continued

| Compound # | Structure | Synthesis Reference Example # | MS (M + 1) | Tau Ki (nM) | Amyloid Ki (nM) |
|---|---|---|---|---|---|
| 21-4 | 21-4 | 21 step 3 | 264.1 | 3.35 | 10000 |
| 22 | 22 | 22 | 252.1 | 1.43 | 10000 |
| 23 | 23 | 23 | 250.1 | 2.10 | — |
| 24 | 24 | 24 | 295.2 | 12.8 | — |
| 24-4 | 24-4 | 24 step 4 | 277.1 | 1.55 | — |
| 24-5 | 24-5 | 24 step 5 | 263.2 | 11.1 | — |
| 25 | 25 | 25 | 265.0 | 14.1 | — |

TABLE 1-continued

| Compound # | Structure | Synthesis Reference Example # | MS (M + 1) | Tau Ki (nM) | Amyloid Ki (nM) |
| --- | --- | --- | --- | --- | --- |
| 26 | 26 | 26 | 247.2 | 2.27 | 10000 |
| 27 | 27 | 27 | 277.2 | 2.31 | — |
| 28 | 28 | 28 | 262.2 | 184.6 | — |
| 29 | 29 | 29 | 308.9 | 2.41 | 10000 |
| 30 | 30 | 30 | 278.1 | 2.44 | 39960 |
| 31 | 31 | 31 | 341.1 | 2.88 | 10000 |
| 31-1 | 31-1 | 31 step 1 | 323.1 | 3.54 | 10000 |

TABLE 1-continued

| Compound # | Structure | Synthesis Reference Example # | MS (M + 1) | Tau Ki (nM) | Amyloid Ki (nM) |
|---|---|---|---|---|---|
| 32 | *structure 32* | 32 | 272.0 | 2.98 | 17340 |
| 33 | *structure 33* | 33 | 264.1 | 3.34 | 10000 |
| 34 | *structure 34* | 34 | 345.1 | 3.83 | 10000 |
| 35 | *structure 35* | 35 | 271.1 | 3.19 | 10000 |
| 36 | *structure 36* | 36 | 257.2 | 4.96 | 18230 |
| 37 | *structure 37* | 37 | 291.1 | 19.7 | — |
| 38 | *structure 38* | 38 | 264.1 | 52.3 | 92.92 |

TABLE 1-continued

| Compound # | Structure | Synthesis Reference Example # | MS (M + 1) | Tau Ki (nM) | Amyloid Ki (nM) |
|---|---|---|---|---|---|
| 39 | (structure 39) | 39 | 251.0 | 10.8 | — |
| 40 | (structure 40) | 40 | 265.1 | 52.7 | — |
| 41 | (structure 41) | 41 | 263.1 | 8.8 | 10000 |
| 42 | (structure 42) | 42 | 295.1 | 71.1 | — |
| 43 | (structure 43) | 43 | 297.1 | 10 | — |
| 44 | (structure 44) | 44 | 291.0 | 1.13 | 10000 |
| 45 | (structure 45) | 45 | 316.0 | — | — |

TABLE 1-continued
| Compound # | Structure | Synthesis Reference Example # | MS (M + 1) | Tau Ki (nM) | Amyloid Ki (nM) |
|---|---|---|---|---|---|
| 46 | 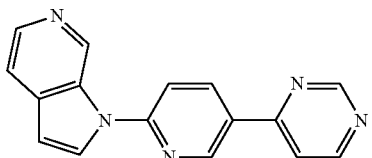<br>46 | 46 | 274.0 | 2.19 | — |
| 47 | 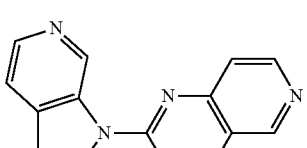<br>47 | 47 | 247.0 | — | 10000 |
| 48 | 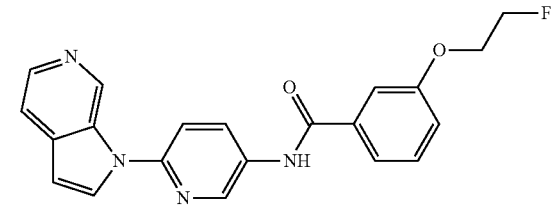<br>48 | 48 | 377.0 | — | — |
| 49 | 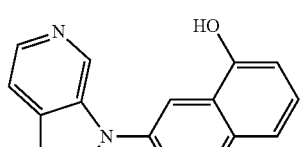<br>49 | 15 | 262.1 | 0.67 | 10000 |
| 50 | 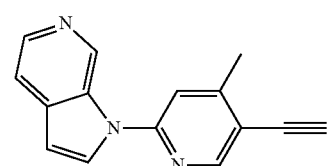<br>50 | 1 | 234.0 | 0.75 | 2495 |
| 51 | 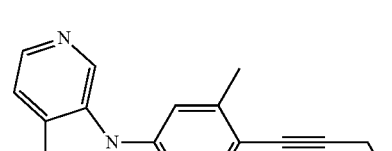<br>51 | 7 | 266.0 | 0.87 | 2781 |
| 52 | 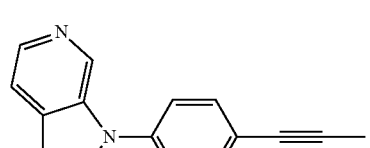<br>52 | 1 | 234.0 | 0.98 | 10000 |

TABLE 1-continued
| Compound # | Structure | Synthesis Reference Example # | MS (M + 1) | Tau Ki (nM) | Amyloid Ki (nM) |
| --- | --- | --- | --- | --- | --- |
| 53 | 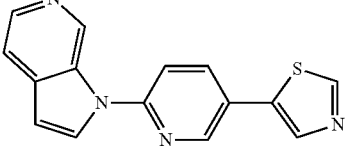 53 | 3 | 279.0 | 1.02 | 10000 |
| 54 | 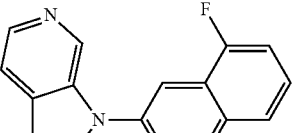 54 | 9 | 264.0 | 1.05 | 10000 |
| 55 | 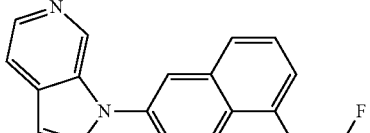 55 | 17 from compound 56 | 294.1 | 1.14 | 10000 |
| 56 | 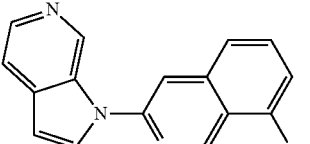 56 | 13 & 15 | 262.1 | 1.16 | 10000 |
| 57 | 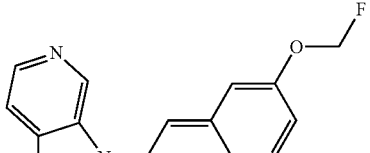 57 | 17 | 294.1 | 1.23 | 10000 |
| 58 | 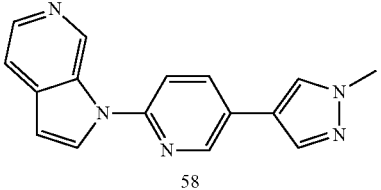 [SMILES: Cn1cc(-c2ccc(-n3ccc4ccncc43)nc2)cn1] 58 | 3 | 276.0 | 1.32 | 10000 |
| 59 | 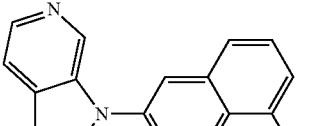 59 | 12 | 261.0 | 0.33 | 10000 |

TABLE 1-continued
| Compound # | Structure | Synthesis Reference Example # | MS (M + 1) | Tau Ki (nM) | Amyloid Ki (nM) |
|---|---|---|---|---|---|
| 60 | 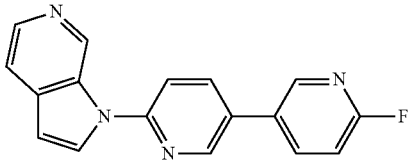 60 | 3 | 291.0 | 2.04 | 10000 |
| 61 | 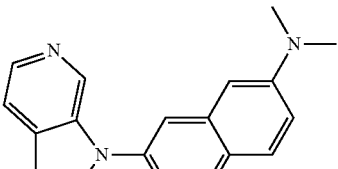 61 | 14 | 289.0 | 2.23 | 10000 |
| 62 | 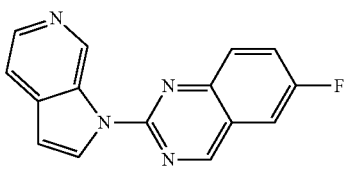 62 | 24 | 265.0 | 2.55 | — |
| 63 | 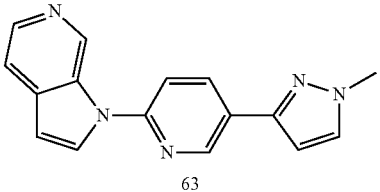 [SMILES: Cn1ccc(-c2ccc(-n3ccc4ccncc43)nc2)n1] 63 | 3 | 276.0 | 2.84 | 1079 |
| 64 | 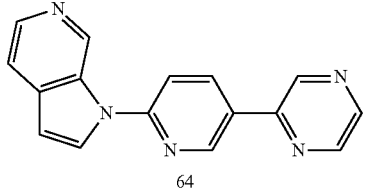 [SMILES: c1cnc(-c2ccc(-n3ccc4ccncc43)nc2)cn1] 64 | 3 | 274.0 | 3.17 | 10000 |
| 65 | 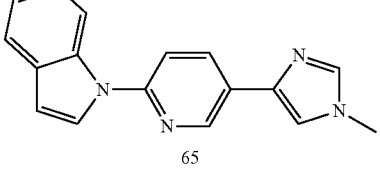 65 | 3 | 276.0 | 3.42 | 25340 |
| 66 | 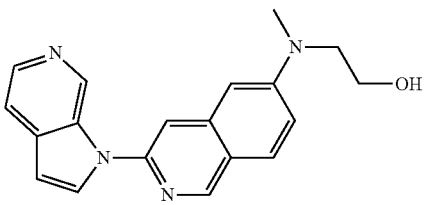 66 | 14 | 319.0 | 4.07 | 10000 |

TABLE 1-continued
| Compound # | Structure | Synthesis Reference Example # | MS (M + 1) | Tau Ki (nM) | Amyloid Ki (nM) |
|---|---|---|---|---|---|
| 67 | 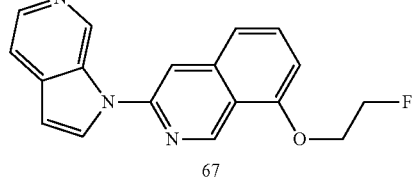 67 | 16 | 308.0 | 6.75 | 10000 |
| 68 | 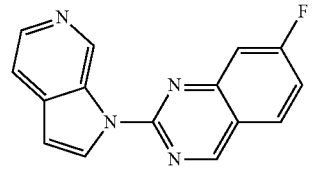 68 | 24 | 265.0 | 8.45 | — |
| 69 | 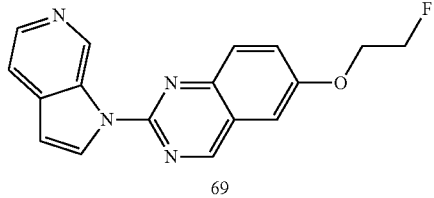 [SMILES: FCCOc1ccc2nc(-n3ccc4ccncc43)ncc2c1] 69 | 24 & 16 | 309.3 | 9.33 | — |
| 70 | 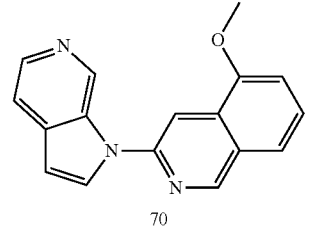 [SMILES: COc1cccc2cnc(-n3ccc4ccncc43)cc12] 70 | 13 | 276.0 | 44.4 | — |
| 71 | 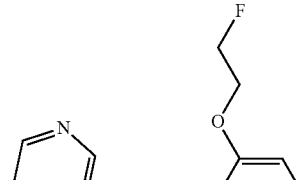 71 | 16 | 308.0 | 172.4 | — |
| 72 | 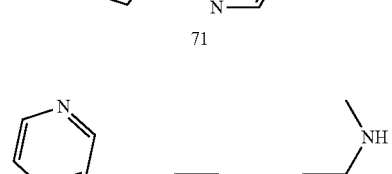 72 | 3 | 301.0 | 0.76 | 1230 |

TABLE 1-continued

| Compound # | Structure | Synthesis Reference Example # | MS (M + 1) | Tau Ki (nM) | Amyloid Ki (nM) |
|---|---|---|---|---|---|
| 73 | 73 | 3 | 301.0 | — | — |
| 74 | 74 | 46 | 274.0 | — | 1050 |
| 75 | 75 | 13 & 15 | 262.1 | 0.48 | 10000 |
| 76 | 76 | 46 | 274.0 | — | — |
| 77 | 77 | 1 | 326.0 | — | — |
| 78 | 78 | 1 | 326.0 | — | — |
| 79 | 79 | 1 | 297.0 | — | — |

TABLE 1-continued
| Compound # | Structure | Synthesis Reference Example # | MS (M + 1) | Tau Ki (nM) | Amyloid Ki (nM) |
|---|---|---|---|---|---|
| 80 | 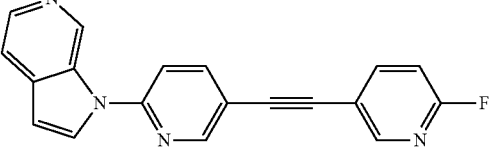 | 1 | 315.0 | — | — |
| 81 | 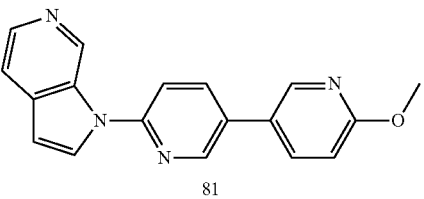 [SMILES: COc1ccc(-c2ccc(-n3ccc4ccncc43)nc2)cn1] | 3 | 303.0 | — | — |
| 82 | 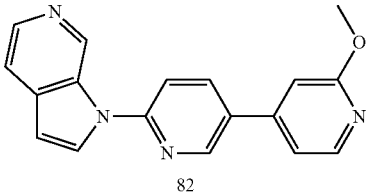 [SMILES: COc1cc(-c2ccc(-n3ccc4ccncc43)nc2)ccn1] | 3 | 303.0 | — | — |
| 83 | 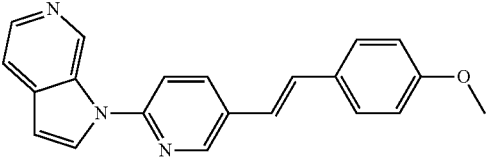 | 2 | 328.0 | — | — |
| 84 | 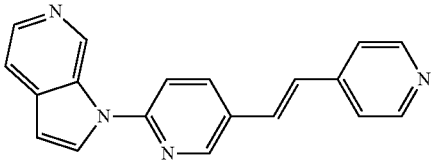 | 2 | 299.0 | — | — |
| 85 | 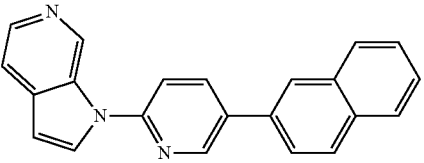 | 3 | 322.0 | — | — |
| 86 | 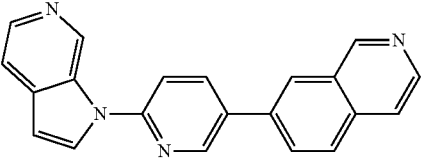 | 3 | 323.0 | — | — |

TABLE 1-continued
| Compound # | Structure | Synthesis Reference Example # | MS (M + 1) | Tau Ki (nM) | Amyloid Ki (nM) |
|---|---|---|---|---|---|
| 87 | 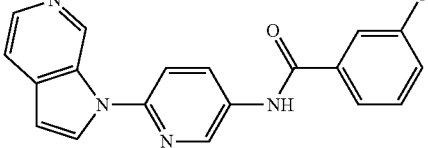 87 | 48 step 1 | 331.0 | — | — |
| 88 | 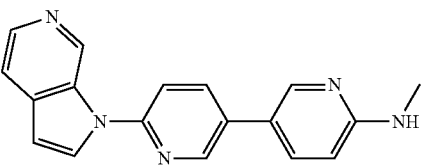 88 | 3 & 14 (step 1) | 302.0 | 0.69 | 2952 |
| 89 | 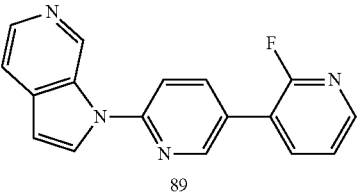 [SMILES: Fc1ncccc1-c1ccc(-n2ccc3ccncc32)nc1] 89 | 3 | 291.0 | — | — |
| 90 | 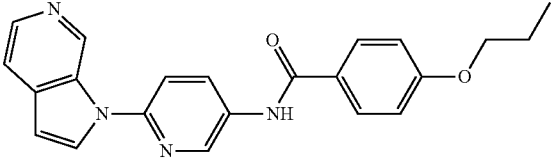 90 | 48 | 373.0 | — | — |
| 91 | 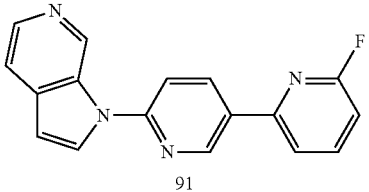 [SMILES: Fc1cccc(-c2ccc(-n3ccc4ccncc43)nc2)n1] 91 | 3 | 291.0 | 1.41 | — |
| 92 | 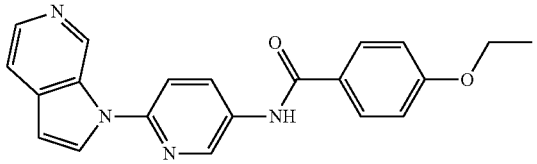 92 | 4 | 359.0 | — | — |
| 93 | 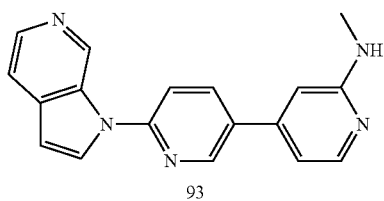 93 | 45 | 302.0 | 0.53 | 5739 |

TABLE 1-continued
| Compound # | Structure | Synthesis Reference Example # | MS (M + 1) | Tau Ki (nM) | Amyloid Ki (nM) |
|---|---|---|---|---|---|
| 94 | 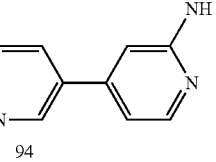 94 | 45 | 316.0 | 1.40 | — |
| 95 | 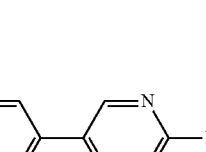 95 | 45 | 316.0 | 0.96 | — |
| 96 | 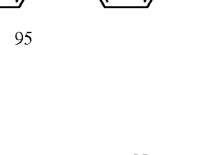 96 | 3 | 262.0 | — | — |
| 97 | 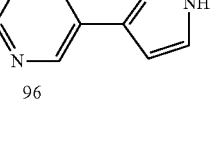 97 | 3 | 262.0 | — | — |
| 98 | 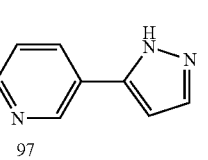 98 | 45 | 316.0 | 1.13 | — |
| 99 | 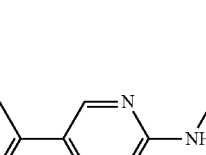 99 | 45 | 288.0 | 0.55 | — |
| 100 | 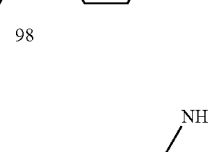 100 | 45 | 288.0 | 1.06 | — |

TABLE 1-continued

| Compound # | Structure | Synthesis Reference Example # | MS (M + 1) | Tau Ki (nM) | Amyloid Ki (nM) |
|---|---|---|---|---|---|
| 101 | 101 | 46 | 273.0 | 1.14 | — |
| 102 | 102 | 6 | 246.3 | — | — |
| 103 | 103 | 13 | 276.0 | 0.32 | 28580 |
| 104 | 104 | 3 & 50 | 308.0 | 1.71 | 1668 |

TABLE 2

| COMPOUND # | Structure | MS (M + 1) | Tau Ki (nM) | Amyloid Ki (nM) |
|---|---|---|---|---|
| 105 | 105 | 279.3 | 0.3826 | 2803 |
| 106 | 106 | 279.3 | 10000 | 17100 |

TABLE 2-continued

| COMPOUND # | Structure | MS (M + 1) | Tau Ki (nM) | Amyloid Ki (nM) |
|---|---|---|---|---|
| 107 | 107 | 279.3 | 10000 | 10000 |
| 108 | 108 | 279.3 | 0.6774 | 10000 |
| 109 | 109 | 279.3 | 0.4235 | 10000 |
| 110 | 110 | 279.3 | 2.155 | 10000 |
| 111 | 111 | 279.3 | 1.095 | 3565 |
| 112 | 112 | 279.3 | 0.6724 | 9990 |
| 113 | 113 | 279.3 | 0.7837 | 9990 |

TABLE 2-continued

| COMPOUND # | Structure | MS (M + 1) | Tau Ki (nM) | Amyloid Ki (nM) |
|---|---|---|---|---|
| 114 | 114 | 279.3 | 0.4945 | 2712 |
| 115 | 115 | 279.3 | 0.2237 | 9990 |
| 116 | 116 | 279.3 | 1.282 | 6653 |
| 117 | 117 | 279.3 | 1.995 | 6653 |
| 118 | 118 | 387.2 | 24.46 | — |
| 119 | 119 | 387.2 | 0.4382 | 9990 |
| 120 | 120 | 387.2 | 93.78 | — |

TABLE 2-continued

| COMPOUND # | Structure | MS (M + 1) | Tau Ki (nM) | Amyloid Ki (nM) |
|---|---|---|---|---|
| 121 | 121 | 387.2 | 0.512 | 739.3 |
| 122 | 122 | 387.2 | 1.767 | 4097 |
| 123 | 123 | 387.2 | 208 | |
| 124 | 124 | 387.2 | 1.066 | 6653 |
| 125 | 125 | 387.2 | 18.63 | |
| 126 | 126 | 387.2 | 0.1796 | 80.32 |
| 127 | 127 | 387.2 | 1.166 | 19960 |

TABLE 2-continued

| COMPOUND # | Structure | MS (M + 1) | Tau Ki (nM) | Amyloid Ki (nM) |
|---|---|---|---|---|
| 128 | 128 | 387.2 | 6.207 | — |
| 129 | 129 | 387.2 | — | — |
| 130 | 130 | 294.3 | 4.03 | — |

Example 1

Synthesis of 1-(5-(2-(2-methylthiazol-4-yl)ethynyl)pyridin-2-yl)-1H-pyrrolo[2,3-c]pyridine (1)

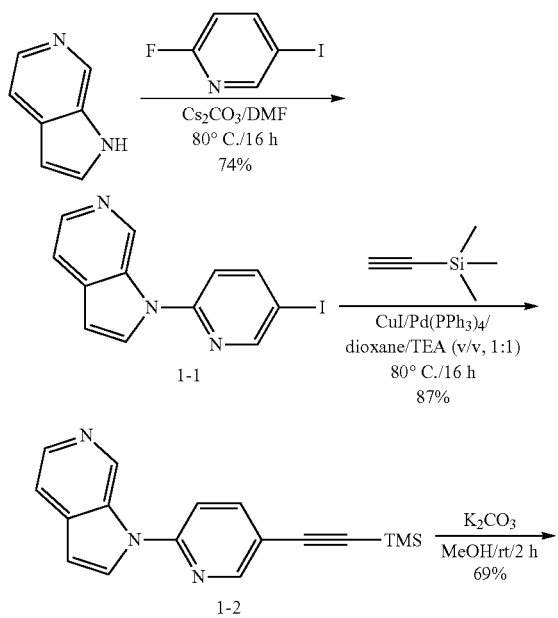

Scheme 1

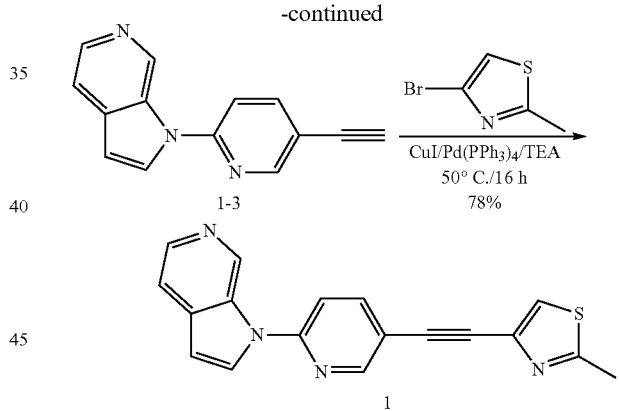

Step 1: Synthesis of 1-(5-iodopyridin-2-yl)-1H-pyrrolo[2,3-c]pyridine (1-1)

To a solution of 1H-pyrrolo[2,3-c]pyridine (20 g, 0.17 mol) in N,N-dimethylformamide (300 mL) were added 2-fluoro-5-iodopyridine (45 g, 0.20 mol) and cesium carbonate (110 g, 0.34 mol). The resulting mixture was stirred for 16 hours at 80° C. under nitrogen atmosphere. After cooling down to ambient temperature, the mixture was diluted with water (1 L) and extracted with dichloromethane (3×200 mL). The combined organic layers was washed with brine (3×100 mL) and dried over anhydrous sodium sulfate. After filtration, the filtrate was concentrated under reduced pressure and the residue was purified by silica gel column chromatography, eluted with 0.5~3% methanol in dichloromethane to afford 1-(5-iodopyridin-2-yl)-1H-pyrrolo[2,3-c]pyridine as a colorless solid: MS (ESI, m/z): 322.0

[M+1]+; 1H NMR (400 MHz, CDCl3) δ 9.61 (s, 1H), 8.77 (d, J=2.0 Hz, 1H), 8.38 (d, J=5.6 Hz, 1H), 8.12-8.09 (m, 1H), 7.81 (d, J=3.6 Hz, 1H), 7.56-7.55 (m, 1H), 7.34-7.28 (m, 1H), 6.72 (d, J=3.6 Hz, 1H).

Step 2: Synthesis of 1-(5-(2-(trimethylsilyl)ethynyl) pyridin-2-yl)-1H-pyrrolo[2,3-c]pyridine (1-2)

To a solution of 1-(5-iodopyridin-2-yl)-1H-pyrrolo[2,3-c]pyridine (4.1 g, 12.5 mmol) in 1,4-dioxane (50 mL) and triethylamine (50 mL) were added ethynyltrimethylsilane (3.7 g, 37.4 mmol), copper(I) iodide (1.4 g, 7.5 mmol) and tetrakis(triphenylphosphine)palladium(0) (1.4 g, 1.2 mmol). The resulting mixture was stirred for 16 hours at 80° C. under nitrogen atmosphere. After cooling down to ambient temperature, the mixture was diluted with water (100 mL) and the organic layer was separated out. The aqueous layer was extracted with dichloromethane (3×100 mL). The combined organic layers was dried over anhydrous sodium sulfate and filtered. The filtrate was concentrated under reduced pressure and the residue was purified by silica gel column chromatography, eluted with 0.3~3% methanol in dichloromethane to afford 1-(5-(2-(trimethylsilyl)ethynyl) pyridin-2-yl)-1H-pyrrolo[2,3-c]pyridine as a yellow solid: MS (ESI, m/z): 292.0 [M+1]+; 1H NMR (300 MHz, DMSO-d6) δ 9.93 (s, 1H), 8.97 (d, J=2.4 Hz, 1H), 8.76 (d, J=1.5 Hz, 1H), 8.51 (d, J=6.3 Hz, 1H), 8.25-8.21 (m, 2H), 8.07 (d, J=8.4 Hz, 1H), 7.24 (d, J=3.3 Hz, 1H), 0.17 (s, 9H).

Step 3: Synthesis of 1-(5-ethynylpyridin-2-yl)-1H-pyrrolo[2,3-c]pyridine (1-3)

A solution of 1-(5-((trimethylsilyl)ethynyl)pyridin-2-yl)-1H-pyrrolo[2,3-c]pyridine (4.5 g, 15.4 mmol) in methanol (50 mL) was treated with potassium carbonate (4.3 g, 30.9 mmol) for 2 hours at ambient temperature. The resulting mixture was neutralized with acetic acid and concentrated under reduced pressure. The residue was purified by silica gel column chromatography, eluted with 0.3~3% methanol in dichloromethane to afford 1-(5-ethynylpyridin-2-yl)-1H-pyrrolo[2,3-c]pyridine as a yellow solid: MS (ESI, m/z): 220.0 [M+1]+1; 1H NMR (300 MHz, DMSO-d6) δ 9.95 (s, 1H), 9.00 (d, J=2.4 Hz, 1H), 8.79 (d, J=1.5 Hz, 1H), 8.53 (d, J=6.3 Hz, 1H), 8.28-8.23 (m, 2H), 8.10 (d, J=8.4 Hz, 1H), 7.28 (d, J=3.3 Hz, 1H), 4.58 (s, 1H).

Step 4: Synthesis of 1-(5-(2-(2-methylthiazol-4-yl) ethynyl)pyridin-2-yl)-1H-pyrrolo[2,3-c]pyridine (1)

To a solution of 1-(5-ethynylpyridin-2-yl)-1H-pyrrolo[2,3-c]pyridine (141 mg, 0.64 mmol) in triethylamine (10 mL) were added 4-bromo-2-methylthiazole (178 mg, 1 mmol), copper(I) iodide (48 mg, 0.26 mmol) and tetrakis(triphenylphosphine)palladium(0) (49 mg, 0.043 mmol). The resulting mixture was stirred for 16 hours at 50° C. under nitrogen atmosphere. After cooling down to ambient temperature, the resulting mixture was concentrated under reduced pressure. The residue was purified by silica gel column chromatography, eluted with 1~3% methanol in dichloromethane to afford 1-(5-(2-(2-methylthiazol-4-yl)ethynyl)pyridin-2-yl)-1H-pyrrolo[2,3-c]pyridine as a colorless solid: MS (ESI, m/z): 317.0 [M+1]+; 1H NMR (400 MHz, CD3OD) δ 9.88 (br s, 1H), 8.79 (d, J=1.6 Hz, 1H), 8.34-8.33 (m, 2H), 8.15-8.12 (m, 1H), 7.85-7.82 (m, 2H), 7.77 (s, 1H), 6.96 (d, J=3.2 Hz, 1H), 2.76 (s, 3H).

Example 2

Synthesis of (E)-1-(5-styrylpyridin-2-yl)-1H-pyrrolo[2,3-c]pyridine (2)

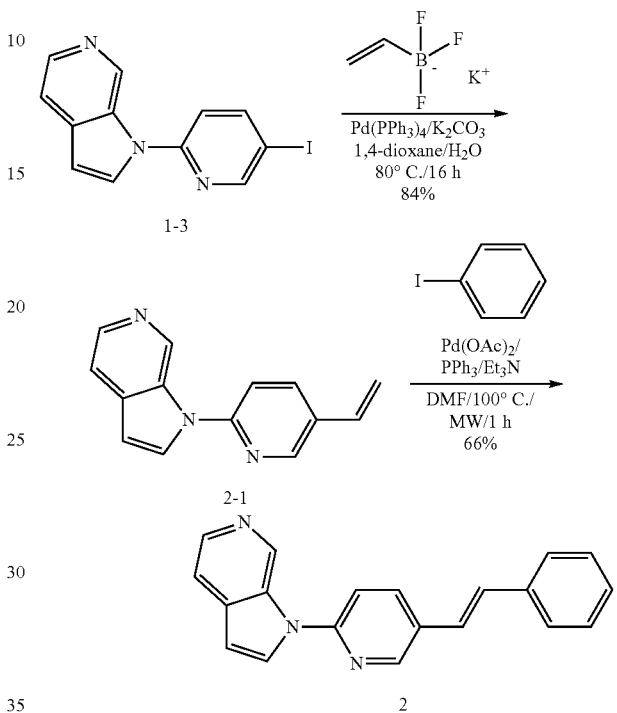

Scheme 2

Step 1: Synthesis of 1-(5-vinylpyridin-2-yl)-1H-pyrrolo[2,3-c]pyridine (2-1)

To a solution of 1-(5-iodopyridin-2-yl)-1H-pyrrolo[2,3-c]pyridine (2 g, 6.23 mmol) in 1,4-dioxane (40 mL) and water (4 mL) were added potassium trifluoro(vinyl)borate (1.25 g, 9.34 mmol), potassium carbonate (1.72 g, 12.46 mmol) and tetrakis(triphenylphosphine)palladium(0) (0.72 g, 0.62 mmol). The resulting mixture was stirred for 16 hours at 80° C. under nitrogen atmosphere. After cooling down to ambient temperature, the mixture was diluted with water (100 mL) and the organic layer was separated out. The aqueous layer was extracted with dichloromethane (3×100 mL). The combined organic layers was dried over anhydrous sodium sulfate and filtered. The filtrate was concentrated under reduced pressure and the residue was purified by silica gel column chromatography, eluted with 0.3~2% methanol in dichloromethane to afford 1-(5-vinylpyridin-2-yl)-1H-pyrrolo[2,3-c]pyridine as a colorless solid: MS (ESI, m/z): 222.0 [M+1]+; 1H NMR (400 MHz, DMSO-d6) δ 9.79 (s, 1H), 8.70 (d, J=2.4 Hz, 1H), 8.35 (d, J=3.6 Hz, 1H), 8.31 (d, J=5.2 Hz, 1H), 8.23 (dd, J=2.0 Hz, 8.4 Hz, 1H), 7.91 (d, J=8.4 Hz, 1H), 7.68 (dd, J=0.8 Hz, 4.4 Hz, 1H), 6.90-6.83 (m, 2H), 6.08 (d, J=17.6 Hz, 1H), 5.46 (d, J=11.2 Hz, 1H).

Step 2: Synthesis of (E)-1-(5-styrylpyridin-2-yl)-1H-pyrrolo[2,3-c]pyridine (2)

To a solution of 1-(5-vinylpyridin-2-yl)-1H-pyrrolo[2,3-c]pyridine (100 mg, 0.4 mmol) in N,N-dimethylformamide (2.5 mL) were added bis(acetato)palladium(II) (10 mg, 0.045 mmol), 1-iodobenzene (138 mg, 0.68 mmol), triphenylphosphine (12 mg, 0.045 mmol) and triethylamine (91 mg, 0.9 mmol). The resulting mixture was irradiated by microwave (100 W) for 1 hour at 100° C. After cooling down to ambient temperature, the resulting mixture was quenched with water (20 mL) and extracted with dichloromethane (3×50 mL). The combined organic layers was washed with brine (3×50 mL) and dried over anhydrous sodium sulfate. After filtration, the filtrate was concentrated under reduced pressure and the residue was purified by silica gel column chromatography, eluted with 0.5~2% methanol in dichloromethane to afford (E)-1-(5-styrylpyridin-2-yl)-1H-pyrrolo[2,3-c]pyridine as a yellow solid: MS (ESI, m/z): 298.0 [M+1]$^+$; $^1$H NMR (300 MHz, DMSO-$d_6$) δ 9.71 (s, 1H), 8.79 (d, J=2.1 Hz, 1H), 8.56-8.32 (m, 3H), 7.93 (d, J=8.7 Hz, 1H), 7.67-7.64 (m, 3H), 7.48-7.29 (m, 5H), 6.83 (d, J=4.2 Hz, 1H).

Example 3

Synthesis of 1-(5-(pyridin-3-yl)pyridin-2-yl)-1H-pyrrolo[2,3-c]pyridine (3)

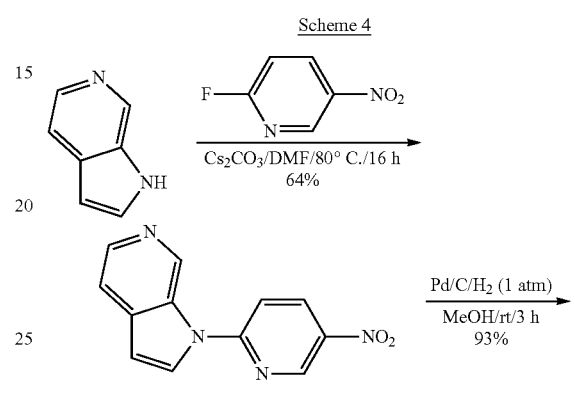

Synthesis of 1-(5-(pyridin-3-yl)pyridin-2-yl)-1H-pyrrolo[2,3-c]pyridine (3)

To a solution of 1-(5-iodopyridin-2-yl)-1H-pyrrolo[2,3-c]pyridine (100 mg, 0.31 mmol) in 1,4-dioxane (20 mL) and water (5 mL) were added 3-(4,4,5,5-tetramethyl-1,3,2-dioxaborolan-2-yl)pyridine (96 mg, 0.47 mmol), potassium carbonate (129 mg, 0.93 mmol) and tetrakis(triphenylphosphine)palladium(0) (18 mg, 0.016 mmol). The resulting mixture was stirred for 3 hours at 80° C. under nitrogen atmosphere. After cooling down to ambient temperature, the mixture was diluted with water (100 mL) and extracted with dichloromethane (3×100 mL). The combined organic layers was dried over anhydrous sodium sulfate and filtered. The filtrate was concentrated under reduced pressure and the residue was purified by silica gel column chromatography, eluted with 1~2% methanol in dichloromethane to afford 1-(5-(pyridin-3-yl)pyridin-2-yl)-1H-pyrrolo[2,3-c]pyridine as a colorless solid: MS (ESI, m/z): 273.0 [M+1]$^+$; $^1$H NMR (300 MHz, DMSO-$d_6$) δ 9.85 (s, 1H), 9.05-9.01 (m, 2H), 8.66-8.64 (m, 1H), 8.44-8.39 (m, 2H), 8.27-8.23 (m, 2H), 8.04 (d, J=8.7 Hz, 1H), 7.75-7.73 (m, 1H), 7.68-7.54 (m, 1H), 6.89 (d, J=3.3 Hz, 1H).

Example 4

Synthesis of N-(6-(1H-pyrrolo[2,3-c]pyridin-1-yl)pyridin-3-yl)-4-methoxybenzamide (4)

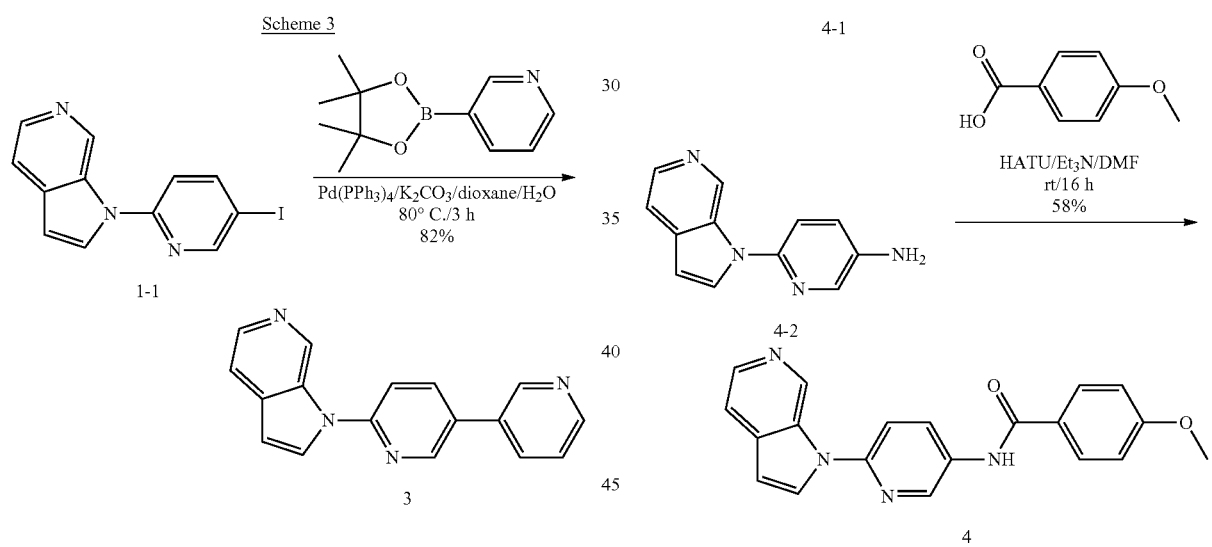

Step 1: Synthesis of 1-(5-nitropyridin-2-yl)-1H-pyrrolo[2,3-c]pyridine (4-1)

To a solution of 1H-pyrrolo[2,3-c]pyridine (2 g, 16.9 mmol) in N,N-dimethylformamide (100 mL) was added 2-fluoro-5-nitropyridine (2.9 g, 20.3 mmol) and cesium carbonate (11.0 g, 33.9 mmol). The resulting mixture was stirred for 16 hours at 80° C. under nitrogen atmosphere. After cooling down to ambient temperature, the mixture was diluted with water (500 mL) and extracted with ethyl acetate (3×100 mL). The combined organic layers was washed with brine (3×100 mL) and dried over anhydrous sodium sulfate. After filtration, the filtrate was concentrated under reduced pressure and the residue was purified by silica gel column chromatography, eluted with 0.3~2% methanol in dichloromethane to afford 1-(5-nitropyridin-2-yl)-1H-pyrrolo[2,3-c]pyridine as an orange solid: MS (ESI, m/z): 241.0 [M+1]$^+$;

¹H NMR (400 MHz, DMSO-d₆) δ 9.95 (s, 1H), 9.46 (d, J=2.4 Hz, 1H), 8.79 (dd, J=2.8 Hz, 6.4 Hz, 1H), 8.50 (d, J=3.6 Hz, 1H), 8.39 (d, J=5.2 Hz, 1H), 8.16 (d, J=9.2 Hz, 1H), 7.72 (d, J=5.2 Hz, 1H), 7.00 (d, J=3.6 Hz, 1H).

Step 2: Synthesis of 6-(1H-pyrrolo[2,3-c]pyridin-1-yl)pyridin-3-amine (4-2)

To a stirred solution of 1-(5-nitropyridin-2-yl)-1H-pyrrolo[2,3-c]pyridine (0.8 g, 3.33 mmol) in methanol (50 mL) was added palladium on charcoal (1.0 g, 10% w/w). The resulting mixture was kept under a hydrogen atmosphere (1 atm.) for 3 hours at ambient temperature. Then, the mixture was filtered through Celite and evaporation of the filtrate under reduced pressure to afford 6-(1H-pyrrolo[2,3-c]pyridin-1-yl)pyridin-3-amine as a yellow solid: MS (ESI, m/z): 211.0 [M+1]⁺; ¹H NMR (400 MHz, DMSO-d₆) δ 9.39 (s, 1H), 8.25 (d, J=2.4 Hz, 1H), 8.09 (dd, J=2.8 Hz, 6.4 Hz, 1H), 7.96 (d, J=3.6 Hz, 1H), 7.63 (d, J=5.2 Hz, 1H), 7.48 (d, J=9.2 Hz, 1H), 7.16 (d, J=5.2 Hz, 1H), 6.71 (d, J=3.6 Hz, 1H), 5.49 (br s, 2H).

Step 3: Synthesis of N-(6-(1H-pyrrolo[2,3-c]pyridin-1-yl)pyridin-3-yl)-4-methoxybenzamide (4)

To a solution of 6-(1H-pyrrolo[2,3-c]pyridin-1-yl)pyridin-3-amine (100 mg, 0.48 mmol) in N,N-dimethylformamide (15 mL) were added 4-methoxybenzoic acid (109 mg, 0.71 mmol), O-(7-azabenzotriazol-1-yl)-N,N,N',N'-tetramethyluronium hexafluorophosphate (HATU) (271 mg, 0.71 mmol) and triethylamine (144 mg, 1.43 mmol). The resulting solution was stirred for 16 hours at ambient temperature under nitrogen atmosphere. The reaction was quenched with water (50 mL) and extracted with ethyl acetate (3×60 mL). The combined organic layers was washed with brine (3×50 mL) and dried over anhydrous sodium sulfate. After filtration, the filtrate was concentrated under reduced pressure and the residue was purified by silica gel column chromatography, eluted with 0.3~2% methanol in dichloromethane to afford N-(6-(1H-pyrrolo[2,3-c]pyridin-1-yl)pyridin-3-yl)-4-methoxybenzamide as a light yellow solid: MS (ESI, m/z): 345.0 [M+1]⁺; ¹H NMR (300 MHz, DMSO-d₆) δ 10.4 (s, 1H), 9.66 (s, 1H), 8.96 (d, J=2.4 Hz, 1H), 8.42 (dd, J=2.7 Hz, 3.3 Hz, 1H), 8.27-8.24 (m, 2H), 8.03-8.00 (m, 2H), 7.89 (d, J=9.0 Hz, 1H), 7.66-7.64 (m, 1H), 7.12-7.09 (m, 2H), 6.82 (d, J=3.0 Hz, 1H), 3.85 (s, 3H).

Example 5

Synthesis of 1-(5-(pyridin-2-ylmethoxy)pyridin-2-yl)-1H-pyrrolo[2,3-c]pyridine (5)

Scheme 5

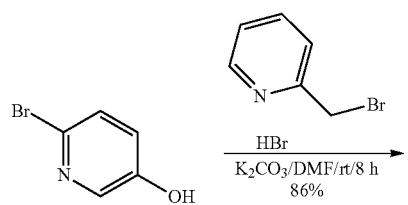

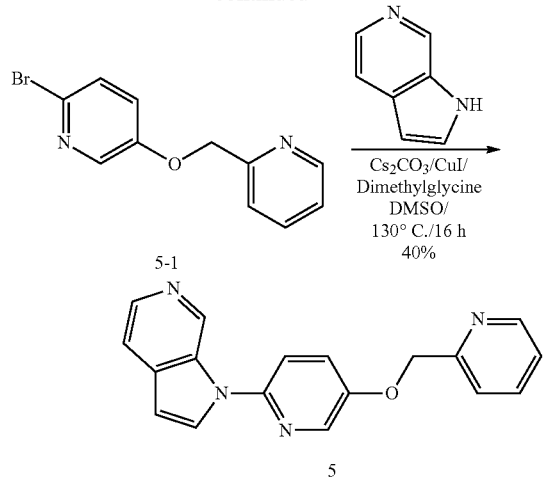

Step 1: Synthesis of 2-((6-bromopyridin-3-yloxy)methyl)pyridine (5-1)

To a solution of 6-bromopyridin-3-ol (0.5 g, 2.87 mmol) in N,N-dimethylformamide (30 mL) were added 2-(bromomethyl)pyridine hydrobromide (0.73 g, 2.87 mmol) and potassium carbonate (1.19 g, 8.62 mmol). The resulting mixture was stirred for 8 hours at ambient temperature under nitrogen atmosphere. The reaction was quenched with water (100 mL) and extracted with ethyl acetate (3×50 mL). The combined organic layers was washed with brine (3×50 mL) and dried over anhydrous sodium sulfate. After filtration, the filtrate was concentrated under reduced pressure and the residue was purified by silica gel column chromatography, eluted with 10~30% ethyl acetate in petroleum ether to afford 2-((6-bromopyridin-3-yloxy)methyl)pyridine as a red solid: MS (ESI, m/z): 265.0, 267.0 [M+1]⁺; ¹H NMR (300 MHz, CDCl₃) δ 8.62 (d, J=4.2 Hz, 1H), 8.16 (d, J=3.0 Hz, 1H), 7.77-7.71 (m, 1H), 7.49 (d, J=10.4 Hz, 1H), 7.38 (d, J=11.7 Hz, 1H), 7.29-7.20 (m, 1H), 7.18-7.17 (m, 1H), 5.22 (s, 2H).

Step 2: Synthesis of 1-(5-(pyridin-2-ylmethoxy)pyridin-2-yl)-1H-pyrrolo[2,3-c]pyridine (5)

To a stirred solution of 1H-pyrrolo[2,3-c]pyridine (0.150 g, 1.27 mmol) in dimethyl sulfoxide (50 mL) were added 2-bromo-5-(pyridin-2-ylmethoxy)pyridine (0.67 g, 2.54 mmol), dimethylglycine (0.13 g, 1.27 mmol), copper (I) iodide (0.24 g, 1.27 mmol) and cesium carbonate (1.65 g, 5.08 mmol). The resulting mixture was stirred for 16 hours at 130° C. under nitrogen atmosphere. After cooling to ambient temperature, the mixture was diluted with water (100 mL) and extracted with ethyl acetate (3×100 mL). The combined organic layers was washed with brine (3×50 mL) and dried with anhydrous sodium sulfate. After filtration, the filtrate was concentrated under reduced pressure and the residue was purified by silica gel column, eluted with 0.3~2% methanol in dichloromethane to afford 1-(5-(pyridin-2-ylmethoxy)pyridin-2-yl)-1H-pyrrolo[2,3-c]pyridine as an off-white solid: MS (ESI, m/z): 303.0 [M+1]⁺; ¹H NMR (300 MHz, DMSO-d₆) δ 9.62 (br s, 1H), 8.62-8.60 (m, 1H), 8.43 (d, J=2.7 Hz, 1H), 8.25 (br s, 1H), 8.17 (d, J=5.7 Hz, 1H), 7.90-7.74 (m, 3H), 7.63-7.59 (m, 2H), 7.41-7.36 (m, 1H), 6.80 (d, J=3.3 Hz, 1H), 5.35 (s, 2H).

Example 6

Synthesis of 3-(1H-pyrrolo[2,3-c]pyridin-1-yl)isoquinoline (6)

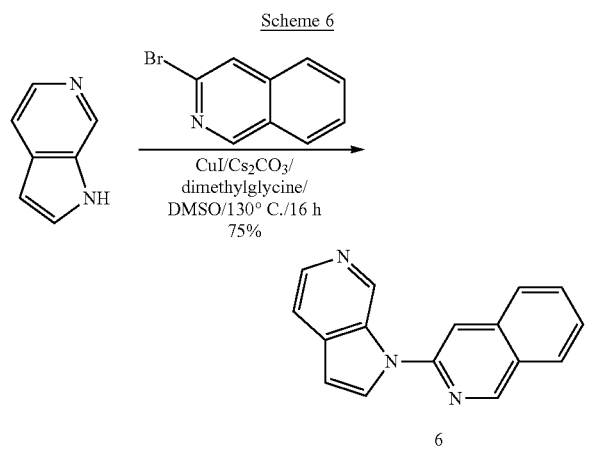

Scheme 6

Synthesis of 3-(1H-pyrrolo[2,3-c]pyridin-1-yl)isoquinoline (6)

To a stirred solution of 1H-pyrrolo[2,3-c]pyridine (0.13 g, 1.08 mmol) in dimethyl sulfoxide (15 mL) were added copper(I) iodide (0.055 g, 0.29 mmol), 3-bromoisoquinoline (0.150 g, 0.72 mmol), cesium carbonate (0.94 g, 2.88 mmol) and dimethylglycine (0.029 g, 0.29 mmol). The resulting mixture was stirred for 16 hours at 130° C. under nitrogen atmosphere. After cooling down to ambient temperature, the reaction was quenched by the addition of water (50 mL) and extracted with ethyl acetate (3×50 mL). The combined organic layers was washed with brine (2×30 mL), dried over anhydrous sodium sulfate and filtered. The filtration was concentrated under reduced pressure and the residue was purified by silica gel column chromatography, eluted with 0.5~2% methanol in dichloromethane to afford 3-(1H-pyrrolo[2,3-c]pyridin-1-yl)isoquinoline as an off-white solid: MS (ESI, m/z): 246.0 [M+1]$^+$; $^1$H NMR (300 MHz, DMSO-d$_6$) δ 9.70 (s, 1H), 9.43 (s, 1H), 8.36 (d, J=3.3 Hz, 1H), 8.30-8.28 (m, 2H), 8.21 (d, J=8.1 Hz, 1H), 8.07 (d, J=8.4 Hz, 1H), 7.88-7.82 (m, 1H), 7.71-7.66 (m, 2H), 6.87 (d, J=3.3 Hz, 1H).

Example 7

Synthesis of 1-(5-(3-fluoroprop-1-ynyl)pyridin-2-yl)-1H-pyrrolo[2,3-c]pyridine (7)

Scheme 7

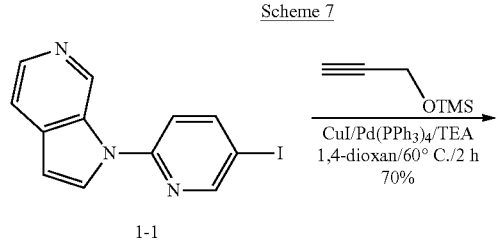

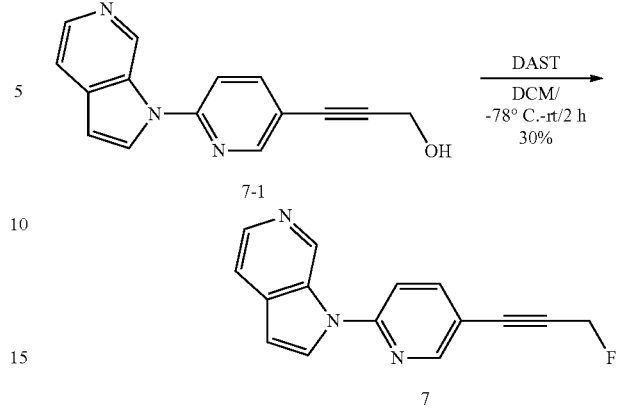

Step 1: Synthesis of 3-(6-(1H-pyrrolo[2,3-c]pyridin-1-yl)pyridin-3-yl)prop-2-yn-1-ol (7-1)

To a solution of 1-(5-iodopyridin-2-yl)-1H-pyrrolo[2,3-c]pyridine (200 mg, 0.62 mmol) in 1,4-dioxane (20 mL) and triethylamine (5 mL) were added trimethyl(prop-2-ynyloxy)silane (96 mg, 0.77 mmol), copper (I) iodide (71 mg, 0.37 mmol) and tetrakis(triphenylphosphine)palladium (0) (140 mg, 0.12 mmol). The resulting mixture was stirred for 2 hours at 60° C. under nitrogen atmosphere. After cooling down to ambient temperature, the mixture was diluted with water (100 mL) and the organic layer was separated out. The aqueous layer was extracted with dichloromethane (3×100 mL). The combined organic layers was dried over anhydrous sodium sulfate and filtered. The filtrate was concentrated under reduced pressure and the residue was purified by silica gel column chromatography, eluted with 0.3~3% methanol in dichloromethane to afford 3-(6-(1H-pyrrolo[2,3-c]pyridin-1-yl)pyridin-3-yl)prop-2-yn-1-ol as a colorless solid: MS (ESI, m/z): 250.0 [M+1]$^+$; $^1$H NMR (300 MHz, DMSO-d$_6$) δ 9.79 (br s, 1H), 8.67 (d, J=1.8 Hz, 1H), 8.34-8.23 (m, 2H), 8.08-8.04 (m, 1H), 7.91 (d, J=8.7 Hz, 1H), 7.67 (d, J=5.1 Hz, 1H), 6.87 (d, J=3.3 Hz, 1H), 5.45 (t, J=6.0 Hz, 1H), 4.37 (d, J=6.0 Hz, 2H).

Step 2: Synthesis of 1-(5-(3-fluoroprop-1-ynyl)pyridin-2-yl)-1H-pyrrolo[2,3-c]pyridine (7)

To a solution of 3-(6-(1H-pyrrolo[2,3-c]pyridin-1-yl)pyridin-3-yl)prop-2-yn-1-ol (100 mg, 0.4 mmol) in dichloromethane (20 mL) was added diethylaminosulfurtrifluoride (DAST) (2 mL) at −78° C. The resulting solution was stirred for 2 hours at ambient temperature and quenched with saturated aqueous solution of sodium bicarbonate (10 mL). The organic layer was separated out and the aqueous layer was extracted with dichloromethane (3×50 mL). The combined organic layers was dried over anhydrous sodium sulfate and filtered. The filtrate was concentrated under reduced pressure and the residue was purified by silica gel column chromatography, eluted with 0.3~3% methanol in dichloromethane to afford 1-(5-(3-fluoroprop-1-ynyl)pyridin-2-yl)-1H-pyrrolo[2,3-c]pyridine as a yellow solid: MS (ESI, m/z): 252.0 [M+1]$^+$; $^1$H NMR (300 MHz, DMSO-d$_6$) δ 9.85 (br s, 1H), 8.76 (d, J=2.1 Hz, 1H), 8.37 (d, J=3.3 Hz, 1H), 8.32 (d, J=5.1 Hz, 1H), 8.17-8.14 (m, 1H), 7.96 (d, J=8.7 Hz, 1H), 7.68 (d, J=5.4 Hz, 1H), 6.90 (d, J=3.3 Hz, 1H), 5.49 (s, 1H), 5.33 (s, 1H).

Example 8

Synthesis of 1-(1H-pyrrolo[2,3-c]pyridin-5-yl)-1H-pyrrolo[2,3-c]pyridine (8)

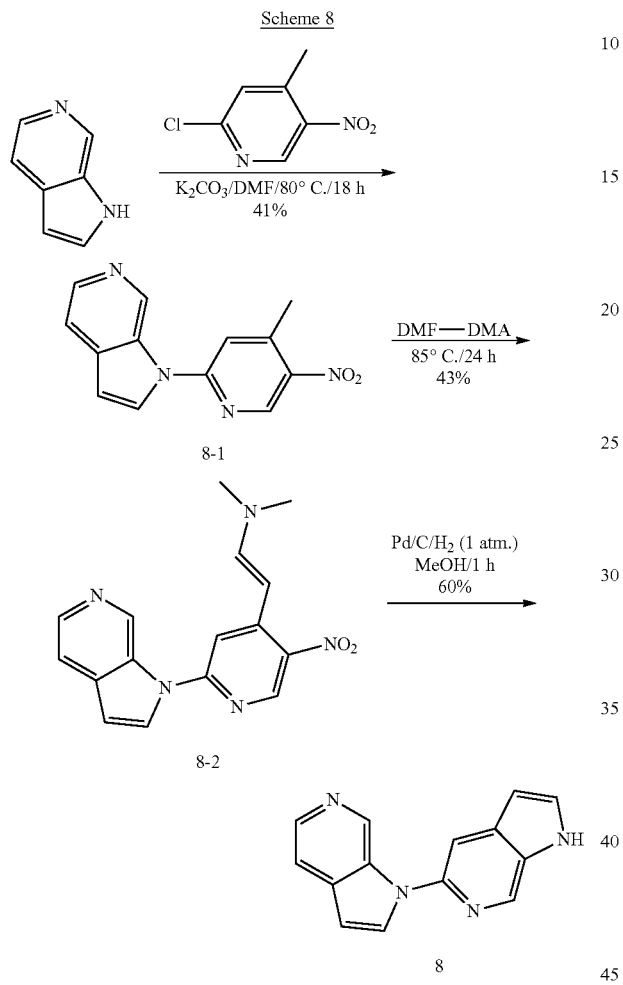

Step 1: Synthesis of 1-(4-methyl-5-nitropyridin-2-yl)-1H-pyrrolo[2,3-c]pyridine (8-1)

To a solution of 1H-pyrrolo[2,3-c]pyridine (1.0 g, 8.7 mmol) in N,N-dimethylformamide (30 mL) were added potassium carbonate (1.6 g, 11.6 mmol) and 2-chloro-4-methyl-5-nitropyridine (1.0 g, 5.8 mmol) at ambient temperature. The resulting mixture was stirred for 18 hours at 80° C. under nitrogen atmosphere. After cooling down to ambient temperature, the reaction was diluted with brine (150 mL) and extracted with ethyl acetate (2×80 mL). The combined organic layers was washed with brine (5×50 mL) and dried over anhydrous sodium sulfate. After filtration, the filtrate was concentrated under reduced pressure and the residue was purified by silica gel column chromatography, eluted with 30~50% ethyl acetate in petroleum ether to afford 1-(4-methyl-5-nitropyridin-2-yl)-1H-pyrrolo[2,3-c]pyridine as a yellow solid: MS (ESI, m/z): 255.0 [M+1]$^+$.

Step 2: Synthesis of (E)-N,N-dimethyl-2-(5-nitro-2-(1H-pyrrolo[2,3-c]pyridin-1-yl)pyridin-4-yl)ethenamine (8-2)

A solution of 1-(4-methyl-5-nitropyridin-2-yl)-1H-pyrrolo[2,3-c]pyridine (140 mg, 0.55 mmol) in N,N-dimethylformamide dimethyl acetal (20 mL) was stirred for 24 hours at 85° C. The solvent was removed under reduced pressure and the residue was purified by silica gel column chromatography, eluted with 50~80% ethyl acetate in petroleum ether to afford (E)-N,N-dimethyl-2-(5-nitro-2-(1H-pyrrolo[2,3-c]pyridin-1-yl)pyridin-4-yl)ethenamine as a yellow solid: MS (ESI, m/z): 310.0 [M+1]$^+$; $^1$H NMR (400 MHz, CDCl$_3$) δ 9.59 (s, 1H), 9.05 (s, 1H), 8.39-8.36 (m, 1H), 8.10 (d, J=3.6 Hz, 1H), 7.69 (d, J=7.0 Hz, 1H), 7.54-7.48 (m, 1H), 7.43 (s, 1H), 6.83 (d, J=3.6 Hz, 1H), 6.18 (d, J=12.4 Hz, 1H), 3.12 (s, 6H).

Step 3: Synthesis of 1-(1H-pyrrolo[2,3-c]pyridin-5-yl)-1H-pyrrolo[2,3-c]pyridine (8)

To a stirred solution of (E)-N,N-dimethyl-2-(5-nitro-2-(1H-pyrrolo[2,3-c]pyridin-1-yl)pyridin-4-yl)ethenamine (40 mg, 0.13 mmol) in methanol (10 mL) was added palladium on charcoal (5.0 mg, 10% w/w). The resulting mixture was kept under a hydrogen atmosphere (1 atm.) for 1 hour at ambient temperature. Then, the mixture was filtered through Celite and the filtrate was concentrated under reduced pressure to dryness. The residue was purified by silica gel column chromatography, eluted with 1~3% methanol in dichloromethane to afford 1-(1H-pyrrolo[2,3-c]pyridin-5-yl)-1H-pyrrolo[2,3-c]pyridine as an off-white solid: MS (ESI, m/z): 235.0 [M+1]$^+$; $^1$H NMR (400 MHz, DMSO-d$_6$) δ 11.80 (br s, 1H), 9.48 (s, 1H), 8.78 (s, 1H), 8.22-8.16 (m, 2H), 7.90 (s, 1H), 7.76-7.75 (m, 1H), 7.64-7.63 (m, 1H), 6.76 (d, J=3.2 Hz, 1H), 6.62 (s, 1H).

Example 9

Synthesis of 6-fluoro-3-(1H-pyrrolo[2,3-c]pyridin-1-yl)isoquinoline (9)

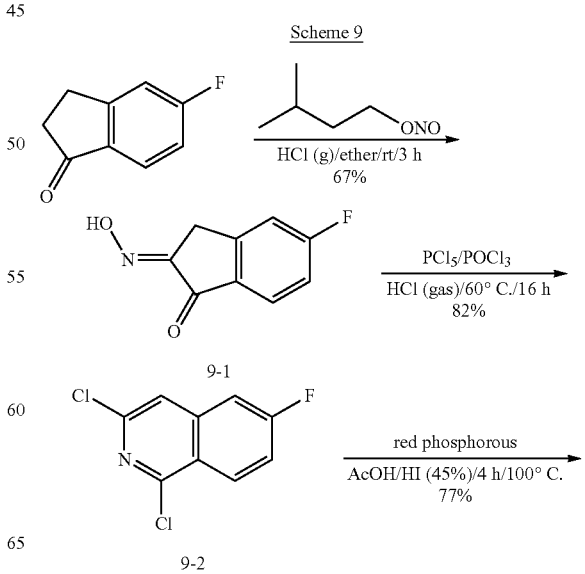

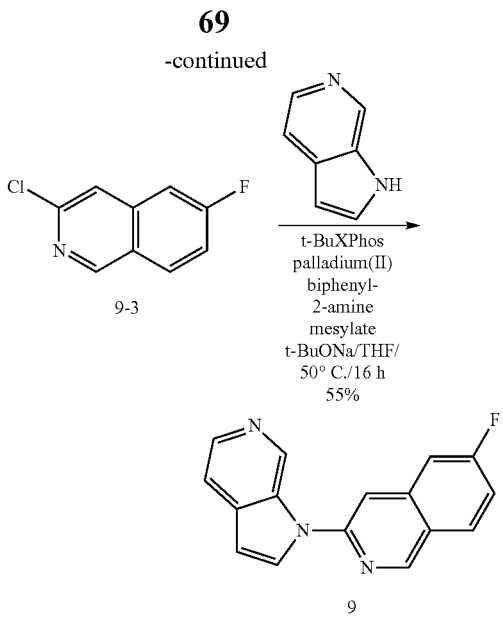

mL). The organic layer was dried over anhydrous sodium sulfate and filtered. The filtrate was concentrated under reduced pressure to afford 3-chloro-6-fluoroisoquinoline as a dark grey solid: MS (ESI, m/z): 182.0 [M+1]$^+$; $^1$H NMR (400 MHz, DMSO-d$_6$) δ 9.24 (s, 1H), 8.32-8.29 (m, 1H), 8.04 (s, 1H), 7.82-7.76 (m, 1H), 7.66-7.61 (m, 1H).

Step 4: Synthesis of 6-fluoro-3-(1H-pyrrolo[2,3-c]pyridin-1-yl)isoquinoline (9)

To a stirred solution of 1H-pyrrolo[2,3-c]pyridine (100 mg, 0.85 mmol) and 3-chloro-6-fluoroisoquinoline (231 mg, 1.27 mmol) in tetrahydrofuran (20 mL) were added sodium 2-methylpropan-2-olate (163 mg, 1.69 mmol) and 2-di-tert-butylphosphino-2',4',6'-tri-iso-propyl-1,1'-biphenyl)(2'''-amino-1'',1'''-biphenyl-2''-yl)palladium(II) mesylate (33.6 mg, 0.042 mmol) at ambient temperature. The resulting mixture was stirred for 16 hours at 50° C. under nitrogen atmosphere. After cooling down to ambient temperature, the reaction was quenched with water (100 mL) and extracted with ethyl acetate (3×50 mL). The combined organic layers was washed with brine (2×100 mL) and dried over anhydrous sodium sulfate. After filtration, the filtrate was concentrated under reduced pressure and the residue was purified by silica gel column chromatography, eluted with 1~5% methanol in dichloromethane to afford 6-fluoro-3-(1H-pyrrolo[2,3-c]pyridin-1-yl)isoquinoline as a light yellow solid: MS (ESI, m/z): 264.0 [M+1]$^+$; $^1$H NMR (300 MHz, DMSO-d$_6$) δ 9.69 (s, 1H), 9.43 (s, 1H), 8.40-8.25 (m, 4H), 8.01-7.95 (m, 1H), 7.71-7.68 (m, 1H), 7.58-7.51 (m, 1H), 6.89 (s, 1H).

Step 1: Synthesis of (E)-5-fluoro-2-(hydroxyimino)-2,3-dihydroinden-1-one (9-1)

To a stirred solution of 5-fluoro-2,3-dihydroinden-1-one (3 g, 20 mmol) in diethyl ether (50 mL) was bubbled with dry hydrochloride gas for 3 hours at 0° C., then isopentyl nitrite (4.7 g, 40 mmol) was added over 5 min. After stirring for 3 hours at ambient temperature, the solid was collected by filtration and washed with diethyl ether (3×30 mL) to afford (E)-5-fluoro-2-(hydroxyimino)-2,3-dihydroinden-1-one as an off-white solid: MS (ESI, m/z): 180.0 [M+1]$^+$; $^1$H NMR (300 MHz, DMSO-d$_6$) δ 12.67 (s, 1H), 7.85-7.81 (m, 1H), 7.46-7.43 (m, 1H), 7.31-7.28 (m, 1H), 3.79 (s, 2H).

Step 2: Synthesis of 1,3-dichloro-6-fluoroisoquinoline (9-2)

To a stirred solution of (E)-5-fluoro-2-(hydroxyimino)-2,3-dihydroinden-1-one (3 g, 13.4 mmol) in phosphorus oxytrichloride (50 mL) was added pentachlorophosphorane (3.2 g, 15.1 mmol) at 0° C. Hydrochloride gas was bubbled into the resulting solution for 3 hours at 0° C. The resulting mixture was stirred for 16 hours at 60° C. After cooling down to ambient temperature, the resulting mixture was concentrated under reduced pressure and the solid was washed with water (3×50 mL), dried in a vacuum oven to afford 1,3-dichloro-6-fluoroisoquinoline as a dark grey solid: MS (ESI, m/z): 216.0 [M+1]$^+$; $^1$H NMR (300 MHz, DMSO-d$_6$) δ 8.41-8.36 (m, 1H), 8.10 (s, 1H), 7.87-7.83 (m, 1H), 7.78-7.69 (m, 1H).

Step 3: Synthesis of 3-chloro-6-fluoroisoquinoline (9-3)

To a stirred solution of 1,3-dichloro-6-fluoroisoquinoline (2.5 g, 11.6 mmol) in acetic acid (40 mL) and hydriodic acid (20 mL, 45% aqueous solution) was added red phosphorus (0.9 g, 28.9 mmol) at ambient temperature. The resulting mixture was stirred for 4 hours at 100° C. After cooling down to ambient temperature, the resulting mixture was concentrated under reduced pressure. The residue was dissolved into dichloromethane (100 mL) and washed with saturated aqueous solution of sodium bicarbonate (2×100

Example 10

Synthesis of N,N-dimethyl-6-(1H-pyrrolo[2,3-c]pyridin-1-yl)pyridin-3-amine (10)

Scheme 10

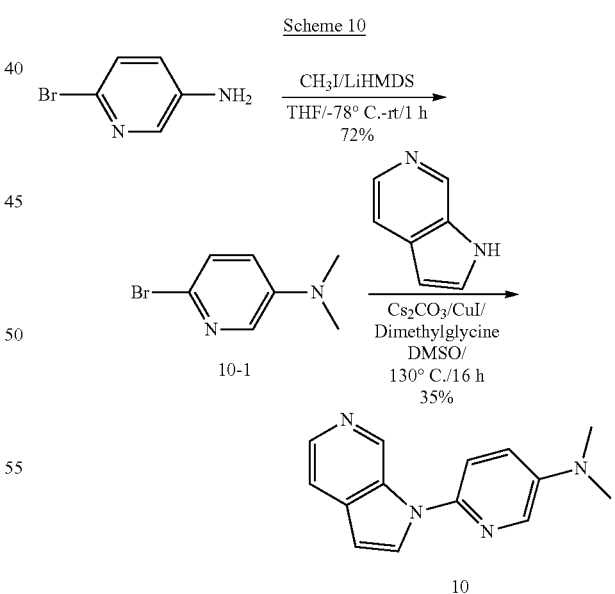

Step 1: Synthesis of 6-bromo-N,N-dimethylpyridin-3-amine (10-1)

To a solution of 6-bromopyridin-3-amine (300 mg, 1.73 mmol) in tetrahydrofuran (30 ml) was added 1 M solution of lithium bis(trimethylsilyl)amide (3.46 mL, 3.46 mmol) in tetrahydrofuran over 5 min at −78° C. under nitrogen atmosphere. After stirring for 30 min at −78° C., iodomethane (566 mg, 3.99 mmol) was added. The resulting mixture was stirred for 1 hour at ambient temperature and then quenched by the addition of saturated aqueous solution of ammonium chloride (50 mL). The resulting mixture was extracted with ethyl acetate (3×50 mL). The combined organic layers was washed with brine (2×50 mL) and dried over anhydrous sodium sulfate. After filtration, the filtrate was concentrated under reduced pressure and the residue was purified by silica gel column chromatography, eluted with 1~10% ethyl acetate in petroleum ether to afford 6-bromo-N,N-dimethylpyridin-3-amine as a light yellow solid: MS (ESI, m/z): 201.0, 203.0 [M+1]$^+$.

Step 2: Synthesis of N,N-dimethyl-6-(1H-pyrrolo[2,3-c]pyridin-1-yl)pyridin-3-amine (10)

To a stirred solution of 1H-pyrrolo[2,3-c]pyridine (100 mg, 0.84 mmol) in dimethyl sulfoxide (30 mL) were added 6-bromo-N,N-dimethylpyridin-3-amine (204 mg, 1.01 mmol), dimethylglycine (52 mg, 0.51 mmol), copper(I) iodide (97 mg, 0.51 mmol) and cesium carbonate (1.1 g, 3.39 mmol) at ambient temperature. The resulting mixture was stirred for 16 hours at 130° C. under nitrogen atmosphere. After cooling down to ambient temperature, the reaction mixture was quenched with water (80 mL) and extracted with ethyl acetate (3×80 mL). The combined organic layers was washed with brine (4×80 mL) and dried over anhydrous sodium sulfate. After filtration, the filtrate was concentrated under reduced pressure and the residue was purified by silica gel column chromatography, eluted with 1~5% methanol in dichloromethane to afford N,N-dimethyl-6-(1H-pyrrolo[2,3-c]pyridin-1-yl)pyridin-3-amine as a light yellow solid: MS (ESI, m/z): 239.0 [M+1]$^+$; $^1$H NMR (300 MHz, DMSO-d$_6$) δ 9.47 (s, 1H), 8.22 (d, J=5.1 Hz, 1H), 8.11-8.09 (m, 2H), 7.66 (s, 1H), 7.62-7.61 (m, 1H), 7.40-7.35 (m, 1H), 6.75 (d, J=3.3 Hz, 1H), 3.02 (s, 6H).

Example 11

Synthesis of 5-iodo-3-(1H-pyrrolo[2,3-c]pyridin-1-yl)isoquinoline (11)

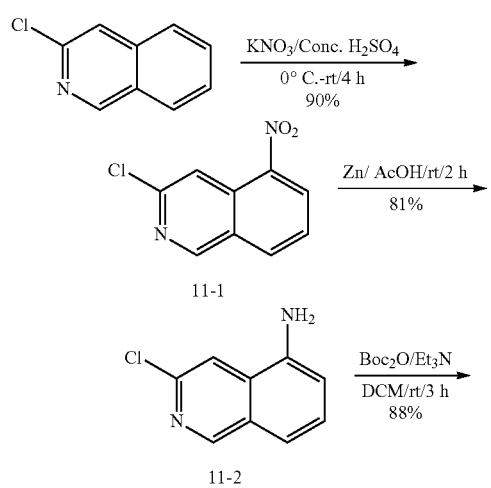
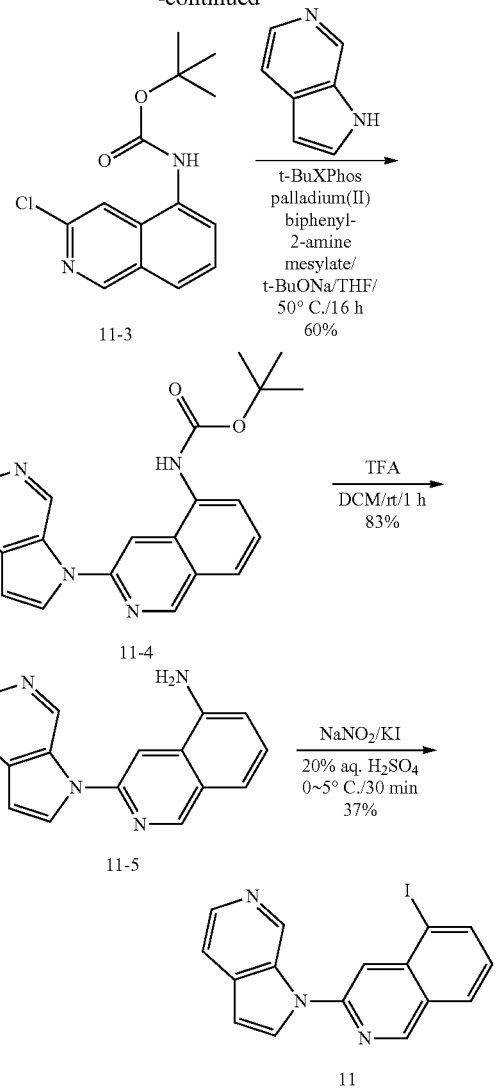

Step 1: Synthesis of 3-chloro-5-nitroisoquinoline (11-1)

To a solution of 3-chloroisoquinoline (2.0 g, 12.2 mmol) in concentrated sulfuric acid (48 mL) was added potassium nitrate (1.48 g, 14.6 mmol) in portions at 0° C. The resulting solution was stirred for 4 hours at ambient temperature and then poured onto ice-water (300 g). The precipitate was collected by filtration and dried to afford 3-chloro-5-nitroisoquinoline as a light yellow solid: MS (ESI, m/z): 209.0 [M+1]$^+$; $^1$H NMR (300 MHz, DMSO-d$_6$) δ 9.46 (s, 1H), 8.75-8.72 (m, 1H), 8.66-8.63 (m, 1H), 8.45 (s, 1H), 7.94-7.89 (m, 1H).

Step 2: Synthesis of 3-chloroisoquinolin-5-amine (11-2)

To a solution of 3-chloro-5-nitroisoquinoline (2.3 g, 11.0 mmol) in acetic acid (100 mL) was added zinc dust (3.5 g, 55.1 mmol) in portions. The resulting mixture was stirred for 2 hours at ambient temperature. Then the resulting mixture was filtered through Celite and the filtrate was concentrated under reduced pressure. The residue was purified by silica gel column chromatography, eluted with 1% methanol in dichloromethane to afford 3-chloroisoquinolin-5-amine as an off-white solid: MS (ESI, m/z): 179.0 [M+1]+; $^1$H NMR (300 MHz, DMSO-$d_6$) δ 8.98 (s, 1H), 8.13 (s, 1H), 7.40-7.35 (m, 1H), 7.28-7.25 (m, 1H), 6.90-6.87 (m, 1H), 6.06 (br s, 2H).

Step 3: Synthesis of tert-butyl 3-chloroisoquinolin-5-ylcarbamate (11-3)

To a solution of 3-chloroisoquinolin-5-amine (1.6 g, 8.96 mmol) in dichloromethane (50 mL) were added triethylamine (1.81 g, 17.92 mmol) and di-tert-butyl dicarbonate (2.34 g, 10.75 mmol). The resulting mixture was stirred for 3 hours at ambient temperature and then concentrated under reduced pressure. The residue was purified by silica gel column chromatography, eluted with 2~10% ethyl acetate in petroleum ether to give tert-butyl (3-chloroisoquinolin-5-yl)carbamate as a light yellow solid: MS (ESI, m/z): 279.0 [M+1]+; $^1$H NMR (400 MHz, DMSO-$d_6$) δ 9.33 (s, 1H), 8.24-8.21 (m, 1H), 7.83-7.77 (m, 2H), 7.57 (s, 1H), 1.32 (s, 9H).

Step 4: Synthesis of tert-butyl 3-(1H-pyrrolo[2,3-c]pyridin-1-yl)isoquinolin-5-ylcarbamate (11-4)

To a solution of 1H-pyrrolo[2,3-c]pyridine (254 mg, 2.15 mmol) in tetrahydrofuran (25 mL) were added tert-butyl (3-chloroisoquinolin-5-yl)carbamate (400 mg, 1.43 mmol), sodium 2-methylpropan-2-olate (276 mg, 2.87 mmol) and 2-di-tert-butylphosphino-2',4',6'-tri-iso-propyl-1,1'-biphenyl)(2'''-amino-1'',1'''-biphenyl-2''-yl)palladium(II) mesylate (114 mg, 0.14 mmol) under nitrogen atmosphere. The resulting solution was stirred for 16 hours at 50° C. After cooling to ambient temperature, the mixture was concentrated under reduced pressure and the residue was purified by silica gel column chromatography, eluted with 1~2% methanol in dichloromethane to afford tert-butyl (3-(1H-pyrrolo[2,3-c]pyridin-1-yl)isoquinolin-5-yl)carbamate as a colorless solid: MS (ESI, m/z): 361.0 [M+1]+; $^1$H NMR (400 MHz, DMSO-$d_6$) δ 9.72 (s, 1H), 9.63 (s, 1H), 9.41 (s, 1H), 8.37-8.31 (m, 1H), 8.29 (s, 2H), 8.07 (d, J=7.6 Hz, 1H), 7.97 (d, J=8.0 Hz, 1H), 7.70 (d, J=4.4 Hz, 1H), 7.68-7.62 (m, 1H), 6.90 (d, J=4.8 Hz, 1H), 1.55 (s, 9H).

Step 5: Synthesis of 3-(1H-pyrrolo[2,3-c]pyridin-1-yl)isoquinolin-5-amine (11-5)

To a solution of tert-butyl (3-(1H-pyrrolo[2,3-c]pyridin-1-yl)isoquinolin-5-yl)carbamate (250 mg, 0.69 mmol) in dichloromethane (20 mL) was added 2,2,2-trifluoroacetic acid (791 mg, 6.94 mmol). After stirring for 1 hour at ambient temperature, the resulting solution was washed with saturated aqueous solution of sodium bicarbonate (2×50 mL) and the organic layer was dried over anhydrous sodium sulfate. After filtration, the filtrate was concentrated under reduced pressure and the residue was purified by silica gel column chromatography, eluted with 0.5~1% methanol in dichloromethane to afford 3-(1H-pyrrolo[2,3-c]pyridin-1-yl)isoquinolin-5-amine as an off-white solid: MS (ESI, m/z): 261.0 [M+1]+; $^1$H NMR (400 MHz, DMSO-$d_6$) δ 9.67 (s, 1H), 9.22 (s, 1H), 8.32-8.26 (m, 3H), 7.68-7.66 (m, 1H), 7.41-7.33 (m, 2H), 6.93-6.84 (m, 2H), 6.12 (br s, 2H).

Step 6: Synthesis of 5-iodo-3-(1H-pyrrolo[2,3-c]pyridin-1-yl)isoquinoline (11)

To a solution of 3-(1H-pyrrolo[2,3-c]pyridin-1-yl)isoquinolin-5-amine (100 mg, 0.38 mmol) in diluted sulfuric acid (10% aqueous solution) was added sodium nitrite (53.0 mg, 0.76 mmol) at 0° C. After stirring for 20 min at 0° C., potassium iodide (128 mg, 0.76 mmol) was added in one portion. After additional 10 min, the resulting mixture was quenched by saturated sodium sulfite (10 mL) and extracted with dichloromethane (3×25 mL). The combined organic layers was dried over anhydrous sodium sulfate and filtered. The filtrate was concentrated under reduced pressure and the residue was purified by silica gel column chromatography, eluted with 0.5~1.5% methanol in dichloromethane to afford 5-iodo-3-(1H-pyrrolo[2,3-c]pyridin-1-yl)isoquinoline as a colorless solid: MS (ESI, m/z): 372.0 [M+1]+; $^1$H NMR (300 MHz, DMSO-$d_6$) δ 9.61 (s, 1H), 9.39 (s, 1H), 8.46-8.27 (m, 4H), 7.99 (s, 1H), 7.72-7.70 (m, 1H), 7.49-7.45 (m, 1H), 6.91 (d, J=3.3 Hz, 1H).

Example 12

Synthesis of 3-(1H-pyrrolo[2,3-c]pyridin-1-yl)isoquinolin-7-amine (12)

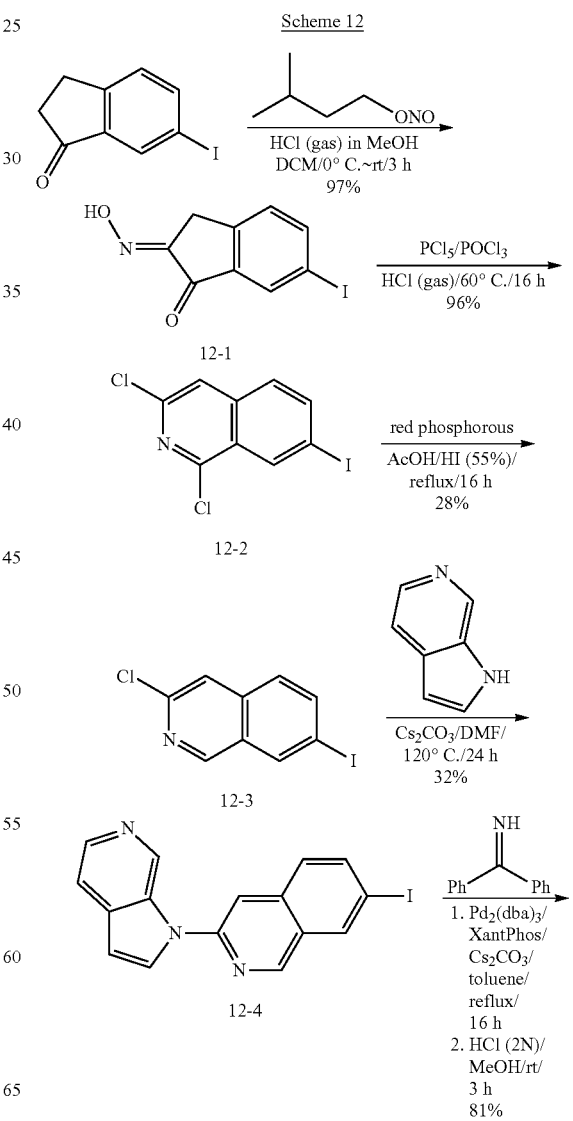

Scheme 12

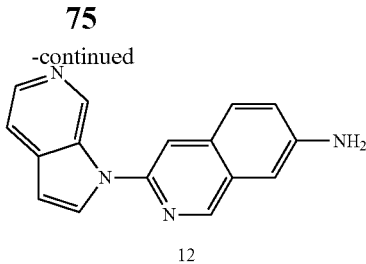

Step 1: Synthesis of (E)-2-(hydroxyimino)-6-iodo-2,3-dihydroinden-1-one (12-1)

To a solution of 6-iodo-2,3-dihydro-1H-inden-1-one (5 g, 19.4 mmol) in dichloromethane (300 mL) and methanol (15 mL, saturated with hydrochloride at 0° C.) was added a solution of isopentyl nitrite (4.5 g, 38.8 mmol) in dichloromethane (10 mL) over 30 min at 0° C. The resulting solution was stirred for 3 hours at ambient temperature. The solvents were removed partially to about 50 mL followed by the dilution with ether (100 mL). Solid was collected by filtration to give (E)-2-(hydroxyimino)-6-iodo-2,3-dihydroinden-1-one as a light yellow solid: MS (ESI, m/z): 288.1 [M+1]$^+$; $^1$H NMR (400 MHz, DMSO-d$_6$) δ 12.75 (s, 1H), 8.06-8.01 (m, 2H), 7.46 (d, J=8.0 Hz, 1H), 3.72 (s, 2H).

Step 2: Synthesis of 1,3-dichloro-7-iodoisoquinoline (12-2)

To a solution of (E)-2-(hydroxyimino)-6-iodo-2,3-dihydroinden-1-one (5.4 g, 18.81 mmol) in phosphoryl trichloride (80 mL) was added pentachlorophosphorane (5.9 g, 28.2 mmol). Then hydrochloride gas was bubbled into the solution for 3 hours at 0° C. The resulting solution was stirred for 16 hours at 60° C. After cooling down to ambient temperature, the mixture was concentrated under reduced pressure and the residue was taken up by dichloromethane (100 mL) and saturated aqueous solution of sodium bicarbonate (100 mL). The organic layer was separated and dried over anhydrous sodium sulfate. After filtration, the filtrate was concentrated under reduced pressure to afford 1,3-dichloro-7-iodoisoquinoline as a brown solid: MS (ESI, m/z): 324.2 [M+1]$^+$; $^1$H NMR (400 MHz, DMSO-d$_6$) δ 8.59 (s, 1H), 8.21 (dd, J=1.2 Hz, 8.4 Hz, 1H), 8.17 (s, 1H), 7.85 (d, J=8.8 Hz, 1H).

Step 3: Synthesis of 3-chloro-7-iodoisoquinoline (12-3)

To a solution of 1,3-dichloro-7-iodoisoquinoline (6 g, 18.52 mmol) in acetic acid (40 mL) were added hydriodic acid (20 mL, 55% w/w) and red phosphorus (1.43 g, 46.3 mmol). The resulting solution was refluxed for 16 hours, then concentrated under reduced pressure. The residue was taken up by dichloromethane (100 mL) and saturated aqueous solution of sodium bicarbonate (100 mL). The organic layer was dried over anhydrous sodium sulfate and filtered. The filtrate was concentrated under reduced pressure and the residue was purified by silica gel column chromatography, eluted with 2~10% ethyl acetate in petroleum ether to afford 3-chloro-7-iodoisoquinoline as a light yellow solid: MS (ESI, m/z): 290.2 [M+1]$^+$; $^1$H NMR (400 MHz, DMSO-d$_6$) δ 9.20 (s, 1H), 8.66 (s, 1H), 8.10 (dd, J=1.2 Hz, 4.8 Hz, 1H), 8.06 (s, 1H), 7.78 (d, J=8.8 Hz, 1H).

Step 4: Synthesis of 7-iodo-3-(1H-pyrrolo[2,3-c]pyridin-1-yl)isoquinoline (12-4)

To a solution of 3-chloro-7-iodoisoquinoline (0.8 g, 2.76 mmol) in N,N-dimethylformamide (30 mL) were added 1H-pyrrolo[2,3-c]pyridine (0.49 g, 4.15 mmol) and cesium carbonate (1.80 g, 5.53 mmol). The resulting mixture was stirred for 24 hours at 120° C. After cooling down to ambient temperature, the resulting mixture was diluted with water (100 mL) and extracted with ethyl acetate (3×100 mL). The combined organic layers was washed with brine (5×50 mL) and dried over anhydrous sodium sulfate. After filtration, the filtrate was concentrated under reduced pressure and the residue was purified by silica gel column chromatography, eluted with 1~2% methanol in dichloromethane to afford 7-iodo-3-(1H-pyrrolo[2,3-c]pyridin-1-yl)isoquinoline as a light yellow solid: MS (ESI, m/z): 372.1 [M+1]$^+$; $^1$H NMR (400 MHz, DMSO-d$_6$) δ 9.70 (s, 1H), 9.39 (s, 1H), 8.70 (s, 1H), 8.36 (d, J=7.2 Hz, 1H), 8.30-8.29 (m, 2H), 8.10 (dd, J=1.6 Hz, 8.4 Hz, 1H), 7.88 (d, J=8.8 Hz, 1H), 7.69 (dd, J=0.8 Hz, 5.2 Hz, 1H), 6.89 (d, J=3.2 Hz, 1H).

Step 5: Synthesis of 3-(1H-pyrrolo[2,3-c]pyridin-1-yl)isoquinolin-7-amine (12)

To a solution of 7-iodo-3-(1H-pyrrolo[2,3-c]pyridin-1-yl)isoquinoline (300 mg, 0.81 mmol) in toluene (30 mL) were added diphenylmethanimine (220 mg, 1.21 mmol), tris(dibenzylideneacetone)dipalladium (0) (41.8 mg, 0.04 mmol), 9,9-dimethyl-4,5-bis(diphenylphosphino)xanthene (46.7 mg, 0.081 mmol) and cesium carbonate (527 mg, 1.62 mmol). The resulting mixture was refluxed for 16 hours under nitrogen atmosphere. After cooling down to ambient temperature, the resulting mixture was concentrated under reduced pressure and the residue was diluted with methanol (30 mL). To the resulting solution was added hydrochloric acid (6 mL, 2 N) and the resulting solution was stirred for 3 hours at ambient temperature. The resulting solution was diluted with sodium bicarbonate (60 mL) and extracted with ethyl acetate (3×80 mL). The combined organic layers was washed with brine (30 mL) and dried over anhydrous sodium sulfate. After filtration, the filtrate was concentrated under reduced pressure and the residue was purified by silica gel column chromatography, eluted with 1~2% methanol in dichloromethane to afford 3-(1H-pyrrolo[2,3-c]pyridin-1-yl)isoquinolin-7-amine as a light yellow solid: MS (ESI, m/z): 261.1 [M+1]$^+$; $^1$H NMR (300 MHz, DMSO-d$_6$) δ 9.52 (s, 1H), 9.00 (s, 1H), 8.23-8.21 (m, 2H), 7.97 (s, 1H), 7.82 (d, J=10.8 Hz, 1H), 7.66 (d, J=5.1 Hz, 1H), 7.26 (d, J=6.9 Hz, 1H), 7.03 (s, 1H), 6.78 (d, J=3.0 Hz, 1H), 5.79 (br s, 2H).

Example 13

Synthesis of 7-methoxy-3-(1H-pyrrolo[2,3-c]pyridin-1-yl)isoquinoline (13)

Scheme 13

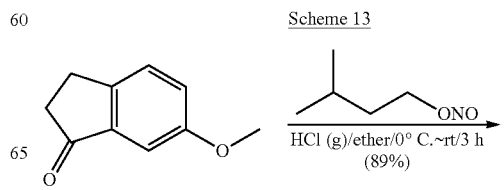

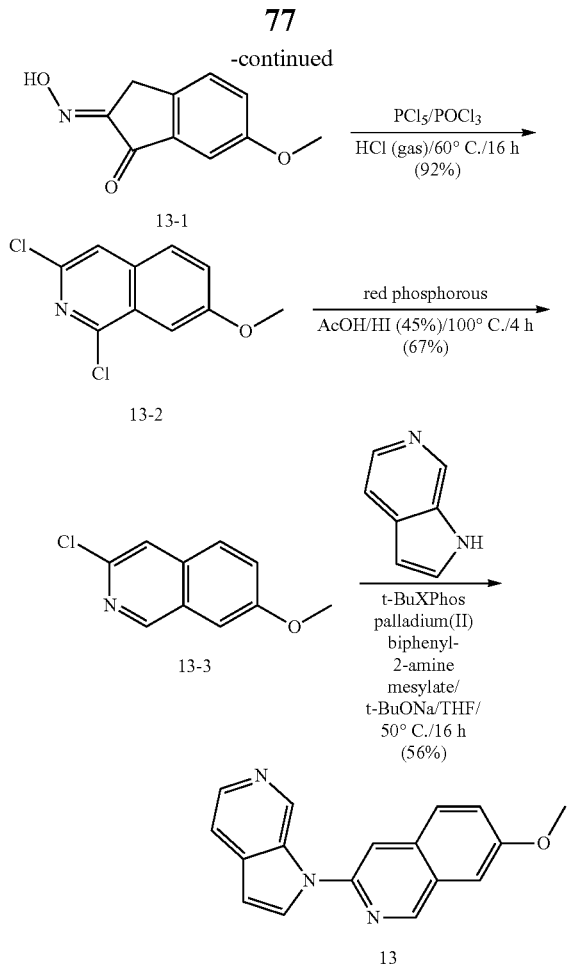

Step 1: Synthesis of (E)-2-(hydroxyimino)-6-methoxy-2,3-dihydroinden-1-one (13-1)

To a stirred solution of 6-methoxy-2,3-dihydroinden-1-one (20 g, 123 mmol) in diethyl ether (300 mL) was bubbled with dry hydrochloride gas at 0° C. for 3 hours, then isopentyl nitrite (22 g, 185 mmol) was added. The resulting solution was stirred for 3 hours at ambient temperature. The solid was collected by filtration and washed with diethyl ether (3×100 mL) to afford (E)-2-(hydroxyimino)-6-methoxy-2,3-dihydroinden-1-one as an off-white solid: MS (ESI, m/z): 192.0 [M+1]+; 1H NMR (400 MHz, DMSO-$d_6$) δ 12.60 (s, 1H), 7.53 (d, J=8.4 Hz, 1H), 7.32 (d, J=8.4 Hz, 1H), 7.21 (s, 1H), 3.80 (s, 3H), 3.69 (s, 2H).

Step 2: Synthesis of 1,3-dichloro-7-methoxyisoquinoline (13-2)

To a stirred solution of (E)-2-(hydroxyimino)-6-methoxy-2,3-dihydroinden-1-one (5.0 g, 26.2 mmol) in phosphorus oxytrichloride (80 mL) was added pentachlorophosphorane (6.0 g, 28.8 mmol) at 0° C. Hydrochloride gas was bubbled into the resulting solution for 3 hours. The resulting mixture was stirred for 16 hours at 60° C. After cooling down to ambient temperature, the resulting mixture was concentrated under reduced pressure and the solid was washed with water (3×50 mL), dried in a vacuum oven to afford 1,3-dichloro-7-methoxyisoquinoline as a light yellow solid: MS (ESI, m/z): 228.0 [M+1]+; 1H NMR (300 MHz, DMSO-$d_6$) δ 8.06 (s, 1H), 8.00 (d, J=9.0 Hz, 1H), 7.60 (dd, J=2.4 Hz, 6.6 Hz, 1H), 7.46 (d, J=2.4 Hz, 1H), 3.97 (s, 3H).

Step 3: Synthesis of 3-chloro-7-methoxyisoquinoline (13-3)

To a stirred solution of 1,3-dichloro-7-methoxyisoquinoline (4.0 g, 17.5 mmol) in acetic acid (60 mL) and hydriodic acid (30 mL, 45% aqueous solution) was added red phosphorus (1.3 g, 43.8 mmol) at ambient temperature. The resulting mixture was stirred for 4 hours at 100° C. After cooling down to ambient temperature, the resulting mixture was concentrated under reduced pressure. The residue was dissolved into dichloromethane (100 mL) and washed with saturated aqueous solution of sodium bicarbonate (2×100 mL). The organic layer was dried over anhydrous sodium sulfate and filtered. The filtrate was concentrated under reduced pressure and the residue was purified by silica gel column chromatography, eluted with 5~10% ethyl acetate in petroleum to afford 3-chloro-7-methoxyisoquinoline as an off-white solid: MS (ESI, m/z): 194.0 [M+1]+; 1H NMR (300 MHz, DMSO-$d_6$) δ 9.00 (s, 1H), 8.00 (s, 1H), 7.89 (d, J=9.0 Hz, 1H), 7.54 (dd, J=2.4 Hz, 6.6 Hz, 1H), 7.46 (d, J=2.4 Hz, 1H), 3.87 (s, 3H).

Step 4: Synthesis of 7-methoxy-3-(1H-pyrrolo[2,3-c]pyridin-1-yl)isoquinoline (13)

To a stirred solution of 1H-pyrrolo[2,3-c]pyridine (79 mg, 0.52 mmol) and 3-chloro-7-methoxyisoquinoline (100 mg, 1.27 mmol) in tetrahydrofuran (20 mL) were added sodium 2-methylpropan-2-olate (163 mg, 1.69 mmol) and 2-di-tert-butylphosphino-2',4',6'-tri-iso-propyl-1,1'-biphenyl)(2'''-amino-1'',1'''-biphenyl-2''-yl)palladium(II) mesylate (33.6 mg, 0.042 mmol) at ambient temperature. The resulting mixture was stirred for 16 hours at 50° C. under nitrogen atmosphere. After cooling down to ambient temperature, the reaction was quenched with water (100 mL) and extracted with ethyl acetate (3×50 mL). The combined organic layers was washed with brine (2×100 mL) and dried over anhydrous sodium sulfate. After filtration, the filtrate was concentrated under reduced pressure and the residue was purified by silica gel column chromatography, eluted with 1~5% methanol in dichloromethane to afford 7-methoxy-3-(1H-pyrrolo[2,3-c]pyridin-1-yl)isoquinoline as a light yellow solid: MS (ESI, m/z): 276.1 [M+1]+; 1H NMR (300 MHz, DMSO-$d_6$) δ 9.64 (s, 1H), 9.30 (s, 1H), 8.31-8.27 (m, 2H), 8.22 (s, 1H), 8.00 (d, J=6.0 Hz, 1H), 7.68 (d, J=5.4 Hz, 1H), 7.61 (d, J=2.4 Hz, 1H), 7.52-7.48 (m, 1H), 6.85 (d, J=3.3 Hz, 1H), 3.95 (s, 3H).

Example 14

Synthesis of N-(2-fluoroethyl)-N-methyl-3-(1H-pyrrolo[2,3-c]pyridin-1-yl)isoquinolin-6-amine (14)

Scheme 14

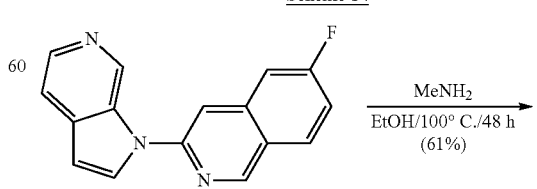

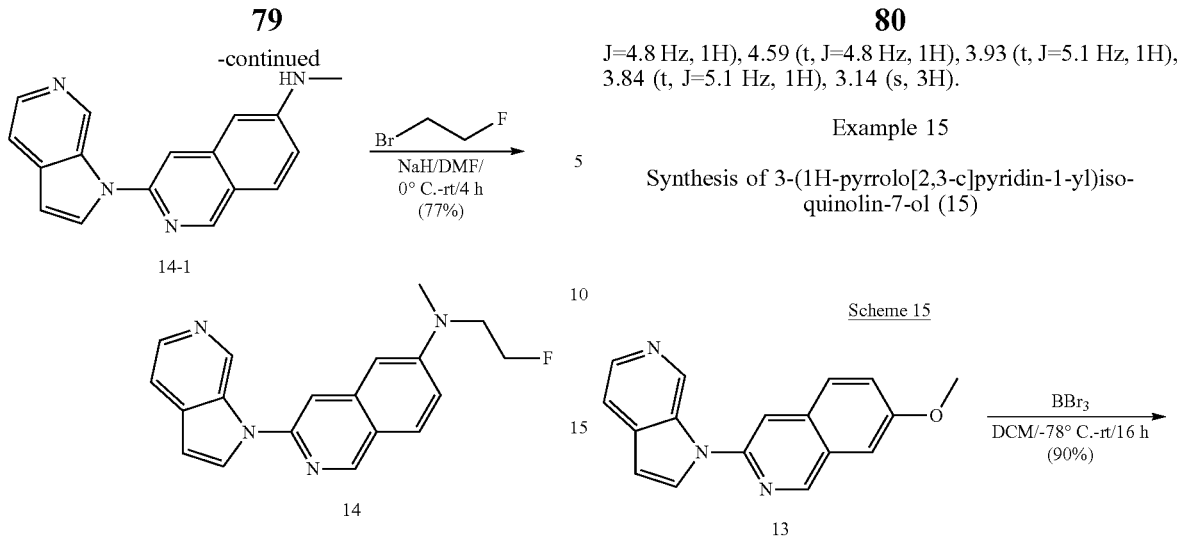

Step 1: Synthesis of N-methyl-3-(1H-pyrrolo[2,3-c]pyridin-1-yl)isoquinolin-6-amine (14-1)

To a sealed tube were added a solution of methanamine in ethanol (30 mL, 30% w/w) and 6-fluoro-3-(1H-pyrrolo[2,3-c]pyridin-1-yl)isoquinoline (150 mg, 0.57 mmol, 9).

The resulting mixture was stirred for 48 hours at 100° C. After cooling down to ambient temperature, the resulting mixture was concentrated under reduced pressure and the residue was purified by silica gel column chromatography, eluted with 1~2% methanol in dichloromethane to afford N-methyl-3-(1H-pyrrolo[2,3-c]pyridin-1-yl)isoquinolin-6-amine as a light yellow solid: MS (ESI, m/z): 275.1 [M+1]$^+$; $^1$H NMR (300 MHz, DMSO-$d_6$) δ 9.63 (s, 1H), 8.94 (s, 1H), 8.27-8.24 (m, 2H), 7.83 (s, 1H), 7.80 (d, J=9.0 Hz, 1H), 7.64 (dd, J=0.9 Hz, 4.5 Hz, 1H), 7.04 (dd, J=5.1 Hz, 6.6 Hz, 1H), 6.82 (d, J=3.0 Hz, 1H), 6.76-6.74 (m, 1H), 6.70 (d, J=1.8 Hz, 1H), 2.83 (d, J=4.8 Hz, 3H).

Step 2: Synthesis of N-(2-fluoroethyl)-N-methyl-3-(1H-pyrrolo[2,3-c]pyridin-1-yl)isoquinolin-6-amine (14)

To a stirred solution of N-methyl-3-(1H-pyrrolo[2,3-c]pyridin-1-yl)isoquinolin-6-amine (50 mg, 0.18 mmol) in N,N-dimethylformamide (10 mL) was added sodium hydride (14 mg, 0.36 mmol, 60% dispersed by mineral oil) at 0° C. under nitrogen atmosphere. The resulting mixture was stirred for 30 min at 0° C. followed by the addition of 1-bromo-2-fluoroethane (46 mg, 0.36 mmol). The resulting mixture was stirred for 4 hours at ambient temperature and quenched with saturated aqueous solution of ammonium chloride (100 mL). The resulting mixture was extracted with ethyl acetate (3×100 mL). The combined organic layers was washed with brine (2×100 mL) and dried over anhydrous sodium sulfate. After filtration, the filtrate was concentrated under reduced pressure and the residue was purified by silica gel column chromatography, eluted with 1~2% methanol in dichloromethane to afford N-(2-fluoroethyl)-N-methyl-3-(1H-pyrrolo[2,3-c]pyridin-1-yl)isoquinolin-6-amine as a light yellow solid: MS (ESI, m/z): 321.2 [M+1]$^+$; $^1$H NMR (300 MHz, DMSO-$d_6$) δ 9.68 (s, 1H), 9.04 (s, 1H), 8.38 (d, J=3.3 Hz, 1H), 8.29 (d, J=5.4 Hz, 1H), 7.96 (d, J=9.0 Hz, 1H), 7.92 (s, 1H), 7.75 (d, J=5.4 Hz, 1H), 7.38 (d, J=9.0 Hz, 1H), 7.01 (d, J=1.8 Hz, 1H), 6.90 (d, J=3.0 Hz, 1H), 4.75 (t, J=4.8 Hz, 1H), 4.59 (t, J=4.8 Hz, 1H), 3.93 (t, J=5.1 Hz, 1H), 3.84 (t, J=5.1 Hz, 1H), 3.14 (s, 3H).

Example 15

Synthesis of 3-(1H-pyrrolo[2,3-c]pyridin-1-yl)isoquinolin-7-ol (15)

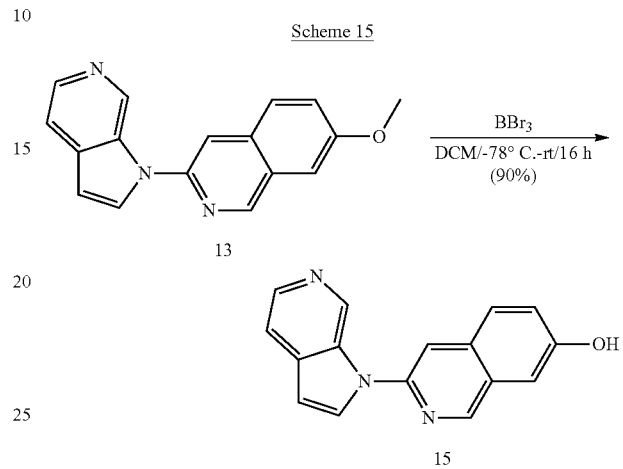

Synthesis of 3-(1H-pyrrolo[2,3-c]pyridin-1-yl)isoquinolin-7-ol (15)

To a stirred solution of 7-methoxy-3-(1H-pyrrolo[2,3-c]pyridin-1-yl)isoquinoline (70 mg, 0.25 mmol, 13) in dichloromethane (15 mL) was added tribromoborane (64 mg, 0.25 mmol) at −78° C. The resulting mixture was stirred for 16 hours at ambient temperature then quenched by the addition of water (10 mL). The mixture was neutralized by the addition of potassium carbonate and extracted with dichloromethane (5×50 mL). The combined organic layers was dried over anhydrous sodium sulfate and filtered. The filtrate was concentrated under reduced pressure and the residue was purified by silica gel column chromatography, eluted with 1~3% methanol in dichloromethane to afford 3-(1H-pyrrolo[2,3-c]pyridin-1-yl)isoquinolin-7-ol as a light-yellow solid: MS (ESI, m/z): 262.1 [M+1]$^+$; $^1$H NMR (300 MHz, DMSO-$d_6$) δ 10.26 (s, 1H), 9.58 (s, 1H), 9.21 (s, 1H), 8.28-8.25 (m, 2H), 8.15 (s, 1H), 7.96 (d, J=9.0 Hz, 1H), 7.66 (d, J=5.1 Hz, 1H), 7.44-7.39 (m, 2H), 6.84 (d, J=3.3 Hz, 1H).

Example 16

Synthesis of 7-(2-fluoroethoxy)-3-(1H-pyrrolo[2,3-c]pyridin-1-yl)isoquinoline (16)

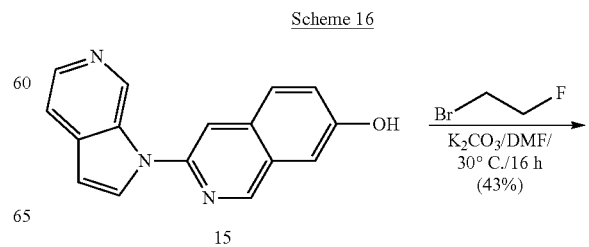

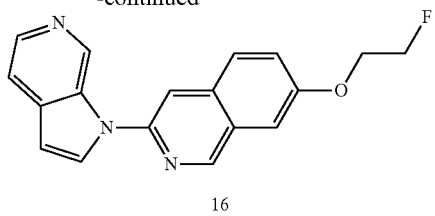

16

Synthesis of 7-(2-fluoroethoxy)-3-(1H-pyrrolo[2,3-c]pyridin-1-yl)isoquinoline (16)

To a stirred solution of 3-(1H-pyrrolo[2,3-c]pyridin-1-yl)isoquinolin-7-ol (40 mg, 0.15 mmol, 15) in N,N-dimethylformamide (5 mL) were added potassium carbonate (42 mg, 0.31 mmol) and 1-bromo-2-fluoroethane (29 mg, 0.23 mmol). The resulting mixture was stirred for 16 hours at 30° C. then quenched with water (30 mL) and extracted with ethyl acetate (3×60 mL). The combined organic layers was dried over anhydrous sodium sulfate and filtered. The filtrate was concentrated under reduced pressure and the residue was purified by silica gel column chromatography, eluted with 1~3% methanol in dichloromethane to afford 7-(2-fluoroethoxy)-3-(1H-pyrrolo[2,3-c]pyridin-1-yl)isoquinoline as a light-yellow solid: MS (ESI, m/z): 308.1 [M+1]$^+$; $^1$H NMR (300 MHz, DMSO-d$_6$) δ 9.90 (s, 1H), 9.38 (s, 1H), 8.94 (d, J=3.3 Hz, 1H), 8.47 (d, J=6.3 Hz, 1H), 8.41 (s, 1H), 8.25 (d, J=6.6 Hz, 1H), 8.05 (d, J=9.0 Hz, 1H), 7.74 (d, J=2.4 Hz, 1H), 7.64-7.60 (m, 1H), 7.26 (d, J=3.3 Hz, 1H), 4.95 (t, J=3.6 Hz, 1H), 4.79 (t, J=3.6 Hz, 1H), 4.51 (t, J=3.6 Hz, 1H), 4.41 (t, J=3.6 Hz, 1H).

Example 17

Synthesis of 7-(fluoromethoxy)-3-(1H-pyrrolo[2,3-c]pyridin-1-yl)isoquinoline (17)

Scheme 17

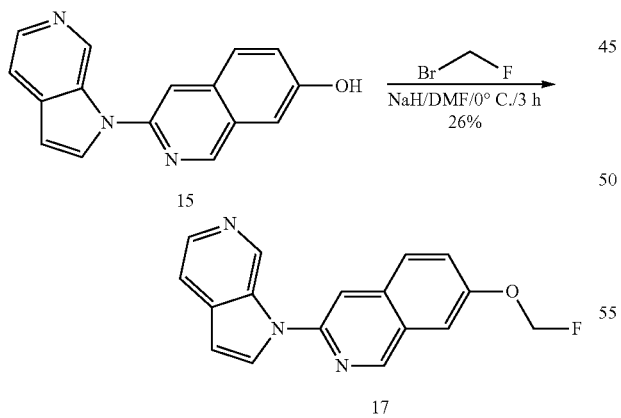

Synthesis of 7-(fluoromethoxy)-3-(1H-pyrrolo[2,3-c]pyridin-1-yl)isoquinoline (17)

A solution of 3-(1H-pyrrolo[2,3-c]pyridin-1-yl)isoquinolin-7-ol (50 mg, 0.19 mmol, 15) in N,N-dimethylformamide (10 mL) was treated with sodium hydride (33 mg, 0.83 mmol, 60% w/w dispersed into mineral oil) at 0° C. for 10 min followed by the addition of bromofluoromethane (108 mg, 0.96 mmol). After additional 3 hours, the reaction was quenched with saturated aqueous solution of ammonium chloride (30 mL) and extracted with ethyl acetate (3×50 mL). The combined organic layers was washed with brine (3×30 mL) and dried over anhydrous sodium sulfate. After filtration, the filtrate was purified by silica gel column chromatography, eluted with 1~2% methanol in dichloromethane to afford 7-(fluoromethoxy)-3-(1H-pyrrolo[2,3-c]pyridin-1-yl)isoquinoline as a light yellow solid: MS (ESI, m/z): 294.2 [M+1]$^+$; $^1$H NMR (300 MHz, DMSO-d$_6$) δ 9.66 (s, 1H), 9.45 (s, 1H), 8.34 (d, J=3.0 Hz, 1H), 8.30-8.27 (m, 2H), 8.12 (d, J=9.0 Hz, 1H), 7.89 (s, 1H), 7.70-7.64 (m, 2H), 6.87 (d, J=2.7 Hz, 1H), 6.15 (s, 1H), 5.97 (s, 1H).

Example 18

Synthesis of 6-fluoro-3-(1H-pyrrolo[2,3-c]pyridin-1-yl)isoquinolin-5-amine (18)

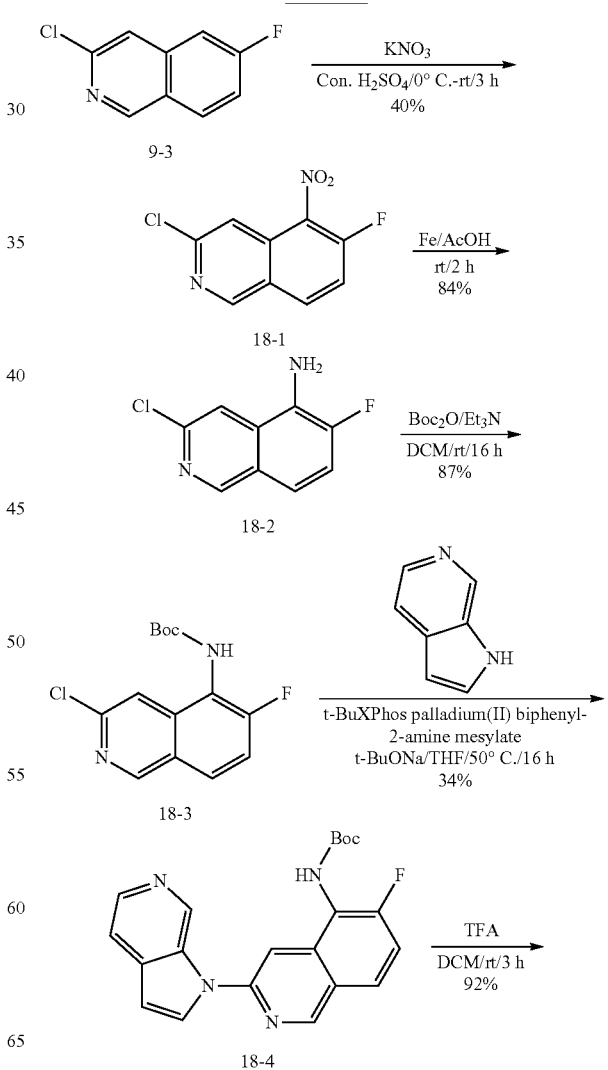

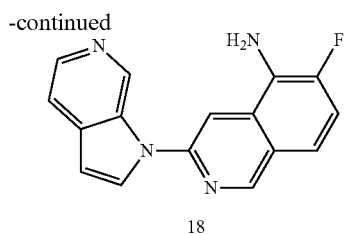

18

Step 1: Synthesis of 3-chloro-6-fluoro-5-nitroisoquinoline (18-1)

To a solution of 3-chloro-6-fluoroisoquinoline (2 g, 11.01 mmol, 9-3) in concentrated sulfuric acid (30 mL) was added potassium nitrate (1.17 g, 11.56 mmol) at 0° C. The resulting mixture was stirred for 3 hours at ambient temperature then poured onto ice/water (200 g). The resulting mixture was extracted with ethyl acetate (3×100 mL). The combined organic layers was dried over anhydrous sodium sulfate. After filtration, the filtrate was concentrated under reduced pressure and the residue was purified by silica gel column chromatography, eluted with 10~20% ethyl acetate in petroleum ether to afford 3-chloro-6-fluoro-5-nitroisoquinoline as a light yellow solid: MS (ESI, m/z): 226.1 [M+1]$^+$; $^1$H NMR (300 MHz, DMSO-d$_6$) δ 9.43 (s, 1H), 8.70-8.65 (m, 1H), 8.07 (s, 1H), 7.70-7.63 (m, 1H).

Step 2: Synthesis of 3-chloro-6-fluoroisoquinolin-5-amine (18-2)

To a solution of 3-chloro-6-fluoro-5-nitroisoquinoline (1 g, 4.41 mmol) in acetic acid (100 mL) was added iron powder (1.27 g, 22.07 mmol). The resulting mixture was stirred for 2 hours at ambient temperature, then filtered through Celite and the filtrate was concentrated under reduced pressure. The residue was purified by silica gel column chromatography, eluted with 2~10% ethyl acetate in petroleum ether to afford 3-chloro-6-fluoroisoquinolin-5-amine as a yellow solid: MS (ESI, m/z): 197.1 [M+1]$^+$; $^1$H NMR (300 MHz, DMSO-d$_6$) δ 9.06 (s, 1H), 8.26 (s, 1H), 7.51-7.44 (m, 1H), 7.40-7.35 (m, 1H), 6.01 (br s, 2H).

Step 3: Synthesis of tert-butyl 3-chloro-6-fluoroisoquinolin-5-ylcarbamate (18-3)

To a solution of 3-chloro-6-fluoroisoquinolin-5-amine (150 mg, 0.76 mmol) in dichloromethane (30 mL) were added di-tert-butyl dicarbonate (216 mg, 0.99 mmol) and triethylamine (116 mg, 1.14 mmol). The resulting mixture was stirred for 16 hours at ambient temperature. After that, the mixture was concentrated under reduced pressure and the residue was purified by silica gel column chromatography, eluted with 2~10% ethyl acetate in petroleum ether to afford tert-butyl 3-chloro-6-fluoroisoquinolin-5-ylcarbamate as a light yellow solid: MS (ESI, m/z): 297.1 [M+1]$^+$; $^1$H NMR (300 MHz, DMSO-d$_6$) δ 9.03 (s, 1H), 7.93-7.88 (m, 1H), 7.83 (s, 1H), 7.41 (t, J=9.3 Hz, 1H), 6.23 (br s, 1H), 1.52 (s, 9H).

Step 4: Synthesis of tert-butyl 6-fluoro-3-(1H-pyrrolo[2,3-c]pyridin-1-yl)isoquinolin-5-ylcarbamate (18-4)

To a solution of 1H-pyrrolo[2,3-c]pyridine (90 mg, 0.76 mmol) in tetrahydrofuran (15 mL) were added tert-butyl (3-chloro-6-fluoroisoquinolin-5-yl)carbamate (150 mg, 0.51 mmol), sodium 2-methylpropan-2-olate (97 mg, 1.01 mmol) and 2-di-tert-butylphosphino-2',4',6'-tri-iso-propyl-1,1'-biphenyl)(2'''-amino-1'',1'''-biphenyl-2''-yl)palladium(II) mesylate (40.2 mg, 0.051 mmol) at ambient temperature. The resulting mixture was stirred for 16 hours at 50° C. under nitrogen atmosphere. After cooling down to ambient temperature, the resulting mixture was diluted with water (50 mL) and extracted with ethyl acetate (3×30 mL). The combined organic layers was washed with brine (2×50 mL) and dried over anhydrous sodium sulfate. After filtration, the filtrate was concentrated under reduced pressure and the residue was purified by silica gel column chromatography, eluted with 0.5~1% methanol in dichloromethane to afford tert-butyl 6-fluoro-3-(1H-pyrrolo[2,3-c]pyridin-1-yl)isoquinolin-5-ylcarbamate as a yellow solid: MS (ESI, m/z): 379.2 [M+1]$^+$; $^1$H NMR (300 MHz, CD$_3$OD) δ 9.62 (s, 1H), 9.34 (s, 1H), 8.25-8.22 (m, 2H), 8.21-8.16 (m, 1H), 8.03 (s, 1H), 7.72 (d, J=5.4 Hz, 1H), 7.57 (t, J=7.8 Hz, 1H), 6.98 (d, J=3.6 Hz, 1H), 1.55 (s, 9H).

Step 5: Synthesis of 6-fluoro-3-(1H-pyrrolo[2,3-c]pyridin-1-yl)isoquinolin-5-amine (18)

A solution of tert-butyl 6-fluoro-3-(1H-pyrrolo[2,3-c]pyridin-1-yl)isoquinolin-5-ylcarbamate (65 mg, 0.17 mmol) in dichloromethane (15 mL) was treated with trifluoroacetic acid (3 mL) for 3 hours at ambient temperature. The resulting mixture was concentrated under reduced pressure and the residue was dissolved into dichloromethane (50 mL), washed with saturated aqueous solution of sodium bicarbonate (50 mL). The organic layer was dried over anhydrous sodium sulfate. After filtration, the filtrate was concentrated under reduced pressure and the residue was purified by silica gel column chromatography, eluted with 1~2% methanol in dichloromethane to afford 6-fluoro-3-(1H-pyrrolo[2,3-c]pyridin-1-yl)isoquinolin-5-amine as a yellow solid: MS (ESI, m/z): 279.0 [M+1]$^+$; $^1$H NMR (300 MHz, DMSO-d$_6$) δ 9.70 (s, 1H), 9.27 (s, 1H), 8.40 (s, 1H), 8.35-8.27 (m, 2H), 7.68-7.66 (m, 1H), 7.45-7.43 (m, 2H), 6.88 (d, J=3.3 Hz, 1H), 6.03 (br s, 2H).

Example 19

Synthesis of 1'-methyl-1,5'-bi(1H-pyrrolo[2,3-c]pyridine) (19)

Scheme 19

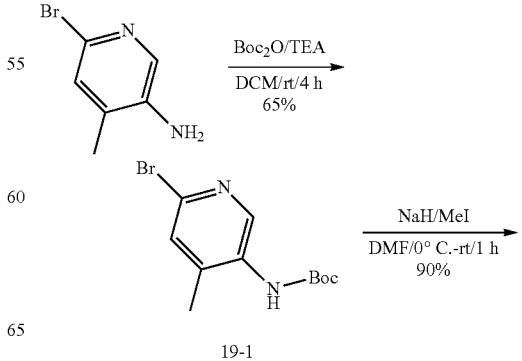

19-1

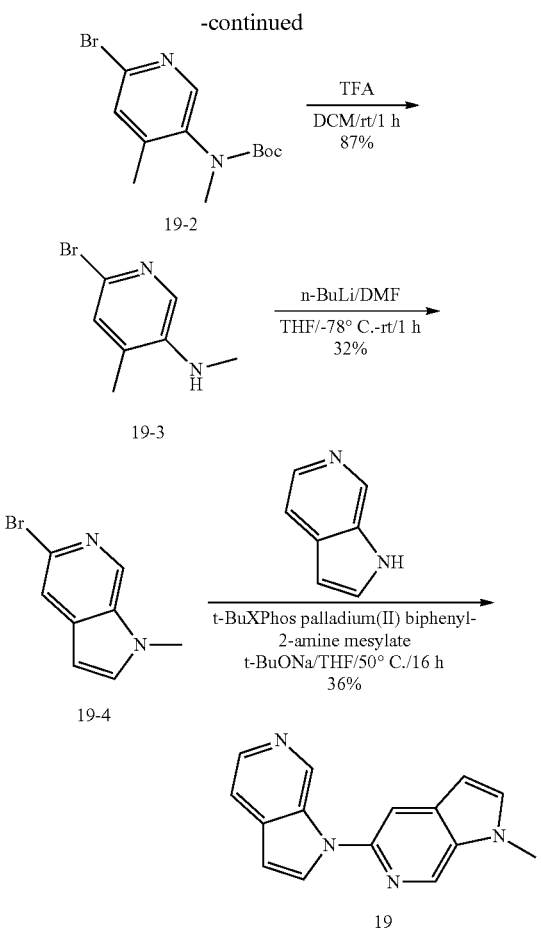

pressure and the residue was purified by silica gel column chromatography, eluted with 10~20% ethyl acetate in petroleum ether to afford tert-butyl 6-bromo-4-methylpyridin-3-yl(methyl)carbamate as a light yellow solid: MS (ESI, m/z): 301.2, 303.2 [M+1]$^+$; $^1$H NMR (300 MHz, CDCl$_3$) δ 8.11 (s, 1H), 7.48 (s, 1H), 3.14 (s, 3H), 2.21 (s, 3H), 1.31 (s, 9H).

Step 3: Synthesis of 6-bromo-N,4-dimethylpyridin-3-amine (19-3)

A solution of tert-butyl 6-bromo-4-methylpyridin-3-yl (methyl)carbamate (3.1 g, 10.3 mmol) in dichloromethane (30 mL) was treated with trifluoroacetic acid (3 mL) for 1 hour at ambient temperature. Then the resulting solution was concentrated under reduced pressure and the residue was dissolved into dichloromethane (100 mL), washed with saturated aqueous solution of sodium bicarbonate (100 mL). The organic layer was dried over anhydrous sodium sulfate and filtered. The filtration was concentrated under reduced pressure to afford 6-bromo-N,4-dimethylpyridin-3-amine as a light yellow solid: MS (ESI, m/z): 201.1, 203.1 [M+1]$^+$; $^1$H NMR (300 MHz, CDCl$_3$) δ 7.66 (s, 1H), 7.11 (s, 1H), 3.48 (br s, 1H), 2.91 (s, 3H), 2.10 (s, 3H).

Step 4: Synthesis of 5-bromo-1-methyl-1H-pyrrolo[2,3-c]pyridine (19-4)

A solution of 6-bromo-N,4-dimethylpyridin-3-amine (1 g, 4.97 mmol) in tetrahyrofuran (30 mL) was treated with 2.5 Mn-butyllithium (4.97 mL, 12.43 mmol) in hexane at −78° C. for 15 min under nitrogen atmosphere, followed by the addition of N,N-dimethylformamide (0.51 g, 6.96 mmol). The resulting solution was stirred for additional 1 hour at ambient temperature and quenched by the addition of saturated aqueous solution of sodium bicarbonate (60 mL). The resulting mixture was extracted with ethyl acetate (3×50 mL). The combined organic layers was washed with brine (3×30 mL) and dried over anhydrous sodium sulfate. After filtration, the filtrate was concentrated under reduced pressure and the residue was purified by silica gel column chromatography, eluted with 10~20% ethyl acetate in petroleum ether to afford 5-bromo-1-methyl-1H-pyrrolo[2,3-c] pyridine as a yellow oil: MS (ESI, m/z): 211.1, 213.1 [M+1]$^+$; $^1$H NMR (400 MHz, CDCl$_3$) δ 9.90 (s, 1H), 7.68 (s, 1H), 7.22 (d, J=2.8 Hz, 1H), 6.44 (d, J=2.4 Hz, 1H), 3.11 (s, 3H).

Step 5: Synthesis of 1'-methyl-1,5'-bi(1H-pyrrolo[2,3-c]pyridine) (19)

To a solution of 5-bromo-1-methyl-1H-pyrrolo[2,3-c] pyridine (70 mg, 0.33 mmol) in tetrahydrofuran (20 mL) were added 1H-pyrrolo[2,3-c]pyridine (59 mg, 0.49 mmol), sodium 2-methylpropan-2-olate (64 mg, 0.66 mmol) and 2-di-tert-butylphosphino-2',4',6'-tri-iso-propyl-1,1'-biphenyl)(2'''-amino-1'',1'''-biphenyl-2''-yl)palladium(II) mesylate (26 mg, 0.033 mmol). The resulting solution was stirred for 16 hours at 50° C. under nitrogen atmosphere. After cooling down to ambient temperature, the resulting solution was concentrated under reduced pressure and the residue was purified by silica gel column chromatography, eluted with 1~2% methanol in dichloromethane to afford 1'-methyl-1,5'-bi(1H-pyrrolo[2,3-c]pyridine) as a light yellow solid: MS (ESI, m/z): 249.1 [M+1]$^+$; $^1$H NMR (400 MHz, DMSO-4) δ 9.49 (s, 1H), 8.88 (s, 1H), 8.23-8.20 (m, Step 1: Synthesis of tert-butyl 6-bromo-4-methylpyridin-3-ylcarbamate (19-1)

To a solution of 6-bromo-4-methylpyridin-3-amine (2 g, 10.69 mmol) in dichloromethane (30 mL) were added triethylamine (2.16 g, 21.39 mmol) and di-tert-butyl dicarbonate (3.03 g, 13.90 mmol). The resulting solution was stirred for 4 hours at ambient temperature, then concentrated under reduced pressure and the residue was purified by silica gel column chromatography, eluted with 5~10% ethyl acetate in petroleum ether to afford tert-butyl 6-bromo-4-methylpyridin-3-ylcarbamate as a colorless solid: MS (ESI, m/z): 287.1, 289.1 [M+1]$^+$; $^1$H NMR (400 MHz, CDCl$_3$) δ 8.72 (s, 1H), 7.30 (s, 1H), 6.18 (br s, 1H), 2.26 (s, 3H), 1.55 (s, 9H).

Step 2: Synthesis of tert-butyl 6-bromo-4-methyl-pyridin-3-yl(methyl)carbamate (19-2)

A solution of tert-butyl 6-bromo-4-methylpyridin-3-ylcarbamate (3.1 g, 10.8 mmol) in N,N-dimethylformamide (30 mL) was treated with sodium hydride (0.86 g, 21.6 mmol, 60% w/w dispersed into mineral oil) for 10 min at 0° C. followed by the addition of iodomethane (3.1 g, 21.6 mmol). The resulting mixture was stirred for 1 hour at ambient temperature and quenched by the addition of water (100 mL). The resulting mixture was extracted with ethyl acetate (3×80 mL). The combined organic layers was washed with brine (4×30 mL) and dried over anhydrous sodium sulfate. After filtration, the filtrate was concentrated under reduced 2H), 7.91 (s, 1H), 7.71 (d, J=3.2 Hz, 1H), 7.66 (d, J=5.6 Hz, 1H), 6.78 (d, J=3.2 Hz, 1H), 6.60 (d, J=2.8 Hz, 1H), 3.97 (s, 3H).

Example 20

Synthesis of 6-iodo-3-(1H-pyrrolo[2,3-c]pyridin-1-yl)isoquinoline (20)

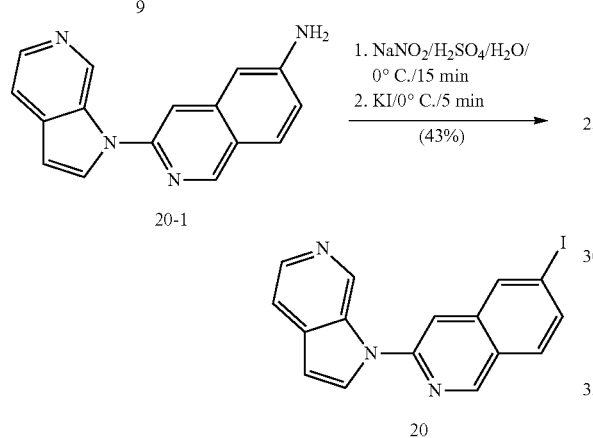

Step 1: Synthesis of 3-(1H-pyrrolo[2,3-c]pyridin-1-yl)isoquinolin-6-amine (20-1)

To a sealed tube were added a saturated solution of ammonia in methanol (300 mL) and 6-fluoro-3-(1H-pyrrolo[2,3-c]pyridin-1-yl)isoquinoline (2.5 g, 9.5 mmol, 9). The resulting mixture was stirred for 5 days at 120° C. After cooling down to ambient temperature, the resulting mixture was concentrated under reduced pressure and the residue was purified by silica gel column chromatography, eluted with 1~10% methanol in dichloromethane to afford 3-(1H-pyrrolo[2,3-c]pyridin-1-yl)isoquinolin-6-amine as a light yellow solid: MS (ESI, m/z): 261.1 [M+1]+; 1H NMR (300 MHz, DMSO-$d_6$) δ 9.41 (s, 1H), 8.93 (s, 1H), 8.29-8.23 (m, 2H), 7.82 (d, J=9.0 Hz, 1H), 7.80 (s, 1H), 7.64 (dd, J=0.9 Hz, 4.5 Hz, 1H), 7.04 (dd, J=5.1 Hz, 6.6 Hz, 1H), 6.83-6.78 (m, 2H), 6.19 (s, 2H).

Step 2: Synthesis of 6-iodo-3-(1H-pyrrolo[2,3-c]pyridin-1-yl)isoquinoline (20)

To a suspension of 3-(1H-pyrrolo[2,3-c]pyridin-1-yl)isoquinolin-6-amine (0.15 g, 0.58 mmol) in water (20 mL) was added concentrated sulfuric acid (2 mL) at ambient temperature. The resulting mixture was heated to 70-80° C. until it gave a clear solution. The resulting solution was cooled down to 0° C. and sodium nitrite (80 mg, 1.15 mmol) was added in one portion. After stirring for 15 min at 0° C., potassium iodide (0.19 g, 1.15 mmol) was added. The resulting mixture was stirred for additional 5 min and quenched with saturated aqueous solution of sodium sulfite (5 mL). The resulting mixture was extracted with dichloromethane (4×50 mL) and the combined organic layers was dried over anhydrous sodium sulfate. After filtration, the filtrate was concentrated under reduced pressure and the residue was purified by silica gel column chromatography, eluted with 0.5~1% methanol in dichloromethane to afford 6-iodo-3-(1H-pyrrolo[2,3-c]pyridin-1-yl)isoquinoline as an off-white solid: MS (ESI, m/z): 372.1 [M+1]+; 1H NMR (400 MHz, DMSO-$d_6$) δ 9.82 (s, 1H), 9.44 (s, 1H), 8.65 (d, J=3.2 Hz, 1H), 8.56 (s, 1H), 8.41 (d, J=5.6 Hz, 1H), 8.29 (s, 1H), 8.05-7.98 (m, 3H), 7.12 (d, J=3.2 Hz, 1H).

Example 21

Synthesis of 1-(4-(fluoromethyl)-5-(prop-1-ynyl)pyridin-2-yl)-1H-pyrrolo[2,3-c]pyridine (21)

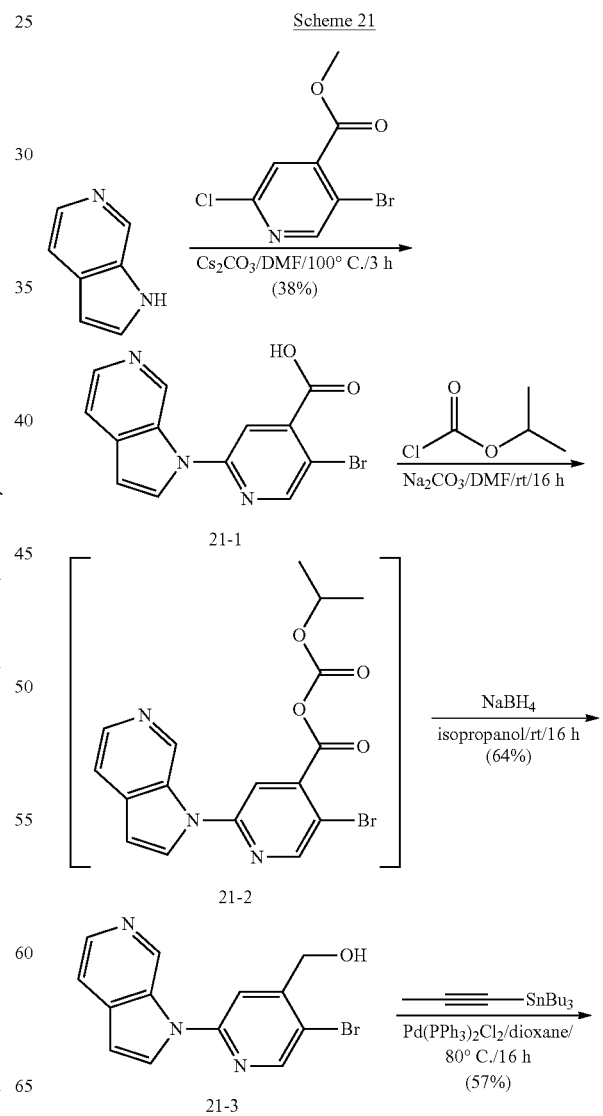

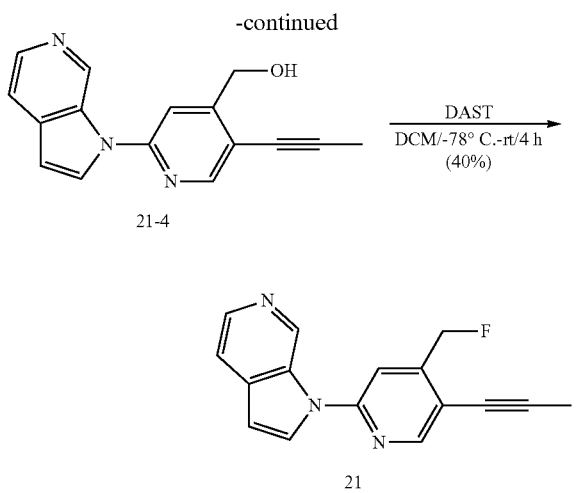

Step 1: Synthesis of 5-bromo-2-(1H-pyrrolo[2,3-c]pyridin-1-yl)isonicotinic acid (21-1)

To a stirred solution of 1H-pyrrolo[2,3-c]pyridine (1.8 g, 15.2 mmol) in N,N-dimethylformamide (80 mL) were added cesium carbonate (14.9 g, 45.7 mmol) and methyl 5-bromo-2-chloroisonicotinate (5.0 g, 16.9 mmol). The resulting mixture was stirred for 3 hours at 100° C. After cooling down to ambient temperature, the resulting mixture was filtered through Celite. The filtrate was diluted with water (200 mL) and acidified with concentrated aqueous hydrochloric acid (pH=5~6). The resulting mixture was extracted with ethyl acetate (3×200 mL). The combined organic layers was washed with brine (2×200 mL) and dried over anhydrous sodium sulfate. After filtration, the filtrate was concentrated under reduced pressure and the residue was purified by silica gel column chromatography, eluted with 1~10% methanol in ethyl acetate to afford 5-bromo-2-(1H-pyrrolo[2,3-c]pyridin-1-yl)isonicotinic acid as a light yellow solid: MS (ESI, m/z): 318.0, 320.0 [M+1]$^+$; $^1$H NMR (400 MHz, DMSO-4) δ 14.3 (br s, 1H), 9.85 (s, 1H), 8.91 (s, 1H), 8.79 (s, 1H), 8.48-8.43 (m, 1H), 8.25 (s, 1H), 8.04 (d, J=6.0 Hz, 1H), 7.13-7.11 (m, 1H).

Step 2: Synthesis of (5-bromo-2-(1H-pyrrolo[2,3-c]pyridin-1-yl)pyridin-4-yl)methanol (21-3)

To a stirred solution of 5-bromo-2-(1H-pyrrolo[2,3-c]pyridin-1-yl)isonicotinic acid (2.0 g, 6.29 mmol) in N,N-dimethylformamide (40 mL) were added sodium carbonate (2.0 g, 18.86 mmol) and isopropyl carbonochloridate (1.54 g, 12.57 mmol) at 0° C. The resulting mixture was stirred for 16 hours at ambient temperature then quenched with water (100 mL) and extracted with ethyl acetate (3×100 mL). The combined organic layers was washed with brine (3×100 mL) and dried over anhydrous sodium sulfate. After filtration, the filtrate was concentrated under reduced pressure to afford crude 5-bromo-2-(1H-pyrrolo[2,3-c]pyridin-1-yl)isonicotinic isobutyric anhydride (21-2, 2 g) as a yellow oil. The resulting crude yellow oil was dissolved into isopropanol (50 mL) at 0° C. and sodium borohydride (0.34 g, 9.02 mmol) was added. The resulting mixture was stirred for 16 hours at ambient temperature and quenched with saturated aqueous solution of ammonium chloride (100 mL). The resulting mixture was extracted with ethyl acetate (3×100 mL). The combined organic layers was washed with brine (2×100 mL) and dried over anhydrous sodium sulfate. After filtration, the filtrate was concentrated under reduced pressure and the residue was purified by silica gel column chromatography, eluted with 1~10% methanol in dichloromethane to afford (5-bromo-2-(1H-pyrrolo[2,3-c]pyridin-1-yl)pyridin-4-yl)methanol as a light yellow solid: MS (ESI, m/z): 304.1, 306.1 [M+1]$^+$; $^1$H NMR (300 MHz, DMSO-d$_6$) δ 9.65 (s, 1H), 8.68 (s, 1H), 8.29 (d, J=5.4 Hz, 1H), 8.27 (d, J=3.6 Hz, 1H), 7.88 (s, 1H), 7.67 (dd, J=0.9 Hz, 4.5 Hz, 1H), 6.85 (d, J=3.6 Hz, 1H), 5.85 (t, J=5.7 Hz, 1H), 4.61 (d, J=5.4 Hz, 2H).

Step 3: Synthesis of (5-(prop-1-ynyl)-2-(1H-pyrrolo[2,3-c]pyridin-1-yl)pyridin-4-yl)methanol (21-4)

To a stirred solution of (5-bromo-2-(1H-pyrrolo[2,3-c]pyridin-1-yl)pyridin-4-yl)methanol (0.72 g, 2.37 mmol) and tributyl(prop-1-yn-1-yl)stannane (1.17 g, 3.55 mmol) in 1,4-dioxane (40 mL) was added bis(triphenylphosphine)palladium(II) chloride (0.17 g, 0.24 mmol) at ambient temperature. The resulting mixture was stirred for 16 hours at 80° C. under nitrogen atmosphere. After cooling down to ambient temperature, the resulting mixture was quenched with water (100 mL) and extracted with ethyl acetate (3×100 mL). The combined organic layers was washed with brine (2×100 mL) and dried over anhydrous sodium sulfate. After filtration, the filtrate was concentrated under reduced pressure and the residue was purified by silica gel column chromatography, eluted with 1~10% methanol in dichloromethane to afford (5-(prop-1-yn-1-yl)-2-(1H-pyrrolo[2,3-c]pyridin-1-yl)pyridin-4-yl)methanol as a light yellow solid: MS (ESI, m/z): 264.1 [M+1]$^+$; $^1$H NMR (300 MHz, DMSO-d$_6$+D$_2$O) δ 9.94 (s, 1H), 8.93 (d, J=3.3 Hz, 1H), 8.59 (s, 1H), 8.46 (d, J=6.3 Hz, 1H), 8.26 (d, J=6.3 Hz, 1H), 7.96 (s, 1H), 7.26 (d, J=3.3 Hz, 1H), 4.73 (s, 2H), 2.16 (s, 3H).

Step 4: Synthesis of 1-(4-(fluoromethyl)-5-(prop-1-ynyl)pyridin-2-yl)-1H-pyrrolo[2,3-c]pyridine (21

To a stirred solution of (5-(prop-1-yn-1-yl)-2-(1H-pyrrolo[2,3-c]pyridin-1-yl)pyridin-4-yl)methanol (50 mg, 0.19 mmol) in dry dichloromethane (20 mL) was added diethylaminosulfurtrifluoride (DAST, 92 mg, 0.57 mmol) at −78° C. under nitrogen atmosphere. The resulting solution was stirred for 4 hours at ambient temperature and quenched with saturated aqueous solution of sodium bicarbonate (50 mL). The resulting mixture was extracted with dichloromethane (3×50 mL). The combined organic layers was washed with brine (2×50 mL) and dried over anhydrous sodium sulfate. After filtration, the filtrate was concentrated under reduced pressure and the residue was purified by silica gel column chromatography, eluted with 1~10% methanol in dichloromethane to afford 1-(4-(fluoromethyl)-5-(prop-1-yn-1-yl)pyridin-2-yl)-1H-pyrrolo[2,3-c]pyridine as a light yellow solid: MS (ESI, m/z): 266.1 [M+1]$^+$; $^1$H NMR (300 MHz, DMSO-d$_6$) δ 9.95 (s, 1H), 8.95 (d, J=3.6 Hz, 1H), 8.69 (s, 1H), 8.48 (d, J=6.0 Hz, 1H), 8.21 (d, J=6.0 Hz, 1H), 8.05 (s, 1H), 7.24 (d, J=3.3 Hz, 1H), 5.78 (s, 1H), 5.62 (s, 1H), 2.17 (s, 3H).

Examples 22 & 23

Synthesis of 1-(4-fluoro-5-(prop-1-ynyl)pyridin-2-yl)-1H-pyrrolo[2,3-c]pyridine (22) and 2-methyl-6-(1H-pyrrolo[2,3-c]pyridin-1-yl)furo[3,2-c]pyridine (23)

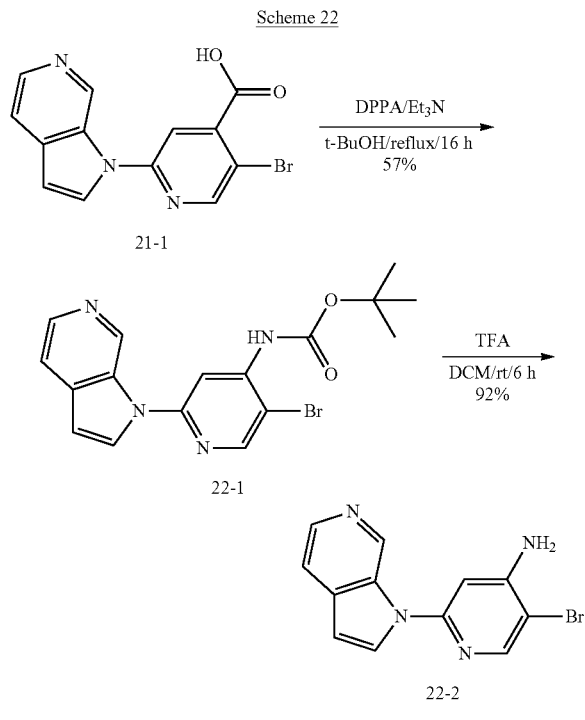

Scheme 22

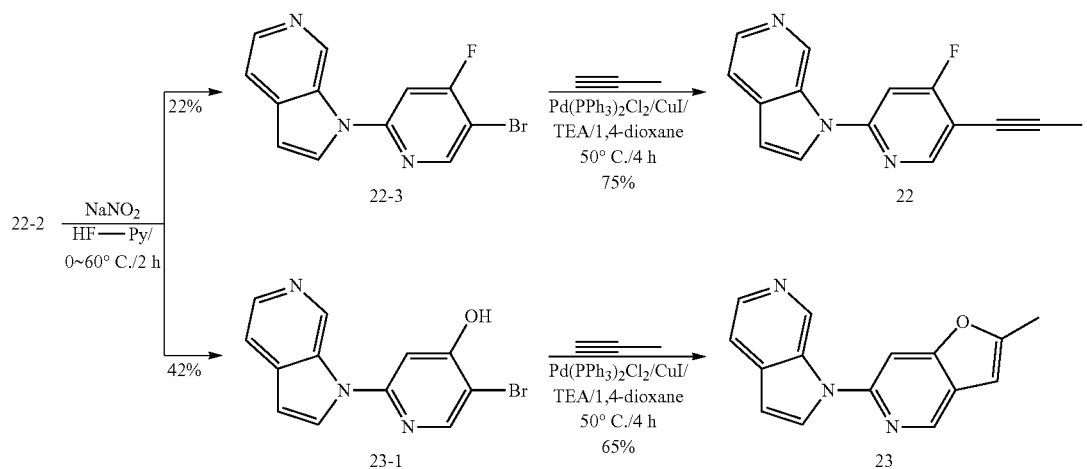

Scheme 23

Step 1: Synthesis of tert-butyl (5-bromo-2-(1H-pyrrolo[2,3-c]pyridin-1-yl)pyridin-4-ylcarbamate (22-1)

To a stirred solution of 5-bromo-2-(1H-pyrrolo[2,3-c]pyridin-1-yl)isonicotinic acid (7.80 g, 8.09 mmol, 21-1) and triethylamine (2.46 g, 24.27 mmol) in tert-butyl alcohol (200 mL) was added diphenyl phosphorazidate (3.34 g, 12.14 mmol) at ambient temperature. The resulting mixture was stirred for 16 hours at 80° C. under nitrogen atmosphere. After cooling down to ambient temperature, the resulting mixture was concentrated under reduced pressure and the residue was dissolved into dichloromethane (200 mL), washed with water (200 mL). The organic layer was dried over anhydrous sodium sulfate and filtered. The filtrate was concentrated under reduced pressure and the residue was purified by silica gel column chromatography, eluted with 1~2% methanol in dichloromethane to afford tert-butyl (5-bromo-2-(1H-pyrrolo[2,3-c]pyridin-1-yl)pyridin-4-yl)carbamate as a yellow solid: MS (ESI, m/z): 289.2, 291.2 [M+1]$^+$; $^1$H NMR (300 MHz, DMSO-$d_6$) δ 9.72 (br s, 1H), 8.93 (s, 1H), 8.69 (s, 1H), 8.29 (d, J=5.1 Hz, 1H), 8.20 (s, 1H), 8.17 (d, J=3.3 Hz, 1H), 7.68 (d, J=0.9 Hz, 1H), 6.86 (d, J=3.0 Hz, 1H), 1.48 (s, 9H).

Step 2: Synthesis of 5-bromo-2-(1H-pyrrolo[2,3-c]pyridin-1-yl)pyridin-4-amine (22-2)

A solution of tert-butyl (5-bromo-2-(1H-pyrrolo[2,3-c]pyridin-1-yl)pyridin-4-yl)carbamate (1.71 g, 4.39 mmol) in dichloromethane (50 mL) was treated with trifluoroacetic acid (5 mL) at ambient temperature for 6 hours. The resulting solution was concentrated under reduced pressure and the residue was dissolved into dichloromethane (100 mL), washed with saturated aqueous solution of sodium bicarbonate (100 mL). The organic layer was dried over anhydrous sodium sulfate and filtered. The filtrate was purified by silica gel column chromatography, eluted with 1~2% methanol in dichloromethane to afford 5-bromo-2-(1H-pyrrolo[2,3-c]pyridin-1-yl)pyridin-4-amine as a light yellow solid: MS (ESI, m/z): 289.2, 291.2 [M+1]$^+$; $^1$H NMR (400 MHz, DMSO-$d_6$) δ 9.53 (br s, 1H), 8.33 (s, 1H), 8.29-8.27 (m, 1H), 8.07 (d, J=3.3 Hz, 1H), 7.66 (d, J=5.1 Hz, 1H), 7.05 (s, 1H), 6.84 (d, J=3.0 Hz, 1H), 6.61 (br s, 2H).

Step 3: Synthesis of 1-(5-bromo-4-fluoropyridin-2-yl)-1H-pyrrolo[2,3-c]pyridine (22-4) and 5-bromo-2-(1H-pyrrolo[2,3-c]pyridin-1-yl)pyridin-4-ol (23-1)

To a stirred solution of 5-bromo-2-(1H-pyrrolo[2,3-c]pyridin-1-yl)pyridin-4-amine (0.5 g, 1.73 mmol) in hydrogen fluoride-pyridine (25 mL, 65-70% w/w) was added sodium nitrite (0.72 g, 10.38 mmol) at 0° C. The resulting mixture was stirred for 2 hours at 60° C. After cooling down to ambient temperature, the resulting mixture was quenched with water (100 mL) and extracted with dichloromethane (3×100 mL). The combined organic layers was washed with brine (2×100 mL) and dried over anhydrous sodium sulfate. After filtration, the filtrate was concentrated under reduced pressure and the residue was purified by silica gel column chromatography, eluted with 1~2% methanol in dichloromethane to afford 1-(5-bromo-4-fluoropyridin-2-yl)-1H-pyrrolo[2,3-c]pyridine as a light yellow solid: MS (ESI, m/z): 292.2, 294.2 [M+1]$^+$; $^1$H NMR (300 MHz, CD$_3$OD) δ 10.08 (br s, 1H), 8.85-8.79 (m, 2H), 8.41 (d, J=3.3 Hz, 1H), 8.23 (d, J=6.3 Hz, 1H), 7.95 (d, J=9.6 Hz, 1H), 7.21 (d, J=3.6 Hz, 1H); and 5-bromo-2-(1H-pyrrolo[2,3-c]pyridin-1-yl) pyridin-4-ol as a light yellow solid (210 mg, 42%): MS (ESI, m/z): 290.1, 292.1 [M+1]$^+$; $^1$H NMR (300 MHz, CD$_3$OD) δ 9.95 (br s, 1H), 8.62 (d, J=2.7 Hz, 1H), 8.55 (s, 1H), 8.35 (d, J=6.9 Hz, 1H), 8.20 (d, J=6.0 Hz, 1H), 7.23 (s, 1H), 7.18 (s, 1H).

Step 4: Synthesis of 1-(4-fluoro-5-(prop-1-ynyl) pyridin-2-yl)-1H-pyrrolo[2,3-c]pyridine (22)

To a stirred solution of 1-(5-bromo-4-fluoropyridin-2-yl)-1H-pyrrolo[2,3-c]pyridine (30 mg, 0.11 mmol) in 1,4-dioxane (15 mL) was bubbled with propyne for 10 min at ambient temperature followed by the addition of triethylamine (5 mL), copper (I) iodide (2 mg, 10 μmol) and bis(triphenylphosphine)palladium(II) dichloride (3.6 mg, 5.14 μmol). The resulting mixture was stirred for 4 hours at 50° C. under nitrogen atmosphere. After cooling down to ambient temperature, the resulting mixture was concentrated under reduced pressure and the residue was purified by silica gel column chromatography, eluted with 1~2% methanol in dichloromethane to afford 1-(4-fluoro-5-(prop-1-ynyl)pyridin-2-yl)-1H-pyrrolo[2,3-c]pyridine as a light yellow solid: MS (ESI, m/z): 252.1 [M+1]$^+$; $^1$H NMR (400 MHz, DMSO-d$_6$) δ 9.81 (br s, 1H), 8.68 (d, J=10.0 Hz, 1H), 8.40 (s, 1H), 8.32 (d, J=5.2 Hz, 1H), 7.92 (d, J=12.0 Hz, 1H), 7.84 (d, J=5.6 Hz, 1H), 6.98 (s, 1H), 2.13 (s, 3H).

Step 5: Synthesis of 2-methyl-6-(1H-pyrrolo[2,3-c] pyridin-1-yl)furo[3,2-c]pyridine (23)

To a stirred solution of 5-bromo-2-(1H-pyrrolo[2,3-c]pyridin-1-yl)pyridin-4-ol (30 mg, 0.11 mmol) in 1,4-dioxane (15 mL) was bubbled with propyne for 10 min at ambient temperature followed by the addition of triethylamine (5 mL), copper (I) iodide (2 mg, 10 μmol) and bis(triphenylphosphine)palladium(II) dichloride (3.6 mg, 5.14 μmol). The resulting mixture was stirred for 4 hours at 50° C. under nitrogen atmosphere. After cooling down to ambient temperature, the resulting mixture was concentrated under reduced pressure and the residue was purified by silica gel column chromatography, eluted with 1~2% methanol in dichloromethane to afford 2-methyl-6-(1H-pyrrolo[2,3-c]pyridin-1-yl)furo[3,2-c]pyridine as a colorless solid: MS (ESI, m/z): 250.1 [M+1]$^+$; $^1$H NMR (300 MHz, CD$_3$OD) δ 9.62 (br s, 1H), 8.77 (s, 1H), 8.22 (d, J=5.4 Hz, 1H), 8.17 (d, J=3.3 Hz, 1H), 7.83 (s, 1H), 7.73 (d, J=5.4 Hz, 1H), 6.86 (d, J=3.3 Hz, 1H), 6.69 (s, 1H), 2.53 (s, 3H).

Example 24

Synthesis of 6-(fluoromethoxy)-2-(1H-pyrrolo[2,3-c]pyridin-1-yl)quinazoline (24)

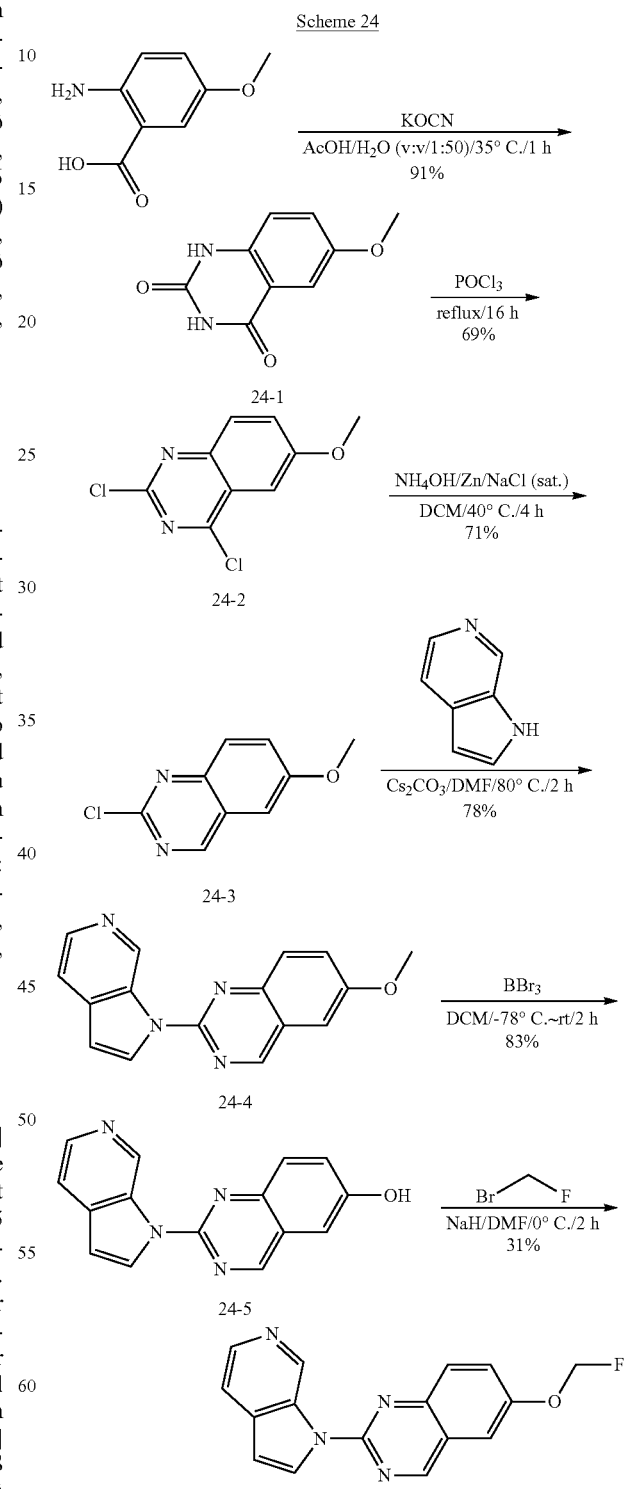

Step 1: Synthesis of 6-methoxyquinazoline-2,4(1H,3H)-dione (24-1)

A suspension of 2-amino-4-methoxybenzoic acid (5 g, 29.9 mmol) in water (35 mL) and acetic acid (0.7 mL, 29.7 mmol) was warmed to 35° C. followed by the addition of a solution of potassium cyanate (6.1 g, 74.8 mmol) in water (10 mL) over 5 min. After additional 1 hour, sodium hydroxide (12 g, 0.3 mol) was carefully added and the reaction system became a clear solution. The resulting solution was acidified by the addition of concentrated hydrochloric acid (27 mL) and solid was precipitated. A filtration was performed and the filter cake was washed with cold water (2×30 mL), dried in a vacuum oven to afford 6-methoxyquinazoline-2,4(1H,3H)-dione as a brown solid: MS (ESI, m/z): 193.1 [M+1]$^+$; $^1$H NMR (300 MHz, DMSO-d$_6$) δ 11.27 (s, 1H), 11.10 (s, 1H), 7.31 (s, 1H), 7.28 (d, J=6.0 Hz, 1H), 7.13 (d, J=5.4 Hz, 1H), 3.76 (s, 3H).

Step 2: Synthesis of 2,4-dichloro-6-methoxyquinazoline (24-2)

A solution of 6-methoxyquinazoline-2,4(1H,3H)-dione (5 g, 26.0 mmol) in trichloro phosphorus oxide (30 mL) was refluxed for 16 hours. After cooling down to ambient temperature, the resulting solution was concentrated under reduced pressure and the residue was purified by silica gel column chromatography, eluted with 1~2% methanol in dichloromethane to afford 2,4-dichloro-6-methoxyquinazoline as a yellow solid: MS (ESI, m/z): 229.1 [M+1]$^+$; $^1$H NMR (300 MHz, CDCl$_3$) δ 7.90 (d, J=9.3 Hz, 1H), 7.61 (dd, J=2.7 Hz, 6.6 Hz, 1H), 7.41 (d, J=2.7 Hz, 1H), 4.00 (s, 3H).

Step 3: Synthesis of 2-chloro-6-methoxyquinazoline (24-3)

To a solution of 2,4-dichloro-6-methoxyquinazoline (3 g, 13.1 mmol) in dichloromethane (50 mL) were added zinc dust (2.57 g, 39.3 mmol), aqueous solution of ammonia (50 mL, 34% w/w) and brine (10 mL). The resulting mixture was stirred for 4 hours at 40° C. under nitrogen atmosphere. After cooling down to ambient temperature, the resulting mixture was filtered through Celite. The organic layer was collected and the aqueous layer was extracted with dichloromethane (2×50 mL). The combined organic layers was dried over anhydrous sodium sulfate. After filtration, the filtrate was concentrated under reduced pressure and the residue was purified by silica gel column chromatography, eluted with 1~2% methanol in dichloromethane to afford 2-chloro-6-methoxyquinazoline as a yellow solid: MS (ESI, m/z): 195.2 [M+1]$^+$; $^1$H NMR (300 MHz, CDCl$_3$) δ 9.19 (s, 1H), 7.91 (d, J=9.3 Hz, 1H), 7.61 (dd, J=2.7 Hz, 6.6 Hz, 1H), 7.16 (d, J=2.7 Hz, 1H), 3.96 (s, 3H).

Step 4: Synthesis of 6-methoxy-2-(1H-pyrrolo[2,3-c]pyridin-1-yl)quinazoline (24-4)

To a solution of 2-chloro-6-methoxyquinazoline (198 mg, 1.02 mmol) in N,N-dimethylformamide (20 mL) were added 1H-pyrrolo[2,3-c]pyridine (176 mg, 1.5 mmol) and cesium carbonate (552 mg, 1.69 mmol). The resulting mixture was stirred for 2 hours at 80° C. After cooling down to ambient temperature, the resulting mixture was diluted with water (60 mL) and extracted with ethyl acetate (3×50 mL). The combined organic layers was washed with brine (2×30 mL) and dried over sodium sulfate. After filtration, the filtrate was concentrated under reduced pressure and the residue was purified by silica gel column chromatography, eluted with 1~2% methanol in dichloromethane to afford 6-methoxy-2-(1H-pyrrolo[2,3-c]pyridin-1-yl)quinazoline as a yellow solid: MS (ESI, m/z): 277.1 [M+1]$^+$; $^1$H NMR (300 MHz, DMSO-d$_6$) δ 10.16 (s, 1H), 9.63 (s, 1H), 8.59 (d, J=3.6 Hz, 1H), 8.35 (d, J=5.1 Hz, 1H), 8.05 (d, J=9.3 Hz, 1H), 7.74-7.69 (m, 2H), 7.62 (d, J=2.7 Hz, 1H), 6.88 (d, J=3.6 Hz, 1H), 3.95 (s, 3H).

Step 5: Synthesis of 2-(1H-pyrrolo[2,3-c]pyridin-1-yl)quinazolin-6-ol (24-5)

To a solution of 6-methoxy-2-(1H-pyrrolo[2,3-c]pyridin-1-yl)quinazoline (1 g, 3.62 mmol) in dichloromethane (50 mL) was added tribromoborane (4.53 g, 18.10 mmol) at −78° C. After additional 2 hours at ambient temperature, the reaction was quenched with water (50 mL) and neutralized with sodium hydroxide (1.45 g, 36.25 mmol). The organic layer was collected and the aqueous layer was extracted with dichloromethane (2×50 mL). The combined organic layers was dried over anhydrous sodium sulfate and filtered. The filtrate was concentrated under reduced pressure and the residue was purified by silica gel column chromatography, eluted with 1~2% methanol in dichloromethane to afford 2-(1H-pyrrolo[2,3-c]pyridin-1-yl)quinazolin-6-ol as a yellow solid: MS (ESI, m/z): 263.2 [M+1]$^+$; $^1$H NMR (300 MHz, DMSO-d$_6$) δ 10.46 (s, 1H), 10.41 (s, 1H), 9.56 (s, 1H), 8.58 (s, 1H), 8.34 (d, J=5.1 Hz, 1H), 8.00 (d, J=9.3 Hz, 1H), 7.73-7.57 (m, 2H), 7.38 (s, 1H), 6.86 (s, 1H).

Step 6: Synthesis of 6-(fluoromethoxy)-2-(1H-pyrrolo[2,3-c]pyridin-1-yl)quinazoline (24)

A solution of 2-(1H-pyrrolo[2,3-c]pyridin-1-yl)quinazolin-6-ol (100 mg, 0.38 mmol) in N,N-dimethylformamide (15 mL) was treated with sodium hydride (76 mg, 1.91 mmol, 60% w/w dispersed by mineral oil) at 0° C. for 10 min followed by the addition of bromofluoromethane (65 mg, 0.57 mmol). After additional 2 hours, the resulting mixture was quenched by water (50 mL) and extracted with dichloromethane (3×50 mL). The combined organic layers was washed with brine (3×50 mL) and dried over anhydrous sodium sulfate. After filtration, the filtrate was concentrated under reduced pressure and the residue was purified by silica gel column chromatography, eluted with 1~2% methanol in dichloromethane to afford 6-(fluoromethoxy)-2-(1H-pyrrolo[2,3-c]pyridin-1-yl)quinazoline as a colorless solid: MS (ESI, m/z): 295.2 [M+1]$^+$; $^1$H NMR (300 MHz, DMSO-d$_6$) δ 10.23 (s, 1H), 9.72 (s, 1H), 8.61 (d, J=3.6 Hz, 1H), 8.37 (d, J=5.1 Hz, 1H), 8.16 (d, J=8.7 Hz, 1H), 7.89-7.84 (m, 2H), 7.71 (d, J=5.1 Hz, 1H), 6.90 (d, J=3.6 Hz, 1H), 6.15 (s, 1H), 5.97 (s, 1H).

Example 25

Synthesis of 1-fluoro-7-(1H-pyrrolo[2,3-c]pyridin-1-yl)-2,6-naphthyridine (25)

Scheme 25

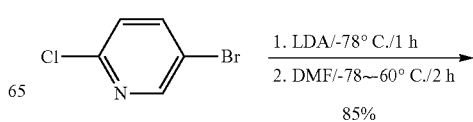

-continued

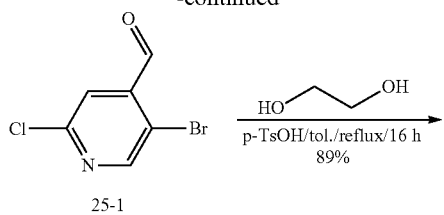

25-1

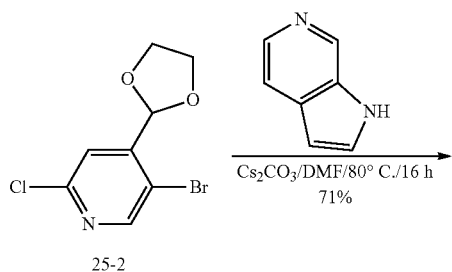

25-2

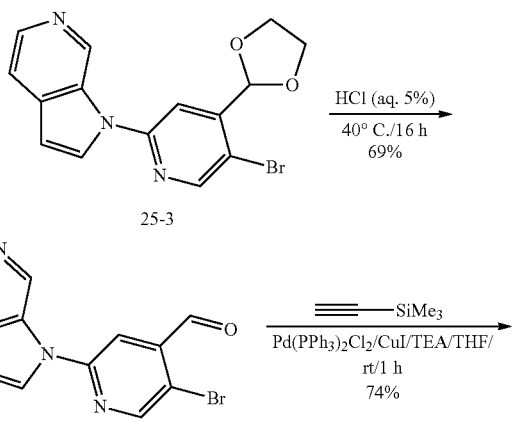

25-3

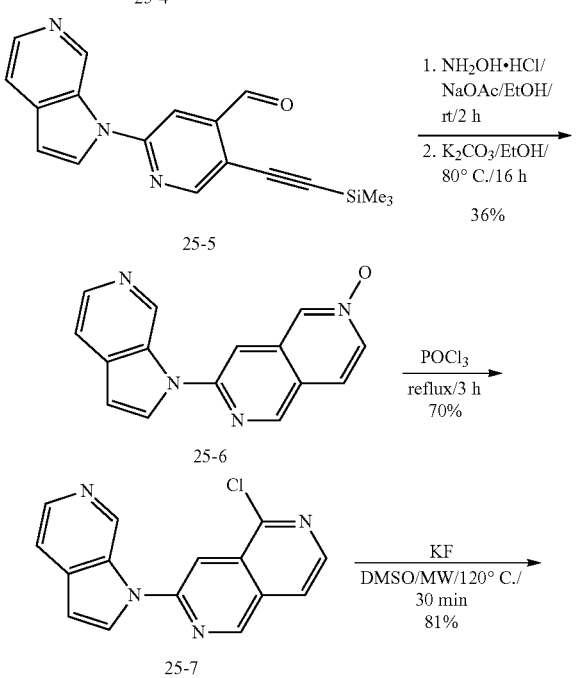

-continued

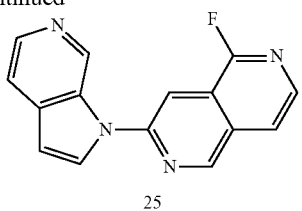

25

Step 1: Synthesis of 5-bromo-2-chloroisonicotinaldehyde (25-1)

A solution of diisopropylamine (31.3 g, 0.31 mol) in tetrahydrofuran (600 mL) was treated with 2.5 Mn-butyllithium (109 mL, 0.27 mol) in hexane for 30 min at −78° C., followed by the addition of a solution of 5-bromo-2-chloropyridine (35 g, 0.18 mol) in tetrahydrofuran (200 mL). The resulting solution was stirred for 30 min at −78° C., then N,N-dimethylformamide (40.4 g, 0.55 mol) was added. After additional 30 min at −60° C., The reaction mixture was quenched by saturated aqueous solution of ammonium chloride (1 L) and extracted with ethyl acetate (3×500 mL). The combined organic layers was washed with brine (2×500 mL) and dried over anhydrous sodium sulfate. After filtration, the filtrate was concentrated under reduced pressure and the residue was purified by silica gel column chromatography, eluted with 1~10% ethyl acetate in petroleum ether to afford 5-bromo-2-chloroisonicotinaldehyde as a light yellow solid: MS (ESI, m/z): 220.2, 222.1 [M+1]$^+$; $^1$H NMR (400 MHz, CDCl$_3$) δ 10.31 (s, 1H), 8.70 (s, 1H), 7.74 (s, 1H).

Step 2: Synthesis of 5-bromo-2-chloro-4-(1,3-dioxolan-2-yl)pyridine (25-2)

To a solution of 5-bromo-2-chloroisonicotinaldehyde (15 g, 61.2 mmol) in toluene (500 mL) were added 4-methylbenzenesulfonic acid (11.6 g, 67.4 mmol) and ethane-1,2-diol (7.6 g, 122 mmol). The resulting mixture was refluxed for 16 hours under nitrogen atmosphere. Water was removed by Dean-Stark trap. After cooling down to ambient temperature, the reaction mixture was quenched with water (300 mL) and neutralized by the addition of sodium hydroxide (2.9 g, 74.1 mmol). The organic layer was separated and the aqueous layer was extracted with ethyl acetate (3×300 mL). The combined organic layers was washed with brine (2×300 mL) and dried over anhydrous sodium sulfate. After filtration, the filtrate was concentrated under reduced pressure to afford 5-bromo-2-chloro-4-(1,3-dioxolan-2-yl)pyridine as a yellow solid: MS (ESI, m/z): 264.2, 266.2 [M+1]$^+$; $^1$H NMR (300 MHz, DMSO-d$_6$) δ 8.69 (s, 1H), 7.59 (s, 1H), 5.93 (s, 1H), 4.13-3.98 (m, 4H).

Step 3: Synthesis of 1-(5-bromo-4-(1,3-dioxolan-2-yl)pyridin-2-yl)-1H-pyrrolo[2,3-c]pyridine (25-3)

To a solution of 5-bromo-2-chloro-4-(1,3-dioxolan-2-yl)pyridine (16 g, 54.4 mmol) in N,N-dimethylformamide (300 mL) were added 1H-pyrrolo[2,3-c]pyridine (6.43 g, 54.4 mmol) and cesium carbonate (53.2 g, 163 mmol). The resulting mixture was stirred for 16 hours at 80° C. After cooling down to ambient temperature, the resulting mixture was filtered through Celite and the filtrate was concentrated under reduced pressure. The residue was purified by silica gel column chromatography, eluted with 1~2% methanol in dichloromethane to afford 1-(5-bromo-4-(1,3-dioxolan-2-yl)pyridin-2-yl)-1H-pyrrolo[2,3-c]pyridine as a light yellow solid: MS (ESI, m/z): 346.2, 348.2 [M+1]⁺; ¹H NMR (300 MHz, DMSO-d₆) δ 9.61 (s, 1H), 8.79 (s, 1H), 8.39 (d, J=3.6 Hz, 1H), 8.30 (d, J=5.4 Hz, 1H), 7.86 (s, 1H), 7.66 (d, J=5.1 Hz, 1H), 6.87 (d, J=3.3 Hz, 1H), 6.04 (s, 1H), 4.21-4.00 (m, 4H).

Step 4: Synthesis of 5-bromo-2-(1H-pyrrolo[2,3-c]pyridin-1-yl)isonicotinaldehyde (25-4)

To a suspension of 1-(5-bromo-4-(1,3-dioxolan-2-yl)pyridin-2-yl)-1H-pyrrolo[2,3-c]pyridine (5 g, 13.72 mmol) in water (200 mL) was added hydrochloric acid (20 mL, 37% w/w). The resulting solution was stirred for 16 hours at 40° C. After cooling down to ambient temperature, the resulting solution was neutralized by the addition of potassium carbonate (14 g, 101 mmol). Solid was collected by filtration and washed with water (3×50 mL), dried in a vacuum oven to afford 5-bromo-2-(1H-pyrrolo[2,3-c]pyridin-1-yl)isonicotinaldehyde as a light yellow solid: MS (ESI, m/z): 302.1, 304.1 [M+1]⁺; ¹H NMR (300 MHz, DMSO-d₆) δ 10.27 (s, 1H), 9.75 (s, 1H), 8.98 (s, 1H), 8.45 (d, J=3.6 Hz, 1H), 8.38 (d, J=3.3 Hz, 1H), 8.17 (s, 1H), 7.68 (d, J=4.5 Hz, 1H), 6.90 (d, J=3.6 Hz, 1H).

Step 5: Synthesis of 2-(1H-pyrrolo[2,3-c]pyridin-1-yl)-5-((trimethylsilyl)ethynyl)isonicotinaldehyde (25-5)

To a stirred solution of 5-bromo-2-(1H-pyrrolo[2,3-c]pyridin-1-yl)isonicotinaldehyde (4 g, 11.92 mmol) and triethylamine (2.41 g, 23.83 mmol) in tetrahydrofuran (120 mL) were added copper (I) iodide (0.23 g, 1.19 mmol), ethynyltrimethylsilane (1.76 g, 17.87 mmol) and bis(triphenylphosphine)palladium(II) dichloride (0.84 g, 1.19 mmol) at ambient temperature under nitrogen atmosphere. After additional 1 hour, the resulting solution was concentrated under reduced pressure and the residue was purified by silica gel column chromatography, eluted with 1~2% methanol in dichloromethane to afford 2-(1H-pyrrolo[2,3-c]pyridin-1-yl)-5-((trimethylsilyl)ethynyl)isonicotinaldehyde as a light yellow solid: MS (ESI, m/z): 320.1 [M+1]⁺; ¹H NMR (300 MHz, CDCl₃) δ 10.55 (s, 1H), 8.85 (s, 1H), 7.93 (d, J=3.6 Hz, 1H), 7.83 (d, J=3.3 Hz, 1H), 7.68-7.64 (m, 1H), 7.55-7.45 (m, 2H), 6.77 (d, J=3.0 Hz, 1H), 0.32 (s, 9H).

Step 6: Synthesis of 7-(1H-pyrrolo[2,3-c]pyridin-1-yl)-2,6-naphthyridine 2-oxide (25-6)

To a stirred solution of 2-(1H-pyrrolo[2,3-c]pyridin-1-yl)-5-((trimethylsilyl)ethynyl)isonicotinaldehyde (3 g, 7.98 mmol) in ethanol (120 mL) were added sodium acetate (1.31 g, 15.97 mmol) and hydroxylamine hydrochloride (0.83 g, 11.97 mmol) at ambient temperature. After additional 2 hours, to the resulting solution was added potassium carbonate (2.64 g, 19.16 mmol) and the resulting mixture was stirred for 16 hours at 80° C. After cooling down to ambient temperature, the resulting mixture was concentrated under reduced pressure and the residue was taken up into dichloromethane (100 mL), washed with water (2×50 mL). The organic layer was dried over anhydrous sodium sulfate. After filtration, the filtrate was concentrated under reduced pressure and the residue was purified by silica gel column chromatography, eluted with 1~2% methanol in dichloromethane to afford 7-(1H-pyrrolo[2,3-c]pyridin-1-yl)-2,6-naphthyridine 2-oxide as a light yellow solid: MS (ESI, m/z): 263.2 [M+1]⁺; ¹H NMR (300 MHz, DMSO-d₆) δ 9.67 (s, 1H), 9.38 (s, 1H), 8.97 (s, 1H), 8.32-8.30 (m, 2H), 8.24 (t, J=7.2 Hz, 1H), 8.19-8.18 (m, 2H), 7.69 (d, J=5.4 Hz, 1H), 6.91 (d, J=3.3 Hz, 1H).

Step 7: Synthesis of 1-chloro-7-(1H-pyrrolo[2,3-c]pyridin-1-yl)-2,6-naphthyridine (25-7)

A solution of 7-(1H-pyrrolo[2,3-c]pyridin-1-yl)-2,6-naphthyridine 2-oxide (0.85 g, 3.21 mmol) in phosphorus oxychloride (30 mL) was refluxed for 3 hours. After cooling down to ambient temperature, the resulting mixture was concentrated under reduced pressure and the residue was dissolved into dichloromethane (50 mL), washed with saturated aqueous solution of sodium bicarbonate (20 mL). The organic layer was dried over anhydrous sodium sulfate. After filtration, the filtrate was concentrated under reduced pressure and the residue was purified by silica gel column chromatography, eluted with 1~2% methanol in dichloromethane to afford 1-chloro-7-(1H-pyrrolo[2,3-c]pyridin-1-yl)-2,6-naphthyridine as a light yellow solid: MS (ESI, m/z): 281.2 [M+1]⁺; ¹H NMR (300 MHz, DMSO-d₆) δ 9.79 (s, 1H), 9.65 (s, 1H), 8.54 (d, J=3.3 Hz, 1H), 8.49 (d, J=2.7 Hz, 1H), 8.34-8.31 (m, 2H), 8.18 (d, J=5.4 Hz, 1H), 7.70 (d, J=5.1 Hz, 1H), 6.93 (d, J=3.3 Hz, 1H).

Step 8: Synthesis of 1-fluoro-7-(1H-pyrrolo[2,3-c]pyridin-1-yl)-2,6-naphthyridine (25)

A mixture of 1-chloro-7-(1H-pyrrolo[2,3-c]pyridin-1-yl)-2,6-naphthyridine (30 mg, 0.11 mmol) and potassium fluoride (60.8 mg, 1.05 mmol) in dimethyl sulfoxide (5 mL) was irradiated for 30 min at 120° C. by a microwave (100 W). After cooling down to ambient temperature, the reaction mixture was quenched with water (30 mL) and extracted with ethyl acetate (3×30 mL). The combined organic layers was washed with brine (2×30 mL) and dried over anhydrous sodium sulfate. After filtration, the filtrate was concentrated under reduced pressure and the residue was purified by silica gel column chromatography, eluted with 1~2% methanol in dichloromethane to afford 1-fluoro-7-(1H-pyrrolo[2,3-c]pyridin-1-yl)-2,6-naphthyridine as a colorless solid: MS (ESI, m/z): 265.0 [M+1]⁺; ¹H NMR (300 MHz, DMSO-d₆) δ 9.81 (s, 1H), 9.65 (s, 1H), 8.55 (d, J=3.3 Hz, 1H), 8.39 (s, 1H), 8.32 (d, J=5.4 Hz, 1H), 8.25 (d, J=5.1 Hz, 1H), 8.08 (d, J=5.4 Hz, 1H), 7.69 (d, J=5.7 Hz, 1H), 6.93 (d, J=3.3 Hz, 1H).

Example 26

Synthesis of 3-(1H-pyrrolo[2,3-c]pyridin-1-yl)-2,6-naphthyridine (26)

Scheme 26

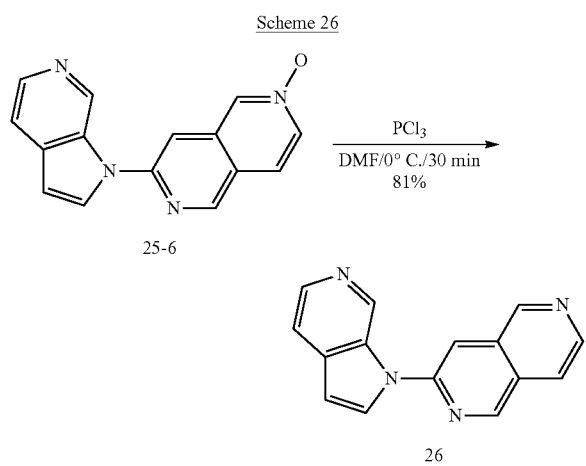

Synthesis of 3-(1H-pyrrolo[2,3-c]pyridin-1-yl)-2,6-naphthyridine (26)

A solution of 7-(1H-pyrrolo[2,3-c]pyridin-1-yl)-2,6-naphthyridine-2-oxide (100 mg, 0.38 mmol, 25-6) in N,N-dimethylformamide (10 mL) was treated with trichlorophosphine (157 mg, 1.14 mmol) at 0° C. for 30 min. The reaction was quenched with saturated aqueous solution of sodium bicarbonate (2 mL) and concentrated under reduced pressure. The residue was purified by silica gel column chromatography, eluted with 1~2% methanol in dichloromethane to afford 3-(1H-pyrrolo[2,3-c]pyridin-1-yl)-2,6-naphthyridine as a light yellow solid: MS (ESI, m/z): 247.2 [M+1]$^+$; $^1$H NMR (400 MHz, DMSO-d$_6$) δ 9.73 (s, 1H), 9.57 (s, 1H), 9.54 (s, 1H), 8.70 (d, J=5.6 Hz, 1H), 8.49 (s, 1H), 8.40 (d, J=3.2 Hz, 1H), 8.32 (d, J=5.2 Hz, 1H), 8.11 (d, J=5.6 Hz, 1H), 7.70 (d, J=1.2 Hz, 1H), 6.92 (d, J=3.2 Hz, 1H).

Examples 27 & 28

Synthesis of 7-(1H-pyrrolo[2,3-c]pyridin-1-yl)-2,6-naphthyridin-1-amine (27) & 1-methoxy-7-(1H-pyrrolo[2,3-c]pyridin-1-yl)-2,6-naphthyridine (28)

Scheme 27

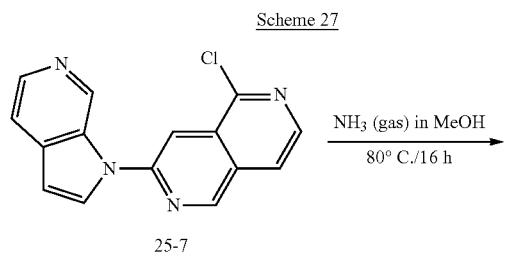

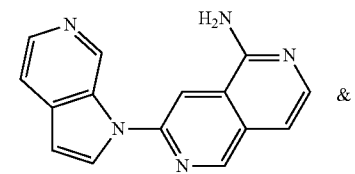

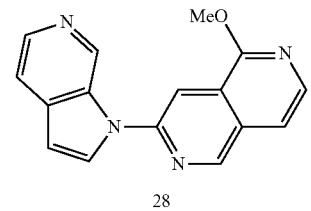 [SMILES: Fc1nccc2cnc(-n3ccc4ccncc43)cc12]

Synthesis of 7-(1H-pyrrolo[2,3-c]pyridin-1-yl)-2,6-naphthyridin-1-amine (27) & 1-methoxy-7-(1H-pyrrolo[2,3-c]pyridin-1-yl)-2,6-naphthyridine (28)

Ammonia gas was bubbled into a solution of 1-chloro-7-(1H-pyrrolo[2,3-c]pyridin-1-yl)-2,6-naphthyridine (20 mg, 0.07 mmol, 25-7) in methanol (5 mL) for 1 h at ambient temperature. The resulting solution was kept for 16 hours at 80° C. in a sealed tube. After cooling down to ambient temperature, the resulting solution was concentrated under reduced pressure and the residue was purified by silica gel column chromatography, eluted with 1~2% methanol in dichloromethane to afford 1-methoxy-7-(1H-pyrrolo[2,3-c]pyridin-1-yl)-2,6-naphthyridine as a light yellow solid: MS (ESI, m/z): 277.2 [M+1]$^+$; $^1$H NMR (300 MHz, CD$_3$OD) δ 9.65 (s, 1H), 9.28 (s, 1H), 8.25-8.20 (m, 3H), 8.09 (d, J=6.9 Hz, 1H), 7.67 (d, J=4.8 Hz, 1H), 7.50 (d, J=5.7 Hz, 1H), 6.85 (d, J=3.3 Hz, 1H), 4.16 (s, 3H); and 7-(1H-pyrrolo[2,3-c]pyridin-1-yl)-2,6-naphthyridin-1-amine as a light yellow solid (6 mg, 32%): MS (ESI, m/z): 262.2 [M+1]$^+$; $^1$H NMR (300 MHz, DMSO-d$_6$) δ 9.69 (s, 1H), 9.22 (s, 1H), 8.44 (s, 1H), 8.30-8.27 (m, 2H), 7.95 (d, J=5.7 Hz, 1H), 7.68 (d, J=5.1 Hz, 1H), 7.24 (br s, 2H), 7.13 (d, J=6.0 Hz, 1H), 6.90 (d, J=3.3 Hz, 1H).

Example 29

Synthesis of 1-(5-(1-(2-fluoroethyl)-1H-pyrazol-3-yl)pyrimidin-2-yl)-1H-pyrrolo[2,3-c]pyridine (29)

Scheme 28

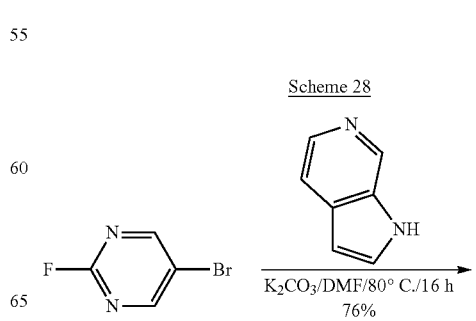

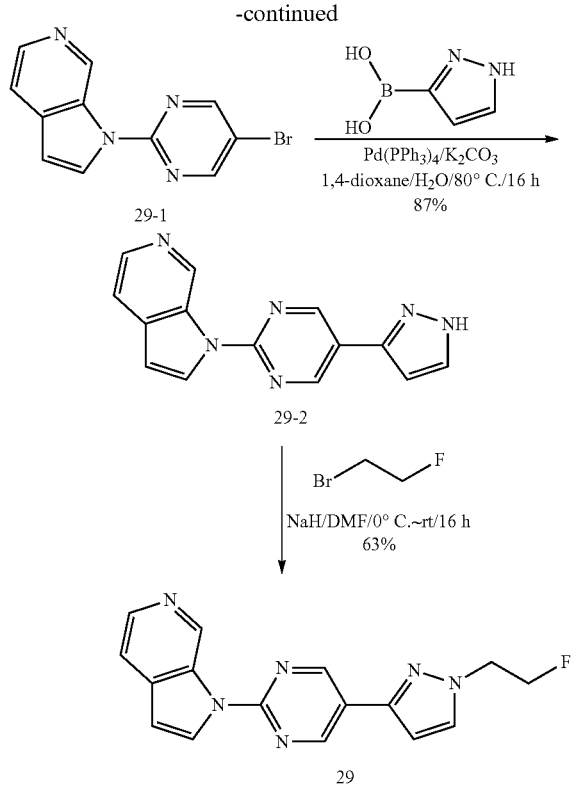

Step 1: Synthesis of 1-(5-bromopyrimidin-2-yl)-1H-pyrrolo[2,3-c]pyridine (29-1)

To a stirred solution of 1H-pyrrolo[2,3-c]pyridine (0.73 g, 6.22 mmol) and 5-bromo-2-fluoropyrimidine (1 g, 5.65 mmol) in N,N-dimethylformamide (50 mL) was added potassium carbonate (1.56 g, 11.30 mmol). The resulting mixture was stirred for 16 hours at 80° C. under nitrogen atmosphere. After cooling down to ambient temperature, the resulting mixture was diluted with water (100 mL) and extracted with ethyl acetate (3×100 mL). The combined organic layers was washed with brine (4×50 mL) and dried over anhydrous sodium sulfate. After filtration, the filtrate was concentrated under reduced pressure and the residue was purified by silica gel column chromatography, eluted with 1~2% methanol in dichloromethane to afford 1-(5-bromopyrimidin-2-yl)-1H-pyrrolo[2,3-c]pyridine as a yellow solid: MS (ESI, m/z): 275.1, 277.1 [M+1]$^+$; $^1$H NMR (400 MHz, CDCl$_3$) δ 9.91 (s, 1H), 8.42 (d, J=4.8 Hz, 1H), 8.28 (d, J=5.2 Hz, 1H), 8.01 (s, 2H), 7.52 (t, J=4.4 Hz, 1H), 6.69 (d, J=4.8 Hz, 1H).

Step 2: Synthesis of 1-(5-(1H-pyrazol-3-yl)pyrimidin-2-yl)-1H-pyrrolo[2,3-c]pyridine (29-2)

A mixture of 1-(5-bromopyrimidin-2-yl)-1H-pyrrolo[2,3-c]pyridine (300 mg, 1.09 mmol), potassium carbonate (301 mg, 2.18 mmol) and tetrakis(triphenylphosphine)palladium (0) (126 mg, 0.11 mmol) in 1,4-dioxane (20 mL) and water (2 mL) was heated to 80° C. under nitrogen atmosphere, followed by the addition of (1H-pyrazol-3-yl)boronic acid (244 mg, 2.18 mmol) in several portions. After additional 16 hours, the resulting mixture was cooled down to ambient temperature and concentrated under reduced pressure. The residue was purified by silica gel column chromatography, eluted with 1~2% methanol in dichloromethane to afford 1-(5-(1H-pyrazol-3-yl)pyrimidin-2-yl)-1H-pyrrolo[2,3-c]pyridine as a colorless solid: MS (ESI, m/z): 263.2 [M+1]$^+$; $^1$H NMR (300 MHz, DMSO-d$_6$) δ 10.08 (s, 1H), 9.40 (s, 2H), 9.08 (s, 1H), 8.59 (d, J=6.3 Hz, 1H), 8.33 (d, J=6.3 Hz, 1H), 7.94 (d, J=1.8 Hz, 1H), 7.29 (d, J=3.3 Hz, 1H), 7.03 (d, J=2.4 Hz, 1H).

Step 3: Synthesis of 1-(5-(1-(2-fluoroethyl)-1H-pyrazol-3-yl)pyrimidin-2-yl)-1H-pyrrolo[2,3-c]pyridine (29)

A solution of 1-(5-(1H-pyrazol-3-yl)pyrimidin-2-yl)-1H-pyrrolo[2,3-c]pyridine (100 mg, 0.38 mmol) in N,N-dimethylformamide (10 mL) was treated with sodium hydride (76 mg, 1.91 mmol, 60% w/w dispersed into mineral oil) for 10 min at 0° C. followed by the addition of 1-bromo-2-fluoroethane (242 mg, 1.91 mmol). After stirring for 16 hours at ambient temperature, the reaction was quenched by water (50 mL) and extracted with ethyl acetate (3×50 mL). The combined organic layers was washed with brine (3×50 mL) and dried over anhydrous sodium sulfate. After filtration, the filtrate was concentrated under reduced pressure and the residue was purified by silica gel column chromatography, eluted with 1~2% methanol in dichloromethane to afford 1-(5-(1-(2-fluoroethyl)-1H-pyrazol-3-yl)pyrimidin-2-yl)-1H-pyrrolo[2,3-c]pyridine as a colorless solid: MS (ESI, m/z): 308.9 [M+1]$^+$; $^1$H NMR (300 MHz, DMSO-d$_6$) δ 9.97 (s, 1H), 9.29 (s, 2H), 8.48 (d, J=3.6 Hz, 1H), 8.35 (d, J=5.1 Hz, 1H), 7.95 (s, 1H), 7.70 (d, J=5.1 Hz, 1H), 6.99 (s, 1H), 6.90 (d, J=3.0 Hz, 1H), 4.92 (t, J=4.2 Hz, 1H), 4.75 (t, J=4.2 Hz, 1H), 4.59 (t, J=4.2 Hz, 1H), 4.48 (t, J=4.2 Hz, 1H).

Example 30

Synthesis of 1-(5-(3-fluoroprop-1-ynyl)-4-vinylpyridin-2-yl)-1H-pyrrolo[2,3-c]pyridine (30)

Scheme 29

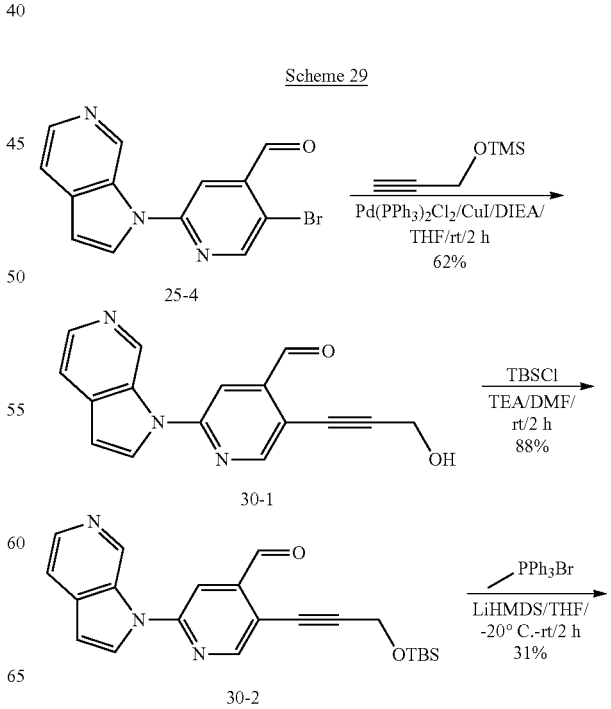

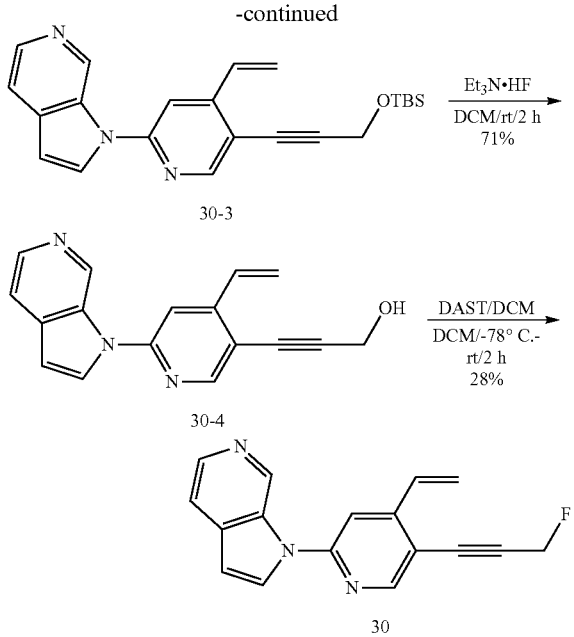

Step 1: Synthesis of 5-(3-hydroxyprop-1-ynyl)-2-(1H-pyrrolo[2,3-c]pyridin-1-yl)isonicotinaldehyde (30-1)

To a stirred solution of 5-bromo-2-(1H-pyrrolo[2,3-c]pyridin-1-yl)isonicotinaldehyde (3 g, 9.43 mmol, 25-4) in tetrahydrofuran (100 mL) were added trimethyl(prop-2-yn-1-yloxy)silane (1.45 g, 11.32 mmol), copper(I) iodide (0.18 g, 0.94 mmol), N-ethyl-N-isopropylpropan-2-amine (24.3 g, 189 mmol) and bis(triphenylphosphine) palladium(II) dichloride (0.33 g, 0.47 mmol). The resulting mixture was stirred for 2 hours at ambient temperature under nitrogen atmosphere. The resulting mixture was concentrated under reduced pressure and the residue was purified by silica gel column chromatography, eluted with 1~2% methanol in dichloromethane to afford 5-(3-hydroxyprop-1-yn-1-yl)-2-(1H-pyrrolo[2,3-c]pyridin-1-yl)isonicotinaldehyde as a yellow solid: MS (ESI, m/z): 278.2 [M+1]$^+$; $^1$H NMR (300 MHz, DMSO-d$_6$) δ 9.72 (s, 1H), 8.64 (s, 1H), 8.31-8.30 (m, 2H), 7.88 (s, 1H), 7.86-7.65 (m, 1H), 7.14 (d, J=7.5 Hz, 1H), 6.87 (d, J=3.3 Hz, 1H), 5.45 (t, J=6.0 Hz, 1H), 4.38 (d, J=6.0 Hz, 2H).

Step 2: Synthesis of 5-(3-(tert-butyldimethylsilyloxy)prop-1-ynyl)-2-(1H-pyrrolo[2,3-c]pyridin-1-yl)isonicotinaldehyde (30-2)

To a stirred solution of 5-(3-hydroxyprop-1-yn-1-yl)-2-(1H-pyrrolo[2,3-c]pyridin-1-yl)isonicotinaldehyde (1.8 g, 6.17 mmol) in N,N-dimethylformamide (50 mL) were added triethylamine (1.25 g, 12.33 mmol) and tert-butylchlorodimethylsilane (1.39 g, 9.25 mmol). The resulting solution was stirred for 2 hours at ambient temperature and quenched with water (150 mL). The resulting mixture was extracted with dichloromethane (3×50 mL). The combined organic layers was washed with brine (2×100 mL) and dried over anhydrous sodium sulfate. After filtration, the filtrate was concentrated under reduced pressure and the residue was purified by silica gel column chromatography, eluted with 1~2% methanol in dichloromethane to afford 5-(3-(tert-butyldimethylsilyloxy)prop-1-ynyl)-2-(1H-pyrrolo[2,3-c]pyridin-1-yl)isonicotinaldehyde as a light yellow solid: MS (ESI, m/z): 392.2 [M+1]$^+$; $^1$H NMR (300 MHz, DMSO-d$_6$) δ 10.37 (s, 1H), 9.82 (s, 1H), 8.90 (s, 1H), 8.52 (d, J=3.6 Hz, 1H), 8.33 (d, J=5.4 Hz, 1H), 8.18 (s, 1H), 7.70 (d, J=5.4 Hz, 1H), 6.92 (d, J=3.3 Hz, 1H), 4.69 (s, 2H), 0.92 (s, 9H), 0.17 (s, 6H).

Step 3: Synthesis of 1-(5-(3-(tert-butyldimethylsilyloxy)prop-1-ynyl)-4-vinylpyridin-2-yl)-1H-pyrrolo[2,3-c]pyridine (30-3)

To a mixture of 5-(3-(tert-butyldimethylsilyloxy)prop-1-ynyl)-2-(1H-pyrrolo[2,3-c]pyridin-1-yl)isonicotinaldehyde (0.4 g, 0.92 mmol) and methyltriphenylphosphonium bromide (0.49 g, 1.38 mmol) in tetrahydrofuran (20 mL) was added 1 M solution of lithium hexamethyldisilazide (1 mL, 1 mmol) in tetrahydrofuran at −20° C. under nitrogen atmosphere. The resulting mixture was stirred for 2 hours at ambient temperature and quenched by saturated aqueous solution of ammonium chloride (50 mL). The resulting mixture was extracted with ethyl acetate (3×50 mL). The combined organic layers was washed with brine (2×50 mL) and dried over anhydrous sodium sulfate. After filtration, the filtrate was concentrated under reduced pressure and the residue was purified by silica gel column chromatography, eluted with 1~2% methanol in dichloromethane to afford 1-(5-(3-(tert-butyldimethylsilyloxy)prop-1-ynyl)-4-vinylpyridin-2-yl)-1H-pyrrolo[2,3-c]pyridine as a light yellow solid: MS (ESI, m/z): 390.2 [M+1]$^+$; $^1$H NMR (300 MHz, DMSO-d$_6$) δ 9.79 (s, 1H), 8.67 (s, 1H), 8.50 (d, J=3.6 Hz, 1H), 8.29 (d, J=5.4 Hz, 1H), 8.11 (s, 1H), 7.66 (d, J=5.1 Hz, 1H), 7.17-7.07 (m, 1H), 6.88 (d, J=3.6 Hz, 1H), 6.53 (d, J=8.7 Hz, 1H), 5.79 (d, J=11.1 Hz, 1H), 4.43 (s, 2H), 0.92 (s, 9H), 0.17 (s, 6H)

Step 4: Synthesis of 3-(6-(1H-pyrrolo[2,3-c]pyridin-1-yl)-4-vinylpyridin-3-yl)prop-2-yn-1-ol (30-4)

A solution of 1-(5-(3-(tert-butyldimethylsilyloxy)prop-1-ynyl)-4-vinylpyridin-2-yl)-1H-pyrrolo[2,3-c]pyridine (0.2 g, 0.51 mmol) in dichloromethane (20 mL) was treated with triethylamine trihydrofluoride (66 mg, 0.41 mmol) for 2 hours at ambient temperature. The reaction was quenched with saturated aqueous solution of sodium bicarbonate (10 mL) and extracted with dichloromethane (3×50 mL). The combined organic layers was washed with brine (20 mL) and dried over anhydrous sodium sulfate. After filtration, the filtrate was concentrated under reduced pressure and the residue was purified by silica gel column chromatography, eluted with 1~2% methanol in dichloromethane to afford 3-(6-(1H-pyrrolo[2,3-c]pyridin-1-yl)-4-vinylpyridin-3-yl)prop-2-yn-1-ol as a light yellow solid: MS (ESI, m/z): 276.2 [M+1]$^+$; $^1$H NMR (300 MHz, DMSO-d$_6$) δ 9.78 (s, 1H), 8.65 (s, 1H), 8.48 (d, J=3.6 Hz, 1H), 8.29 (d, J=5.4 Hz, 1H), 8.10 (s, 1H), 7.66 (d, J=5.1 Hz, 1H), 7.17-7.07 (m, 1H), 6.88 (d, J=3.6 Hz, 1H), 6.53 (d, J=8.7 Hz, 1H), 5.79 (d, J=11.1 Hz, 1H), 5.46 (t, J=6.0 Hz, 1H), 4.41 (d, J=6.0 Hz, 2H).

Step 5: Synthesis of 1-(5-(3-fluoroprop-1-ynyl)-4-vinylpyridin-2-yl)-1H-pyrrolo[2,3-c]pyridine (30)

To a stirred solution of 3-(6-(1H-pyrrolo[2,3-c]pyridin-1-yl)-4-vinylpyridin-3-yl)prop-2-yn-1-ol (140 mg, 0.31 mmol) in dichloromethane (20 mL) was added diethylaminosulfurtrifluoride (492 mg, 3.05 mmol) at −78° C. The resulting mixture was stirred for 2 hours at ambient temperature and quenched with saturated aqueous solution of sodium bicarbonate (50 mL). The resulting mixture was extracted with dichloromethane (3×50 mL). The combined organic layers was washed with brine (100 mL) and dried over anhydrous sodium sulfate. After filtration, the filtrate was concentrated under reduced pressure and the residue was purified by silica gel column chromatography, eluted with 1~2% methanol in dichloromethane to afford 1-(5-(3-fluoroprop-1-ynyl)-4-vinylpyridin-2-yl)-1H-pyrrolo[2,3-c]pyridine as a light yellow solid: MS (ESI, m/z): 278.1 [M+1]$^+$; $^1$H NMR (300 MHz, CD$_3$OD) δ 9.74 (s, 1H), 8.65 (s, 1H), 8.27 (d, J=3.6 Hz, 1H), 8.21 (d, J=5.4 Hz, 1H), 7.92 (s, 1H), 7.67 (d, J=6.3 Hz, 1H), 7.20-7.11 (m, 1H), 6.84 (d, J=3.9 Hz, 1H), 6.36 (d, J=17.7 Hz, 1H), 5.73 (d, J=11.1 Hz, 1H), 5.39 (s, 1H), 5.36 (s, 1H).

Example 31

Synthesis of 1-(5-(4-(2-chloroethyl)piperidin-1-yl)pyridin-2-yl)-1H-pyrrolo[2,3-c]pyridine (31)

Scheme 30

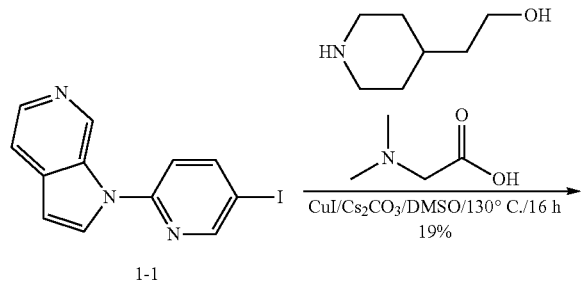

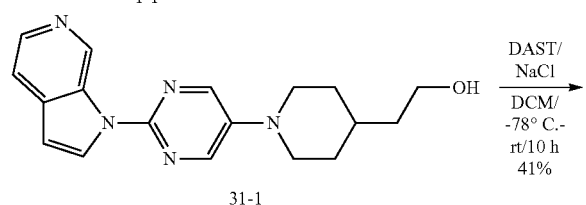

Step 1: Synthesis of 2-(1-(6-(1H-pyrrolo[2,3-c]pyridin-1-yl)pyridin-3-yl)piperidin-4-yl)ethanol (31-1)

To a solution of 1-(5-iodopyridin-2-yl)-1H-pyrrolo[2,3-c]pyridine (0.8 g, 2.49 mmol, 1-1) in dimethyl sulfoxide (30 mL) were added 2-(piperidin-4-yl)ethanol (0.64 g, 4.98 mmol), copper(I) iodide (0.28 g, 1.49 mmol), cesium carbonate (3.24 g, 9.97 mmol) and 2-(dimethylamino)acetic acid (0.1 g, 0.99 mmol). The resulting mixture was stirred for 16 hours at 130° C. under nitrogen atmosphere. After cooling down to ambient temperature, the resulting mixture was diluted with water (100 mL) and extracted with ethyl acetate (3×50 mL). The combined organic layers was washed with brine (3×100 mL) and dried over anhydrous sodium sulfate. After filtration, the filtrate was concentrated under reduced pressure and the residue was purified by silica gel column chromatography, eluting with 1~2% methanol in dichloromethane to afford 2-(1-(6-(1H-pyrrolo[2,3-c]pyridin-1-yl)pyridin-3-yl)piperidin-4-yl)ethanol as a colorless solid: MS (ESI, m/z): 323.1 [M+1]$^+$; $^1$H NMR (300 MHz, DMSO-d$_6$) δ 8.90 (s, 1H), 8.30-8.27 (m, 2H), 8.06 (d, J=6.0 Hz, 1H), 7.99 (d, J=3.6 Hz, 1H), 7.78 (s, 2H), 6.84 (d, J=3.6 Hz, 1H), 4.35 (t, J=5.7 Hz, 1H), 3.84-3.78 (m, 2H), 3.48-3.43 (m, 2H), 2.78-2.71 (m, 2H), 1.79-1.73 (m, 2H), 1.68-1.54 (m, 1H), 1.42-1.37 (m, 2H), 1.29-1.21 (m, 2H).

Step 2: Synthesis of 1-(5-(4-(2-chloroethyl)piperidin-1-yl)pyridin-2-yl)-1H-pyrrolo[2,3-c]pyridine (31)

To a solution of 2-(1-(6-(1H-pyrrolo[2,3-c]pyridin-1-yl)pyridin-3-yl)piperidin-4-yl)ethanol (100 mg, 0.31 mmol) in dichloromethane (10 mL) was added diethylaminosulfurtrifluoride (DAST, 548 mg, 3.40 mmol) at −78° C. The resulting solution was stirred for 10 hours at ambient temperature and quenched with brine (30 mL), extracted with dichloromethane (3×50 mL). The combined organic layers was washed with brine (50 mL) and dried over anhydrous sodium sulfate. After filtration, the filtrate was concentrated under reduced pressure and the residue was purified by silica gel column chromatography, eluted with 1~2% methanol in dichloromethane to afford 1-(5-(4-(2-chloroethyl)piperidin-1-yl)pyridin-2-yl)-1H-pyrrolo[2,3-c]pyridine as a colorless solid: MS (ESI, m/z): 341.1 [M+1]$^+$; $^1$H NMR (400 MHz, CDCl$_3$) δ 9.53 (s, 1H), 8.34-8.31 (m, 1H), 8.27 (d, J=2.4 Hz, 1H), 7.88 (d, J=3.2 Hz, 1H), 7.66 (t, J=4.8 Hz, 1H), 7.45-7.43 (m, 2H), 6.76 (d, J=7.2 Hz, 1H), 3.79-3.76 (m, 2H), 3.65 (t, J=7.6 Hz, 2H), 2.89-2.83 (m, 2H), 1.91-1.89 (m, 2H), 1.81-1.77 (m, 3H), 1.49-1.41 (m, 2H).

Example 32

Synthesis of 1-(5-(2-fluoroethoxy)-4-methylpyridin-2-yl)-1H-pyrrolo[2,3-c]pyridine (32)

Scheme 31

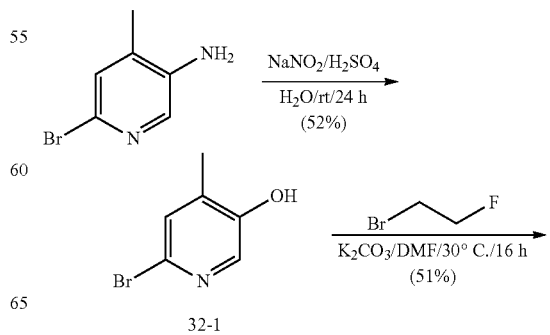

-continued

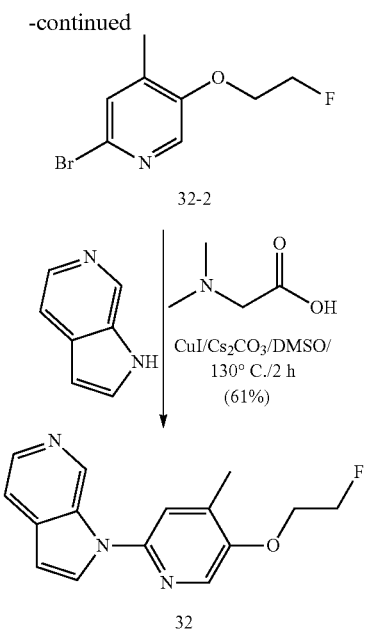

Step 1: Synthesis of 6-bromo-4-methylpyridin-3-ol (32-1)

To a stirred solution of 6-bromo-4-methylpyridin-3-amine (2.0 g, 10.7 mmol) in aqueous 40% sulfuric acid (20 mL) was added sodium nitrite (1.1 g, 16.1 mmol) at 0° C. The resulting mixture was stirred for 30 min at 0° C. and 24 hours at ambient temperature. The resulting mixture was diluted with water (200 mL) and neutralized by potassium carbonate. The resulting mixture was extracted with ethyl acetate (3×100 mL). The combined organic layers was washed with brine (2×100 mL) and dried over anhydrous sodium sulfate. After filtration, the filtrate was concentrated under reduced pressure and the residue was purified by silica gel column chromatography, eluted with 0.5~1.5% methanol in dichloromethane to afford 6-bromo-4-methylpyridin-3-ol as a light yellow solid: MS (ESI, m/z): 188.0, 190.0 [M+1]$^+$; $^1$H NMR (300 MHz, DMSO-d$_6$) δ 7.89 (s, 1H), 7.83 (s, 1H), 7.35 (s, 1H), 2.13 (s, 3H).

Step 2: Synthesis of 2-bromo-5-(2-fluoroethoxy)-4-methylpyridine (32-2)

To a stirred solution of 6-bromo-4-methylpyridin-3-ol (0.50 g, 1.31 mmol) in N,N-dimethylformamide (20 mL) were added potassium carbonate (0.55 g, 3.95 mmol) and 1-bromo-2-fluoroethane (0.25 mg, 1.99 mmol). The resulting mixture was stirred for 16 hours at 30° C. and quenched with water (150 mL). The resulting mixture was extracted with ethyl acetate (3×50 mL). The combined organic layers was washed with brine (2×50 mL) and dried over anhydrous sodium sulfate. After filtration, the filtrate was concentrated under reduced pressure and the residue was purified by silica gel column chromatography, eluted with 0.5~1% methanol in dichloromethane to afford 2-bromo-5-(2-fluoroethoxy)-4-methylpyridine as a light yellow solid: MS (ESI, m/z): 234.1, 236.1 [M+1]$^+$; $^1$H NMR (300 MHz, DMSO-d$_6$) δ 8.07 (s, 1H), 7.48 (s, 1H), 4.85-4.82 (m, 1H), 4.69-4.66 (m, 1H), 4.41-4.38 (m, 1H), 4.31-4.27 (m, 1H), 2.18 (s, 3H).

Step 3: Synthesis of 1-(5-(2-fluoroethoxy)-4-methylpyridin-2-yl)-1H-pyrrolo[2,3-c]pyridine (32)

To a stirred mixture of 1H-pyrrolo[2,3-c]pyridine (70 mg, 0.59 mmol) and cesium carbonate (770 mg, 2.37 mmol) in dimethyl sulfoxide (20 ml) were added 2-bromo-5-(2-fluoroethoxy)-4-methylpyridine (173 mg, 0.59 mmol), dimethylglycine (36.7 mg, 0.36 mmol) and copper (I) iodide (67.7 mg, 0.36 mmol). The resulting mixture was stirred for 2 hours at 130° C. under a nitrogen atmosphere. After cooling down to ambient temperature, the reaction mixture was quenched with water (100 mL) and extracted with ethyl acetate (3×50 mL). The combined organic layers was washed with brine (2×50 mL) and dried over anhydrous sodium sulfate. After filtration, the filtrate was concentrated under reduced pressure and the residue was purified by silica gel column chromatography, eluted with 0.5~1% methanol in dichloromethane to afford 1-(5-(2-fluoroethoxy)-4-methylpyridin-2-yl)-1H-pyrrolo[2,3-c]pyridine as a light yellow solid: MS (ESI, m/z): 272.2 [M+1]$^+$; $^1$H NMR (300 MHz, DMSO-d$_6$) δ 9.61 (s, 1H), 8.28 (s, 1H), 8.24 (d, J=5.1 Hz, 1H), 8.19 (d, J=3.3 Hz, 1H), 7.75 (s, 1H), 7.64-7.62 (m, 1H), 6.78 (d, J=3.0 Hz, 1H), 4.89 (t, J=3.6 Hz, 1H), 4.73 (t, J=3.6 Hz, 1H), 4.49 (t, J=3.6 Hz, 1H), 4.39 (t, J=3.6 Hz, 1H), 2.33 (s, 3H).

Example 33

Synthesis of 1-(4-methoxy-5-(prop-1-ynyl)pyridin-2-yl)-1H-pyrrolo[2,3-c]pyridine (33)

Scheme 32

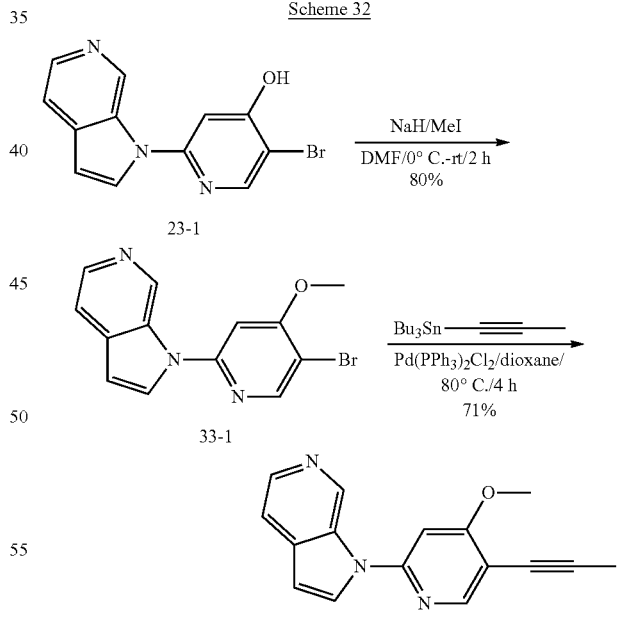

Step 1: Synthesis of 1-(5-bromo-4-methoxypyridin-2-yl)-1H-pyrrolo[2,3-c]pyridine (33-1)

A solution of 5-bromo-2-(1H-pyrrolo[2,3-c]pyridin-1-yl)pyridin-4-ol (100 mg, 0.35 mmol, 23-1) in N,N-dimethylformamide (10 mL) was treated with sodium hydride (15 mg, 0.38 mmol, 60% w/w dispersed by mineral oil) for 10 min at 0° C. followed by the addition of iodomethane (54 mg, 0.38 mmol). The resulting solution was stirred for 2 hours at ambient temperature, then quenched with water (50 mL) and extracted with dichloromethane (3×30 mL). The combined organic layers was washed with brine (3×20 mL) and dried over anhydrous sodium sulfate. After filtration, the filtrate was concentrated under reduced pressure and the residue was purified by silica gel column chromatography, eluted with 1~2% methanol in dichloromethane to afford 1-(5-bromo-4-methoxypyridin-2-yl)-1H-pyrrolo[2,3-c]pyridine as a light yellow solid: MS (ESI, m/z): 304.1, 306.1 [M+1]$^+$; $^1$H NMR (300 MHz, CD$_3$OD) δ 9.72 (s, 1H), 8.54 (s, 1H), 8.28-8.23 (m, 2H), 7.72 (d, J=5.4 Hz, 1H), 7.37 (s, 1H), 6.87 (d, J=3.3 Hz, 1H), 4.11 (s, 3H).

Step 2: Synthesis of 1-(4-methoxy-5-(prop-1-ynyl) pyridin-2-yl)-1H-pyrrolo[2,3-c]pyridine (33)

To a stirred solution of 1-(5-bromo-4-methoxypyridin-2-yl)-1H-pyrrolo[2,3-c]pyridine (60 mg, 0.18 mmol) in 1,4-dioxane (20 mL) were added dibutyl(prop-1-yn-1-yl)(propyl)stannane (84 mg, 0.27 mmol) and bis(triphenylphosphine)palladium(II) chloride (6 mg, 0.09 mmol). The resulting mixture was stirred at 80° C. for 4 hours under nitrogen atmosphere. After cooling down to ambient temperature, the resulting mixture was concentrated under reduced pressure and the residue was purified by silica gel column chromatography, eluted with 1~2% methanol in dichloromethane to afford 1-(4-methoxy-5-(prop-1-ynyl) pyridin-2-yl)-1H-pyrrolo[2,3-c]pyridine as a light yellow solid: MS (ESI, m/z): 264.1 [M+1]$^+$; $^1$H NMR (300 MHz, CD$_3$OD) δ 9.70 (s, 1H), 8.38 (s, 1H), 8.23-8.21 (m, 2H), 7.68 (d, J=8.1 Hz, 1H), 7.27 (s, 1H), 6.84 (d, J=3.3 Hz, 1H), 4.06 (s, 3H), 2.11 (s, 3H).

Example 34

Synthesis of N-(4-methoxyphenyl)-6-(1H-pyrrolo[2,3-c]pyridin-1-yl)nicotinamide (34)

Scheme 33

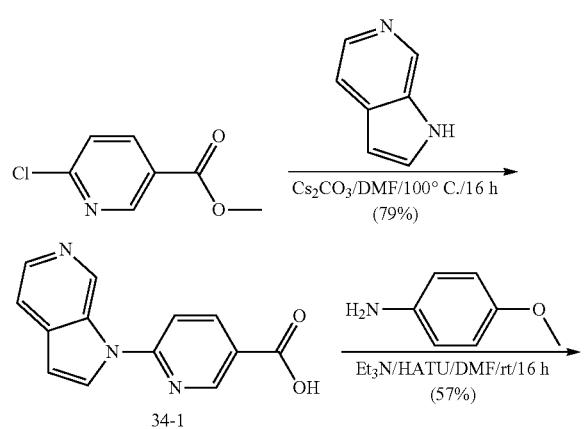

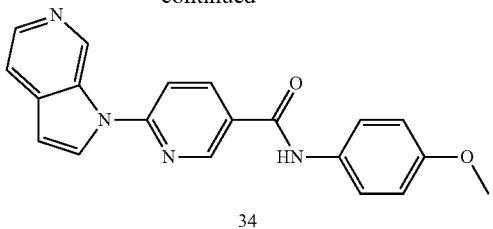

34

Step 1: Synthesis of 6-(1H-pyrrolo[2,3-c]pyridin-1-yl)nicotinic acid (34-1)

To a solution of 1H-pyrrolo[2,3-c]pyridine (1.0 g, 8.5 mmol) in N,N-dimethylformamide (30 mL) were added methyl 6-chloronicotinate (1.7 g, 10.2 mmol) and cesium carbonate (8.3 g, 25.4 mmol) at ambient temperature. The resulting mixture was stirred for 16 hours at 100° C. After cooling down to ambient temperature, the resulting mixture was filtered through Celite and the filtrate was concentrated under reduced pressure. The residue was purified by silica gel column chromatography, eluted with 1~3% methanol (1% acetic acid, v/v) in dichloromethane to afford 6-(1H-pyrrolo[2,3-c]pyridin-1-yl)nicotinic acid as a colorless solid: MS (ESI, m/z): 240.1 [M+1]$^+$; $^1$H NMR (300 MHz, DMSO-d$_6$) δ 13.80 (br s, 1H), 10.08 (s, 1H), 9.18 (s, 1H), 9.00 (d, J=3.3 Hz, 1H), 8.55-8.51 (m, 2H), 8.24 (d, J=6.0 Hz, 1H), 8.16 (d, J=8.7 Hz, 1H), 7.28 (d, J=3.6 Hz, 1H).

Step 2: Synthesis of N-(4-methoxyphenyl)-6-(1H-pyrrolo[2,3-c]pyridin-1-yl)nicotinamide (34)

To a solution of 6-(1H-pyrrolo[2,3-c]pyridin-1-yl)nicotinic acid (239 mg, 1 mmol) in N,N-dimethylformamide (30 mL) were added 4-methoxybenzenamine (246 mg, 2 mmol), triethylamine (202 mg, 2 mmol) and O-(7-azabenzotriazol-1-yl)-N,N,N',N'-tetramethyluronium hexafluorophosphate (HATU, 760 mg, 2 mmol). The resulting solution was stirred for 16 hours at ambient temperature, then quenched with water (100 mL) and extracted with ethyl acetate (3×100 mL). The combined organic layers was washed with brine (5×50 mL) and dried over anhydrous sodium sulfate. After filtration, the filtrate was concentrated under reduced pressure and the residue was purified by silica gel column chromatography, eluted with 0.5~2% methanol in dichloromethane to afford N-(4-methoxyphenyl)-6-(1H-pyrrolo[2,3-c]pyridin-1-yl)nicotinamide as a light yellow solid: MS (ESI, m/z): 345.1 [M+1]$^+$; $^1$H NMR (400 MHz, DMSO-d$_6$) δ 10.34 (s, 1H), 9.88 (s, 1H), 9.15 (s, 1H), 8.61-8.52 (m, 1H), 8.43 (d, J=3.3 Hz, 1H), 8.33 (d, J=5.1 Hz, 1H), 8.05 (d, J=8.7 Hz, 1H), 7.72-7.68 (m, 3H), 6.98-6.92 (m, 3H), 3.76 (s, 3H).

Example 35

Synthesis of N-(3-fluoropropyl)-6-(1H-pyrrolo[2,3-c]pyridin-1-yl)pyridin-3-amine (35)

Scheme 34

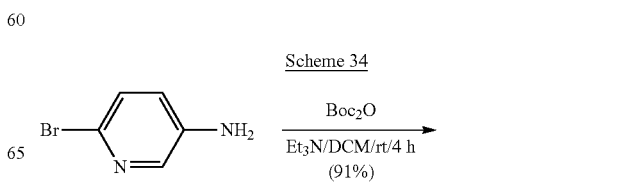

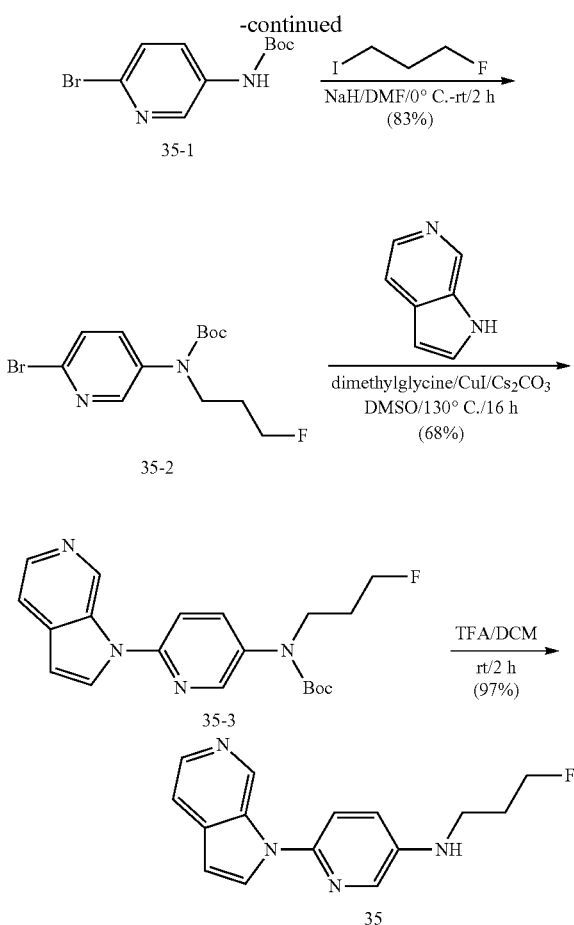

Step 1: Synthesis of tert-butyl 6-bromopyridin-3-ylcarbamate (35-1)

To a solution of 6-bromopyridin-3-amine (5.4 g, 28.9 mmol) in dichloromethane (200 mL) were added triethylamine (4.4 g, 43.3 mmol) and di-tert-butyl dicarbonate (7.6 g, 34.7 mmol). The resulting solution was stirred for 4 hours at ambient temperature and quenched with water (300 mL). The organic layer was separated and dried over anhydrous sodium sulfate. After filtration, the filtrate was concentrated under reduced pressure and the residue was purified by silica gel column chromatography, eluted with 2~10% ethyl acetate in petroleum ether to afford tert-butyl (6-bromopyridin-3-yl)carbamate as a colorless solid: MS (ESI, m/z): 273.1, 275.1 [M+1]$^+$; $^1$H NMR (300 MHz, DMSO-d$_6$) δ 9.72 (s, 1H), 8.45 (d, J=1.8 Hz, 1H), 7.83 (d, J=5.4 Hz, 1H), 7.53 (d, J=5.7 Hz, 1H), 1.48 (s, 9H).

Step 2: Synthesis of tert-butyl 6-bromopyridin-3-yl(3-fluoropropyl)carbamate (35-2)

To a solution of tert-butyl (6-bromopyridin-3-yl)carbamate (2.0 g, 7.3 mmol) in dimethylformamide (50 mL) was added sodium hydride (0.6 g, 14.7 mmol, 60% dispersed into mineral oil) at 0° C. After stirring for 10 min, 1-fluoro-3-iodopropane (2.7 g, 14.7 mmol) was added to the resulting solution. The resulting solution was stirred for 2 hours at ambient temperature, then quenched with water (200 mL) and extracted with ethyl acetate (3×100 mL). The combined organic layers was washed with brine (5×50 mL) and dried over anhydrous sodium sulfate. After filtration, the filtrate was concentrated under reduced pressure, and the residue was purified by silica gel column chromatography, eluted with 5~10% ethyl acetate in petroleum ether to afford tert-butyl 6-bromopyridin-3-yl(3-fluoropropyl)carbamate as a light yellow solid: MS (ESI, m/z): 333.2, 335.2 [M+1]$^+$; $^1$H NMR (400 MHz, DMSO-d$_6$) δ 8.28 (s, 1H), 7.49-7.47 (m, 2H), 4.57 (t, J=5.6 Hz, 1H), 4.45 (t, J=5.6 Hz, 1H), 3.81 (t, J=7.2 Hz, 2H), 2.05-2.00 (m, 1H), 1.99-1.92 (m, 1H), 1.49 (s, 9H).

Step 3: Synthesis of tert-butyl 6-(1H-pyrrolo[2,3-c]pyridin-1-yl)pyridin-3-yl(3-fluoropropyl)carbamate (35-3)

To a solution of 1H-pyrrolo[2,3-c]pyridine (125 mg, 1.1 mmol) in dimethyl sulfoxide (15 mL) were added cesium carbonate (919 mg, 2.8 mmol), tert-butyl (6-bromopyridin-3-yl)(3-fluoropropyl)carbamate (235 mg, 0.7 mmol), dimethylglycine (29.1 mg, 0.3 mmol) and copper(I) iodide (81 mg, 0.4 mmol) at ambient temperature under nitrogen atmosphere. After stirring for 16 hours at 130° C., the resulting mixture was cooled down to ambient temperature and diluted with water (100 mL). The resulting mixture was extracted with ethyl acetate (3×60 mL). The combined organic layers was washed with brine (3×50 mL) and dried over anhydrous sodium sulfate. After filtration, the filtrate was concentrated under reduced pressure and the residue was purified by silica gel column chromatography, eluted with 0.5~1.5% methanol in dichloromethane to afford tert-butyl 6-(1H-pyrrolo[2,3-c]pyridin-1-yl)pyridin-3-yl(3-fluoropropyl)carbamate as a light yellow solid: MS (ESI, m/z): 371.1 [M+1]$^+$; $^1$H NMR (400 MHz, CDCl$_3$) δ 9.67 (br s, 1H), 8.53 (d, J=2.0 Hz, 1H), 8.40 (br s, 1H), 7.88 (d, J=3.2 Hz, 1H), 7.82 (d, J=7.2 Hz, 1H), 7.61 (d, J=4.4 Hz, 1H), 7.51 (d, J=8.4 Hz, 1H), 6.76 (d, J=3.2 Hz, 1H), 4.75 (t, J=4.8 Hz, 1H), 4.64 (t, J=4.8 Hz, 1H), 4.01 (t, J=4.8 Hz, 1H), 3.95 (t, J=4.8 Hz, 1H), 1.49 (s, 9H), 1.33-1.24 (m, 2H).

Step 4: Synthesis of N-(3-fluoropropyl)-6-(1H-pyrrolo[2,3-c]pyridin-1-yl)pyridin-3-amine (35)

A solution of tert-butyl (6-(1H-pyrrolo[2,3-c]pyridin-1-yl)pyridin-3-yl)(3-fluoropropyl)carbamate (150 mg, 0.4 mmol) in dichloromethane (10 mL) was treated with trifluoroacetic acid (3 mL) for 2 hours at ambient temperature. The reaction was diluted with water (30 mL) and neutralized with potassium carbonate. The resulting mixture was extracted with dichloromethane (3×100 mL). The combined organic layers was dried over anhydrous sodium sulfate. After filtration, the filtrate was concentrated under reduced pressure and the residue was purified by a silica gel column, eluted with 0.5-1.5% methanol in dichloromethane to afford N-(3-fluoropropyl)-6-(1H-pyrrolo[2,3-c]pyridin-1-yl)pyridin-3-amine as an off white solid: MS (ESI, m/z): 271.1 [M+1]$^+$; $^1$H NMR (400 MHz, CDCl$_3$) δ 9.38 (s, 1H), 8.33 (d, J=5.2 Hz, 1H), 8.02 (s, 1H), 7.80 (s, 1H), 7.60 (d, J=4.4 Hz, 1H), 7.32 (d, J=8.4 Hz, 1H), 7.17-7.11 (m, 1H), 6.71 (d, J=3.2 Hz, 1H), 4.75 (t, J=4.8 Hz, 1H), 4.64 (t, J=4.8 Hz, 1H), 4.05 (br s, 1H), 3.45 (t, J=4.8 Hz, 2H), 2.16-2.12 (m, 1H), 2.10-2.03 (m, 1H).

Example 36

Synthesis of N-(2-fluoroethyl)-6-(1H-pyrrolo[2,3-c]pyridin-1-yl)pyridin-3-amine (36)

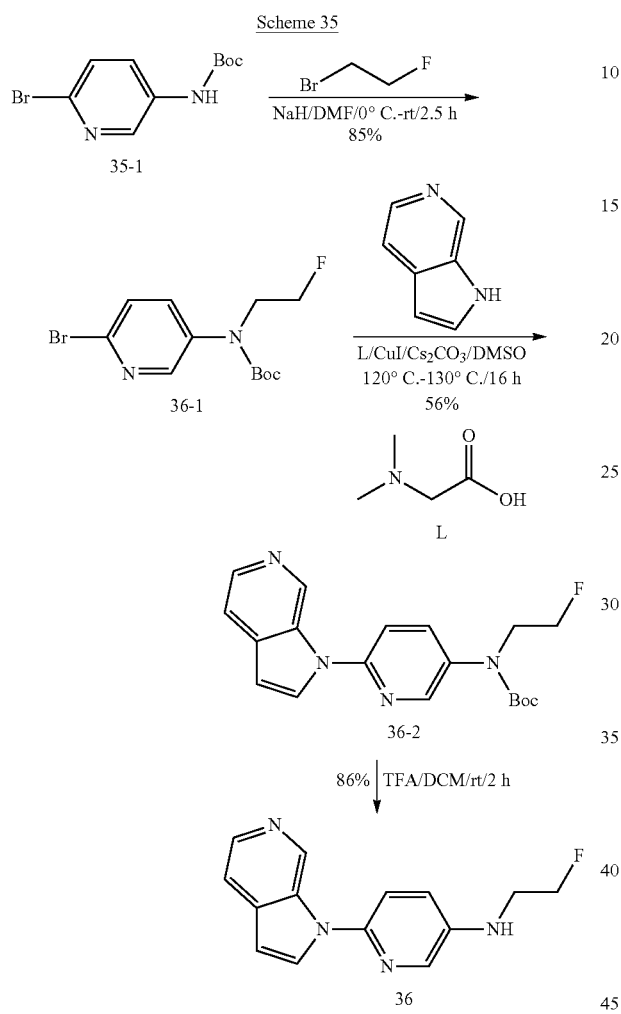

Step 1: Synthesis of tert-butyl 6-bromopyridin-3-yl(2-fluoroethyl)carbamate (36-1)

A solution of tert-butyl (6-bromopyridin-3-yl)carbamate (200 mg, 0.73 mmol, 35-1) in N,N-dimethylformamide (20 mL) was treated with sodium hydride (117 mg, 2.93 mmol, 60% w/w dispersed by mineral oil) at 0° C. for 40 min, followed by the addition of 1-bromo-2-fluoroethane (186 mg, 1.46 mmol). After additional 2 hours at ambient temperature, the reaction was diluted with water (50 mL) and extracted with ethyl acetate (2×60 mL). The combined organic layers was washed with brine (5×50 mL) and dried over anhydrous sodium sulfate. After filtration, the filtrate was concentrated under reduced pressure to give tert-butyl 6-bromopyridin-3-yl(2-fluoroethyl)carbamate as a light yellow solid: MS (ESI, m/z): 319.0, 321.0 [M+1]$^+$; $^1$H NMR (400 MHz, CDCl$_3$) δ 8.32 (s, 1H), 7.51-7.45 (m, 2H), 4.70 (t, J=4.8 Hz, 1H), 4.58 (t, J=4.8 Hz, 1H), 3.92 (t, J=4.8 Hz, 1H), 3.86 (t, J=4.8 Hz, 1H), 1.46 (s, 9H).

Step 2: Synthesis of tert-butyl 6-(1H-pyrrolo[2,3-c]pyridin-1-yl)pyridin-3-yl(2-fluoroethyl)carbamate (36-2)

To a solution of 1H-pyrrolo[2,3-c]pyridine (129 mg, 1.09 mmol) in dimethyl sulfoxide (15 mL) were added cesium carbonate (951 mg, 2.92 mmol), tert-butyl (6-bromopyridin-3-yl)(2-fluoroethyl)carbamate (233 mg, 0.73 mmol), 2-(dimethylamino)acetic acid (30 mg, 0.29 mmol) and copper(I) iodide (83 mg, 0.44 mmol) at ambient temperature under an atmosphere of nitrogen. After stirring for 16 hour at 120° C., the reaction was cooled down to ambient temperature and diluted with water (80 mL). The resulting mixture was extracted with ethyl acetate (2×60 mL) and the combined organic layers was washed with brine (2×50 mL), dried over anhydrous sodium sulfate. After filtration, the filtrate was concentrated under reduced pressure and the residue was purified by silica gel column chromatography, eluted with 1~2% methanol in dichloromethane to give tert-butyl 6-(1H-pyrrolo[2,3-c]pyridin-1-yl)pyridin-3-yl(2-fluoroethyl)carbamate as a colorless solid: MS (ESI, m/z): 357.2 [M+1]$^+$; $^1$H NMR (400 MHz, CDCl$_3$) δ 9.67 (br s, 1H), 8.53 (d, J=2.0 Hz, 1H), 8.40 (br s, 1H), 7.88 (d, J=2.8 Hz, 1H), 7.82 (d, J=7.8 Hz, 1H), 7.62 (d, J=4.4 Hz, 1H), 7.51 (d, J=8.4 Hz, 1H), 6.76 (d, J=3.2 Hz, 1H), 4.76 (t, J=4.8 Hz, 1H), 4.64 (t, J=4.8 Hz, 1H), 4.01 (t, J=4.8 Hz, 1H), 3.94 (t, J=4.8 Hz, 1H), 1.49 (s, 9H).

Step 3: Synthesis of N-(2-fluoroethyl)-6-(1H-pyrrolo[2,3-c]pyridin-1-yl)pyridin-3-amine (36)

A solution of tert-butyl (6-(1H-pyrrolo[2,3-c]pyridin-1-yl)pyridin-3-yl)(2-fluoroethyl)carbamate (150 mg, 0.41 mmol) in dichloromethane (10 mL) was treated with trifluoroacetic acid (3 mL) for 2 hours at ambient temperature. The resulting solution was concentrated under reduced pressure and the residue was dissolved into dichloromethane again (50 mL). The resulting solution was washed with saturated aqueous solution of sodium bicarbonate (2×50 mL) and dried over anhydrous sodium sulfate. After filtration, the filtrate was concentrated under reduced pressure and the residue was purified by silica gel column chromatography, eluted with 1~2% methanol in dichloromethane to give N-(2-fluoroethyl)-6-(1H-pyrrolo[2,3-c]pyridin-1-yl)pyridin-3-amine as a colorless solid: MS (ESI, m/z): 257.2 [M+1]$^+$; $^1$H NMR (400 MHz, CDCl$_3$) δ 9.40 (s, 1H), 8.34 (d, J=5.2 Hz, 1H), 8.06 (d, J=2.8 Hz, 1H), 7.77 (d, J=3.2 Hz, 1H), 7.59 (d, J=5.2 Hz, 1H), 7.39 (t, J=9.6 Hz, 1H), 7.18-7.15 (m, 1H), 6.70 (d, J=3.2 Hz, 1H), 4.77 (t, J=4.8 Hz, 1H), 4.66 (t, J=4.8 Hz, 1H), 4.21 (br s, 1H), 3.56 (t, J=4.8 Hz, 1H), 3.53 (t, J=4.8 Hz, 1H).

Example 37

Synthesis of 1-(2-fluoro-3,3'-bipyridin-6-yl)-1H-pyrrolo[2,3-c]pyridine (37)

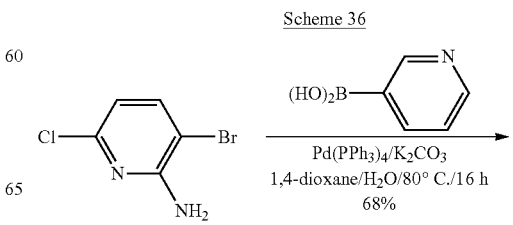

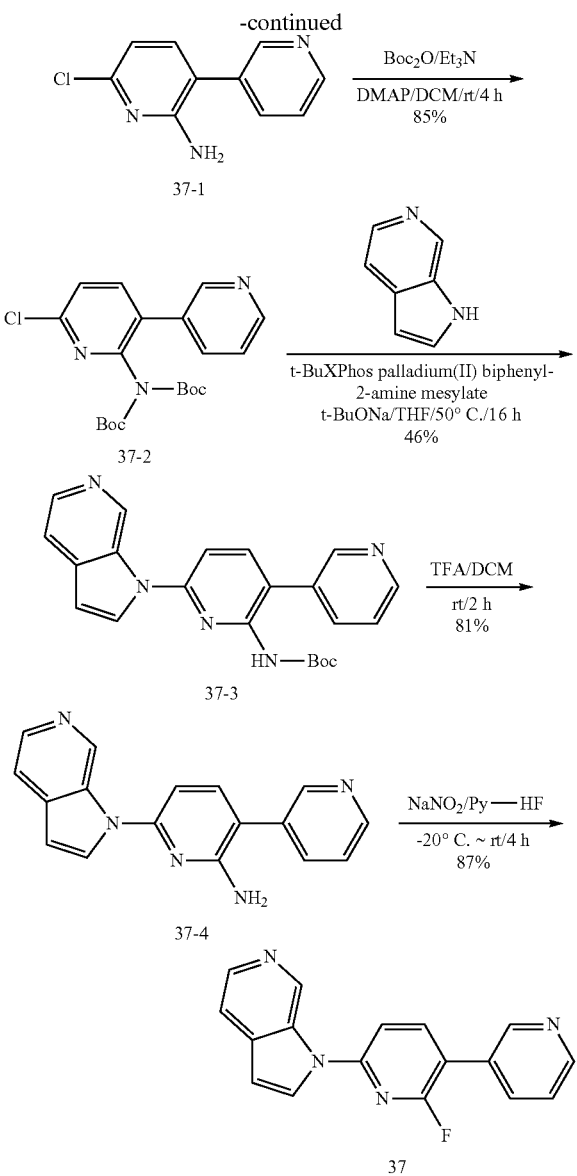

(s, 1H), 8.57 (dd, J=2.0 Hz, 4.4 Hz, 1H), 7.84-7.82 (m, 1H), 7.48-7.45 (m, 1H), 7.38 (d, J=7.6 Hz, 1H), 6.69 (d, J=11.6 Hz, 1H), 6.28 (br s, 2H).

Step 2: Synthesis of N,N-di-Boc protected 6-chloro-3,3'-bipyridin-2-amine (37-2)

To a solution of 6-chloro-3,3'-bipyridin-2-amine (0.68 g, 3.31 mmol) in dichloromethane (30 mL) were added di-tert-butyl dicarbonate (1.51 g, 6.95 mmol), triethylamine (0.67 g, 6.61 mmol) and N,N-dimethylpyridin-4-amine (40 mg, 0.33 mmol). The resulting solution was stirred for 4 hours at ambient temperature then concentrated under reduced pressure. The residue was purified by silica gel column chromatography, eluted with 0.5~1% methanol in dichloromethane to afford N,N-di-Boc protected 6-chloro-3,3'-bipyridin-2-amine as a light yellow solid: MS (ESI, m/z): 406.1 [M+1]$^+$; $^1$H NMR (300 MHz, DMSO-d$_6$) δ 8.64 (dd, J=1.2 Hz, 4.8 Hz, 1H), 8.59 (d, J=2.1 Hz, 1H), 8.10 (d, J=8.1 Hz, 1H), 7.81-7.75 (m, 2H), 7.58-7.54 (m, 1H), 1.23 (s, 9H), 1.20 (s, 9H).

Step 3: Synthesis of tert-butyl 6-(1H-pyrrolo[2,3-c]pyridin-1-yl)-3,3'-bipyridin-2-ylcarbamate (3)

To a solution of tert-butyl N-tert-butyloxycarbonyl-6-chloro-3,3'-bipyridin-2-ylcarbamate (0.9 g, 2.22 mmol) in tetrahydrofuran (40 mL) were added 1H-pyrrolo[2,3-c]pyridine (0.39 g, 3.33 mmol), sodium 2-methylpropan-2-olate (0.43 g, 4.43 mmol) and 2-di-tert-butylphosphino-2',4',6'-tri-iso-propyl-1,1'-biphenyl)(2'''-amino-1'',1'''-biphenyl-2''-yl)palladium(II) mesylate (0.18 g, 0.22 mmol) under nitrogen atmosphere. The resulting solution was stirred for 16 hours at 50° C. After cooling down to ambient temperature, the resulting mixture was concentrated under reduced pressure and the residue was purified by silica gel column chromatography, eluted with 1~2% methanol in dichloromethane to afford tert-butyl 6-(1H-pyrrolo[2,3-c]pyridin-1-yl)-3,3'-bipyridin-2-ylcarbamate as a light yellow solid: MS (ESI, m/z): 388.2 [M+1]$^+$; $^1$H NMR (400 MHz, DMSO-d$_6$) δ 10.06 (s, 1H), 9.75 (s, 1H), 8.70 (s, 1H), 8.55 (d, J=4.0 Hz, 1H), 8.40 (d, J=3.2 Hz, 1H), 8.30 (d, J=5.2 Hz, 1H), 8.05 (d, J=8.4 Hz, 1H), 7.92 (d, J=4.4 Hz, 1H), 7.83 (d, J=8.4 Hz, 1H), 7.65 (d, J=5.2 Hz, 1H), 7.48 (dd, J=4.8 Hz, 11.6 Hz, 1H), 6.87 (d, J=3.2 Hz, 1H), 1.24 (s, 9H).

Step 4: Synthesis of 6-(1H-pyrrolo[2,3-c]pyridin-1-yl)-3,3'-bipyridin-2-amine (37-4)

A solution of tert-butyl 6-(1H-pyrrolo[2,3-c]pyridin-1-yl)-3,3'-bipyridin-2-ylcarbamate (0.5 g, 1.29 mmol) in dichloromethane (30 mL) was treated with trifluoroacetic acid (3 mL) for 2 hours at ambient temperature. The resulting solution was concentrated under reduced pressure and the residue was dissolved into dichloromethane (100 mL), washed with saturated aqueous solution of sodium bicarbonate (100 mL). The organic layer was dried over anhydrous sodium sulfate and filtered. The filtration was concentrated under reduced pressure and the residue was purified by silica gel column chromatography, eluted with 1~2% methanol in dichloromethane to afford 6-(1H-pyrrolo[2,3-c]pyridin-1-yl)-3,3'-bipyridin-2-amine as a light yellow solid: MS (ESI, m/z): 288.2 [M+1]$^+$; $^1$H NMR (400 MHz, DMSO-d$_6$) δ 10.00 (s, 1H), 8.68 (d, J=5.6 Hz, 1H), 8.58 (t, J=3.6 Hz, 1H), 8.27-8.26 (m, 2H), 7.92 (d, J=8.0 Hz, 1H), Step 1: Synthesis of 6-chloro-3,3'-bipyridin-2-amine (37-1)

To a solution of 3-bromo-6-chloropyridin-2-amine (1 g, 4.82 mmol) in 1,4-dioxane (40 mL) and water (4 mL) were added pyridin-3-ylboronic acid (0.65 g, 5.30 mmol), potassium carbonate (1.33 g, 9.64 mmol) and tetrakis(triphenylphosphine)palladium(0) (0.56 g, 0.48 mmol). The resulting solution was stirred for 16 hours at 80° C. under nitrogen atmosphere. After cooling down to ambient temperature, the resulting mixture was diluted with water (100 mL) and extracted with ethyl acetate (3×100 mL). The combined organic layers was washed with brine (30 mL) and dried over anhydrous sodium sulfate. After filtration, the filtrate was concentrated under reduced pressure and the residue was purified by silica gel column chromatography, eluted with 1~2% methanol in dichloromethane to afford 6-chloro-3,3'-bipyridin-2-amine as a light yellow solid: MS (ESI, m/z): 206.1 [M+1]$^+$; $^1$H NMR (400 MHz, DMSO-d$_6$) δ 8.66

7.62 (d, J=5.2 Hz, 1H), 7.58 (d, J=7.6 Hz, 1H), 7.49 (dd, J=4.8 Hz, 7.6 Hz, 1H), 7.07 (d, J=8.0 Hz, 1H), 6.78 (d, J=3.2 Hz, 1H), 6.33 (br s, 2H).

Step 5: Synthesis of 1-(2-fluoro-3,3'-bipyridin-6-yl)-1H-pyrrolo[2,3-c]pyridine (37)

To a solution of 6-(1H-pyrrolo[2,3-c]pyridin-1-yl)-3,3'-bipyridin-2-amine (100 mg, 0.35 mmol) in hydrogenfluoride-pyridine (3 mL, 64~70% w/w) was added sodium nitrite (144 mg, 2.09 mmol) at −20° C. The resulting solution was stirred for 2 hours at ambient temperature and diluted with water (50 mL). The resulting mixture was extracted with ethyl acetate (3×80 mL). The combined organic layers was washed with brine (3×30 mL) and dried over anhydrous sodium sulfate. After filtration, the filtrate was concentrated under reduced pressure and the residue was purified by silica gel column chromatography, eluted with 1~2% methanol in dichloromethane to afford 1-(2-fluoro-3,3'-bipyridin-6-yl)-1H-pyrrolo[2,3-c]pyridine as an off-white solid: MS (ESI, m/z): 291.1 [M+1]$^+$; $^1$H NMR (400 MHz, DMSO-d$_6$) δ 9.80 (s, 1H), 8.91 (s, 1H), 8.66 (dd, J=1.6 Hz, 4.8 Hz, 1H), 8.48-8.43 (m, 2H), 8.34 (d, J=5.2 Hz, 1H), 8.13 (dd, J=1.2 Hz, 8.0 Hz, 1H), 8.02 (dd, J=1.2 Hz, 8.4 Hz, 1H), 7.70 (d, J=0.8 Hz, 1H), 7.58 (dd, J=4.8 Hz, 8.0 Hz, 1H), 6.93 (d, J=3.2 Hz, 1H).

Example 38

Synthesis of 3-(5-fluoro-1H-pyrrolo[2,3-c]pyridin-1-yl)isoquinoline (38)

Scheme 37

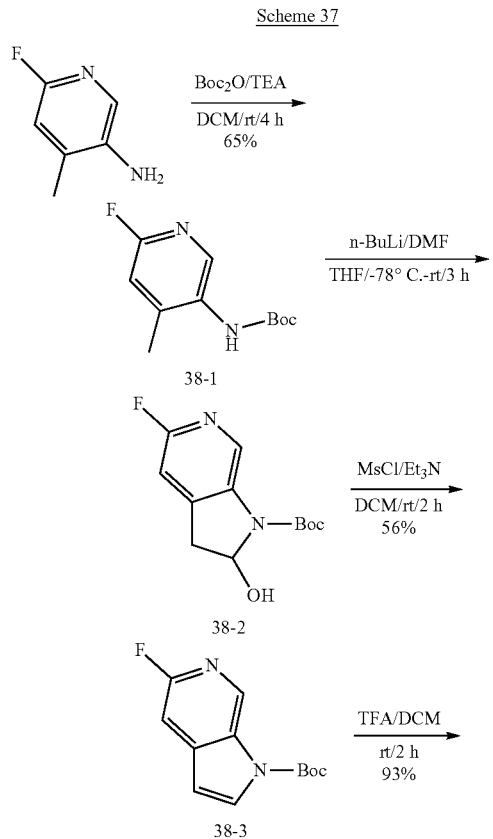

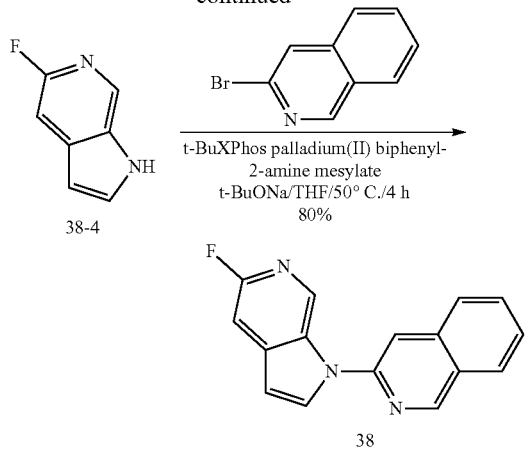

Step 1: Synthesis of tert-butyl 6-fluoro-4-methylpyridin-3-ylcarbamate (38-1)

To a solution of 6-fluoro-4-methylpyridin-3-amine (5.0 g, 39.6 mmol) in dichloromethane (100 mL) were added triethylamine (6.1 g, 59.5 mmol) and di-tert-butyl dicarbonate (10.4 g, 47.6 mmol). The resulting mixture was stirred for 4 hours at ambient temperature then concentrated under reduced pressure and the residue was purified by silica gel column chromatography, eluted with 5~10% ethyl acetate in petroleum ether to afford tert-butyl 6-fluoro-4-methylpyridin-3-ylcarbamate as a colorless solid: MS (ESI, m/z): 227.1 [M+1]$^+$; $^1$H NMR (300 MHz, CDCl$_3$) δ 8.38 (s, 1H), 6.76 (s, 1H), 6.16 (br s, 1H), 2.30 (s, 3H), 1.51 (s, 9H).

Step 2: Synthesis of tert-butyl 5-fluoro-1H-pyrrolo[2,3-c]pyridine-1-carboxylate (38-3)

A solution of tert-butyl (6-fluoro-4-methylpyridin-3-yl)carbamate (3.7 g, 16.3 mmol) in dry tetrahydrofuran (50 mL) was treated with 2.5 M solution of n-butyllithium (16.3 mL, 40.9 mmol) in hexane at −78° C. for 30 min, followed by the addition of N,N-dimethylformamide (1.4 g, 19.6 mmol). After additional 3 hours at ambient temperature, the reaction was quenched by saturated aqueous solution of ammonium chloride (50 mL) and extracted with ethyl acetate (3×100 mL). The combined organic layers was washed with brine (3×100 mL) and dried over anhydrous sodium sulfate. After filtration, the filtrate was concentrated under reduced pressure and the residue was dissolved into dichloromethane (25 mL) followed by the addition of triethylamine (1.6 g, 16.3 mmol) and methanesulfonyl chloride (1.8 g, 16.3 mmol). The resulting mixture was stirred for 2 hours at ambient temperature and concentrated under reduced pressure. The residue was purified by silica gel column chromatography, eluted with 10~20% ethyl acetate in petroleum ether to afford tert-butyl 5-fluoro-1H-pyrrolo[2,3-c]pyridine-1-carboxylate as a light yellow solid: MS (ESI, m/z): 237.1 [M+1]$^+$; $^1$H NMR (300 MHz, CDCl$_3$) δ 9.01 (s, 1H), 7.87 (d, J=3.3 Hz, 1H), 7.14 (s, 1H), 6.64 (d, J=3.6 Hz, 1H), 1.69 (s, 9H).

Step 3: Synthesis of 5-fluoro-1H-pyrrolo[2,3-c]pyridine (38-4)

A solution of tert-butyl 5-fluoro-1H-pyrrolo[2,3-c]pyridine-1-carboxylate (1.3 g, 5.5 mmol) in dichloromethane (20 mL) was treated with trifluoroacetic acid (2 mL) for 2 hours at ambient temperature. The resulting solution was concentrated under reduced pressure and the residue was dissolved into dichloromethane (50 mL), washed with saturated aqueous solution of sodium bicarbonate (100 mL). The organic layer was dried over anhydrous sodium sulfate and filtered. The filtration was concentrated under reduced pressure to afford 5-fluoro-1H-pyrrolo[2,3-c]pyridine as a colorless solid: MS (ESI, m/z): 137.1 [M+1]$^+$; $^1$H NMR (300 MHz, DMSO-d$_6$) δ 11.66 (br s, 1H), 8.34 (s, 1H), 7.71 (t, J=2.7 Hz, 1H), 7.17 (s, 1H), 6.51 (t, J=2.1 Hz, 1H).

Step 4: Synthesis of 3-(5-fluoro-1H-pyrrolo[2,3-c] pyridin-1-yl)isoquinoline (38)

To a solution of 5-fluoro-1H-pyrrolo[2,3-c]pyridine (50 mg, 0.37 mmol) in tetrahydrofuran (10 mL) were added 3-bromoisoquinoline (115 mg, 0.55 mmol), sodium 2-methylpropan-2-olate (70.6 mg, 0.74 mmol) and 2-di-tert-butylphosphino-2',4',6'-tri-iso-propyl-1,1'-biphenyl)(2'''-amino-1'',1'''-biphenyl-2''-yl)palladium(II) mesylate (29.2 mg, 0.037 mmol) under nitrogen atmosphere. The resulting mixture was kept for 4 hours at 50° C. After cooling down to ambient temperature, the mixture was concentrated under reduced pressure and the residue was purified by silica gel column chromatography, eluted with 1~2% methanol in dichloromethane to afford 3-(5-fluoro-1H-pyrrolo[2,3-c] pyridin-1-yl)isoquinoline as a colorless solid: MS (ESI, m/z): 264.1 [M+1]$^+$; $^1$H NMR (300 MHz, DMSO-d$_6$) δ 9.42 (s, 1H), 9.33 (s, 1H), 8.49 (d, J=3.3 Hz, 1H), 8.29 (s, 1H), 8.21 (d, J=8.1 Hz, 1H), 8.06 (d, J=8.4 Hz, 1H), 7.85 (t, J=8.1 Hz, 1H), 7.68 (t, J=7.8 Hz, 1H), 7.37 (d, J=1.2 Hz, 1H), 6.90 (d, J=3.3 Hz, 1H).

Example 39

Synthesis of 7-(1H-pyrrolo[2,3-c]pyridin-1-yl)-1,2,3,4-tetrahydro-1,6-naphthyridine (39)

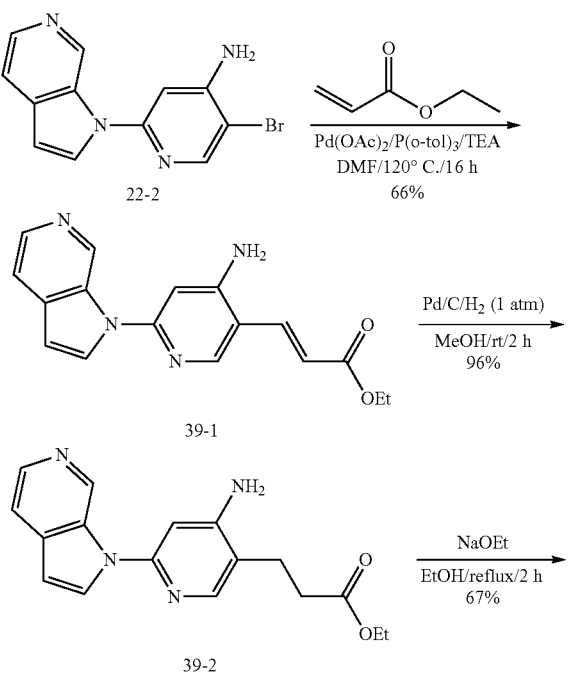

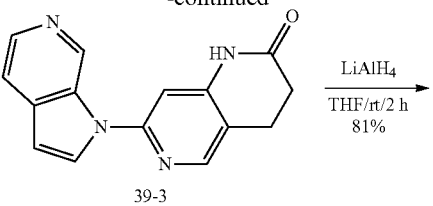

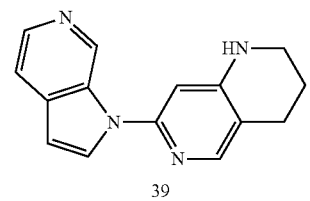

Step 1: Synthesis of (E)-ethyl 3-(4-amino-6-(1H-pyrrolo[2,3-c]pyridin-1-yl)pyridin-3-yl)acrylate (39-1)

To a solution of 5-bromo-2-(1H-pyrrolo[2,3-c]pyridin-1-yl)pyridin-4-amine (1 g, 3.46 mmol, 22-2) in N,N-dimethylformamide (50 mL) were added ethyl acrylate (1.38 g, 13.83 mmol), triethylamine (1.40 g, 13.83 mmol), palladium (II) acetate (0.078 g, 0.35 mmol) and tri-o-tolylphosphine (0.21 g, 0.69 mmol) at ambient temperature under nitrogen atmosphere. The resulting solution was stirred for 16 hours at 120° C. After cooling down to ambient temperature, the resulting mixture was concentrated under reduced pressure and the residue was purified by silica gel column chromatography, eluted with 1~3% methanol in dichloromethane to afford (E)-ethyl 3-(4-amino-6-(1H-pyrrolo[2,3-c]pyridin-1-yl)pyridin-3-yl)acrylate as a light yellow solid: MS (ESI, m/z): 309.2 [M+1]$^+$; $^1$H NMR (300 MHz, DMSO-d$_6$) δ 9.65 (s, 1H), 8.56 (s, 1H), 8.36-8.32 (m, 2H), 7.94-7.83 (m, 2H), 6.97 (t, J=4.2 Hz, 2H), 6.90 (br s, 2H), 6.60 (d, J=15.9 Hz, 1H), 4.21 (q, J=7.8 Hz, 2H), 1.21 (t, J=7.8 Hz, 3H).

Step 2: Synthesis of ethyl 3-(4-amino-6-(1H-pyrrolo[2,3-c]pyridin-1-yl)pyridin-3-yl)propanoate (39-2)

To a stirred solution of (E)-ethyl 3-(4-amino-6-(1H-pyrrolo[2,3-c]pyridin-1-yl)pyridin-3-yl)acrylate (0.5 g, 1.62 mmol) in methanol (120 mL) was added palladium on charcoal (50 mg, 10% w/w). The resulting mixture was kept under a hydrogen atmosphere (1 atm.) for 2 hours at ambient temperature. Then, the mixture was filtered through Celite and the filtrate was concentrated under reduced pressure to dryness to afford ethyl 3-(4-amino-6-(1H-pyrrolo[2,3-c] pyridin-1-yl)pyridin-3-yl)propanoate as a light yellow solid: MS (ESI, m/z): 311.1 [M+1]$^+$; $^1$H NMR (300 MHz, DMSO-d$_6$) δ 9.34 (s, 1H), 8.22 (d, J=5.4 Hz, 1H), 8.02 (d, J=3.3 Hz, 1H), 7.97 (s, 1H), 7.62 (d, J=4.5 Hz, 1H), 6.87 (s, 1H), 6.74 (d, J=7.2 Hz, 1H), 6.26 (br s, 2H), 4.08 (q, J=7.8 Hz, 2H), 2.75-2.71 (m, 2H), 2.54-2.51 (m, 2H), 1.15 (t, J=7.8 Hz, 3H).

Step 3: Synthesis of 7-(1H-pyrrolo[2,3-c]pyridin-1-yl)-3,4-dihydro-1,6-naphthyridin-2(1H)-one (39-3)

A solution of ethyl 3-(4-amino-6-(1H-pyrrolo[2,3-c]pyridin-1-yl)pyridin-3-yl)propanoate (50 mg, 0.16 mmol) and sodium ethanolate (54.8 mg, 0.81 mmol) in ethanol (5 mL) was refluxed for 2 hours. After cooling down to ambient temperature, the resulting mixture was neutralized by the addition of acetic acid (0.2 mL) and concentrated under reduced pressure, the residue was purified by silica gel column chromatography, eluted with 1~3% methanol in dichloromethane to afford 7-(1H-pyrrolo[2,3-c]pyridin-1-yl)-3,4-dihydro-1,6-naphthyridin-2(1H)-one as a colorless solid: MS (ESI, m/z): 265.0 [M+1]$^+$; $^1$H NMR (300 MHz, DMSO-d$_6$) δ 10.56 (br s, 1H), 9.49 (s, 1H), 8.32 (s, 1H), 8.26 (d, J=5.4 Hz, 1H), 8.07 (d, J=3.3 Hz, 1H), 7.66 (d, J=5.4 Hz, 1H), 7.16 (s, 1H), 6.82 (d, J=2.7 Hz, 1H), 2.96 (t, J=4.8 Hz, 2H), 2.57 (t, J=4.8 Hz, 2H).

Step 4: Synthesis of 7-(1H-pyrrolo[2,3-c]pyridin-1-yl)-1,2,3,4-tetrahydro-1,6-naphthyridine (39)

A solution of 7-(1H-pyrrolo[2,3-c]pyridin-1-yl)-3,4-dihydro-1,6-naphthyridin-2(1H)-one (28 mg, 0.11 mmol) in tetrahydrofuran (10 mL) was treated with lithium aluminum hydride (6 mg, 0.16 mmol) at ambient temperature for 2 hours. The reaction was quenched by the addition of sodium sulfate decahydrate (322 mg, 0.1 mmol) and filtered. The filtrate was concentrated under reduced pressure and the residue was purified by silica gel column chromatography, eluted with 1~3% methanol in dichloromethane to afford 7-(1H-pyrrolo[2,3-c]pyridin-1-yl)-1,2,3,4-tetrahydro-1,6-naphthyridine as a colorless solid: MS (ESI, m/z): 251.0 [M+1]$^+$; $^1$H NMR (300 MHz, DMSO-d$_6$) δ 9.43 (s, 1H), 8.21 (d, J=5.4 Hz, 1H), 8.00 (d, J=3.3 Hz, 1H), 7.85 (s, 1H), 7.61 (d, J=5.4 Hz, 1H), 6.91 (s, 1H), 6.79 (d, J=6.3 Hz, 1H), 6.68 (s, 1H), 3.27 (t, J=4.8 Hz, 2H), 2.68 (t, J=6.0 Hz, 2H), 1.83-1.79 (m, 2H).

Example 40

Synthesis of 2-fluoro-7-(1H-pyrrolo[2,3-c]pyridin-1-yl)-1,6-naphthyridine (40)

Scheme 39

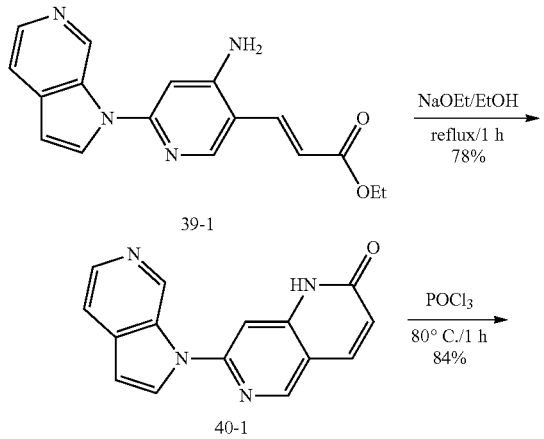

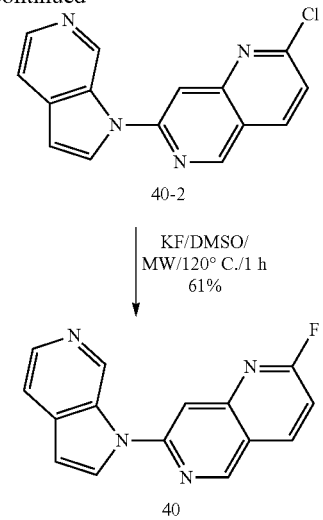

Step 1: Synthesis of 7-(1H-pyrrolo[2,3-c]pyridin-1-yl)-1,6-naphthyridin-2(1H)-one (40-1)

A solution of (E)-ethyl 3-(4-amino-6-(1H-pyrrolo[2,3-c]pyridin-1-yl)pyridin-3-yl)acrylate (150 mg, 0.49 mmol, 39-1) in ethanol (5 mL) was treated with sodium ethanolate (166 mg, 2.43 mmol) for 1 hour at 78° C. After cooling down to ambient temperature, the reaction was quenched by water (2 mL) and neutralized with acetic acid (0.2 mL). The resulting mixture was concentrated under reduced pressure and the residue was purified by silica gel column chromatography, eluted with 1~5% methanol in dichloromethane to afford 7-(1H-pyrrolo[2,3-c]pyridin-1-yl)-1,6-naphthyridin-2(1H)-one as an off white solid: MS (ESI, m/z): 263.1 [M+1]$^+$; $^1$H NMR (300 MHz, DMSO-d$_6$) δ 12.11 (br s, 1H), 9.59 (s, 1H), 8.89 (s, 1H), 8.31 (d, J=5.4 Hz, 1H), 8.18 (d, J=3.6 Hz, 1H), 8.05 (d, J=3.6 Hz, 1H), 7.66-7.64 (m, 1H), 7.49 (s, 1H), 6.88 (d, J=3.3 Hz, 1H), 6.55 (d, J=9.0 Hz, 1H).

Step 2: Synthesis of 2-chloro-7-(1H-pyrrolo[2,3-c]pyridin-1-yl)-1,6-naphthyridine (40-2)

A solution of 7-(1H-pyrrolo[2,3-c]pyridin-1-yl)-1,6-naphthyridin-2(1H)-one (100 mg, 0.38 mmol) in trichloro phosphorous oxide (5 mL) was stirred for 1 hour at 80° C. After cooling down to ambient temperature, the resulting mixture was concentrated under reduced pressure and the residue was taken up by dichloromethane (50 mL) and washed with saturated aqueous solution of sodium bicarbonate (2×20 mL). The organic layer was dried over anhydrous sodium sulfate. After filtration, the filtrate was concentrated under reduced pressure and the residue was purified by silica gel column chromatography, eluted with 1~2% methanol in dichloromethane to afford 2-chloro-7-(1H-pyrrolo[2,3-c]pyridin-1-yl)-1,6-naphthyridine as an off white solid: MS (ESI, m/z): 381.1 [M+1]$^+$; $^1$H NMR (300 MHz, DMSO-d$_6$) δ 9.85 (s, 1H), 9.55 (s, 1H), 8.71 (d, J=8.4 Hz, 1H), 8.50 (d, J=3.3 Hz, 1H), 8.32-8.28 (m, 2H), 7.72-7.61 (m, 2H), 6.93 (d, J=3.3 Hz, 1H).

Step 3: Synthesis of 2-fluoro-7-(1H-pyrrolo[2,3-c]pyridin-1-yl)-1,6-naphthyridine (40)

A mixture of 2-chloro-7-(1H-pyrrolo[2,3-c]pyridin-1-yl)-1,6-naphthyridine (100 mg, 0.37 mmol) and potassium fluoride (62 mg, 1.07 mmol) in dimethylsulfoxide (3 mL) was irradiated with microwave (100 W) for 1 hour at 120° C. After cooling down to ambient temperature, the mixture was diluted with water (20 mL) and extracted with dichloromethane (3×30 mL). The combined organic layer was washed with brine (3×50 mL) and dried over anhydrous sodium sulfate. After filtration, the filtrate was concentrated under reduced pressure and the residue was purified by column chromatography, eluted with 1~2% methanol in dichloromethane to afford 2-fluoro-7-(1H-pyrrolo[2,3-c]pyridin-1-yl)-1,6-naphthyridine as an off white solid: MS (ESI, m/z): 265.1 [M+1]$^+$; $^1$H NMR (300 MHz, DMSO-d$_6$) δ 10.08 (s, 1H), 9.59 (s, 1H), 9.16 (d, J=3.3 Hz, 1H), 8.96 (t, J=8.7 Hz, 1H), 8.56-8.51 (m, 2H), 8.13 (t, J=9.0 Hz, 1H), 7.61-7.58 (m, 1H), 7.35-7.58 (d, J=6.6 Hz, 1H).

Example 41

Synthesis of 1-(5-(1H-1,2,4-triazol-3-yl)pyridin-2-yl)-1H-pyrrolo[2,3-c]pyridine (41)

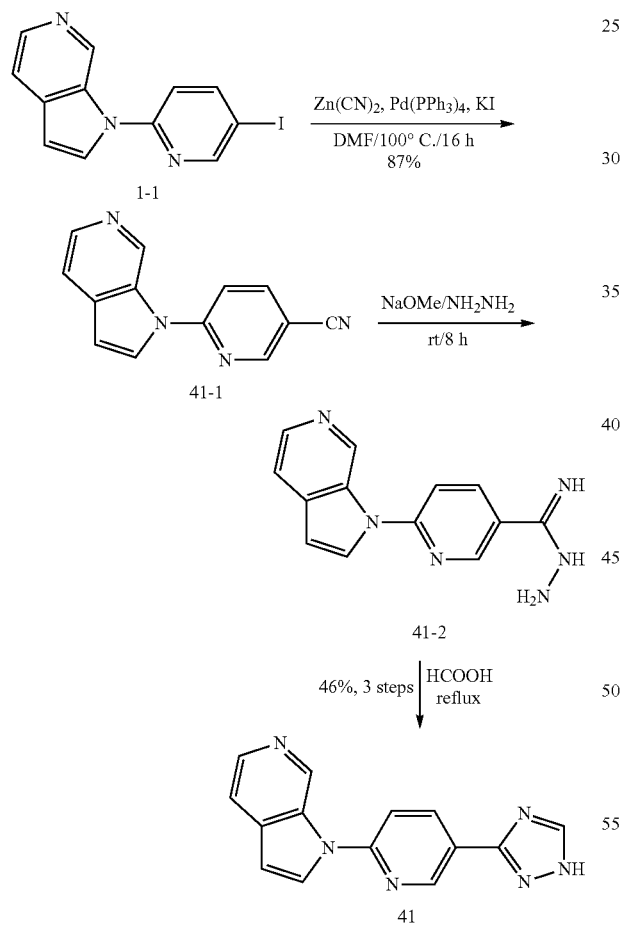

Scheme 40

Step 1: Synthesis of 6-(1H-pyrrolo[2,3-c]pyridin-1-yl)nicotinonitrile (41-1)

To a solution of 1-(5-iodopyridin-2-yl)-1H-pyrrolo[2,3-c]pyridine (1 g, 3.11 mmol, 1-1) in N,N-dimethylformamide (50 mL) were added dicyanozinc (0.73 g, 6.23 mmol), tetrakis(triphenylphosphine)palladium(0) (0.36 g, 0.31 mmol) and potassium iodide (0.052 g, 0.311 mmol). The resulting mixture was stirred for 16 hours at 100° C. under nitrogen atmosphere. After cooling down to ambient temperature, the reaction was diluted with water (150 mL) and extracted with dichloromethane (3×100 mL). The combined organic layers was washed with brine (5×80 mL) and dried over anhydrous sodium sulfate. After filtration, the filtrate was concentrated under reduced pressure and the residue was purified by a silica gel column chromatography, eluted with 20~30% ethyl acetate in petroleum ether to afford 6-(1H-pyrrolo[2,3-c]pyridin-1-yl)nicotinonitrile as an off white solid: MS (ESI, m/z): 221.0 [M+1]$^+$; $^1$H NMR (400 MHz, DMSO-d$_6$) δ 9.85 (s, 1H), 9.07 (d, J=1.2 Hz, 1H), 8.50 (d, J=2.0 Hz, 1H), 8.42 (d, J=3.6 Hz, 1H), 8.34 (d, J=5.2 Hz, 1H), 8.08 (d, J=8.4 Hz, 1H), 7.68 (d, J=5.2 Hz, 1H), 6.94 (d, J=3.2 Hz, 1H).

Step 2: Synthesis of 6-(1H-pyrrolo[2,3-c]pyridin-1-yl)nicotinimidohydrazide (41-2)

A solution of 6-(1H-pyrrolo[2,3-c]pyridin-1-yl)nicotinonitrile (600 mg, 2.72 mmol) in methanol (20 mL) was treated with sodium methanolate (736 mg, 13.63 mmol) for 4 hours at ambient temperature, followed by the addition of hydrazine (190, 5.95 mmol). After additional 4 hours at ambient temperature, the mixture was concentrated under reduced pressure and the residue was used in the next step without further purification: (ESI, m/z): 253.2 [M+1]$^+$.

Step 3: Synthesis of 1-(5-(1H-1,2,4-triazol-3-yl)pyridin-2-yl)-1H-pyrrolo[2,3-c]pyridine (41)

A solution of the above crude 6-(1H-pyrrolo[2,3-c]pyridin-1-yl)nicotinimidohydrazide in formic acid (15 mL) was refluxed for 16 hours. After cooling down to ambient temperature, the resulting mixture was concentrated under reduced pressure and the residue was purified by silica gel column chromatography, eluted with 1~2% methanol in dichloromethane to afford 1-(5-(1H-1,2,4-triazol-3-yl)pyridin-2-yl)-1H-pyrrolo[2,3-c]pyridine as a colorless solid: MS (ESI, m/z): 263.1 [M+1]$^+$; $^1$H NMR (400 MHz, DMSO-d$_6$) δ 10.08 (s, 1H), 9.26 (d, J=2.0 Hz, 1H), 9.04 (d, J=3.6 Hz, 1H), 8.68 (br s, 1H), 8.65-8.62 (m, 1H), 8.54 (d, J=6.4 Hz, 1H), 8.30 (d, J=8.4 Hz, 1H), 8.16 (d, J=8.8 Hz, 1H), 7.31 (t, J=3.2 Hz, 1H).

Examples 42 & 43

Synthesis of 1-(6-(1H-pyrrolo[2,3-c]pyridin-1-yl)pyridin-3-yl)piperidin-4-ol (42) and 1-(5-(4-fluoropiperidin-1-yl)pyridin-2-yl)-1H-pyrrolo[2,3-c]pyridine (43)

Scheme 41

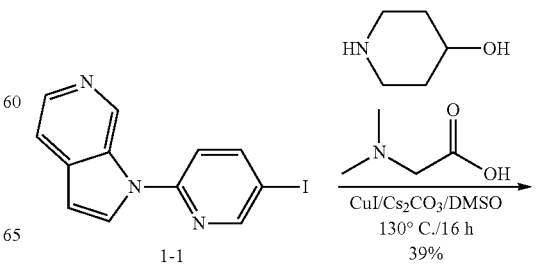

-continued

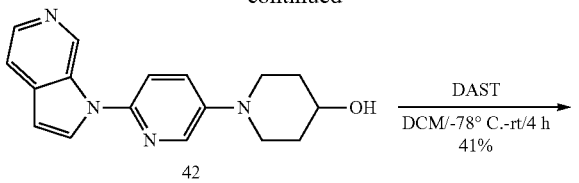

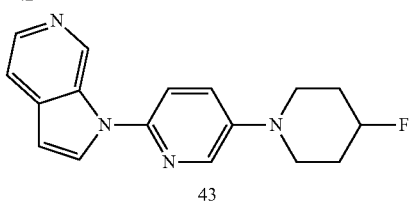

Step 1: Synthesis of 1-(6-(1H-pyrrolo[2,3-c]pyridin-1-yl)pyridin-3-yl)piperidin-4-ol (42)

To a solution of 1-(5-iodopyridin-2-yl)-1H-pyrrolo[2,3-c]pyridine (0.5 g, 1.56 mmol, 1-1) in dimethyl sulfoxide (20 mL) were added piperidin-4-ol (0.3 g, 3.11 mmol), cesium carbonate (2.1 g, 6.23 mmol), copper(I) iodide (0.18 g, 0.93 mmol) and 2-(dimethylamino)acetic acid (64.2 mg, 0.62 mmol). The resulting mixture was stirred for 16 hours at 130° C. under nitrogen atmosphere. After cooling down to ambient temperature, the resulting mixture was diluted with water (100 mL) and extracted with ethyl acetate (3×50 mL). The combined organic layers was washed with brine (3×60 mL) and dried over anhydrous sodium sulfate. After filtration, the filtrate was concentrated under reduced pressure and the residue was purified by silica gel column chromatography, eluted with 1~2% methanol in dichloromethane to afford 1-(6-(1H-pyrrolo[2,3-c]pyridin-1-yl)pyridin-3-yl)piperidin-4-ol as a light yellow solid: MS (ESI, m/z): 295.1 [M+1]$^+$; $^1$H NMR (300 MHz, DMSO-$d_6$) δ 8.91 (s, 1H), 8.30-8.21 (m, 2H), 8.06 (d, J=5.7 Hz, 1H), 8.00 (d, J=3.3 Hz, 1H), 7.62 (s, 2H), 6.84 (d, J=3.3 Hz, 1H), 4.74 (d, J=5.2 Hz, 1H), 3.71-3.57 (m, 3H), 2.98-2.91 (m, 2H), 1.89-1.81 (m, 2H), 1.53-1.42 (m, 2H).

Step 2: Synthesis of 1-(5-(4-fluoropiperidin-1-yl)pyridin-2-yl)-1H-pyrrolo[2,3-c]pyridine (43)

To a solution of 1-(6-(1H-pyrrolo[2,3-c]pyridin-1-yl)pyridin-3-yl)piperidin-4-ol (100 mg, 0.34 mmol) in dichloromethane (10 mL) was added diethylaminosulfurtrifluoride (DAST, 548 mg, 3.40 mmol) at −78° C. The resulting solution was stirred for 4 hours at ambient temperature and quenched with water (30 mL), extracted with dichloromethane (3×50 mL). The combined organic layers was washed with brine (50 mL) and dried over anhydrous sodium sulfate. After filtration, the filtrate was concentrated under reduced pressure and the residue was purified by silica gel column chromatography, eluted with 1~2% methanol in dichloromethane to afford 1-(5-(4-fluoropiperidin-1-yl)pyridin-2-yl)-1H-pyrrolo[2,3-c]pyridine as a colorless solid: MS (ESI, m/z): 297.1 [M+1]$^+$; $^1$H NMR (400 MHz, CD$_3$OD) δ 8.87 (s, 1H), 8.31 (d, J=3.2 Hz, 1H), 8.27 (d, J=6.0 Hz, 1H), 8.06 (d, J=6.0 Hz, 1H), 7.86 (d, J=3.6 Hz, 1H), 6.67 (dd, J=3.2 Hz, 8.8 Hz, 1H), 7.55 (d, J=8.8 Hz, 1H), 6.89 (d, J=3.6 Hz, 1H), 4.93-4.91 (m, 0.5H), 4.84-4.79 (m, 0.5H), 3.53-3.47 (m, 2H), 3.35-3.31 (m, 2H), 2.17-1.94 (m, 4H).

Examples 44 & 45

Synthesis of 1-(6'-fluoro-3,4'-bipyridin-6-yl)-1H-pyrrolo[2,3-c]pyridine (44) & Synthesis of N,N-dimethyl-6-(1H-pyrrolo[2,3-c]pyridin-1-yl)-3,4'-bipyridin-2'-amine (45)

Scheme 42

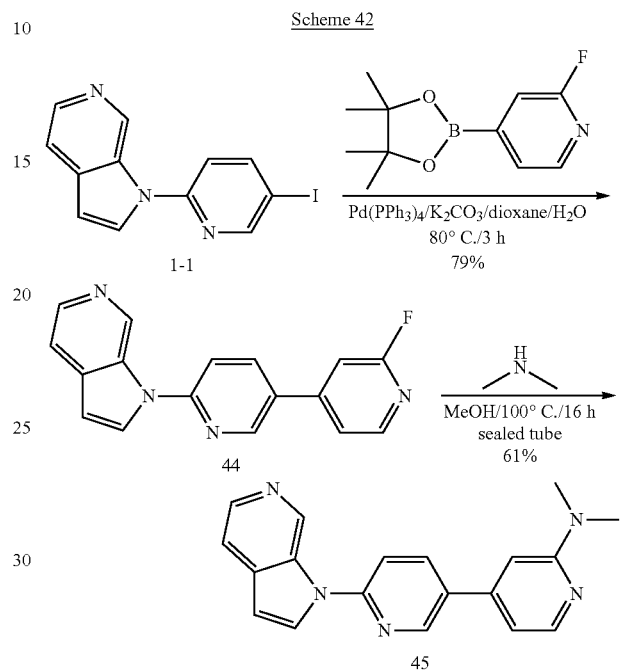

Step 1: Synthesis of 1-(6'-fluoro-3,4'-bipyridin-6-yl)-1H-pyrrolo[2,3-c]pyridine (44)

To a solution of 1-(5-iodopyridin-2-yl)-1H-pyrrolo[2,3-c]pyridine (100 mg, 0.31 mmol, 1-1) in 1,4-dioxane (20 mL) and water (5 mL) was added 2-fluoro-4-(4,4,5,5-tetramethyl-1,3,2-dioxaborolan-2-yl)pyridine (105 mg, 0.47 mmol), potassium carbonate (129 mg, 0.93 mmol) and tetrakis(triphenylphosphine)palladium(0) (18 mg, 0.016 mmol). The resulting mixture was stirred for 3 hours at 80° C. under nitrogen atmosphere. After cooling down to ambient temperature, the mixture was diluted with water (100 mL) and extracted with dichloromethane (3×100 mL). The combined organic layers was dried over anhydrous sodium sulfate and filtered. The filtrate was concentrated under reduced pressure and the residue was purified by silica gel column chromatography, eluted with 1~5% methanol in dichloromethane to afford 1-(5-(pyridin-3-yl)pyridin-2-yl)-1H-pyrrolo[2,3-c]pyridine as a colorless solid: MS (ESI, m/z): 291.0 [M+1]$^+$; $^1$H NMR (300 MHz, DMSO-$d_6$) δ 9.87 (s, 1H), 9.16 (d, J=2.1 Hz, 1H), 8.54 (dd, J=2.4 Hz, 8.7 Hz, 1H), 8.43 (d, J=3.3 Hz, 1H), 8.38 (d, J=5.1 Hz, 1H), 8.32 (d, J=5.1 Hz, 1H), 8.07 (d, J=8.7 Hz, 1H), 7.90 (dd, J=1.8 Hz, 3.6 Hz, 1H), 7.76 (s, 1H), 7.69 (dd, J=0.9 Hz, 5.4 Hz, 1H), 6.90 (d, J=3.3 Hz, 1H).

Step 2: Synthesis of N,N-dimethyl-6-(1H-pyrrolo[2,3-c]pyridin-1-yl)-3,4'-bipyridin-2'-amine (45)

To a solution of dimethylamine in methanol (5 mL, 33% w/w) was added 1-(6'-fluoro-3,4'-bipyridin-6-yl)-1H-pyrrolo[2,3-c]pyridine (50 mg, 0.17 mmol). The resulting solution was kept for 16 hours at 100° C. in a sealed tube. After cooling down to ambient temperature, the resulting solution was concentrated under reduced pressure and the residue was purified by silica gel column chromatography, eluted with 0.3~3% methanol in dichloromethane to afford N,N-dimethyl-6-(1H-pyrrolo[2,3-c]pyridin-1-yl)-3,4'-bipyridin-2'-amine as a colorless solid: MS (ESI, m/z): 316.0 [M+1]$^+$; $^1$H NMR (300 MHz, DMSO-d$_6$) δ 9.84 (s, 1H), 9.04 (d, J=2.1 Hz, 1H), 8.43-8.39 (m, 2H), 8.30 (d, J=5.4 Hz, 1H), 8.20 (d, J=6.0 Hz, 1H), 8.00 (d, J=8.7 Hz, 1H), 7.67 (dd, J=0.6 Hz, 5.1 Hz, 1H), 7.03-6.89 (m, 2H), 6.89 (d, J=3.3 Hz, 1H).

Example 46

Synthesis of 1-(5-(pyrimidin-4-yl)pyridin-2-yl)-1H-pyrrolo[2,3-c]pyridine (46)

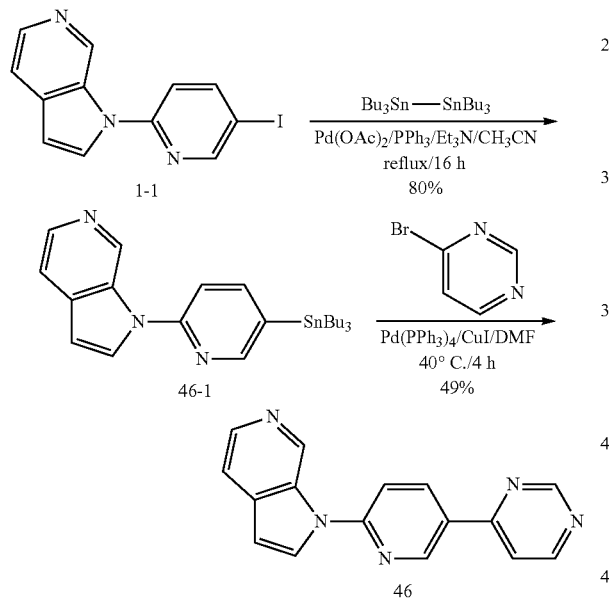

Step 1: Synthesis of 1-(5-(tributylstannyl)pyridin-2-yl)-1H-pyrrolo[2,3-c]pyridine (46-1)

To a solution of 1-(5-iodopyridin-2-yl)-1H-pyrrolo[2,3-c]pyridine (1.51 g, 4.67 mmol, 1-1) in acetonitrile (50 mL) were added 1,1,1,2,2,2-hexabutyldistannane (8.13 g, 14.01 mmol), triphenylphosphine (0.37 g, 1.40 mmol), triethylamine (4.73 g, 46.71 mmol) and palladium(II) acetate (0.11 g, 0.47 mmol). The resulting solution was refluxed for 16 hours under nitrogen atmosphere. After cooling down to ambient temperature, the resulting mixture was diluted with water (100 mL) and extracted with ethyl acetate (3×100 mL). The combined organic layers was washed with brine (30 mL) and dried over anhydrous sodium sulfate. After filtration, the filtrate was concentrated under reduced pressure and the residue was purified by silica gel column chromatography, eluted with 1~2% methanol in dichloromethane to afford 1-(5-(tributylstannyl)pyridin-2-yl)-1H-pyrrolo[2,3-c]pyridine as a yellow solid: MS (ESI, m/z): 486.0 [M+1]$^+$; $^1$H NMR (400 MHz, CDCl$_3$) δ 9.66 (s, 1H), 9.60 (s, 1H), 8.38 (d, J=5.6 Hz, 1H), 7.95 (d, J=1.6 Hz, 1H), 7.73 (d, J=4.8 Hz, 1H), 7.62 (d, J=6.4 Hz, 1H), 7.48 (d, J=8.4 Hz, 1H), 6.74 (d, J=2.8 Hz, 1H), 1.65-1.61 (m, 6H), 1.42-1.35 (m, 6H), 1.15-1.13 (m, 6H), 0.95-0.91 (m, 9H).

Step 2: Synthesis of 1-(5-(pyrimidin-4-yl)pyridin-2-yl)-1H-pyrrolo[2,3-c]pyridine (46)

To a solution of 1-(5-(tributylstannyl)pyridin-2-yl)-1H-pyrrolo[2,3-c]pyridine (120 mg, 0.25 mmol) in N,N-dimethylformamide (20 mL) were added 4-bromopyrimidine (59 mg, 0.37 mmol), copper(I) iodide (5 mg, 0.026 mmol) and tetrakis(triphenylphosphine)palladium(0) (29 mg, 0.025 mmol). The resulting mixture was stirred for 4 hours at 40° C. under nitrogen atmosphere. After cooling down to ambient temperature, the resulting mixture was diluted with water (60 mL) and extracted with ethyl acetate (3×80 mL). The combined organic layers was washed with brine (3×30 mL) and dried over anhydrous sodium sulfate. After filtration, the filtrate was concentrated under reduced pressure and the residue was purified by silica gel column chromatography, eluted with 1~2% methanol in dichloromethane to afford 1-(5-(pyrimidin-4-yl)pyridin-2-yl)-1H-pyrrolo[2,3-c]pyridine as a yellow solid: MS (ESI, m/z): 274.0 [M+1]$^+$; $^1$H NMR (400 MHz, DMSO-d$_6$) δ 9.89 (s, 1H), 9.44 (d, J=2.0 Hz, 1H), 9.32 (d, J=1.2 Hz, 1H), 8.95 (d, J=5.6 Hz, 1H), 8.78 (dd, J=2.4 Hz, 8.8 Hz, 1H), 8.45 (d, J=3.6 Hz, 1H), 8.33 (d, J=5.2 Hz, 1H), 8.28 (dd, J=1.2 Hz, 5.2 Hz, 1H), 8.10 (d, J=8.8 Hz, 1H), 7.68 (d, J=5.2 Hz, 1H), 6.92 (d, J=3.6 Hz, 1H).

Example 47

Synthesis of 2-(1H-pyrrolo[2,3-c]pyridin-1-yl)-1,6-naphthyridine (47)

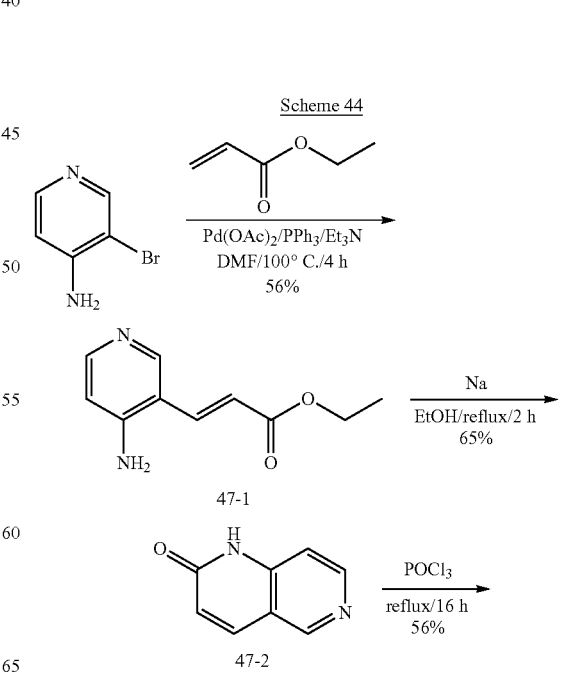

131

-continued

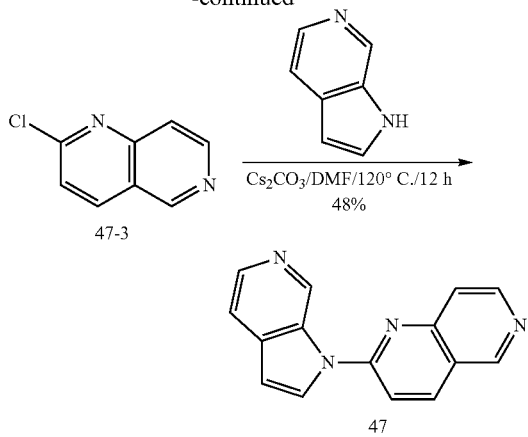

Step 1: Synthesis of (E)-ethyl 3-(4-aminopyridin-3-yl)acrylate (47-1)

To a solution of 3-bromopyridin-4-amine (5 g, 28.9 mmol) in N,N-dimethylformamide (50 mL) were added ethyl acrylate (4.4 g, 43.3 mmol), triphenylphosphine (1.7 g, 6.4 mmol), palladium(II) acetate (0.65 g, 2.9 mmol) and triethylamine (2.9 g, 28.9 mmol). The resulting mixture was stirred for 4 hours at 100° C. under nitrogen atmosphere. After cooling down to ambient temperature, the resulting mixture was diluted with water (200 mL) and extracted with ethyl acetate (3×100 mL). The combined organic layers was washed with brine (5×50 mL) and dried over anhydrous sodium sulfate. After filtration, the filtrate was concentrated under reduced pressure and the residue was purified by silica gel column chromatography, eluted with 1~2% methanol in dichloromethane to afford (E)-ethyl 3-(4-aminopyridin-3-yl)acrylate as a yellow solid: MS (ESI, m/z): 193.0 [M+1]$^+$; $^1$H NMR (400 MHz, CDCl$_3$) δ 7.86 (s, 1H), 7.65 (d, J=8.0 Hz, 1H), 7.45 (d, J=16.4 Hz, 1H), 7.10 (d, J=8.0 Hz, 1H), 6.65 (d, J=16.4 Hz, 1H), 5.10 (br s, 2H), 4.25 (q, J=7.2 Hz, 2H), 1.34 (t, J=7.2 Hz, 3H).

Step 2: Synthesis of 1,6-naphthyridin-2(1H)-one (47-2)

Sodium (0.96 g, 41.6 mmol) was dissolved into anhydrous ethanol (60 mL) at 0° C. followed by the addition of (E)-ethyl 3-(4-aminopyridin-3-yl)acrylate (2.1 g, 10.4 mmol). The resulting solution was refluxed for 2 hours, then cooled down to ambient temperature and neutralized with acetic acid (2.5 g, 41.6 mmol). The resulting solution was concentrated under reduced pressure and the residue was purified by silica gel column chromatography, eluted with 1~2% methanol in dichloromethane to afford 1,6-naphthyridin-2(1H)-one as a yellow solid: MS (ESI, m/z): 147.0 [M+1]$^+$; $^1$H NMR (300 MHz, DMSO-d$_6$) δ 12.18 (br s, 1H), 8.83 (s, 1H), 8.46 (d, J=5.7 Hz, 1H), 8.00 (d, J=9.3 Hz, 1H), 7.20 (d, J=5.7 Hz, 1H), 6.57 (d, J=9.6 Hz, 1H).

Step 3: Synthesis of 2-chloro-1,6-naphthyridine (47-3)

A solution of 1,6-naphthyridin-2(1H)-one (2 g, 13.68 mmol) in phosphoryl trichloride (20 mL) was refluxed for 16 hours. After cooling down to ambient temperature, the resulting solution was concentrated under reduced pressure

132 and the residue was taken up by dichloromethane (100 mL) and washed with saturated aqueous solution of sodium bicarbonate (100 mL). The organic layer was dried over anhydrous sodium sulfate. After filtration, the filtrate was concentrated under reduced pressure and the residue was purified by silica gel column chromatography, eluted with 1~2% methanol in dichloromethane to afford 2-chloro-1,6-naphthyridine as a yellow solid: MS (ESI, m/z): 165.0 [M+1]$^+$; $^1$H NMR (300 MHz, DMSO-d$_6$) δ 9.43 (s, 1H), 8.83 (d, J=6.0 Hz, 1H), 8.69 (d, J=11.7 Hz, 1H), 7.88 (d, J=5.7 Hz, 1H), 7.86 (d, J=9.6 Hz, 1H).

Step 4: Synthesis of 2-(1H-pyrrolo[2,3-c]pyridin-1-yl)-1,6-naphthyridine (47)

To a solution of 1H-pyrrolo[2,3-c]pyridine (48 mg, 0.41 mmol) in N,N-dimethylformamide (10 mL) were added 2-chloro-1,6-naphthyridine (60 mg, 0.37 mmol) and cesium carbonate (119 mg, 0.37 mmol). The resulting mixture was stirred for 12 hours at 120° C. under nitrogen atmosphere. After cooling down to ambient temperature, the resulting mixture was diluted with water (50 mL) and extracted with ethyl acetate (3×50 mL). The combined organic layers was washed with brine (3×30 mL) and dried over anhydrous sodium sulfate. After filtration, the filtrate was concentrated under reduced pressure and the residue was purified by a silica gel column chromatography, eluted with 1~2% methanol in dichloromethane to afford 2-(1H-pyrrolo[2,3-c]pyridin-1-yl)-1,6-naphthyridine as a yellow solid: MS (ESI, m/z): 247.0 [M+1]$^+$; $^1$H NMR (300 MHz, DMSO-d$_6$) δ 10.24 (br s, 1H), 9.37 (s, 1H), 8.78-8.74 (m, 2H), 8.58 (d, J=3.6 Hz, 1H), 8.38 (d, J=4.8 Hz, 1H), 8.27 (d, J=9.0 Hz, 1H), 8.02 (d, J=6.0 Hz, 1H), 7.71 (d, J=5.1 Hz, 1H), 6.96 (d, J=3.6 Hz, 1H).

Example 48

Synthesis of N-(6-(1H-pyrrolo[2,3-c]pyridin-1-yl)pyridin-3-yl)-3-(2-fluoroethoxy)benzamide (48)

Scheme 45

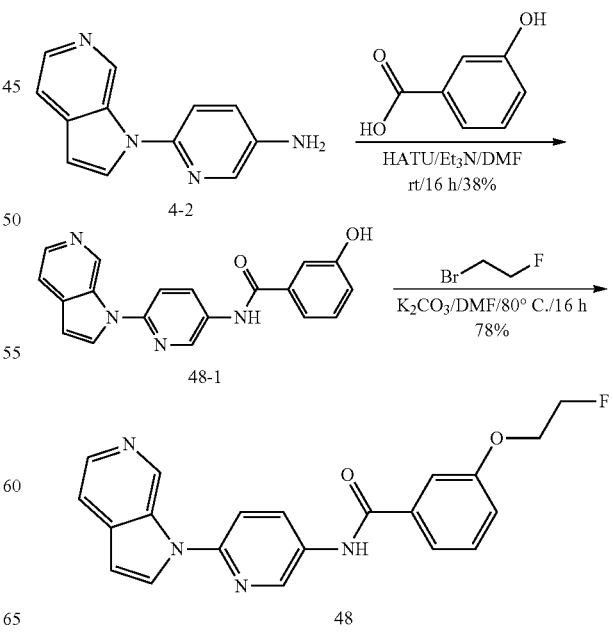

Step 1: Synthesis of N-(6-(1H-pyrrolo[2,3-c]pyridin-1-yl)pyridin-3-yl)-3-hydroxybenzamide (48-1)

To a solution of 6-(1H-pyrrolo[2,3-c]pyridin-1-yl)pyridin-3-amine (100 mg, 0.48 mmol) in N,N-dimethylformamide (15 mL) was added 4-methoxybenzoic acid (98 mg, 0.71 mmol), O-(7-azabenzotriazol-1-yl)-N,N,N',N'-tetramethyluronium hexafluorophosphate (HATU) (271 mg, 0.71 mmol) and triethylamine (144 mg, 1.43 mmol). The resulting solution was stirred for 16 hours at ambient temperature under nitrogen atmosphere. The reaction was quenched with water (50 mL) and extracted with ethyl acetate (3×60 mL). The combined organic layers was washed with brine (3×50 mL) and dried over anhydrous sodium sulfate. After filtration, the filtrate was concentrated under reduced pressure and the residue was purified by silica gel column chromatography, eluted with 0.3~2% methanol in dichloromethane to afford N-(6-(1H-pyrrolo[2,3-c]pyridin-1-yl)pyridin-3-yl)-3-hydroxybenzamide as a light yellow solid: MS (ESI, m/z): 331.0 [M+1]$^+$; $^1$H NMR (300 MHz, DMSO-d$_6$) δ 10.58 (s, 1H), 9.83 (br s, 1H), 9.67 (s, 1H), 8.97 (d, J=2.4 Hz, 1H), 8.40 (dd, J=2.7 Hz, 9.0 Hz, 1H), 8.28-8.25 (m, 2H), 7.88 (d, J=8.7 Hz, 1H), 7.65 (d, J=5.4 Hz, 1H), 7.45-7.33 (m, 3H), 7.03 (dd, J=2.7 Hz, 9.0 Hz, 1H), 6.83 (d, J=3.3 Hz, 1H).

Step 2: Synthesis of N-(6-(1H-pyrrolo[2,3-c]pyridin-1-yl)pyridin-3-yl)-3-(2-fluoroethoxy)benzamide (48)

To a solution of N-(6-(1H-pyrrolo[2,3-c]pyridin-1-yl)pyridin-3-yl)-3-hydroxybenzamide (40 mg, 0.12 mmol) in N,N-dimethylformamide (10 mL) were added 1-bromo-2-fluoroethane (23 mg, 0.18 mmol) and potassium carbonate (50 mg, 0.36 mmol) at ambient temperature. The resulting mixture was stirred for 16 hours at 80° C. After cooling down to ambient temperature, the resulting mixture was diluted with water (50 mL) and extracted with ethyl acetate (3×50 mL). The combined organic layers was washed with brine (3×50 mL) and dried over anhydrous sodium sulfate. After filtration, the filtrate was concentrated under reduced pressure and the residue was purified by silica gel column chromatography, eluted with 1~2% methanol in dichloromethane to afford N-(6-(1H-pyrrolo[2,3-c]pyridin-1-yl)pyridin-3-yl)-3-(2-fluoroethoxy)benzamide as a colorless solid: MS (ESI, m/z): 377.0 [M+1]$^+$; $^1$H NMR (300 MHz, DMSO-d$_6$) δ 10.58 (s, 1H), 9.68 (br s, 1H), 8.98 (d, J=2.4 Hz, 1H), 8.41 (dd, J=2.7 Hz, 8.7 Hz, 1H), 8.28-8.25 (m, 2H), 7.92 (d, J=8.7 Hz, 1H), 7.72-7.48 (m, 4H), 7.24 (dd, J=2.4 Hz, 7.5 Hz, 1H), 6.84 (d, J=3.6 Hz, 1H), 4.88 (d, J=3.9 Hz, 1H), 4.72 (d, J=3.9 Hz, 1H), 4.41 (d, J=3.9 Hz, 1H), 4.30 (d, J=3.9 Hz, 1H).

Example 49

Radiochemical Synthesis of [$^3$H]-6

Scheme 46

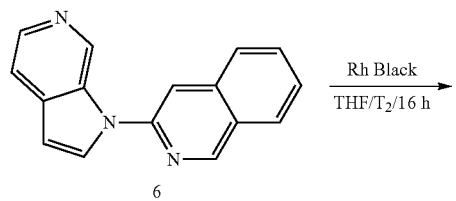

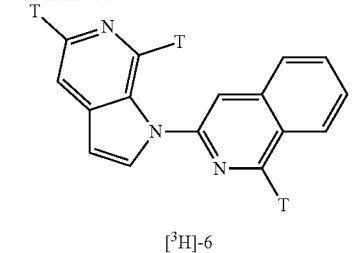

[$^3$H]-6

Radiochemical Synthesis of [$^3$H]-6

To a tritiation vessel were added 3-(1H-pyrrolo[2,3-c]pyridin-1-yl)isoquinoline (2.8 mg, 11.4 μmol) and Rhodium black (2.4 mg, 23.3 μmol), followed by THF (0.3 mL). The vessel was hooked up to the tritiation manifold and put through two freeze-thaw cycles (liquid nitrogen). While the reaction was frozen, tritium gas (1.02 Ci) was added. The black suspension was warmed to RT and stirred for 16 h. The reaction was frozen with liquid nitrogen and excess tritium gas was removed, then the vessel was removed from the reaction port. When the suspension had warmed to RT, it was filtered through a small plug of celite using EtOH. The filtrate was concentrated to give a thin film that was taken up in EtOH, concentrated, taken up in 10 mL EtOH and counted resulting in a total of 494.7 mCi. Analysis by RP-HPLC (Gemini C18, 4.6×150 mm, 254 nm, (55:45) 0.05M pH 9.5 TEAA:CH3CN, 1 mL/min). A portion of the batch was purified by reverse phase HPLC (Gemini C18, 10×250 mm, 254 nm, (60:40) 0.05M pH 9.5 TEAA:CH$_3$CN, 5 mL/min, to give a batch of 135.18 mCi of [$^3$H]-6 in 99.4 mL EtOH. The specific activity was determined to be 37.8 Ci/mmol.

Example 50

Synthesis of 6-fluoro-3-(5-methoxy-1H-pyrrolo[2,3-c]pyridin-1-yl)isoquinoline (L-005587122-000U)

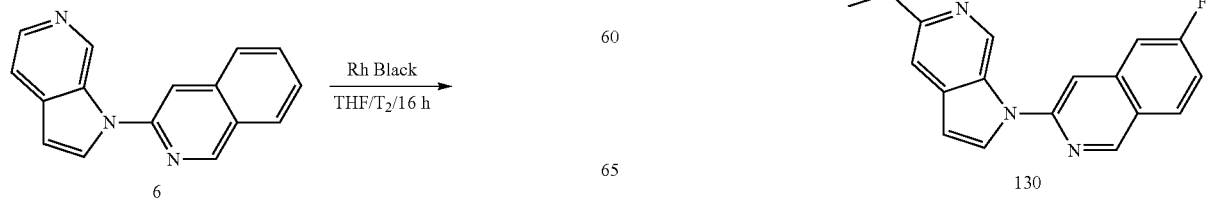

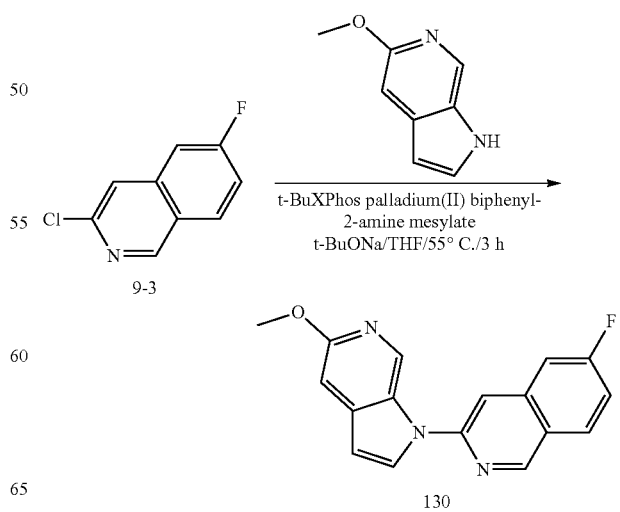

Synthesis of 6-fluoro-3-(5-methoxy-1H-pyrrolo[2,3-c]pyridin-1-yl)isoquinoline

To a stirred solution of 1H-pyrrolo[2,3-c]pyridine (163 mg, 1.10 mmol) and 3-chloro-6-fluoroisoquinoline 9-3 (200 mg, 1.10 mmol) in tetrahydrofuran (50 mL) was added sodium 2-methylpropan-2-olate (212 mg, 2.20 mmol) and t-BuXPhos palladium(II) biphenyl-2-amine mesylate (351 mg, 0.44 mmol) at ambient temperature. The resulting mixture was stirred for 3 hours at 55° C. under a nitrogen atmosphere. After cooling down to ambient temperature, the reaction was quenched with water (100 mL) and extracted with ethyl acetate (3×50 mL). The combined organic layers was washed with brine (2×100 mL) and dried over anhydrous sodium sulfate. After filtration, the filtrate was concentrated under reduced pressure and the residue was purified by silica gel column chromatography, eluted with 1~5% methanol in dichloromethane to afford 6-fluoro-3-(5-methoxy-1H-pyrrolo[2,3-c]pyridin-1-yl)isoquinoline as a light yellow solid (270 mg, 83%): MS (ESI, m/z): 293.9 [M+1]$^+$; $^1$H NMR (300 MHz, DMSO-d$^6$) δ 9.41 (s, 1H), 9.36 (s, 1H), 8.35 (d, J=3.6 Hz, 1H), 8.34-8.30 (dd, J=9.2 Hz, 6.0 Hz, 1H), 8.24 (s, 1H), 7.80 (dd, J=2.0 Hz, 10.0 Hz, 1H), 7.59-7.54 (m, 1H), 7.03 (d, J=0.8 Hz, 1H), 6.77 (d, J=3.6 Hz, 1H), 3.91 (s, 3H).

Radiochemical Synthesis of [$^{18}$F]-Ligands

General Methods

[$^{18}$F]Fluoride was transported to the radiochemistry lab on an anion exchange resin and eluted prior to use. Unless specifically stated, the [$^{18}$F]fluoride containing anion exchange resin was eluted with Kryptofix222 (7 mg, 19 μmol) and K$_2$CO$_3$ (2.1 mg, 15 μmol) in acetonitrile/water (80/20, 0.7 ml) and transferred to a vented 1-ml V-shaped vial in a microwave cavity. The fluoride was dried under argon flow and microwave heating (35 W/90° C.). Additional aliquots of acetonitrile (3×0.5 ml) were added for azeotropic drying at 35 W/90° C.

Synthetic Procedure for Precursors to [$^{18}$F]-Ligands

1. Synthesis of 6-nitro-3-(1H-pyrrolo[2,3-c]pyridin-1-yl)isoquinoline (9a)

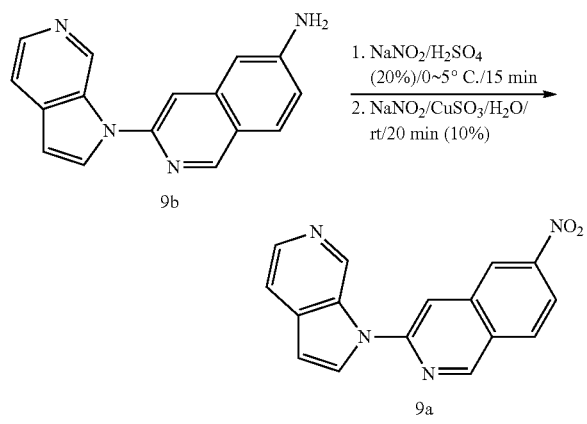

Synthesis of 6-nitro-3-(1H-pyrrolo[2,3-c]pyridin-1-yl)isoquinoline (9a)

Step 1: A solution of cupric sulfate (1 g, 6.29 mmol) in water (5 mL) was added to a stirred solution of sodium sulfite (1 g, 7.94 mmol) in water (5 mL) at ambient temperature. After 10 minutes, a filtration was performed and the filter cake was washed with water (3×10 mL) to afford wet cupric sulfite as a brown solid, which was dissolved into saturated aqueous solution of sodium nitrite (50 mL) at ambient temperature.

Step 2: 3-(1H-pyrrolo[2,3-c]pyridin-1-yl)isoquinolin-6-amine (300 mg, 1.15 mmol) was dissolved into 20% (w/w) aqueous solution of sulfuric acid (5 mL) followed by the addition of sodium nitrite (95 mg, 1.38 mmol) at 0° C. After stirring for 15 min, the resulting solution was added to the above solution over 10 minutes at ambient temperature. After stirring for 10 minutes, the reaction was quenched with 25% (w/w) aqueous solution of ammonia (5 mL) and exacted with dichloromethane (3×50 mL). The combined organic layers was dried over anhydrous sodium sulfate and filtered. The filtrate was concentrated under reduced pressure and the residue was purified by silica gel column chromatography, eluted with 0.5~1% methanol in dichloromethane to afford 6-nitro-3-(1H-pyrrolo[2,3-c]pyridin-1-yl)isoquinoline as a yellow solid (31.6 mg, 10%): MS (ESI, m/z): 291.1 [M+1]$^+$; $^1$H NMR (300 MHz, CDCl$_3$) δ 9.81-9.77 (m, 1H), 9.45 (s, 1H), 8.84 (d, J=1.8 Hz, 1H), 8.43-8.41 (m, 1H), 8.35 (d, J=2.1 Hz, 1H), 8.28 (d, J=9.3 Hz, 1H), 8.09 (s, 1H), 8.03 (s, 1H), 7.75-7.68 (m, 1H), 6.88 (t, J=9.0 Hz, 1H).

2. Synthesis of ditert-butyl (6-nitro-3-(1H-pyrrolo[2,3-c]pyridin-1-yl)isoquinolin-5-yl)carbamate (18a)

Step 1: Synthesis of N-(3-chloro-6-nitroisoquinolin-5-yl)acetamide

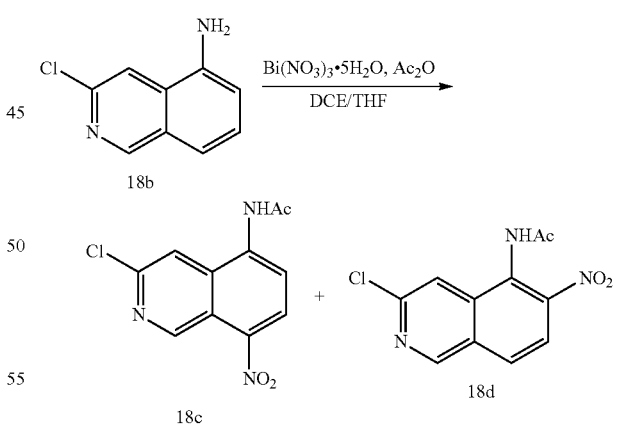

Into a 2000-mL 4-necked round-bottom flask, was placed a solution of 3-chloroisoquinolin-5-amine (33 g, 184.75 mmol, 1.00 equiv) in DCE/THF (550/183 mL), acetic anhydride (150.77 g, 1.48 mol, 8.00 equiv), Bi(NO$_3$)$_3$.5H$_2$O (79.6 g, 184.69 mmol, 1.00 equiv). The resulting solution was stirred for 2 h at 50° C. in an oil bath. The resulting mixture was concentrated under vacuum. The residue was applied onto a silica gel column with ethyl acetate/petroleum ether (3:1). This resulted in 19 g mixture (38%) of N-(3- chloro-8-nitroisoquinolin-5-yl)acetamide and N-(3-chloro-6-nitroisoquinolin-5-yl)acetamide as a yellow solid.

Step 2: Synthesis of N-(6-nitro-3-[1H-pyrrolo[2,3-c]pyridin-1-yl]isoquinolin-5-yl)acetamide; N-(8-nitro-3-[1H-pyrrolo[2,3-c]pyridin-1-yl]isoquinolin-5-yl)

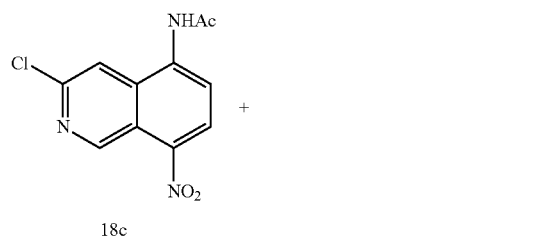

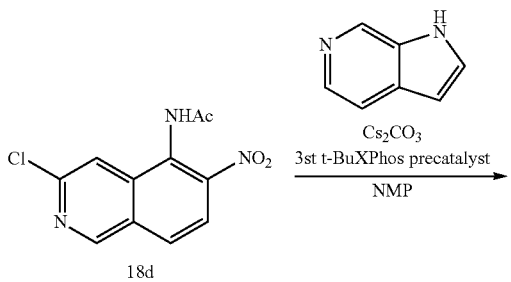

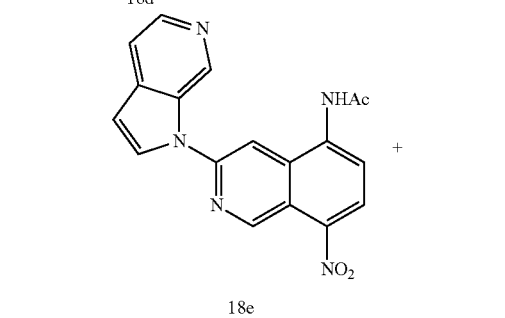

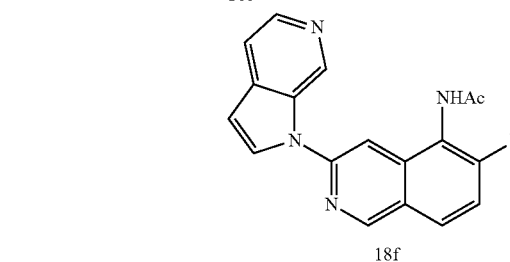

of N-(6-nitro-3-[1H-pyrrolo[2,3-c]pyridin-1-yl]isoquinolin-5-yl)acetamide; N-(8-nitro-3-[1H-pyrrolo[2,3-c]pyridin-1-yl]isoquinolin-5-yl)acetamide as red oil.

Step 3: Synthesis of tert-butyl N-acetyl-N-(6-nitro-3-[1H-pyrrolo[2,3-c]pyridin-1-yl]isoquinolin-5-yl)carbamate

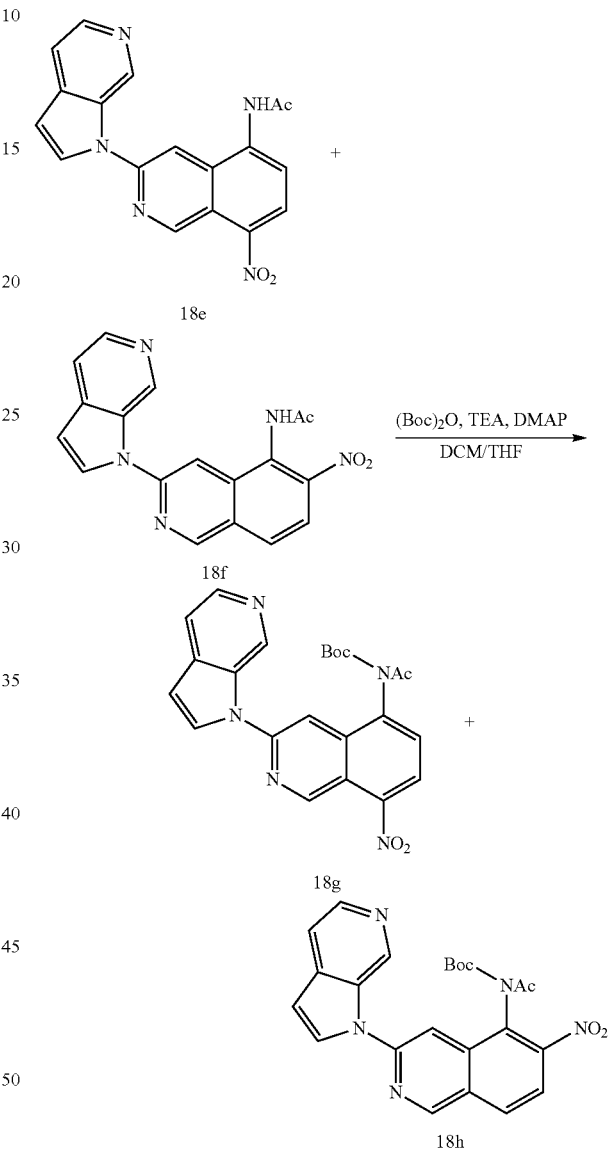

Into a 1000-mL 4-necked round-bottom flask purged and maintained with an inert atmosphere of nitrogen, was placed a solution of N-(3-chloro-8-nitroisoquinolin-5-yl)acetamide and N-(3-chloro-6-nitroisoquinolin-5-yl)acetamide (19 g mixture, 35.76 mmol, 1.00 equiv) in NMP (480 mL), 3st t-BuXPhos precatalyst (5.7 g, 7.18 mmol, 0.10 equiv), $Cs_2CO_3$ (70 g, 215.52 mmol, 3.00 equiv). The resulting solution was stirred for 2 h at 60° C. in an oil bath. The reaction was then quenched by the addition of 3000 mL of water. The resulting solution was extracted with 3×500 mL of ethyl acetate and the organic layers combined. The resulting mixture was washed with 2×500 mL of water. The mixture was dried over anhydrous sodium sulfate and concentrated under vacuum. This resulted in 20 g mixture (81%)

Into a 1000-mL 4-necked round-bottom flask, was placed a solution of N-(8-nitro-3-[1H-pyrrolo[2,3-c]pyridin-1-yl]isoquinolin-5-yl)acetamide/N-(6-nitro-3-[1H-pyrrolo[2,3-c]pyridin-1-yl]isoquinolin-5-yl)acetamide (20 g, 57.58 mmol, 1.00 equiv) in DCM/THF (500/50 mL), $(Boc)_2O$ (18.8 g, 86.14 mmol, 1.50 equiv), TEA (17.46 g, 172.55 mmol, 3.00 equiv), DMPA (1.4 g, 11.48 mmol, 0.20 equiv). The resulting solution was stirred overnight at room temperature. The resulting mixture was concentrated under vacuum. The residue was applied onto a silica gel column with ethyl acetate/petroleum ether (3:1). This resulted in 6.8 g (26%) of tert-butyl N-acetyl-N-(6-nitro-3-[1H-pyrrolo[2,3-c]pyridin-1-yl]isoquinolin-5-yl)carbamate as a yellow solid.

Step 4: Synthesis of tert-butyl N-(6-nitro-3-[1H-pyrrolo[2,3-c]pyridin-1-yl]isoquinolin-5-yl)carbamate

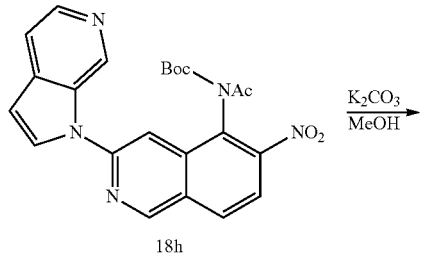

18h

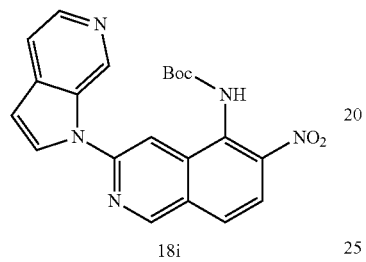

18i

Into a 250-mL 4-necked round-bottom flask, was placed a solution of tert-butyl N-acetyl-N-(6-nitro-3-[1H-pyrrolo[2,3-c]pyridin-1-yl]isoquinolin-5-yl)carbamate (6.8 g, 15.20 mmol, 1.00 equiv) in methanol (100 mL), potassium carbonate (20.9 g, 151.45 mmol, 10.00 equiv). The resulting solution was stirred for 2 h at room temperature. The solids were filtered out. The filtrate was concentrated under vacuum. The residue was applied onto a silica gel column with ethyl acetate/petroleum ether (3:1). This resulted in 4.8 g (78%) of tert-butyl N-(6-nitro-3-[1H-pyrrolo[2,3-c]pyridin-1-yl]isoquinolin-5-yl)carbamate as a yellow solid.

Step 5: Synthesis of tert-butyl N-[(tert-butoxy)carbonyl]-N-(6-nitro-3-[1H-pyrrolo[2,3-c]pyridin-1-yl]isoquinolin-5-yl)carbamate (18a)

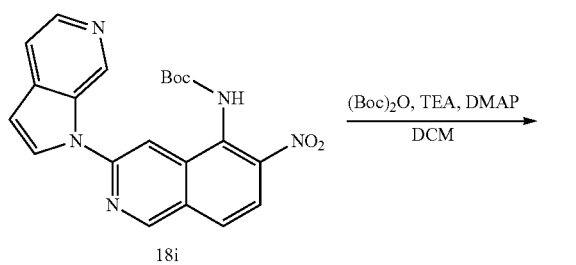

18i

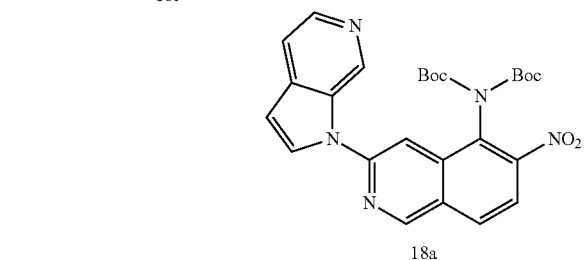

18a

Into a 100-mL 4-necked round-bottom flask, was placed tert-butyl N-(6-nitro-3-[1H-pyrrolo[2,3-c]pyridin-1-yl]iso- quinolin-5-yl)carbamate (4.8 g, 11.84 mmol, 1.00 equiv), (Boc)$_2$O (3.86 g, 17.69 mmol, 1.50 equiv), TEA (3.59 g, 35.48 mmol, 3.00 equiv), 4-dimethylaminopyridine (290 mg, 2.37 mmol, 0.20 equiv), dichloromethane (100 mL). The resulting solution was stirred for 2 h at room temperature. The resulting mixture was concentrated under vacuum. The residue was applied onto a silica gel column with ethyl acetate/petroleum ether (3:1). This resulted in 3.52 g (59%) of tert-butyl N-[(tert-butoxy)carbonyl]-N-(6-nitro-3-[1H-pyrrolo[2,3-c]pyridin-1-yl]isoquinolin-5-yl)carbamate as a yellow solid: MS (ESI, m/z): 505 [M+1]$^+$; $^1$H-NMR (300 MHz, CDCl$_3$): δ 1.39 (18H, s), 6.85 (1H, d), 7.65 (1H, d), 7.88 (1H, s), 7.95 (1H, d), 8.10 (1H, d), 8.21 (1H, d), 8.43 (1H, d), 9.43 (1H, s), 9.750 (1H, d).

3. Synthesis of tert-butyl N-[(tert-butoxy)carbonyl]-N-(6-nitro-3-{1H-pyrrolo[2,3-c]pyridin-1-yl}isoquinolin-7-yl)carbamate (105a)

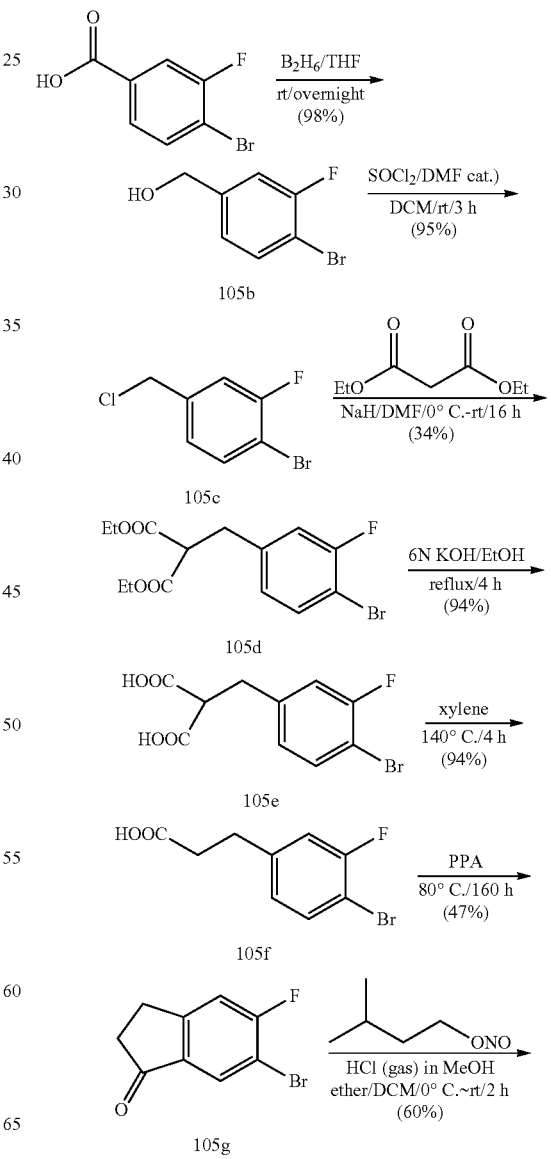

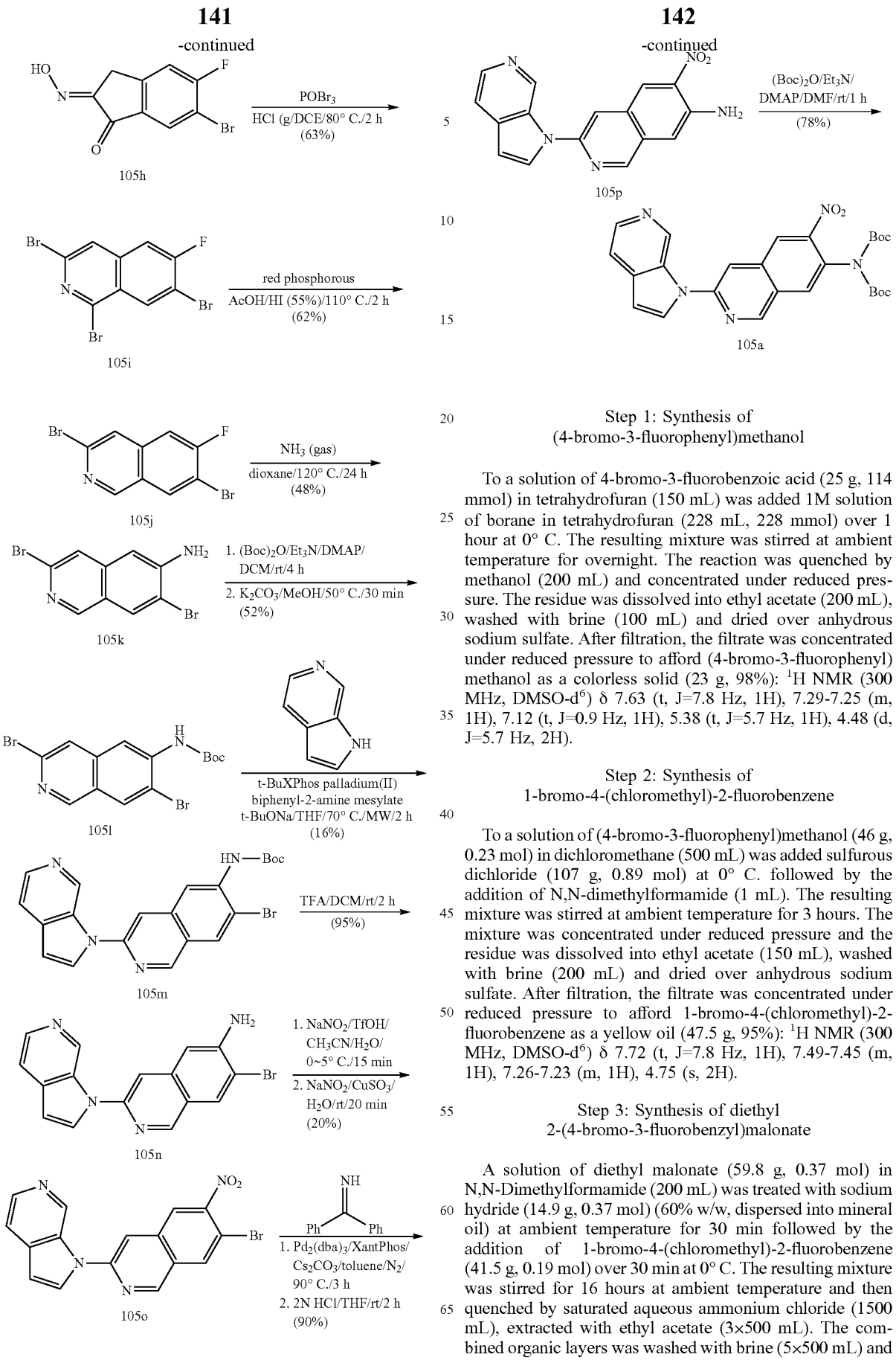

Step 1: Synthesis of
(4-bromo-3-fluorophenyl)methanol

To a solution of 4-bromo-3-fluorobenzoic acid (25 g, 114 mmol) in tetrahydrofuran (150 mL) was added 1M solution of borane in tetrahydrofuran (228 mL, 228 mmol) over 1 hour at 0° C. The resulting mixture was stirred at ambient temperature for overnight. The reaction was quenched by methanol (200 mL) and concentrated under reduced pressure. The residue was dissolved into ethyl acetate (200 mL), washed with brine (100 mL) and dried over anhydrous sodium sulfate. After filtration, the filtrate was concentrated under reduced pressure to afford (4-bromo-3-fluorophenyl)methanol as a colorless solid (23 g, 98%): $^1$H NMR (300 MHz, DMSO-d$^6$) δ 7.63 (t, J=7.8 Hz, 1H), 7.29-7.25 (m, 1H), 7.12 (t, J=0.9 Hz, 1H), 5.38 (t, J=5.7 Hz, 1H), 4.48 (d, J=5.7 Hz, 2H).

Step 2: Synthesis of
1-bromo-4-(chloromethyl)-2-fluorobenzene

To a solution of (4-bromo-3-fluorophenyl)methanol (46 g, 0.23 mol) in dichloromethane (500 mL) was added sulfurous dichloride (107 g, 0.89 mol) at 0° C. followed by the addition of N,N-dimethylformamide (1 mL). The resulting mixture was stirred at ambient temperature for 3 hours. The mixture was concentrated under reduced pressure and the residue was dissolved into ethyl acetate (150 mL), washed with brine (200 mL) and dried over anhydrous sodium sulfate. After filtration, the filtrate was concentrated under reduced pressure to afford 1-bromo-4-(chloromethyl)-2-fluorobenzene as a yellow oil (47.5 g, 95%): $^1$H NMR (300 MHz, DMSO-d$^6$) δ 7.72 (t, J=7.8 Hz, 1H), 7.49-7.45 (m, 1H), 7.26-7.23 (m, 1H), 4.75 (s, 2H).

Step 3: Synthesis of diethyl
2-(4-bromo-3-fluorobenzyl)malonate

A solution of diethyl malonate (59.8 g, 0.37 mol) in N,N-Dimethylformamide (200 mL) was treated with sodium hydride (14.9 g, 0.37 mol) (60% w/w, dispersed into mineral oil) at ambient temperature for 30 min followed by the addition of 1-bromo-4-(chloromethyl)-2-fluorobenzene (41.5 g, 0.19 mol) over 30 min at 0° C. The resulting mixture was stirred for 16 hours at ambient temperature and then quenched by saturated aqueous ammonium chloride (1500 mL), extracted with ethyl acetate (3×500 mL). The combined organic layers was washed with brine (5×500 mL) and dried over anhydrous sodium sulfate. After filtration, the filtrate was concentrated under reduced pressure and the residue was purified by silica gel column chromatography, eluted with 1~2% ethyl acetate in petroleum ether to afford diethyl 2-(4-bromo-3-fluorobenzyl)malonate as a colorless oil (36 g, 34%): MS (ESI, m/z): 346.9, 348.9 [M+1]+; $^1$H NMR (400 MHz, DMSO-d$^6$) δ 7.40-7.38 (m, 1H), 7.33 (s, 1H), 7.18-7.16 (m, 1H), 4.13-4.05 (m, 4H), 3.94 (t, J=8.0 Hz, 1H), 3.10 (d, J=8.0 Hz, 2H), 1.15-1.08 (m, 6H).

Step 4: Synthesis of 2-(4-bromo-3-fluorobenzyl)malonic acid

A solution of diethyl 2-(4-bromo-3-fluorobenzyl)malonate (34 g, 58.8 mmol) in ethanol (100 mL) was treated with 6 N aqueous solution of potassium hydroxide (50 mL, 300 mmol) at reflux for 4 hours. After cooling down to ambient temperature, the resulting solution was concentrated under reduced pressure and the residue was diluted with water (200 mL) and acidified with concentrated hydrochloric acid (12 N) to pH=1. Solid was collected by filtration and dried in a vacuo oven to afford 2-(4-bromo-3-fluorobenzyl)malonic acid as a white solid (16 g, 94%): $^1$H NMR (400 MHz, DMSO-d$^6$) δ 12.89 (br s, 2H), 7.39-7.32 (m, 1H), 7.29 (d, J=13.2 Hz, 1H), 7.17-7.11 (m, 1H), 3.69 (t, J=8.0 Hz, 1H), 3.02 (d, J=8.0 Hz, 2H).

Step 5: Synthesis of 3-(4-bromo-3-fluorophenyl)propanoic acid

A suspension of 2-(4-bromo-3-fluorobenzyl)malonic acid (16 g, 55 mmol) in xylene (150 mL) was refluxed for 4 hours. After cooling down to ambient temperature, xylene was removed by evaporation under reduced pressure to afford 3-(4-bromo-3-fluorophenyl)propanoic acid as a colorless solid (13 g, 94%): $^1$H NMR (400 MHz, DMSO-d$^6$) δ 12.21 (br s, 1H), 7.32-7.29 (m, 2H), 7.16-7.13 (m, 1H), 2.83 (t, J=7.6 Hz, 2H), 2.56 (d, J=7.6 Hz, 2H).

Step 6: Synthesis of 6-bromo-5-fluoro-2,3-dihydro-1H-inden-1-one

A mixture of 3-(4-bromo-3-fluorophenyl)propanoic acid (60 g, 0.24 mol) and polyphosphoric acid (300 mL) was kept at 80° C. for 160 hours. After cooling down to ambient temperature, the mixture was poured into ice-water (1200 g) and extracted with ethyl acetate (3×500 mL). The combined organic layers was washed with brine (300 mL) and dried over anhydrous sodium sulfate. After filtration, the filtrate was concentrated under reduced pressure and the residue was purified by silica gel column chromatography, eluted with 5~10% ethyl acetate in petroleum ether to afford 6-bromo-5-fluoro-2,3-dihydro-1H-inden-1-one as a light yellow solid (26 g, 47%): MS (ESI, m/z): 229.0, 231.0 [M+1]+; $^1$H NMR (300 MHz, DMSO-d$^6$) δ 7.92 (d, J=6.9 Hz, 1H), 7.64 (d, J=8.1 Hz, 1H), 3.08 (t, J=5.4 Hz, 2H), 2.68 (d, J=5.4 Hz, 2H).

Step 7: Synthesis of (E)-6-bromo-5-fluoro-2-(hydroxyimino)-2,3-dihydro-1H-inden-1-one To a solution of 6-bromo-5-fluoro-2,3-dihydro-1H-inden-1-one (22 g, 96 mmol) in diethyl ether (150 mL) and dichloromethane (50 mL) were added methanol (25 mL, saturated with HCl at ambient temperature) and isopentyl nitrite (16.9 g, 144 mmol) at 0° C. The resulting mixture was stirred at ambient temperature for 2 hours. A filtration was performed and the filter cake was washed with cold diethyl ether (2×50 mL) to afford (E)-6-bromo-5-fluoro-2-(hydroxyimino)-2,3-dihydro-1H-inden-1-one as a light yellow solid (15 g, 60%): MS (ESI, m/z): 258.0, 260.0 [M+1]+; $^1$H NMR (300 MHz, DMSO-d$^6$) δ 12.78 (s, 1H), 8.06 (d, J=6.9 Hz, 1H), 7.68 (d, J=9.0 Hz, 1H), 3.75 (s, 2H).

Step 8: Synthesis of 1,3,7-tribromo-6-fluoroisoquinoline (8)

To a solution of (E)-6-bromo-1-fluoro-2-(hydroxyimino)-2,3-dihydro-1H-inden-1-one (13.5 g, 52.3 mmol) in 1,2-dichloroethane (200 mL, saturated with dry HCl) was added phosphoryl tribromide (30.0 g, 105 mmol) at ambient temperature. The resulting mixture was stirred for 2 hours at 80° C. After cooling down to ambient temperature, the mixture was concentrated under reduced pressure and the residue was poured into ice-water (500 g) carefully. A filtration was performed and the filter cake was washed with water (2×100 mL), dried in a vacuo oven to afford 1,3,7-tribromo-6-fluoroisoquinoline as a light yellow solid (14 g, 63%): MS (ESI, m/z): 384.0, 386.0 [M+1]+; $^1$H NMR (300 MHz, DMSO-d$^6$) δ 8.38 (d, J=6.6 Hz, 1H), 8.24 (s, 1H), 7.96 (d, J=9.3 Hz, 1H).

Step 9: Synthesis of 3,7-dibromo-6-fluoroisoquinoline

To a stirred solution of 1,3,7-tribromo-6-fluoroisoquinoline (13.5 g, 35.2 mmol) in acetic acid (100 mL) were added 55% aqueous solution of HI (50 mL) and red phosphorus (2.7 g, 88.1 mmol) at ambient temperature. The resulting solution was stirred at 110° C. for 2 hours. After cooling down to ambient temperature, the mixture was concentrated under reduced pressure. The residue was taken up with ethyl acetate (300 mL), washed with saturated aqueous solution of sodium bicarbonate (100 mL) and dried over anhydrous sodium sulfate. After filtration, the filtrate was concentrated under reduced pressure and the residue was purified by silica gel column chromatography, eluted with 1~6% ethyl acetate in petroleum ether to afford 3,7-dibromo-6-fluoroisoquinoline as an off white solid (7 g, 62%): MS (ESI, m/z): 306.0 [M+1]+; $^1$H NMR (300 MHz, DMSO-d$^6$) δ 9.15 (s, 1H), 8.68 (d, J=6.9 Hz, 1H), 8.20 (s, 1H), 7.94 (d, J=9.3 Hz, 1H).

Step 10: Synthesis of 3,7-dibromoisoquinolin-6-amine (10)

To a solution of 3,7-dibromo-6-fluoroisoquinoline (5.0 g, 16.4 mmol) in 1,4-dioxane (150 mL) was bubbled with dry ammonia gas until the resulting solution was saturated at 0° C. The resulting solution was put into a high-pressure autoclave and stirred at 120° C. for 24 hours. After cooling down to ambient temperature, the resulting mixture was concentrated under reduced pressure and the residue was purified by silica gel column chromatography, eluted with 1~8% ethyl acetate in petroleum ether to afford 3,7-dibromoisoquinolin-6-amine as a light yellow solid (2.5 g, 48%): MS (ESI, m/z): 302.7 [M+1]+; $^1$H NMR (300 MHz, DMSO-d$^6$) δ 8.76 (s, 1H), 8.27 (s, 1H), 7.73 (s, 1H), 6.93 (s, 1H), 6.34 (br s, 2H).

Step 11: Synthesis of tert-butyl (3,7-dibromoisoquinolin-6-yl)carbamate (11)

To a solution of 3,7-dibromoisoquinolin-6-amine (2.50 g, 8.28 mmol) in dichloromethane (50 mL) were added triethylamine (2.51 g, 24.84 mmol), di-tert-butyl dicarbonate (5.42 g, 24.84 mmol) and N,N-dimethylpyridin-4-amine (51 mg, 0.41 mmol) at ambient temperature. After additional 4 hours, the resulting solution was concentrated under reduced pressure and the residue was dissolved into methanol (50 mL) followed by the addition of potassium carbonate (2.5 g, 18.11 mmol). The resulting mixture was stirred at 50° C. for 30 min. After cooling down to ambient temperature, a filtration was performed and the filtrate was concentrated under reduced pressure to give a residue, which was purified by silica gel column chromatography, eluted with 1~5% ethyl acetate in petroleum ether to afford tert-butyl (3,7-dibromoisoquinolin-6-yl)carbamate as an off white solid (1.8 g, 52%): MS (ESI, m/z): 402.8 [M+1]$^+$; $^1$H NMR (300 MHz, DMSO-d$^6$) δ 9.05 (s, 1H), 8.75 (s, 1H), 8.54 (s, 1H), 8.20 (s, 1H), 8.18 (s, 1H), 1.50 (s, 9H).

Step 12: Synthesis of tert-butyl (7-bromo-3-(1H-pyrrolo[2,3-c]pyridin-1-yl)isoquinolin-6-yl)carbamate (12)

To a stirred solution of tert-butyl (3,7-dibromoisoquinolin-6-yl)carbamate (1.2 g, 2.98 mmol) in tetrahydrofuran (10 mL) were added 1H-pyrrolo[2,3-c]pyridine (0.71 g, 5.97 mmol), t-BuXPhos palladium(II) biphenyl-2-amine mesylate (0.71 g, 0.89 mmol) and sodium 2-methylpropan-2-olate (1.15 g, 11.94 mmol) at ambient temperature under nitrogen atmosphere. The resulting mixture was irradiated with microwave at 70° C. for 2 hours. After cooling down to ambient temperature, the resulting mixture was concentrated under reduced pressure and the residue was purified by silica gel column chromatography, eluted with 1~2% methanol in dichloromethane to afford tert-butyl (7-bromo-3-(1H-pyrrolo[2,3-c]pyridin-1-yl)isoquinolin-6-yl)carbamate as a light yellow solid (0.2 g, 16%): MS (ESI, m/z): 439.0, 441.0 [M+1]$^+$; $^1$H NMR (300 MHz, DMSO-d$^6$) δ 9.72 (s, 1H), 9.31 (s, 1H), 8.73 (s, 1H), 8.59 (s, 1H), 8.37-8.34 (m, 2H), 8.29-8.28 (m, 2H), 7.67 (d, J=4.8 Hz, 1H), 6.88 (d, J=3.3 Hz, 1H), 1.50 (s, 9H).

Step 13: Synthesis of 7-bromo-3-(1H-pyrrolo[2,3-c]pyridin-1-yl)isoquinolin-6-amine A solution of tert-butyl (7-bromo-3-(1H-pyrrolo[2,3-c]pyridin-1-yl)isoquinolin-6-yl)carbamate (0.47 g, 1.07 mmol) in dichloromethane (20 mL) was treated with 2,2,2-trifluoroacetic acid (1.14 g, 10 mmol) for 2 hours at ambient temperature. The reaction was quenched with water (50 mL) and neutralized with sodium bicarbonate (0.84 g, 10 mmol). The resulting mixture was extracted with dichloromethane (3×100 mL) and the combined organic layers was dried over anhydrous sodium sulfate. After filtration, the filtrate was concentrated under reduced pressure to afford 7-bromo-3-(1H-pyrrolo[2,3-c]pyridin-1-yl)isoquinolin-6-amine as a light yellow solid (0.35 g, 95%): MS (ESI, m/z): 339.0, 341.0 [M+1]$^+$; $^1$H NMR (300 MHz, DMSO-d$^6$) δ 9.65 (s, 1H), 9.06 (s, 1H), 8.34 (s, 1H), 8.31-8.17 (m, 2H), 7.84 (s, 1H), 7.65 (d, J=5.4 Hz, 1H), 7.10 (s, 1H), 6.82 (d, J=3.0 Hz, 1H), 6.31 (br s, 2H).

Step 14: Synthesis of 7-bromo-6-nitro-3-(1H-pyrrolo[2,3-c]pyridin-1-yl)isoquinoline Step 1: A solution of cupric sulfate (1 g, 6.29 mmol) in water (5 mL) was added to a stirred solution of sodium sulfite (1 g, 7.94 mmol) in water (5 mL) at ambient temperature. After 10 minutes, a filtration was performed and the filter cake was washed with water (3×10 mL) to afford wet cupric sulfite as a brown solid, which was dissolved into saturated aqueous solution of sodium nitrite (50 mL) at ambient temperature.

Step 2: To a suspension of 7-bromo-3-(1H-pyrrolo[2,3-c]pyridin-1-yl)isoquinolin-6-amine (0.3 g, 0.88 mmol) in acetonitrile (20 mL) and water (20 mL) was added trifluoromethanesulfonic acid (0.65, 4.4 mmol) followed by the addition of sodium nitrite (61 mg, 0.88 mmol) at 0° C. After 15 minutes, the resulting solution was added to the above solution over 10 minutes. After additional 10 minutes, 25% aqueous solution of ammonia (10 mL) was added and the resulting mixture was extracted with dichloromethane (3×100 mL). The combined organic layers was dried over anhydrous sodium sulfate and filtered. The filtrate was concentrated under reduced pressure and the residue was purified by silica gel column chromatography, eluted with 1% methanol in dichloromethane to afford 7-bromo-6-nitro-3-(1H-pyrrolo[2,3-c]pyridin-1-yl)isoquinoline as a light yellow solid (70 mg, 20%): MS (ESI, m/z): 368.8, 370.8 [M+1]$^+$; $^1$H NMR (300 MHz, DMSO-d$^6$) δ 9.75 (s, 1H), 9.55 (s, 1H), 8.86 (s, 1H), 8.77 (s, 1H), 8.47 (s, 1H), 8.37 (s, 1H), 8.33 (d, J=7.2 Hz, 1H), 7.69 (d, J=5.4 Hz, 1H), 6.93 (d, J=3.3 Hz, 1H).

Step 15: Synthesis of 6-nitro-3-(1H-pyrrolo[2,3-c]pyridin-1-yl)isoquinolin-7-amine To a suspension of 7-bromo-6-nitro-3-(1H-pyrrolo[2,3-c]pyridin-1-yl)isoquinoline (50 mg, 0.14 mmol) in toluene (15 mL) were added diphenylmethanimine (73.6 mg, 0.41 mmol), cesium carbonate (88 mg, 0.27 mmol), XantPhos (15.7 mg, 0.027 mmol) and tris(dibenzylideneacetone)dipalladium (0) (14 mg, 0.014 mmol) under nitrogen atmosphere. The resulting mixture was stirred for 3 hours at 90° C. After cooling down to ambient temperature, the resulting mixture was concentrated under reduced pressure and the residue was taken up with tetrahydrofuran (20 mL) followed by the addition of 2 N aqueous solution of hydrochloride (3.0 mL). After stirring for 2 hours at ambient temperature, the resulting mixture was quenched with saturated aqueous solution of sodium bicarbonate (50 mL) and extracted with dichloromethane (3×50 mL). The combined organic layers was dried over anhydrous sodium sulfate. After filtration, the filtrate was concentrated under reduced pressure and the residue was purified by silica gel column chromatography, eluted with 1~2% methanol in dichloromethane to afford 6-nitro-3-(1H-pyrrolo[2,3-c]pyridin-1-yl)isoquinolin-7-amine as a purple solid (35 mg, 90%): MS (ESI, m/z): 305.9 [M+1]$^+$; $^1$H NMR (300 MHz, DMSO-d$^6$) δ 9.52 (s, 1H), 9.23 (s, 1H), 8.86 (s, 1H), 8.27-8.199 (m, 3H), 7.66 (d, J=5.1 Hz, 1H), 7.57 (s, 1H), 6.97 (br s, 2H), 6.83 (d, J=3.0 Hz, 1H).

Step 16: Synthesis of tert-butyl N-[(tert-butoxy)carbonyl]-N-(6-nitro-3-{1H-pyrrolo[2,3-c]pyridin-1-yl}isoquinolin-7-yl)carbamate (105a)

To a solution of 6-nitro-3-(1H-pyrrolo[2,3-c]pyridin-1-yl)isoquinolin-7-amine (35 mg, 0.11 mmol) in N,N-dimethylformamide (10 mL) were added triethylamine (35 mg, 0.34 mmol), di-tert-butyl dicarbonate (75 mg, 0.34 mmol) and N,N-dimethylpyridin-4-amine (5 mg, 0.04 mmol) at ambient temperature. After 1 hour, the reaction was quenched with water (50 mL) and extracted with dichloromethane (3×50 mL). The combined organic layers was washed with brine (3×30 mL) and dried over anhydrous sodium sulfate. After filtration, the filtrate was concentrated under reduced pressure and the residue was purified by prep-TLC, eluted with 4% methanol in dichloromethane to afford tert-butyl N-[(tert-butoxy)carbonyl]-N-(6-nitro-3-{1H-pyrrolo[2, 3-c]pyridin-1-yl}isoquinolin-7-yl)carbamate as a yellow solid (45 mg, 78%): MS (ESI, m/z): 506.0 [M+1]$^+$; $^1$H NMR (300 MHz, DMSO-d$^6$) δ 9.74 (s, 1H), 9.59 (s, 1H), 8.94 (s, 1H), 8.60 (s, 1H), 8.48 (s, 1H), 8.37 (d, J=3.6 Hz, 1H), 8.32 (d, J=5.1 Hz, 1H), 7.71 (d, J=5.4 Hz, 1H), 6.94 (d, J=3.3 Hz, 1H), 1.36 (s, 18H).

Example 51

Synthesis of [$^{18}$F]1-(5-(1-(2-fluoroethyl)-1H-pyrazol-3-yl)pyridin-2-yl)-1H-pyrrolo[2,3-c]pyridine ([$^{18}$F]-104)

water (100 mL) and extracted with dichloromethane (3×100 mL). The combined organic layers was dried over anhydrous sodium sulfate and filtered. The filtrate was concentrated under reduced pressure and the residue was purified by silica gel column chromatography, eluted with 1~5% methanol in dichloromethane to afford 1-(5-(1H-pyrazol-3-yl)pyridin-2-yl)-1H-pyrrolo[2,3-c]pyridine as a colorless solid: MS (ESI, m/z): 262.1 [M+1]$^+$; $^1$H NMR (400 MHz, d$^6$-DMSO) δ 13.09 (s, 1H), 9.78 (s, 1H), 9.06 (s, 1H), 8.40 (dd, J=1.6 Hz, 6.8 Hz, 1H), 8.30 (s, 1H), 8.28 (d, J=5.2 Hz, 1H), 7.92 (d, J=8.8 Hz, 1H), 7.89 (s, 1H), 7.67 (d, J=5.6 Hz, 1H), 6.91 (s, 1H), 6.86 (d, J=3.2 Hz, 1H).

Step 2: Synthesis of 2-(3-(6-(1H-pyrrolo[2,3-c]pyridin-1-yl)pyridin-3-yl)-1H-pyrazol-1-yl)ethyl 4-methylbenzenesulfonate (50-2)

To a solution of 1-(5-(1H-pyrazol-3-yl)pyridin-2-yl)-1H-pyrrolo[2,3-c]pyridine (0.20 g, 0.77 mmol) in acetonitrile

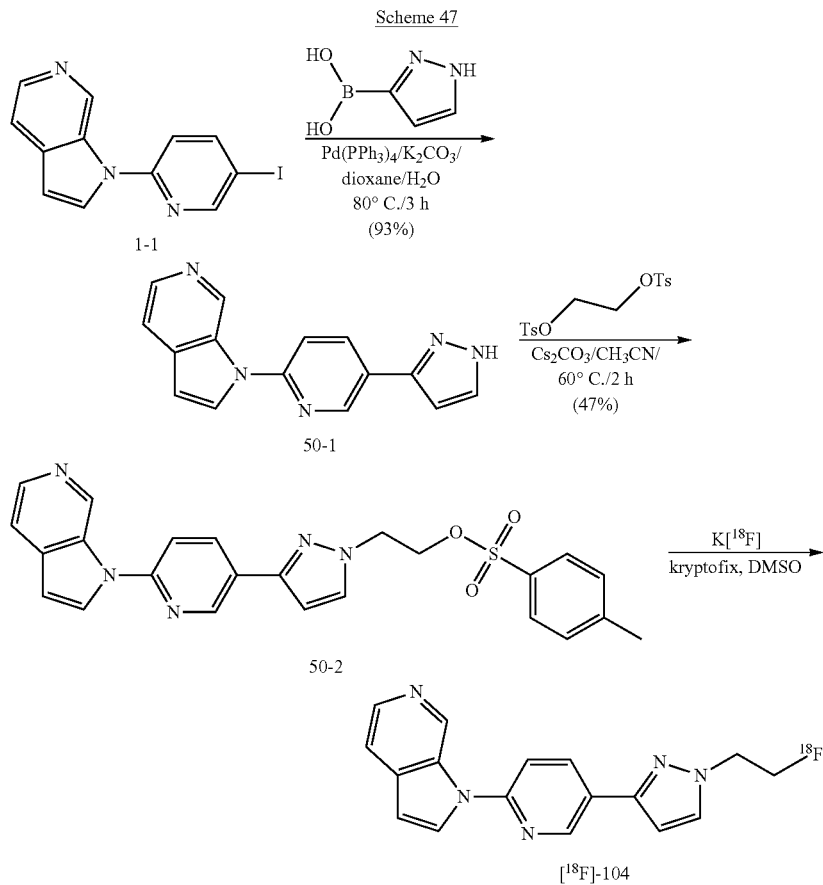

Step 1: Synthesis of 1-(5-(1H-pyrazol-3-yl)pyridin-2-yl)-1H-pyrrolo[2,3-c]pyridine (50-1)

To a solution of 1-(5-iodopyridin-2-yl)-1H-pyrrolo[2,3-c]pyridine (100 mg, 0.31 mmol, 1-1) in 1,4-dioxane (20 mL) and water (5 mL) were added 1H-pyrazol-3-ylboronic acid (53 mg, 0.47 mmol), potassium carbonate (129 mg, 0.93 mmol) and tetrakis(triphenylphosphine)palladium(0) (18 mg, 0.016 mmol). The resulting mixture was stirred for 3 hours at 80° C. under nitrogen atmosphere. After cooling down to ambient temperature, the mixture was diluted with (20 mL) were added cesium carbonate (0.50 g, 1.53 mmol) and ethane-1,2-diyl bis(4-methylbenzenesulfonate) (0.42 g, 1.15 mmol) at ambient temperature. After stirring for 2 hours at 60° C., the reaction was concentrated under reduced pressure and the residue was purified by silica gel column chromatography, eluted with 0.5~1.5% methanol in dichloromethane to afford 2-(3-(6-(1H-pyrrolo[2,3-c]pyridin-1-yl)pyridin-3-yl)-1H-pyrazol-1-yl)ethyl 4-methylbenzenesulfonate as an off white solid: MS (ESI, m/z): 460.2 [M+1]$^+$; $^1$H NMR (300 MHz, d$^6$-DMSO) δ 10.03 (s, 1H), 9.02 (d, J=3.3 Hz, 1H), 8.98 (d, J=2.1 Hz, 1H), 8.52 (d, J=5.7 Hz, 1H), 8.37 (dd, J=2.4 Hz, 6.3 Hz, 1H), 8.30 (d, J=6.3 Hz, 1H), 8.09 (d, J=9.3 Hz, 1H), 7.83 (d, J=2.4 Hz, 1H), 7.60 (d, J=8.4 Hz, 2H), 7.32 (d, J=8.4 Hz, 2H), 7.30 (s, 1H), 6.88 (d, J=1.5 Hz, 1H), 4.45 (br s, 4H), 2.23 (s, 3H).

Step 3: Radiochemical synthesis of [$^{18}$F] 1-(5-(1-(2-fluoroethyl)-1H-pyrazol-3-yl)pyridin-2-yl)-1H-pyrrolo[2,3-c]pyridine ([$^{18}$F]-104)

A solution of 2-(3-(6-(1H-pyrrolo[2,3-c]pyridin-1-yl)pyridin-3-yl)-1H-pyrazol-1-yl)ethyl 4-methylbenzenesulfonate (1 mg) in DMSO or DMF (0.25 ml) was added to the microwave vial containing the dry [$^{18}$F]fluoride, the vent line was removed, and the reaction mixture was heated at 110° C. (75 W) for 10 min. After cooling to <50° C., the reaction was diluted with H$_2$O (0.6 ml), mixed and injected into the semi-preparative HPLC column. The product was purified using Zorbax Eclipse XDB-C-18, 5 μm, 9.4×250 mm (Agilent), at a flow rate of 5 mL/min. The mobile phase was acetonitrile/aq. NaH$_2$PO$_4$ (10 mM) from 30 to 70% in 15 min. The radioactive fraction of interest was collected, evaporated under negative pressure diluted with 0.9% saline solution (3 mL) and transferred into a sterile container. The final product was tested for chemical and radiochemical purity by means of an analytical HPLC system (Waters) using a Gemini, 5 μm, 4.6×150 mm column (Phenomenex) at a flow rate of 1 mL/min. The mobile phase was a mixture consisting of 50% of acetonitrile and 50% of 0.1% trifluoroacetic acid in water. Concentration of [$^{18}$F]-104 was determined by means of an ultraviolet detector (254 nm). Confirmation of the identity of the product was determined by coinjection of a sample of compound 104, and radiochemical purity was determined using a sodium iodide detector (Bioscan). The retention time for compound [$^{18}$F]-404 was 4.2 min, the chemical and radiochemical purities were 100%.

Example 52

Radiochemcial Synthesis of [$^{18}$F] 7-(fluoromethoxy)-3-(1H-pyrrolo[2,3-c]pyridin-1-yl)isoquinoline ([$^{18}$F]-17)

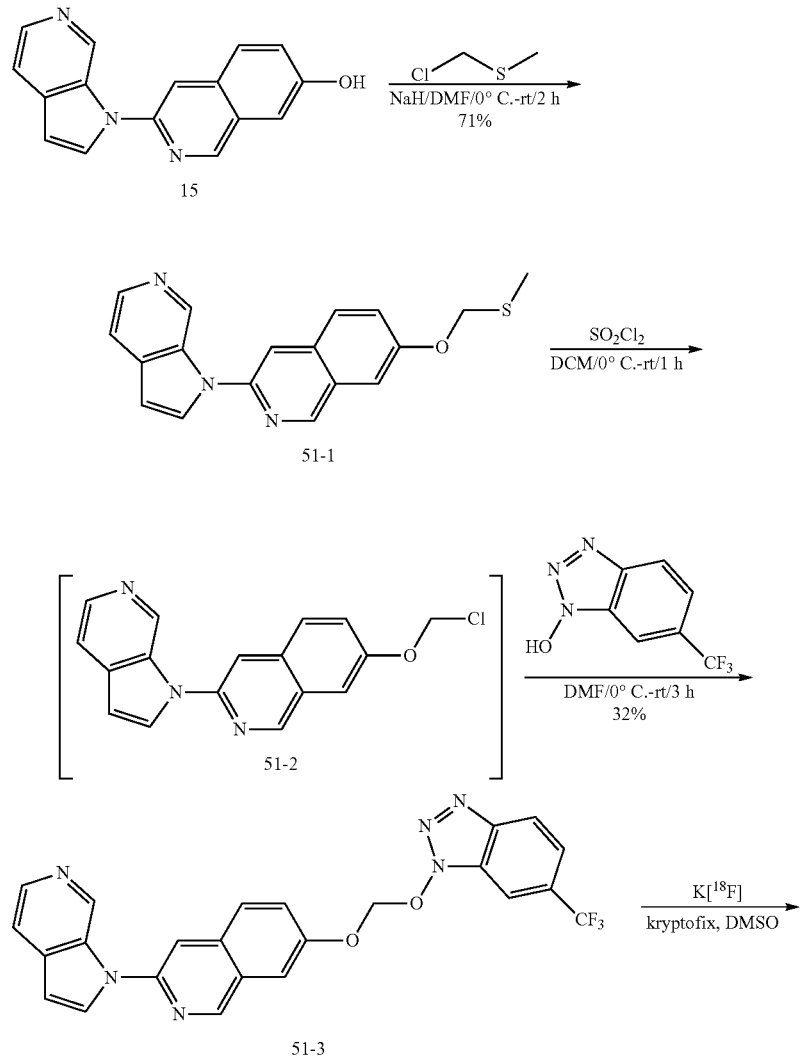

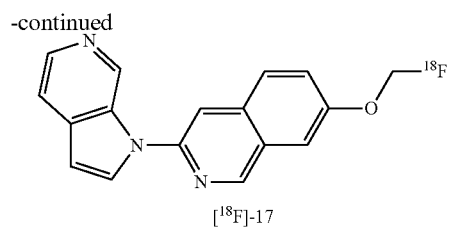

[¹⁸F]-17

Step 1: Synthesis of 7-(methylthiomethoxy)-3-(1H-pyrrolo[2,3-c]pyridin-1-yl)isoquinoline (51-1)

A solution of 3-(1H-pyrrolo[2,3-c]pyridin-1-yl)isoquinolin-7-ol (0.4 g, 1.53 mmol, 15) in N,N-dimethylformamide (6 mL) was treated with sodium hydride (80 mg, 2 mmol, 60% w/w dispersed into mineral oil) at 0° C. for 10 min, followed by the addition of (chloromethyl)(methyl)sulfane (289 mg, 3 mmol). The resulting mixture was stirred for 2 hours at ambient temperature and quenched with saturated aqueous solution of ammonium chloride (30 mL). The resulting mixture was extracted with ethyl acetate (3×60 mL). The combined organic layers was washed with brine (3×20 mL) and dried over anhydrous sodium sulfate. After filtration, the filtrate was concentrated under reduced pressure and the residue was purified by silica gel column chromatography, eluted with 1~2% methanol in dichloromethane to afford 7-(methylthiomethoxy)-3-(1H-pyrrolo[2,3-c]pyridin-1-yl)isoquinoline as a light yellow solid: MS (ESI, m/z): 322.1 [M+1]$^+$; $^1$H NMR (300 MHz, DMSO-$d_6$) δ 9.64 (s, 1H), 9.30 (s, 1H), 8.32 (d, J=3.3 Hz, 1H), 8.28 (d, J=5.4 Hz, 1H), 8.24 (s, 1H), 8.04 (d, J=9.0 Hz, 1H), 7.72 (d, J=2.4 Hz, 1H), 7.68 (dd, J=0.9 Hz, 5.1 Hz, 1H), 7.57 (dd, J=2.4 Hz, 9.0 Hz, 1H), 6.86 (d, J=3.3 Hz, 1H), 5.47 (s, 2H), 2.25 (d, J=4.5 Hz, 3H).

Step 2: Synthesis of 3-(1H-pyrrolo[2,3-c]pyridin-1-yl)-7-((6-(trifluoromethyl)-1H-benzo[d][1,2,3]triazol-1-yloxy)methoxy)isoquinoline (51-3)

To a solution of 7-(methylthiomethoxy)-3-(1H-pyrrolo[2,3-c]pyridin-1-yl)isoquinoline (0.15 g, 0.46 mmol) in dichloromethane (10 mL) was added sulfuryl dichloride (0.18 g, 1.31 mmol) at 0° C. The resulting solution was stirred for 1 hour at ambient temperature and concentrated under reduced pressure to afford crude 7-(chloromethoxy)-3-(1H-pyrrolo[2,3-c]pyridin-1-yl)isoquinoline. A solution of the above crude 7-(chloromethoxy)-3-(1H-pyrrolo[2,3-c]pyridin-1-yl)isoquinoline in dichloromethane (10 mL) was added to a solution of 6-(trifluoromethyl)-1H-benzo[d][1,2,3]triazol-1-ol (0.3 g, 1.48 mmol) and sodium hydride (59 mg, 1.48 mmol) in N,N-dimethylformamide (20 mL) at 0° C. After additional 3 hours at ambient temperature, the reaction was quenched by the addition of saturated aqueous solution of ammonium chloride (50 mL) and extracted with ethyl acetate (3×60 mL). The combined organic layers was washed with brine (3×20 mL) and dried over anhydrous sodium sulfate. After filtration, the filtrate was concentrated under reduced pressure and the residue was purified by silica gel column chromatography, eluted with 1~3% methanol in dichloromethane to afford 3-(1H-pyrrolo[2,3-c]pyridin-1-yl)-7-((6-(trifluoromethyl)-1H-benzo[d][1,2,3]triazol-1-yloxy)methoxy)isoquinoline as a colorless solid: MS (ESI, m/z): 477.1 [M+1]$^+$; $^1$H NMR (400 MHz, DMSO-$d_6$) δ 9.68 (s, 1H), 9.42 (s, 1H), 8.36-8.33 (m, 3H), 8.30 (d, J=5.6 Hz, 1H), 8.15 (s, 1H), 8.13-8.11 (m, 1H), 7.91 (s, 1H), 7.77 (d, J=8.8 Hz, 1H), 7.68 (dd, J=0.4 Hz, 5.2 Hz, 1H), 7.64 (dd, J=2.4 Hz, 8.8 Hz, 1H), 6.88 (d, J=3.2 Hz, 1H), 6.48 (s, 2H).

Step 3: Radiochemical synthesis [¹⁸F] 7-(fluoromethoxy)-3-(1H-pyrrolo[2,3-c]pyridin-1-yl)isoquinoline ([¹⁸F]-17)

A solution of 3-(1H-pyrrolo[2,3-c]pyridin-1-yl)-7-((6-(trifluoromethyl)-1H-benzo[d][1,2,3]triazol-1-yloxy)methoxy)isoquinoline (0.6 mg, 51-3) in DMSO (0.25 mL) and acetonitrile (0.15 mL) was added to the microwave vial containing the dry [¹⁸F]fluoride, the vent line was removed, and the reaction mixture was heated at 90° C. for 5 min, then at 110° C. for 5 min and 120° C. for 5 min (50 W). After cooling down to <50° C., the reaction was diluted with H$_2$O (0.6 mL), mixed and injected into the semi-preparative HPLC column. The product was purified using Zorbax Eclipse XDB-C-18, 5 μm, 9.4×250 mm (Agilent), at a flow rate of 5 mL/min. The mobile phase was acetonitrile/aq. NaH$_2$PO$_4$ (10 mM) from 30 to 70% in 15 min. The radioactive fraction of interest was collected, evaporated under negative pressure diluted with 0.9% saline solution (3 mL) and transferred into a sterile container. The final product was tested for chemical and radiochemical purity by means of an analytical HPLC system (Waters) using a Xbridge Phenyl, 3.5 μm, 4.6×150 mm column (Waters) at a flow rate of 2 mL/min. The mobile phase was a mixture consisting of 50% of acetonitrile and 50% of 0.1% trifluoroacetic acid in water. Concentration of [¹⁸F]-17 was determined by means of an ultraviolet detector (254 nm). Confirmation of the identity of the product was determined by coinjection of a sample of compound 17, and radiochemical purity was determined using a sodium iodide detector (Bioscan). The retention time for compound [¹⁸F]-17 was 5.3 min.

Example 53

Radiochemcial Synthesis of [¹⁸F]1-(2'-fluoro-[3,4'-bipyridin]-6-yl)-1H-pyrrolo[2,3-c]pyridine ([¹⁸F]-44)

Scheme 49

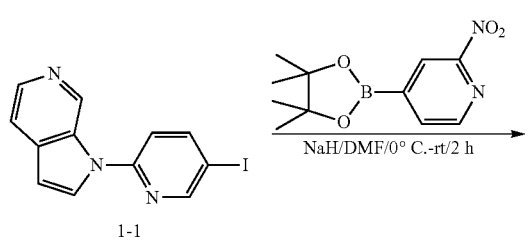

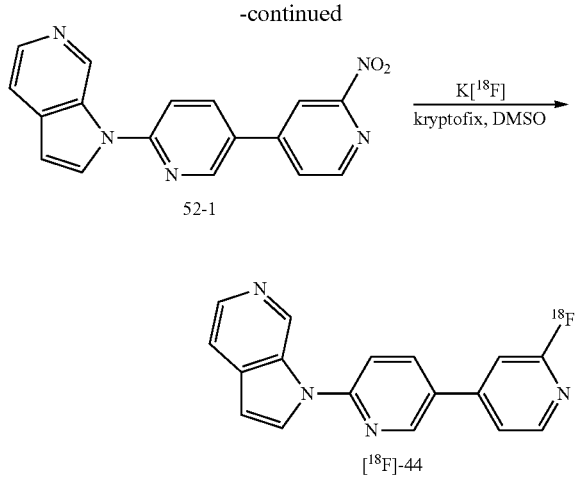

Step 1: Synthesis of 1-(6'-nitro-3,4'-bipyridin-6-yl)-1H-pyrrolo[2,3-c]pyridine (52-1)

To a solution of 1-(5-iodopyridin-2-yl)-1H-pyrrolo[2,3-c]pyridine (100 mg, 0.31 mmol) in 1,4-dioxane (30 mL) were added bis(pinacolato)diboron (158 mg, 0.62 mmol), potassium acetate (60 mg, 0.62 mmol) and [1,1'-bis(diphenylphosphino)ferrocene]-dichloropalladium(II) (23 mg, 0.031 mmol) at ambient temperature. The resulting mixture was stirred for 3 hours at 80° C. under nitrogen atmosphere. After cooling down to ambient temperature, 4-bromo-2-nitropyridine (125 mg, 0.62 mmol) was added to the mixture followed by the addition of potassium carbonate (85 mg, 0.62 mmol), water (3 mL) and tetrakis(triphenyl-phosphine)palladium(0) (35 mg, 0.031 mmol). The resulting mixture was stirred for 4 hours at 80° C. under nitrogen atmosphere. After cooling down to ambient temperature, the mixture was diluted with water (100 mL) and extracted with dichloromethane (3×50 mL). The combined organic layers was dried over anhydrous sodium sulfate and filtered. The filtrate was concentrated under reduced pressure and the residue was purified by silica gel column chromatography, eluted with 0.3~3% methanol in dichloromethane to afford 1-(6'-nitro-3,4'-bipyridin-6-yl)-1H-pyrrolo[2,3-c]pyridine as a yellow solid: MS (ESI, m/z): 318.1 [M+1]$^+$; $^1$H NMR (300 MHz, DMSO-$d_6$) δ 9.93 (s, 1H), 9.24 (d, J=2.1 Hz, 1H), 8.81-7.92 (m, 2H), 8.65 (dd, J=2.4 Hz, 8.7 Hz, 1H), 8.47 (d, J=3.3 Hz, 1H), 8.41 (dd, J=1.5 Hz, 5.1 Hz, 1H), 8.33 (d, J=5.1 Hz, 1H), 8.10 (d, J=8.4 Hz, 1H), 7.69 (d, J=5.7 Hz, 1H), 6.93 (d, J=3.6 Hz, 1H).

Step 2. Radiochemical synthesis [$^{18}$F] 1-(2'-fluoro-[3,4'-bipyridin]-6-yl)-1H-pyrrolo[2,3-c]pyridine ([$^{18}$F]-44)

A solution of 1-(2'-nitro-[3,4'-bipyridin]-6-yl)-1H-pyrrolo[2,3-c]pyridine (0.4 mg, 52-1) in DMSO (0.25 mL) was added to the microwave vial containing the dry [$^{18}$F]fluoride, the vent line was removed, and the reaction mixture was heated at 140° C. (75 W) for 3 min. After cooling down to <50° C., the reaction was diluted with H$_2$O (0.6 mL), mixed and injected into the semi-preparative HPLC column. The product was purified using Zorbax Eclipse XDB-C-18, 5 μm, 9.4×250 mm (Agilent), at a flow rate of 5 mL/min. The mobile phase was acetonitrile/aq. NaH$_2$PO$_4$ (10 mM) 45/55. The radioactive fraction of interest was collected, evaporated under negative pressure diluted with 0.9% saline solution (3 mL) and transferred into a sterile container. The final product was tested for chemical and radiochemical purity by means of an analytical HPLC system (Waters) using a Gemini, 5 μm, 4.6×150 mm column (Phenomenex) at a flow rate of 1 mL/min. The mobile phase was acetonitrile/0.1% trifluoroacetic acid in water (10 mM) from 50 to 85% in 10 min. Concentration of [$^{18}$F]-52 was determined by means of an ultraviolet detector (254 nm). Confirmation of the identity of the product was determined by coinjection of a sample of compound 52, and radiochemical purity was determined using a sodium iodide detector (Bioscan). The retention time for compound [$^{18}$F]-52 was 6.6 min.

Example 54

Radiochemcial Synthesis of [$^{18}$F]$d_2$-7-(fluoromethoxy)-3-(1H-pyrrolo[2,3-c]pyridin-1-yl)isoquinoline ($d_2$, [$^{18}$F]-17)

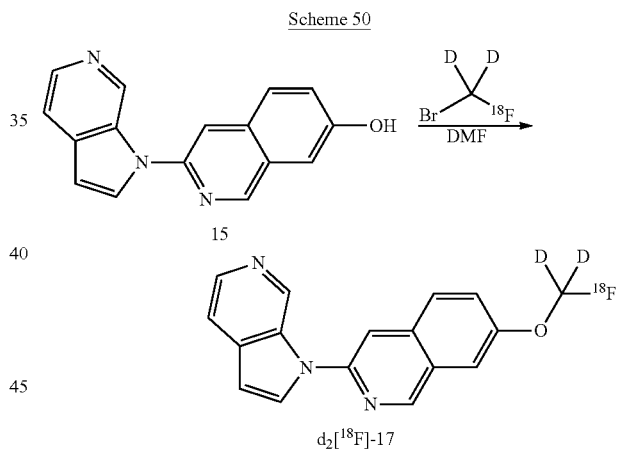

Step 1 Radiochemcial synthesis of [$d_2$, $^{18}$F]-7-(fluoromethoxy)-3-(1H-pyrrolo[2,3-c]pyridin-1-yl)isoquinoline [$d_2$, $^{18}$F]-17)

The [$^{18}$F]fluoride containing anion exchange resin was eluted with Kryptofix222 (7 mg, 19 μmol) and K$_2$CO$_3$ (2.1 mg, 15 μmol) in acetonitrile/water (80/20, 0.7 mL) and transferred to a vented 5-ml V-shaped. The [$^{18}$F]fluoride was dried under argon flow heating (95° C.). Additional aliquots of acetonitrile (3×0.5 mL) were added for azeotropic drying at 90° C. Dibromomethane-$d_2$ (50 μL) in dry acetonitrile was added to the dry [$^{18}$F]fluoride and the reaction vessel sealed. The mixture was heated at 95° C. for 5 minutes. After cooling, the reaction vessel was opened and the [$d_2$, $^{18}$F] bromofluoromethane was transfer true teflon tubing to a 0.9 mL vial containing 15 (0.36 mg, 1.38 μmol) and cesium carbonate (4 mg, 120 μmol) in dimethylformamide (300 μL) at rt. The resulting reaction mixture was heated for 15 minutes at 70° C. The solution was transferred in a 0.9 mL vial containing water (700 μL) at rt, mixed and injected into the semi-preparative HPLC column. The product was purified using Zorbax Eclipse XDB-C-18, 5 μm, 9.4×250 mm (Agilent), at a flow rate of 5 mL/min. The mobile phase was acetonitrile/aq. $NaH_2PO_4$ (10 mM) from 30 to 70% in 15 min. The radioactive fraction of interest was collected, evaporated under negative pressure diluted with 0.9% saline solution (3 mL) and transferred into a sterile container. The final product was tested for chemical and radiochemical purity by means of an analytical HPLC system (Waters) using a Xbridge Phenyl, 3.5 μm, 4.6×150 mm column (Waters) at a flow rate of 2 mL/min. The mobile phase was a mixture consisting of 50% of acetonitrile and 50% of 0.1% trifluoroacetic acid in water. [$d_2$, $^{18}F$]-17 concentration was determined by means of an ultraviolet detector (254 nm). Confirmation of the identity of the product was determined by coinjection of a sample of 17, and radiochemical purity was determined using a sodium iodide detector (Bioscan). The retention time for [$d_2$, $^{18}F$]-17 was 5.3 min.

Example 55

Radiochemical Synthesis of [$^{18}F$]6-fluoro-3-(1H-pyrrolo[2,3-c]pyridin-1-yl)isoquinoline [$^{18}F$]-9

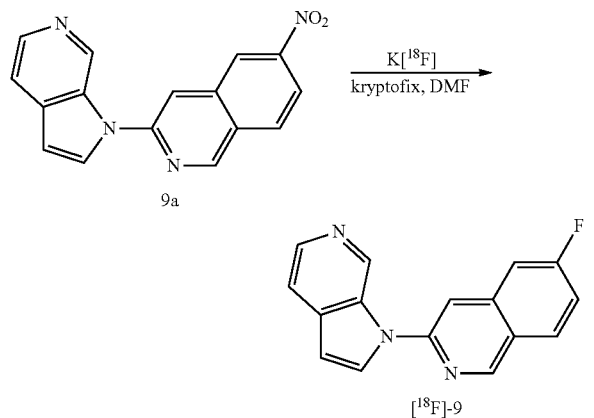

A solution of 6-nitro-3-(1H-pyrrolo[2,3-c]pyridin-1-yl) isoquinoline name (0.3 mg, 9a) in DMF (0.25 mL) was added to the microwave vial containing the dry [$^{18}F$]fluoride, the vent line was removed, and the reaction mixture was heated at 140° C. (65 W) for 4 min. After cooling down to <50° C., the reaction was diluted with H2O (0.6 mL), mixed and injected into the semi-preparative HPLC column. The product was purified using Zorbax Eclipse XDB-C-18, 5 μm, 9.4×250 mm (Agilent), at a flow rate of 5 mL/min. The mobile phase was acetonitrile/aq. NaH2PO4 (10 mM) 50 to 80% in 15 min. The radioactive fraction of interest was collected, evaporated under negative pressure diluted with 0.9% saline solution (3 mL) and transferred into a sterile container. The final product was tested for chemical and radiochemical purity by means of an analytical HPLC system (Waters) using a Onix Monolithic C-18 100×3.0 mm column (Phenomenex) at a flow rate of 1 mL/min. The mobile phase was acetonitrile/0.1% trifluoroacetic acid in water: 30/70. Concentration of [$^{18}F$]-9 was determined by means of an ultraviolet detector (254 nm). Confirmation of the identity of the product was determined by coinjection of a sample of compound 9, and radiochemical purity was determined using a sodium iodide detector (Bioscan). The retention time for compound [$^{18}F$]-9 was 3.2 min.

Example 56

Radiochemical Synthesis [$^{18}F$] 6-fluoro-3-(1H-pyrrolo[2,3-c]pyridin-1-yl)isoquinolin-5-amine. ([$^{18}F$]-18)

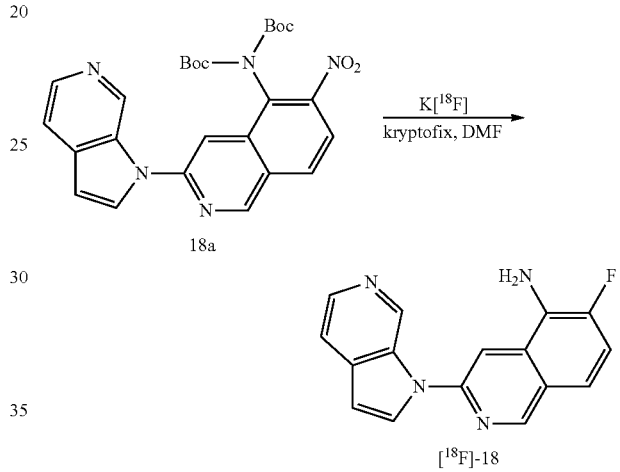

A solution of tert-butyl N-[(tert-butoxy)carbonyl]-N-(6-nitro-3-[1H-pyrrolo[2,3-c]pyridin-1-yl]isoquinolin-5-yl) carbamate (1 mg, 18a) in DMF (0.25 mL) was added to the microwave vial containing the dry [18F]fluoride, the vent line was removed, and the reaction mixture was heated at 90° C. (55 W) for 3 min, then 110° C. (55 W) for 3 min, then 120° C. (55 W) for 3 min and 140° C. (55 W) for 3 min. TFA (5% in water) was added and the mixture was heated at 110° C. (55 W) for 3 min. After cooling down to <50° C., the reaction was injected into the semi-preparative HPLC column. The product was purified using Gemini C6-Phenyl 110A, 5 μm, 10×250 mm (Phenomenex), at a flow rate of 4 mL/min. The mobile phase was Ethanol/sodium acetate pH 4 (10 mM) 25/75. The radioactive fraction of interest was collected, evaporated under negative pressure diluted with 0.9% saline solution (3 mL) and transferred into a sterile container. The final product was tested for chemical and radiochemical purity by means of an analytical HPLC system (Agilent) using a Xbridge Phenyl 3.5 μ4.6×150 mm column (Waters) at a flow rate of 2 mL/min. The mobile phase was acetonitrile/sodium acetate pH4 (10 mM): 20/80. Concentration of [$^{18}F$]-18 was determined by means of an ultraviolet detector (254 nm). Confirmation of the identity of the product was determined by coinjection of a sample of compound 18, and radiochemical purity was determined using a sodium iodide detector (Bioscan). The retention time for compound [$^{18}F$]-18 was 7.1 min.

Example 57

Radiochemical Synthesis [$^{18}$F]6-fluoro-3-(1H-pyrrolo[2,3-c]pyridin-1-yl)isoquinolin-7-amine-([$^{18}$F]-105)

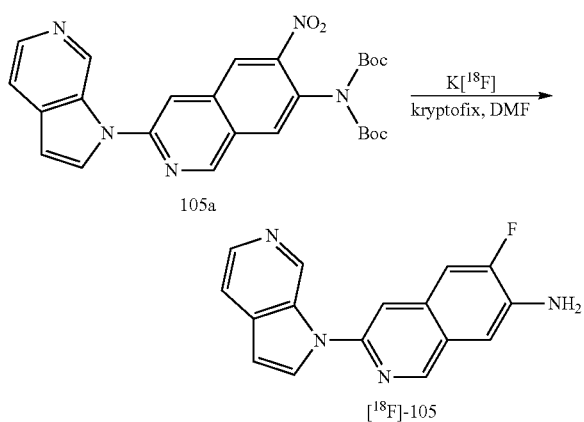

[$^{18}$F]-105

A solution of tert-butyl N-[(tert-butoxy)carbonyl]-N-(6-nitro-3-{1H-pyrrolo[2, 3-c]pyridin-1-yl}isoquinolin-7-yl)carbamate (1.5 mg, 105a) in DMF (0.25 mL) was added to the microwave vial containing the dry [$^{18}$F]fluoride, the vent line was removed, and the reaction mixture was heated at 90° C. (55 W) for 3 min, then 110° C. (55 W) for 3 min, then 120° C. (55 W) for 3 min and 140° C. (55 W) for 3 min. TFA (5% in water) was added and the mixture was heated at 110° C. (55 W) for 3 mM. After cooling down to <50° C., the reaction was injected into the semi-preparative HPLC column. The product was purified using Zorbax Eclipse XDB-C-18, 5 µm, 9.4×250 mm (Agilent), at a flow rate of 5 mL/min. The mobile phase was acetonitrile/aq. NaH$_2$PO$_4$ (10 mM) with an 30 to 70% in 15 min gradient. The radioactive fraction of interest was collected, evaporated under negative pressure diluted with 0.9% saline solution (3 mL) and transferred into a sterile container. The final product was tested for chemical and radiochemical purity by means of an analytical HPLC system (Agilent) using a Xbridge Phenyl 3.5 µ4.6×150 mm column (Waters) at a flow rate of 2 mL/min. The mobile phase was acetonitrile/sodium acetate pH4 (10 mM): 20/80. Concentration of [$^{18}$F]-105 was determined by means of an ultraviolet detector (254 nm). Confirmation of the identity of the product was determined by coinjection of a sample of compound 105, and radiochemical purity was determined using a sodium iodide detector (Bioscan). The retention time for compound [$^{18}$F]-105 was 5.4 min.

Procedures for Tissue Homogenate Binding Assays

The frozen human brain samples of Alzheimer's disease (AD) were purchased from Analytic Biological Services Inc. They were postmortem tissue from donors with clinical diagnosis of AD. As much of the white matter was dissected out of the frontal cortex in order to enrich the tissue preparations for gray matter. Brain homogenates of gray matter enriched frontal cortex were prepared by homogenizing the tissue in ice cold Phosphate Buffered Saline (PBS), pH 7.4 at 80 mg wet weight tissue per 1 mL for 45 seconds at 4° C. on setting 16 of Polytron. The homogenate was further diluted with ice cold PBS to 30 mg wet weight tissue per 1 mL and homogenized for an additional minute as described above. Homogenates were aliquotted in 5 ml/tube and store at −70° C. until use.

For hot saturation binding assay, various concentrations of radioligand were prepared in Assay Buffer (PBS plus 0.1% BSA) plus 20% DMSO ranging from 0.02 to 57 nM for [$^3$H]compound of Example 49. 25 µl of radioligand was added to 225 µl of membranes diluted to 0.5 mg/ml in Assay Buffer) for final conc of radioligand ranging from 0.002 to 5.7 nM and final membrane of 100 µg wet weight/assay tube (incubation, filtration, and determination of amount of radioligand used in assay are described below). Self-block with unlabeled compound was used to determine non-specific binding. Saturation data was analyzed using Graphpad/Prism software. FIG. 1 shows an example of hot saturation binding of [$^3$11]-6. The radioligand shows high affinity for tau in AD brain homogenates with measured dissociation constant of 0.2 nM.

For displacement tau binding assay, unlabeled test compounds were dissolved in DMSO at 1 mM. Dilutions of tests compounds to various concentrations were made in 100% DMSO at 1000× final assay concentration and 0.225 µl aliquots were dispensed into assay plates. Brain homogenates were diluted to 0.5 mg/mL from original 30 mg/mL volume in Assay Buffer, and 200 µl were added to the assay plate for a final concentration of 100 µg wet weight/assay tube. [$^3$H]-6 was prepared at 10× final concentration in Assay Buffer plus 20% DMSO and 25 µl was added to the assay plate for final assay concentration of 0.25 nM. The assay plate was incubated at room temperature (25° C.) for 90 minutes. Unbound and bound ligand were separated by filtration of bound onto GF/C filter plates (pre-treated for 30 min with 0.2% polyethyleninamine) using a Packard Uni-Filter Harvester and washing away unbound with 2.5 ml per well ice cold 5 mM Tris at pH 7.4. Filter plates were dried for 1 hour in a vacuum oven and 50 µl/well MicroScint-20 were added. Plates were counted 1 min per well by Packard Topcount. Total amount of radioligand used in the assay was determined by counting 25 µl of 10× ligand stock. Data was analyzed using Activity Base software to generate 4p fit of dose responses; and, Ki values were calculated. Tau Ki data for representative compounds of the invention are found in Table 1. As shown in FIG. 2, compound 6 (unlabeled) self-displaced [$^3$H]-6 with Ki value of 0.43 nM Homogenates from AD and non-AD human brain samples were assessed for their immunoreactivity to anti-Aβ antibody 6E10 and an anti-phospho-tau antibody PHF6 or AT8. The brain sections with the highest levels of PHF6 or AT8 immunoreactivity were chosen for the displacement tau binding assay and the brain sections with the highest levels of 6E10 combined with low levels of PHF6 or AT8 immunoreactivity were chosen for the amyloid tissue homogenate binding assay.

Procedure for the amyliod binding assay (counterscreen) was identical to the Tau binding assay using [$^3$H]-131

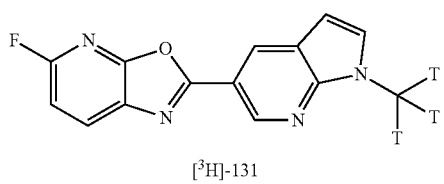

[$^3$H]-131 as the reference radioligand.

Tau Ki and/or Amyloid Ki data for representative compounds of the instant invention are found in Table 1.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

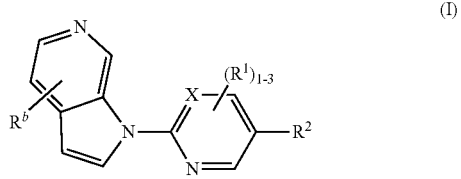

(I)

or a pharmaceutically acceptable salt thereof wherein;
X represents CH, or N;
R represents hydrogen, or —$C_{1-6}$alkyl, said alkyl optionally substituted with 1 to 3 groups of $R^a$;
$R^1$ represents hydrogen, —$C_{1-6}$alkyl, —CN, —$(CH_2)_n$NH $(CH_2)_nN(R)_2$, —$C_{2-6}$alkenyl, —$(CH_2)_n$OR, or —$(CH_2)_n$halogen;
$R^2$ represents —$OC_{1-6}$ alkyl, —$C_{2-6}$alkenyl$R^3$ —$(CH_2)_n$OR, —$(CH_2)_n$halogen, —$O(CH_2)_n$halogen, —$C_{6-10}$ aryl, —$C_{5-10}$ heterocyclyl, —$O(CH_2)_nR^a$, —$N(CH_3)(CH_2)_n$OR, —NRC(O)R, —NH$(CH_2)_n$halo, —NC(O)$C_{6-10}$ aryl, —NC(O)$C_{5-10}$ heterocyclyl, —N(CH$_3$)(CH$_2$)$_n$halogen, —C(O)NC$_{6-10}$ aryl, said alkyl, aryl, and heterocyclyl optionally substituted with 1 to 3 groups of $R^a$;
or an adjacent $R^1$ can combine with $R^2$ to form a nine to ten membered bicyclic ring together with the ring to which $R^1$ and $R^2$ are attached, optionally interrupted with N, S, and/or O, said bicyclic ring optionally substituted with 1 to 3 groups of $R^a$;
$R^3$ represents hydrogen, —$C_{1-6}$alkyl, —$(CH_2)_n$halogen, —$(CH_2)_nN(R)_2$, —$(CH_2)_nNR(CH_2)_nN(R)_2$, —$C_{6-10}$ aryl, —$C_{5-10}$ heteroaryl, said alkyl, aryl, and heteroaryl optionally substituted with 1 to 3 groups of $R^a$;
$R^a$ represents —CN, CF$_3$, —$C_{1-6}$alkyl, —$C_{2-6}$alkenyl, —$C_{2-6}$alkynyl, $C_{6-10}$ aryl, —$C_{5-10}$ heterocyclyl, —CN, NO$_2$, (CH$_2$) halogen, —O(CH$_2$)$_n$halogen, (CH$_2$)$_n$OR, —O(CH$_2$)$_n$$C_{6-10}$ aryl, —(CH$_2$)$_n$N(R)$_2$, —C(O)N(R)$_2$, —N(CH$_3$)(CH$_2$)$_n$OR, —NRCOR, —COR, —NH (CH$_2$)$_n$halo, —N(CH$_3$)(CH$_2$)$_n$halogen, C(O)C$_{6-10}$ aryl, or —CO$_2$R, said alkyl, alkenyl, alkynyl, aryl, and heterocyclyl optionally substituted with 1 to 3 groups of $R^b$;
$R^b$ represents hydrogen, —$C_{1-6}$alkyl, —OR, —$(CH_2)_n$N (R)$_2$, or halogen; and
n represents 0-4.

2. The compound according to claim 1 wherein X is CH.

3. The compound according to claim 1 wherein X is N.

4. The compound according to claim 1 wherein $R^2$ is selected from the group consisting of —$C_{2-6}$alkenyl$R^3$, —$C_{2-6}$alkynyl$R^3$, —NC(O)$C_{6-10}$ aryl, —NC(O)$C_{5-10}$ heterocyclyl, —$C_{6-10}$ aryl, and —$C_{5-10}$ heterocyclyl said aryl and heterocyclyl optionally substituted with 1 to 3 groups of $R^a$.

5. The compound according to claim 1 wherein an adjacent $R^1$ is combined with an $R^2$ to form a 9 to 10 membered bicycle ring, said ring optionally interrupted with N, S, and/or O, and said ring optionally substituted with 1 to 3 groups of $R^a$.

6. The compound according to claim 5 wherein the bicycle formed is selected from the group consisting of optionally substituted pyrrolopyridinyl, furopyridinyl, naphthryidinyl, tetrahydronaphthyridinyl, quinazolinyl, quinolinyl, and isoquinolinyl.

7. The compound according to claim 1 wherein X is CH and $R^2$ is selected from the group consisting of —$C_{2-6}$alkenyl$R^3$, —$C_{2-6}$alkynyl$R^3$, —NC(O)$C_{6-10}$ aryl, —NC(O)$C_{5-10}$ heterocyclyl, —$C_{6-10}$ aryl, and —$C_{5-10}$ heterocyclyl, said aryl and heterocyclyl optionally substituted with 1 to 3 groups of $R^a$ and $R^3$ is selected from the group consisting of methyl, ethyl, propyl, (CH$_2$)$_n$F, —(CH$_2$)$_n$N (R)$_2$, —(CH$_2$)$_n$NR(CH$_2$)$_n$N(R)$_2$, optionally substituted phenyl, pyridyl and thiazolyl.

8. The compound according to claim 1 wherein X is CH and $R^2$ is combined with an adjacent $R^1$ to form a 9 to 10 membered bicycle ring together with the ring to which $R^1$ and $R^2$ are attached, said bicyclic ring optionally interrupted with N, S and/or O, said bicycle optionally substituted with 1 to 3 groups of $R^a$.

9. The compound according to claim 8 wherein the bicycle ring formed is selected from the group consisting of optionally substituted pyrrolopyridinyl, furopyridinyl, naphthryidinyl, tetrahydronaphthyridinyl, quinolinyl, or isoquinolinyl.

10. The compound according to claim 7 wherein X is N, $R^2$ is selected from the group consisting of —$C_{2-6}$alkenyl$R^3$, —$C_{2-6}$alkynyl$R^3$, —NC(O)$C_{6-10}$ aryl, —NC(O)$C_{5-10}$ heterocyclyl, —$C_{6-10}$ aryl, and —$C_{5-10}$ heterocyclyl, said aryl and heterocyclyl optionally substituted with 1 to 3 groups of $R^a$ and $R^3$ is selected from the group consisting of methyl, ethyl, propyl, (CH$_2$)$_n$F, —(CH$_2$)$_n$N(R)$_2$, —(CH$_2$)$_n$NR (CH$_2$)$_n$N(R)$_2$, optionally substituted phenyl, pyridyl and thiazolyl.

11. The compound according to claim 1 wherein X is N and $R^2$ is combined with an adjacent $R^1$ to form a 9 to 10 membered bicycle ring together with the ring to which $R^1$ and $R^2$ are attached, said bicyclic ring optionally interrupted with N, S and/or O, said bicycle optionally substituted with 1 to 3 groups of $R^a$.

12. The compound according to claim 1 which are isotopically labeled with $^2$H, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{76}$Br, $^{77}$Br, $^{123}$I, $^{124}$I or $^{131}$I.

13. The compound according to claim 1 presented by structural formula Ia:

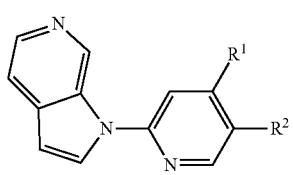

Ia or a pharmaceutically acceptable salt thereof.

14. The compound according to claim 13 wherein $R^2$ is selected from the group consisting of —$C_{2-6}$alkenyl$R^3$, —$C_{2-6}$alkynyl$R^3$, $C_{6-10}$ aryl, —$C_{5-10}$ heterocyclyl, —NC(O)

$C_{6-10}$ aryl, —NC(O) $C_{5-10}$ heterocyclyl, —N(CH$_3$)(CH$_2$)$_n$halogen, and C(O)NC$_{6-10}$ aryl, said aryl and heterocyclyl optionally substituted with 1 to 3 groups of R$^a$, and R$^3$ is selected from the group consisting of hydrogen, —(CH$_2$)$_n$halogen, —(CH$_2$)$_n$N(R)$_2$, (CH$_2$)$_n$NR(CH$_2$)$_n$N(R)$_2$, $C_{6-10}$ aryl, and —$C_{5-10}$ heteroaryl, said aryl and heteroaryl optionally substituted with 1 to 3 groups of R$^a$.

15. The compound according to claim 13 wherein R$^2$ combines with an adjacent R$^1$ to form a 9 to 10 membered bicycle ring together with the ring to which R$^1$ and R$^2$ are attached, said bicyclic ring optionally interrupted by N, S, O, said bicycle optionally substituted by 1 to 3 groups of R$^a$.

16. The compound according to claim 13 which are isotopically labeled with $^2$H, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{76}$Br, $^{77}$Br, $^{123}$I, $^{124}$I or $^{131}$I.

17. The compound of claim 1 represented by structural formula II:

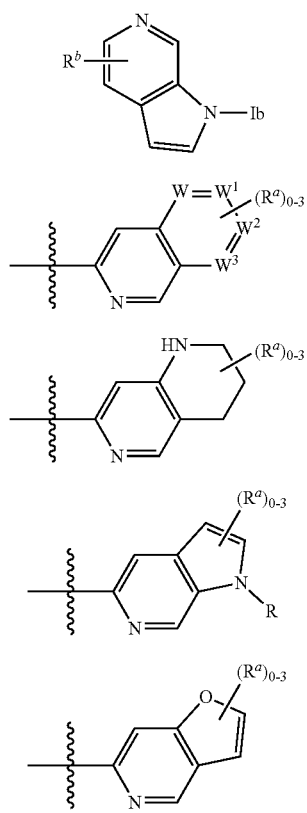

or a pharmaceutically acceptable salt there of wherein Ib=Ib1, Ib2, Ib3, or Ib4, and W, W$^1$, W$^2$, W$^3$ independently are selected from —CH— and —N— and R, R$^a$ and R$^b$ are as originally described.

18. The compound according to claim 1 represented by structural formula II:

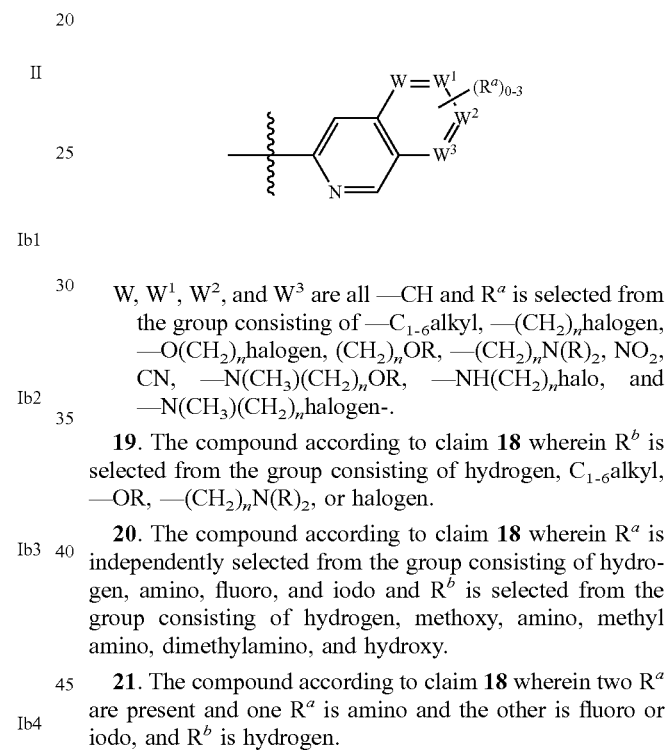

wherein Ib is N

W, W$^1$, W$^2$, and W$^3$ are all —CH and R$^a$ is selected from the group consisting of —$C_{1-6}$alkyl, —(CH$_2$)$_n$halogen, —O(CH$_2$)$_n$halogen, (CH$_2$)$_n$OR, —(CH$_2$)$_n$N(R)$_2$, NO$_2$, CN, —N(CH$_3$)(CH$_2$)$_n$OR, —NH(CH$_2$)$_n$halo, and —N(CH$_3$)(CH$_2$)$_n$halogen-.

19. The compound according to claim 18 wherein R$^b$ is selected from the group consisting of hydrogen, $C_{1-6}$alkyl, —OR, —(CH$_2$)$_n$N(R)$_2$, or halogen.

20. The compound according to claim 18 wherein R$^a$ is independently selected from the group consisting of hydrogen, amino, fluoro, and iodo and R$^b$ is selected from the group consisting of hydrogen, methoxy, amino, methyl amino, dimethylamino, and hydroxy.

21. The compound according to claim 18 wherein two R$^a$ are present and one R$^a$ is amino and the other is fluoro or iodo, and R$^b$ is hydrogen.

22. The compound according to claim 18 which is an isotopically labeled with a group selected from $^2$H, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{76}$Br, $^{77}$Br, $^{123}$I, $^{124}$I and $^{131}$I.

23. A compound which is selected from the group consisting of:

| Compound # | Structure |
|---|---|
| 1 | 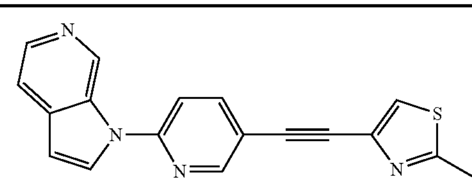 |

-continued
| Compound # | Structure |
|---|---|
| 2 | 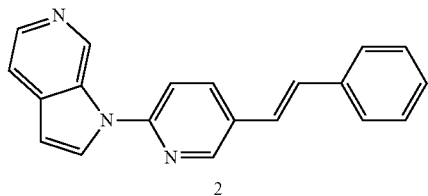 [SMILES: C(=C\c1ccc(-n2ccc3ccncc32)nc1)/c1ccccc1] |
| 3 | 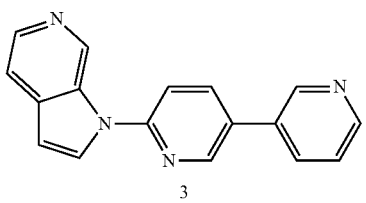 [SMILES: c1cncc(-c2ccc(-n3ccc4ccncc43)nc2)c1] |
| 4 | 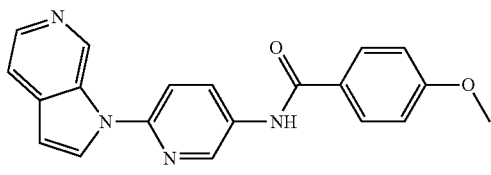 |
| 5 | 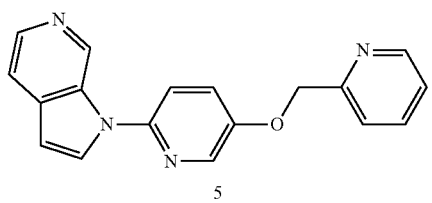 [SMILES: c1ccc(COc2ccc(-n3ccc4ccncc43)nc2)nc1] |
| 6 | 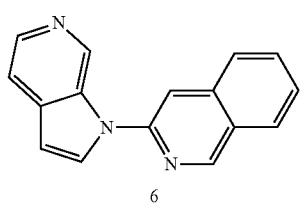 [SMILES: c1ccc2cc(-n3ccc4ccncc43)ncc2c1] |
| 7 | 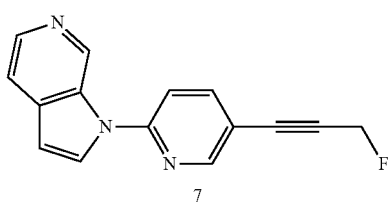 [SMILES: FCC#Cc1ccc(-n2ccc3ccncc32)nc1] |
| 8 | 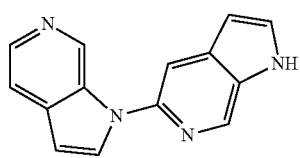 |

-continued
| Compound # | Structure |
|---|---|
| 9 | 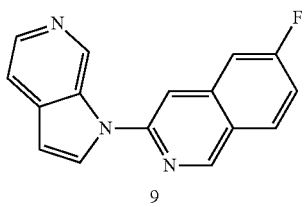 [SMILES: Fc1ccc2cnc(-n3ccc4ccncc43)cc2c1]<br>9 |
| 10 | 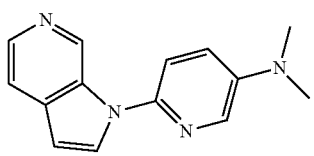<br>10 |
| 11 | 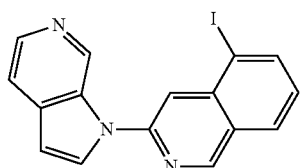<br>11 |
| 11-5 | 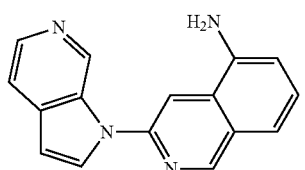<br>11-5 |
| 12 | 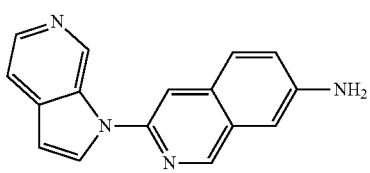<br>12 |
| 13 | 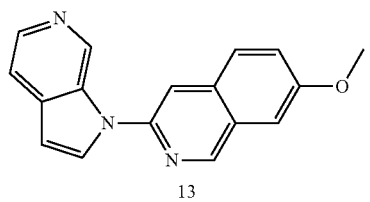 [SMILES: COc1ccc2cc(-n3ccc4ccncc43)ncc2c1]<br>13 |
| 14 | 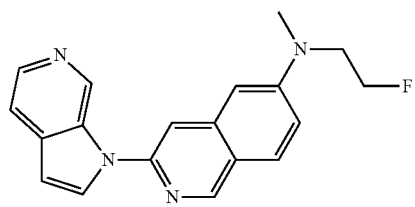<br>14 |

-continued
| Compound # | Structure |
|---|---|
| 14-1 | 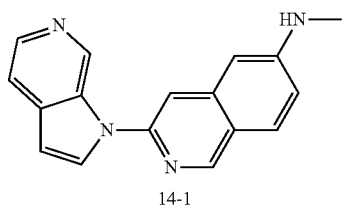 [SMILES: CNc1ccc2cnc(-n3ccc4ccncc43)cc2c1]<br>14-1 |
| 15 | 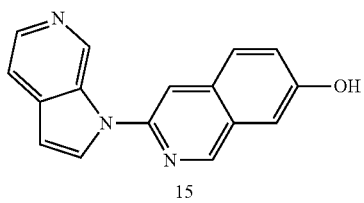 [SMILES: Oc1ccc2cc(-n3ccc4ccncc43)ncc2c1]<br>15 |
| 16 | 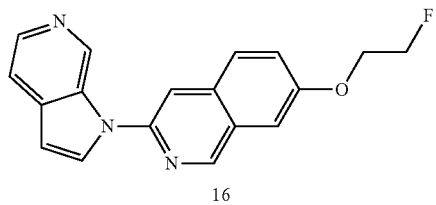<br>16 |
| 17 | 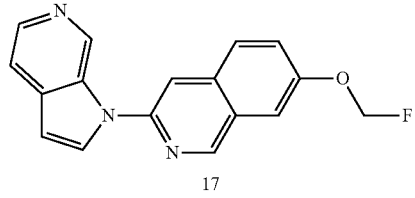 [SMILES: FCOc1ccc2cc(-n3ccc4ccncc43)ncc2c1]<br>17 |
| 18 | 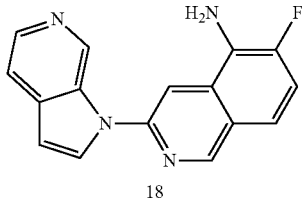 [SMILES: Nc1c(F)ccc2cnc(-n3ccc4ccncc43)cc12]<br>18 |
| 19 | 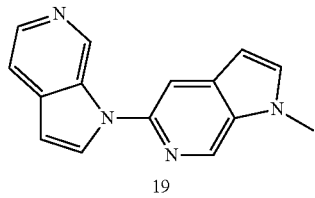 [SMILES: Cn1ccc2cc(-n3ccc4ccncc43)ncc21]<br>19 |
| 20 | 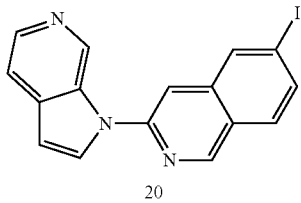 [SMILES: Ic1ccc2cnc(-n3ccc4ccncc43)cc2c1]<br>20 |

-continued

| Compound # | Structure |
|---|---|
| 21 | 21 |
| 21-4 | 21-4 |
| 22 | 22 |
| 23 | 23 |
| 24 | 24 |
| 24-4 | 24-4 |
| 24-5 | 24-5 |

-continued
| Compound # | Structure |
|---|---|
| 25 | 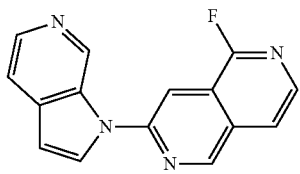<br>25 |
| 26 | 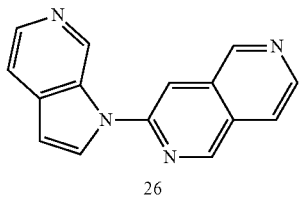 [SMILES: c1cc2cnc(-n3ccc4ccncc43)cc2cn1]<br>26 |
| 27 | 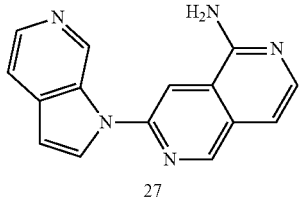<br>27 |
| 28 | 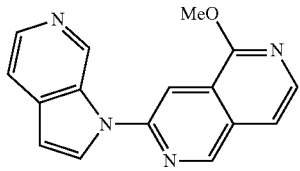<br>28 |
| 29 | 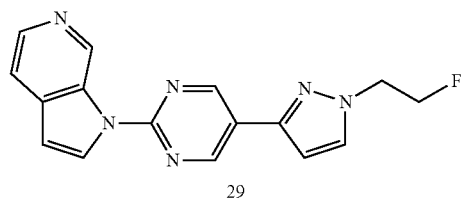 [SMILES: FCCn1ccc(-c2cnc(-n3ccc4ccncc43)nc2)n1]<br>29 |
| 30 | 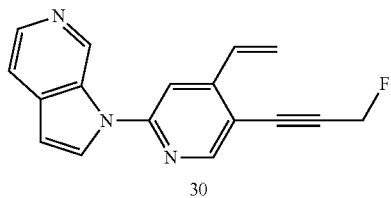 [SMILES: C=Cc1cc(-n2ccc3ccncc32)ncc1C#CCF]<br>30 |
| 31 | 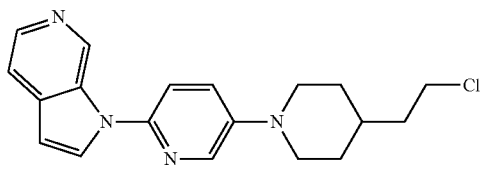<br>31 |

-continued
| Compound # | Structure |
|---|---|
| 31-1 | 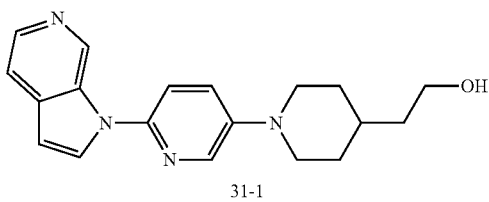 [SMILES: OCCC1CCN(c2ccc(-n3ccc4ccncc43)nc2)CC1]
31-1 |
| 32 | 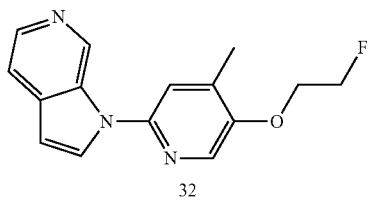 [SMILES: Cc1cc(-n2ccc3ccncc32)ncc1OCCF]
32 |
| 33 | 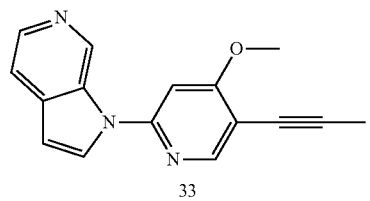
33 |
| 34 | 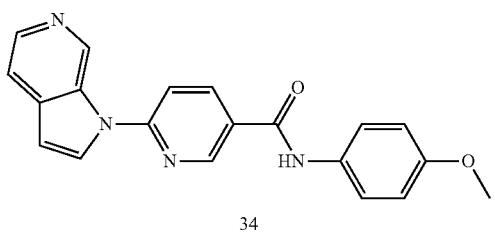 [SMILES: COc1ccc(NC(=O)c2ccc(-n3ccc4ccncc43)nc2)cc1]
34 |
| 35 | 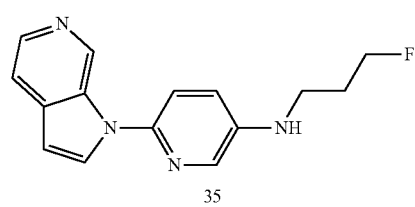 [SMILES: FCCCNc1ccc(-n2ccc3ccncc32)nc1]
35 |
| 36 | 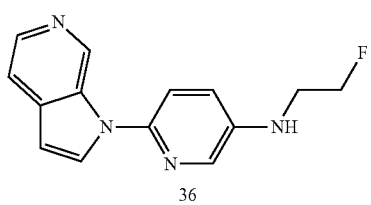 [SMILES: FCCNc1ccc(-n2ccc3ccncc32)nc1]
36 |
| 37 | 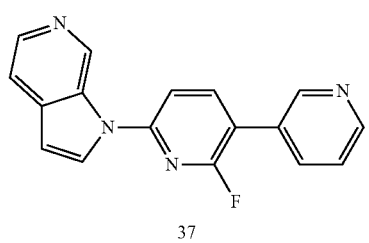 [SMILES: Fc1nc(-n2ccc3ccncc32)ccc1-c1cccnc1]
37 |

| Compound # | Structure |
|---|---|
| 38 | 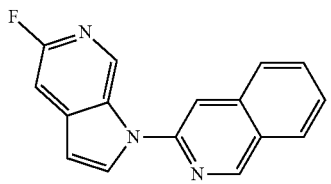
38 |
| 39 | 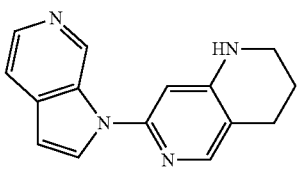
39 |
| 40 | 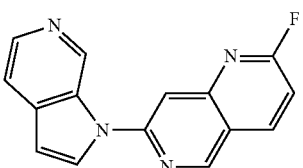
40 |
| 41 | 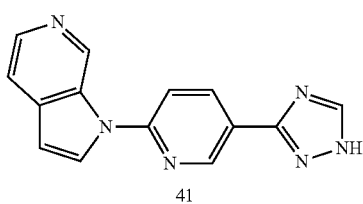 [SMILES: c1cc2ccn(-c3ccc(-c4nc[nH]n4)cn3)c2cn1]
41 |
| 42 | 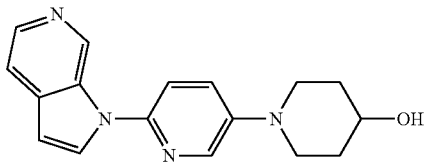
42 |
| 43 | 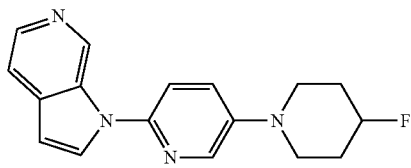
43 |
| 44 | 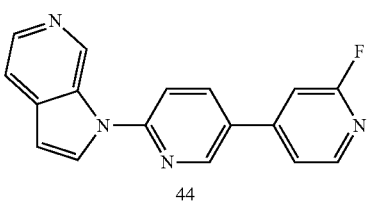 [SMILES: Fc1cc(-c2ccc(-n3ccc4ccncc43)nc2)ccn1]
44 |

-continued
| Compound # | Structure |
|---|---|
| 45 | 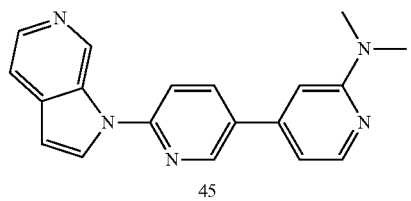 [SMILES: CN(C)c1cc(-c2ccc(-n3ccc4ccncc43)nc2)ccn1]<br>45 |
| 46 | 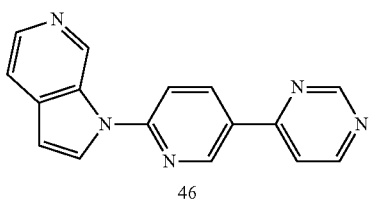 [SMILES: c1cc(-c2ccc(-n3ccc4ccncc43)nc2)ncn1]<br>46 |
| 47 | 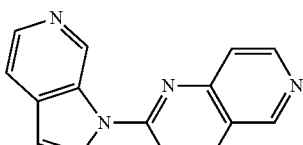<br>47 |
| 48 | 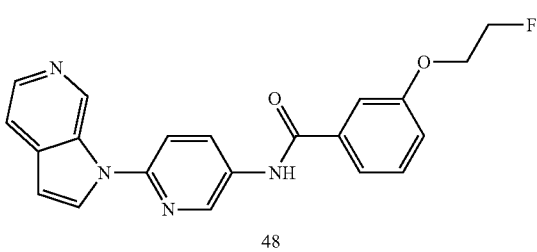 [SMILES: O=C(Nc1ccc(-n2ccc3ccncc32)nc1)c1cccc(OCCF)c1]<br>48 |
| 49 | 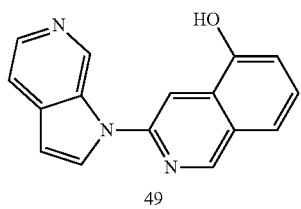 [SMILES: Oc1cccc2cnc(-n3ccc4ccncc43)cc12]<br>49 |
| 50 | 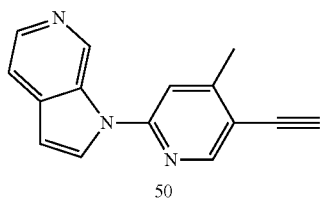 [SMILES: C#Cc1cnc(-n2ccc3ccncc32)cc1C]<br>50 |
| 51 | 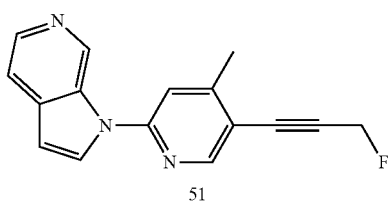 [SMILES: Cc1cc(-n2ccc3ccncc32)ncc1C#CCF]<br>51 |

-continued
| Compound # | Structure |
|---|---|
| 52 | 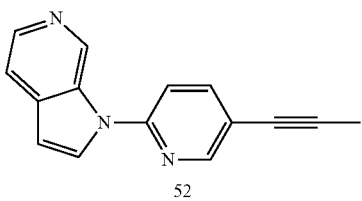 [SMILES: CC#Cc1ccc(-n2ccc3ccncc32)nc1]<br>52 |
| 53 | 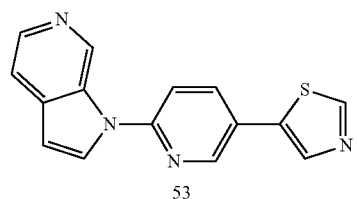 [SMILES: c1cc2ccn(-c3ccc(-c4cncs4)cn3)c2cn1]<br>53 |
| 54 | 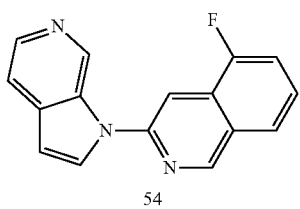<br>54 |
| 55 | 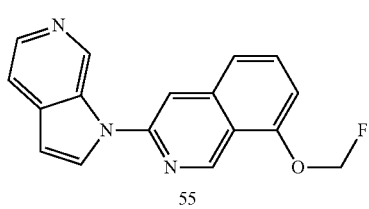 [SMILES: FCOc1cccc2cc(-n3ccc4ccncc43)ncc12]<br>55 |
| 56 | 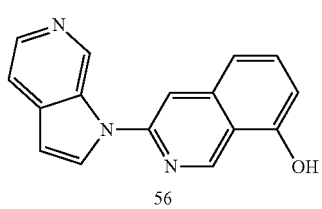 [SMILES: Oc1cccc2cc(-n3ccc4ccncc43)ncc12]<br>56 |
| 57 | 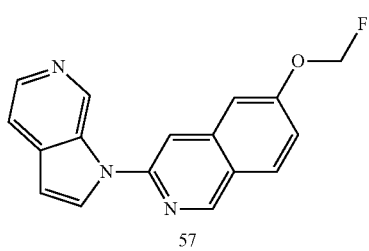 [SMILES: FCOc1ccc2cnc(-n3ccc4ccncc43)cc2c1]<br>57 |
| 58 | 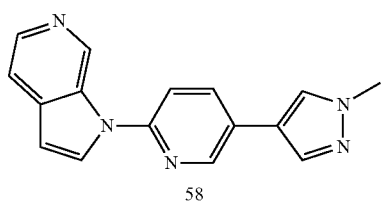 [SMILES: Cn1cc(-c2ccc(-n3ccc4ccncc43)nc2)cn1]<br>58 |

-continued
| Compound # | Structure |
|---|---|
| 59 | 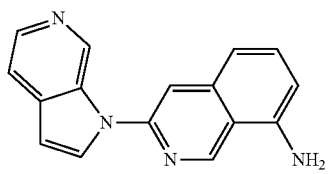
59 |
| 60 | 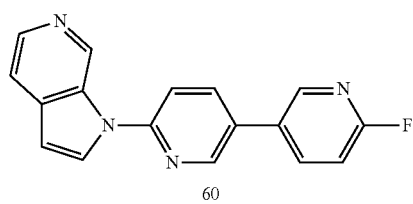 [SMILES: Fc1ccc(-c2ccc(-n3ccc4ccncc43)nc2)cn1]
60 |
| 61 | 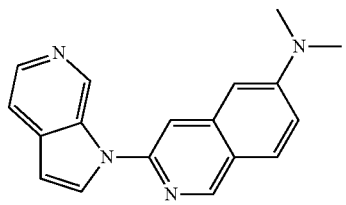
61 |
| 62 | 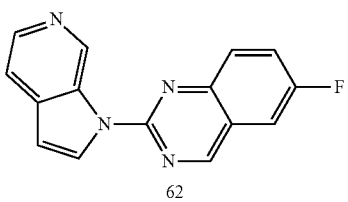 [SMILES: Fc1ccc2nc(-n3ccc4ccncc43)ncc2c1]
62 |
| 63 | 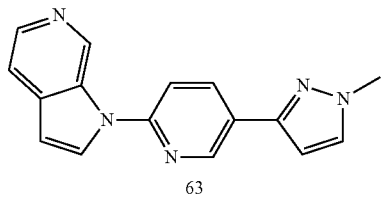 [SMILES: Cn1ccc(-c2ccc(-n3ccc4ccncc43)nc2)n1]
63 |
| 64 | 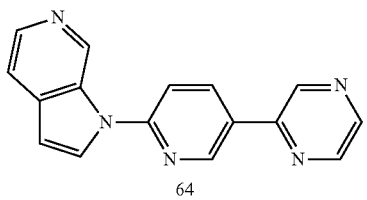 [SMILES: c1cnc(-c2ccc(-n3ccc4ccncc43)nc2)cn1]
64 |
| 65 | 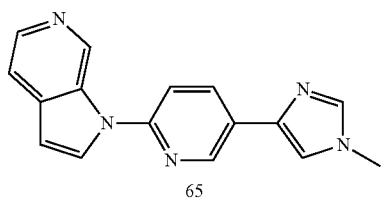 [SMILES: Cn1cnc(-c2ccc(-n3ccc4ccncc43)nc2)c1]
65 |

| Compound # | Structure |
|---|---|
| 66 | 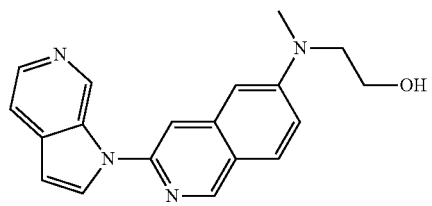<br>66 |
| 67 | 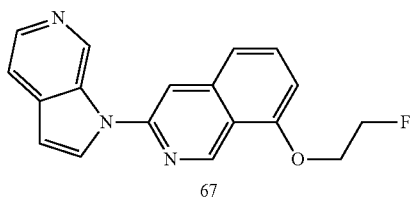 [SMILES: FCCOc1cccc2cc(-n3ccc4ccncc43)ncc12]<br>67 |
| 68 | 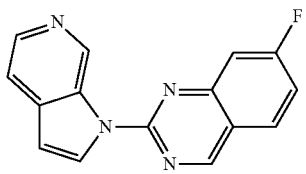<br>68 |
| 69 | 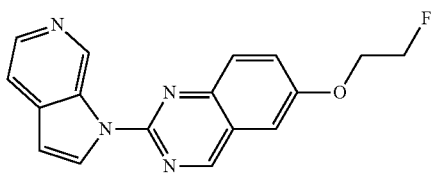<br>69 |
| 70 | 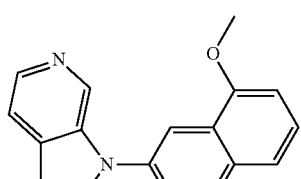<br>70 |
| 71 | 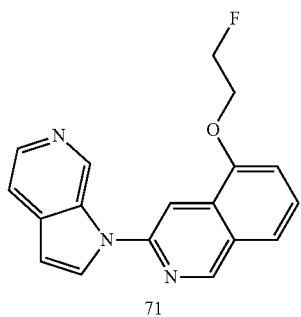 [SMILES: FCCOc1cccc2cnc(-n3ccc4ccncc43)cc12]<br>71 |

-continued
| Compound # | Structure |
|---|---|
| 72 | 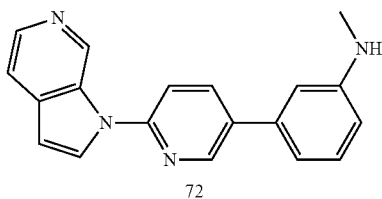 |
| 73 | 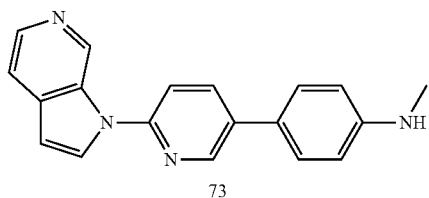 |
| 74 | 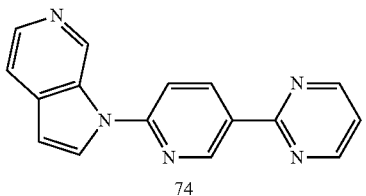 [SMILES: c1cnc(-c2ccc(-n3ccc4ccncc43)nc2)nc1] |
| 75 | 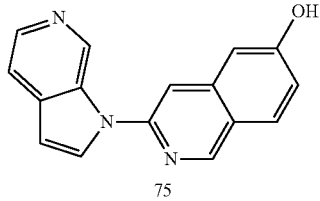 [SMILES: Oc1ccc2cnc(-n3ccc4ccncc43)cc2c1] |
| 76 | 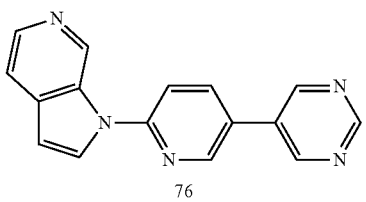 [SMILES: c1cc2ccn(-c3ccc(-c4cncnc4)cn3)c2cn1] |
| 77 | 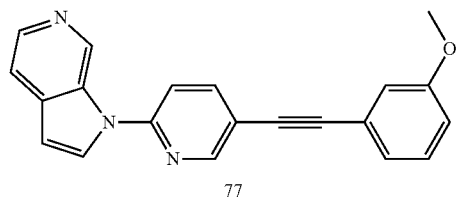 [SMILES: COc1cccc(C#Cc2ccc(-n3ccc4ccncc43)nc2)c1] |
| 78 | 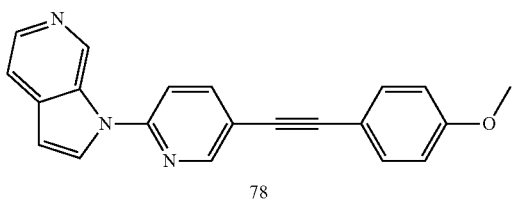 [SMILES: COc1ccc(C#Cc2ccc(-n3ccc4ccncc43)nc2)cc1] |

-continued
| Compound # | Structure |
|---|---|
| 79 | 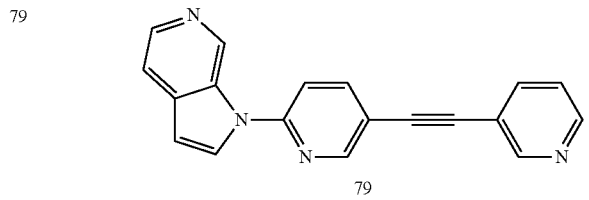 79 |
| 80 | 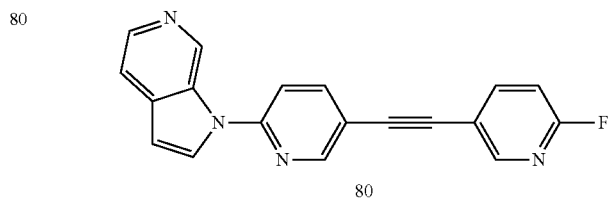 80 |
| 81 | 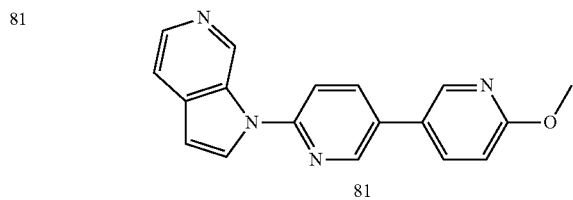 81 |
| 82 | 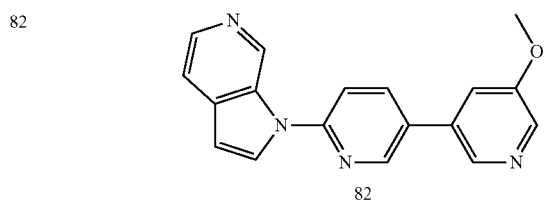 82 |
| 83 | 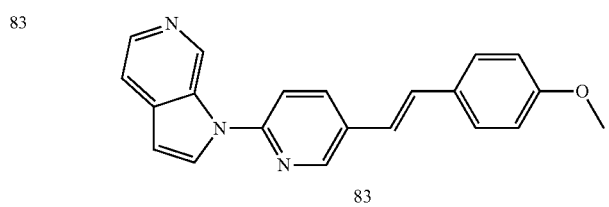 83 |
| 84 | 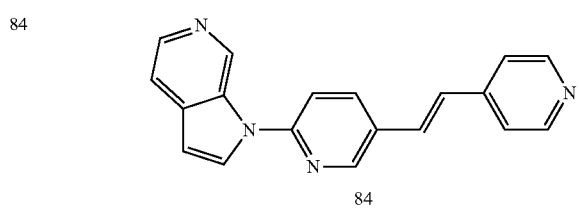 84 |
| 85 | 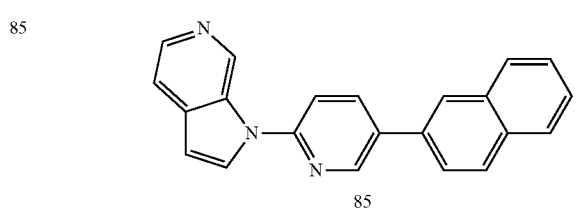 85 |

-continued
| Compound # | Structure |
|---|---|
| 86 | 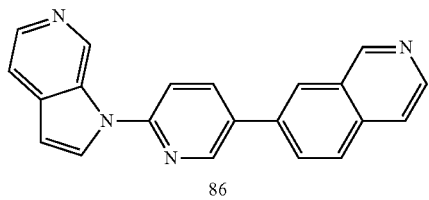 [SMILES: c1cc2ccc(-c3ccc(-n4ccc5ccncc54)nc3)cc2cn1] 86 |
| 87 | 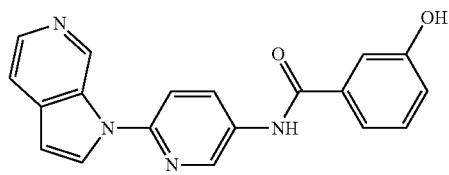 87 |
| 88 | 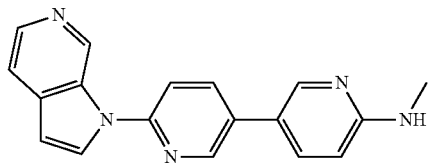 88 |
| 89 | 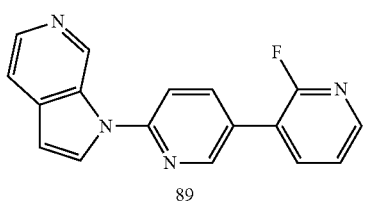 [SMILES: Fc1ncccc1-c1ccc(-n2ccc3ccncc32)nc1] 89 |
| 90 | 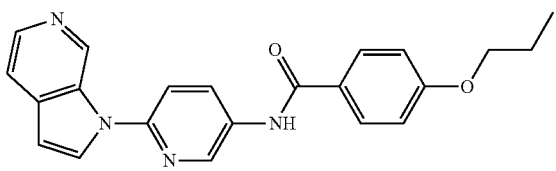 90 |
| 91 | 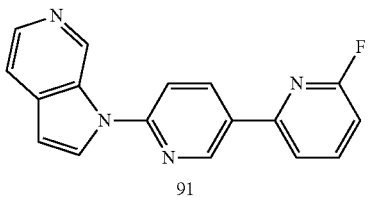 91 |
| 92 | 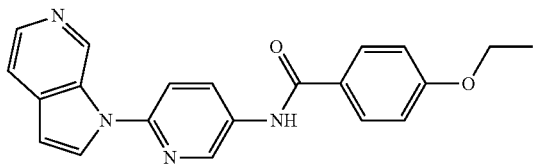 92 |

| Compound # | Structure |
|---|---|
| 93 | 93 |
| 94 | 94 |
| 95 | 95 |
| 96 | 96 |
| 97 | 97 |
| 98 | 98 |
| 99 | 99 |

| Compound # | Structure |
|---|---|
| 100 | 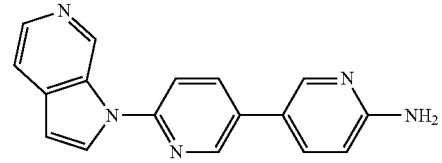<br>100 |
| 101 | 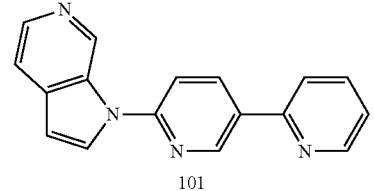 [SMILES: c1ccc(-c2ccc(-n3ccc4ccncc43)nc2)nc1]<br>101 |
| 102 | 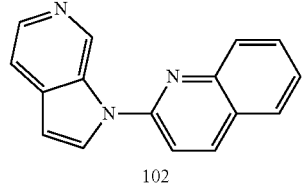 [SMILES: c1ccc2nc(-n3ccc4ccncc43)ccc2c1]<br>102 |
| 103 | 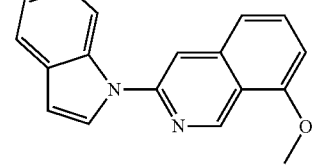<br>103 |
| 104 | 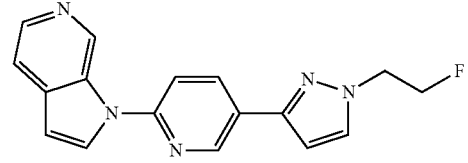<br>104 | or a pharmaceutically acceptable salt thereof.

24. The compound according to claim 23 which is isotopically labeled as $^2$H, $^3$H, $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{76}$Br, $^{77}$Br, $^{123}$I, $^{124}$I or $^{131}$I.

25. The compound according to claim 24 wherein the isotopically labeled compound is $^{18}$F.

26. A compound which is

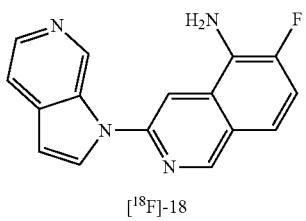 [SMILES: Nc1c(F)ccc2cnc(-n3ccc4ccncc43)cc12]

18 or a pharmaceutically acceptable salt thereof.

27. The compound according to claim 26 which is isotopically labeled as $^2$H, $^3$H, $^{11}$C, $^{13}$C, $^{14}$C, $^{13}$N, $^{15}$N, $^{18}$F.

28. An isotopically labeled compound represented by structural formula [$^{18}$F]-18:

[$^{18}$F]-18 or pharmaceutically acceptable salt thereof.

29. An isotopically labeled compound represented by structural formula [$^{18}$F]-18:

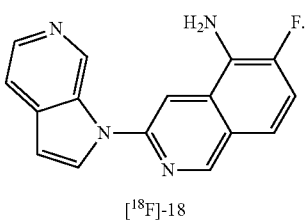 [SMILES: Nc1c(F)ccc2cnc(-n3ccc4ccncc43)cc12]

[¹⁸F]-18

30. A pharmaceutically acceptable salt of an isotopically labeled compound represented by structural formula [¹⁸F]-18:

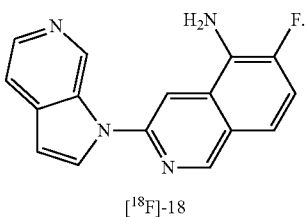 [SMILES: Nc1c(F)ccc2cnc(-n3ccc4ccncc43)cc12]

[¹⁸F]-18

31. A pharmaceutical composition comprising a compound according to claim 1 and a pharmaceutically acceptable carrier.

32. A pharmaceutical composition comprising a compound according to claim 30 and a pharmaceutically acceptable carrier.

33. A composition for imaging of tau aggregates, comprising a radio-labeled compound of claim 7 and a pharmaceutically acceptable carrier.

34. A method of inhibiting tau aggregation in a mammal, comprising administering the composition of claim 30 in an amount effective to inhibit tau aggregation.

35. A method for measuring tau deposits in a patient comprising the steps of administering a detectable quantity of a compound of formula I of claim 1 or a pharmaceutically acceptable salt thereof, and detecting the binding of the compound to tau deposits in the patient.

36. The method according to claim 35 wherein detection is carried out by performing positron emission tomography (PET) imaging, single photon emission computed tomography (SPECT), magnetic resonance imaging, or autoradiography.

37. The method according to claim 35 for diagnosing and monitoring the treatment of Alzheimer's Disease, familial Alzheimer's Disease, Down's Syndrome, Cognitive Deficit in Schizophrenia, frontotemporal dementia (FTD), progressive supranuclear palsy (PSP), corticobasal degeneration (CBD), chronic traumatic encephalopathy (CTE), Pick's disease, schizophrenia, pain disorders, sleep disorders, and Parkinson's Disease.

* * * * *

UNITED STATES PATENT AND TRADEMARK OFFICE
CERTIFICATE OF CORRECTION

PATENT NO. : 9,808,542 B2
APPLICATION NO. : 15/317333
DATED : November 7, 2017
INVENTOR(S) : Abbas W. Walji et al.

It is certified that error appears in the above-identified patent and that said Letters Patent is hereby corrected as shown below:

In the Claims

Column 159, Claim 4: Line 67, delete "-$C_{2-6}$ alkynyl$R^3$".

Column 160, Claim 7: Line 16, delete "-$C_{2-6}$ alkynyl$R^3$".

Column 160, Claim 10: Line 36, delete "-$C_{2-6}$ alkynyl$R^3$".

Column 160, Claim 14: Line 67, delete "-$C_{2-6}$ alkynyl$R^3$".

Signed and Sealed this
Nineteenth Day of June, 2018

Andrei Iancu
*Director of the United States Patent and Trademark Office*